United States Patent
Carlson et al.

(10) Patent No.: US 8,916,686 B2
(45) Date of Patent: Dec. 23, 2014

(54) TDF-RELATED COMPOUNDS AND ANALOGS THEREOF

(71) Applicant: Thrasos Innovation, Inc., Montreal, Quebec (CA)

(72) Inventors: William D. Carlson, Weston, MA (US); Peter C. Keck, Millbury, MA (US); Michael Sworin, Marlborough, MA (US); Dattatreyamurty Bosukonda, Shrewsbury, MA (US)

(73) Assignee: Thrasos Innovation, Inc., Montreal (CA)

( * ) Notice: Subject to any disclaimer, the term of this patent is extended or adjusted under 35 U.S.C. 154(b) by 0 days.

(21) Appl. No.: 13/777,658

(22) Filed: Feb. 26, 2013

(65) Prior Publication Data

US 2014/0044754 A1     Feb. 13, 2014

Related U.S. Application Data

(63) Continuation of application No. 11/629,558, filed as application No. PCT/US2005/021444 on Jun. 17, 2005, now Pat. No. 8,410,246.

(60) Provisional application No. 60/580,511, filed on Jun. 17, 2004, provisional application No. 60/608,625, filed on Sep. 10, 2004, provisional application No. 60/610,054, filed on Sep. 15, 2004, provisional application No. 60/618,735, filed on Oct. 14, 2004.

(51) Int. Cl.
| | | |
|---|---|---|
| C07K 1/00 | (2006.01) | |
| A61K 38/00 | (2006.01) | |
| C07K 7/08 | (2006.01) | |
| C07K 14/475 | (2006.01) | |
| C07K 7/06 | (2006.01) | |
| A61K 38/10 | (2006.01) | |

(52) U.S. Cl.
CPC .................. *C07K 7/08* (2013.01); *C07K 14/475* (2013.01); *C07K 7/06* (2013.01); *A61K 38/10* (2013.01)
USPC .......................................... 530/350; 530/300

(58) Field of Classification Search
None
See application file for complete search history.

(56) References Cited

U.S. PATENT DOCUMENTS

| 6,444,802 B1 | 9/2002 | Kapeller-Libermann et al. |
| 2003/0185792 A1 | 10/2003 | Keck et al. |

FOREIGN PATENT DOCUMENTS

| WO | WO 97/26277 | 7/1997 |
| WO | 0239118 A1 | 5/2002 |
| WO | 03106656 A2 | 12/2003 |
| WO | 03106972 A2 | 12/2003 |
| WO | 2004044838 A2 | 5/2004 |

OTHER PUBLICATIONS

Nishijima et al., A Human GM-CSF Receptor Expressed in Transgenic Mice Stimulates Proliferation and Differentiation of Hemopoietic Progenitors to All Lineages in Response to Human GM, Molecular Biology of the Cell; 6: 497-508 (1995).
Guy et al., E2F-1 Blocks Terminal Differentiation and Causes Proliferation in Transgenic Megakaryocytes, Molecular and Cellular Biology, 16(2): 685-693 (1996).
Takahashi et al., Role of GATA-1 in Proliferation and Differentiation of Definitive Erythroid and Megakaryocytic Cells In Vivo, Blood 92(2): 434-442 (1998).
Celeste et al., Identification of Transforming Growth Factor b Family Members Present in Bone-Inducive Protein Puriied from Bovine Bone, Proc. Natl. Acad. Sci. USA, 87: 9843-9847 (1990).
International Search Report PCT/US03/19203 mailed Jun. 22, 2005.
International Search Report PCT/US03/19229 completed May 11, 2004.

*Primary Examiner* — Sean Aeder
(74) *Attorney, Agent, or Firm* — McCarter & English, LLP; Jonathan M. Sparks

(57) ABSTRACT

The present invention relates generally to tissue differentiation factor (TDF) analogs. More specifically, the invention relates to structure-based methods and compositions useful in designing, identifying, and producing molecules which act as functional modulators of TDF-like receptors. The invention further relates to methods of detecting, preventing, and treating TDF-associated disorders.

10 Claims, 26 Drawing Sheets

FIG. 2

In Vitro Data Using Vascular Endothelial Cell-based Assay

| TDFRP Compound (SEQ ID NO.) | SMAD 1/5 Phosphorylation |
|---|---|
| 45 | + |
| 43 | + |
| 24 | + |
| 209 | + |
| 33 | + |
| 221 | + |
| 16 | No activity |

FIG. 3

*In vitro* showing Smad 1/5 phosphorylation by Thrasos compounds in LNCaP human prostate cancer cells

| SEQ ID NO. | Smad 1/5 Phosphorylation |
|---|---|
| 45 | + |
| 16 | No activity |

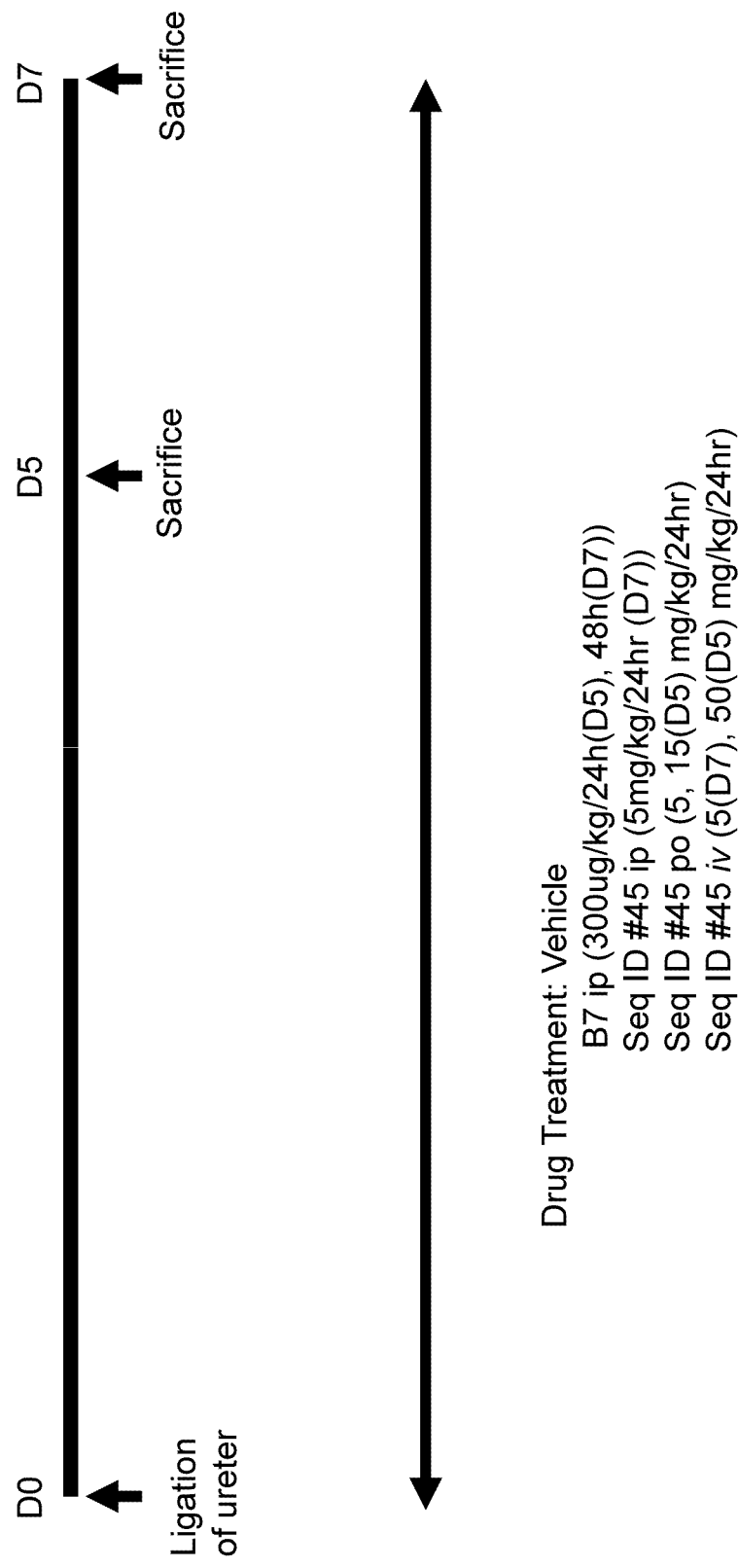

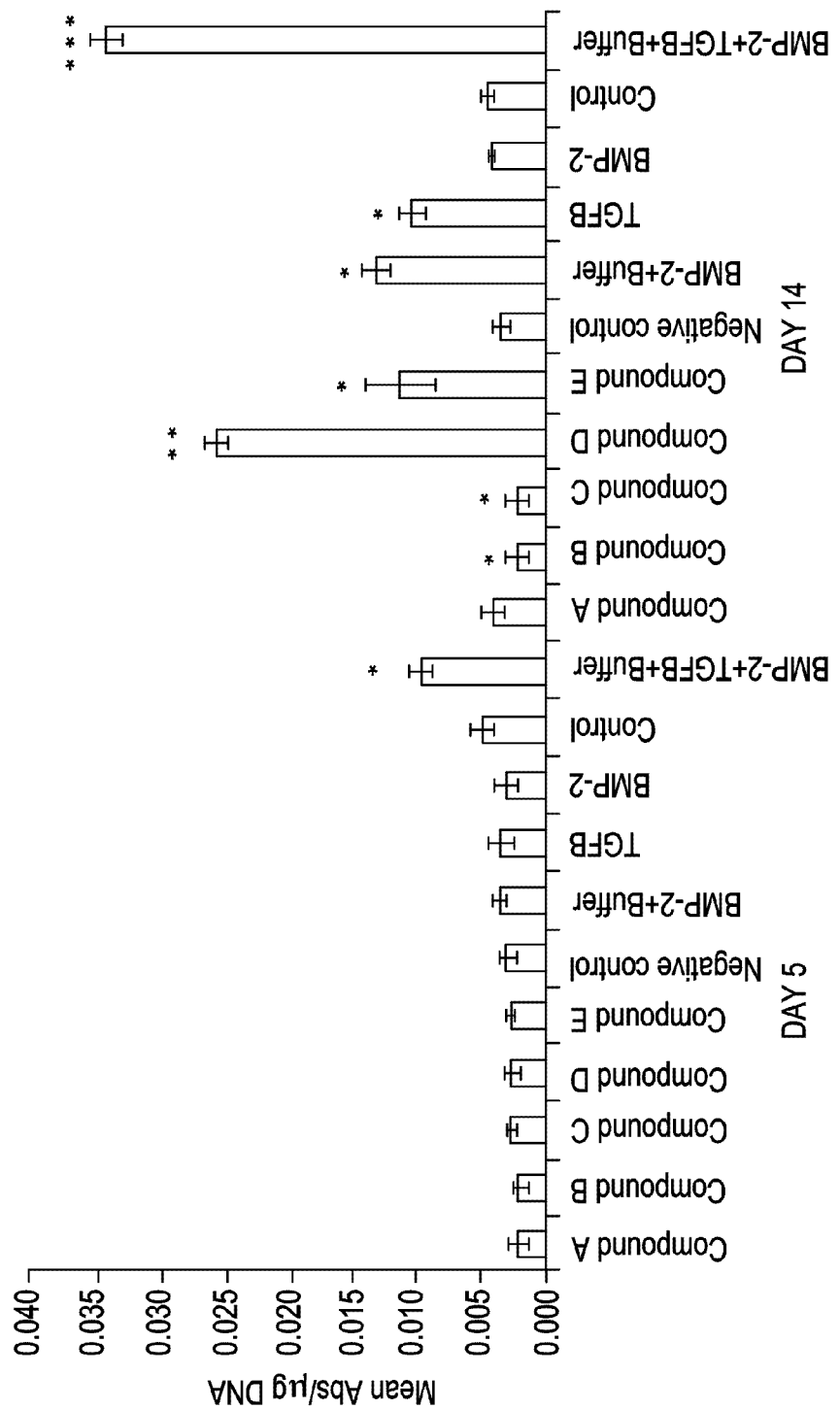

FIG. 10

*In vitro* data using the respective HK-2 cell-based assays

| SEQ ID NO | IL-6 TNF-α | IL-8 TNF-α | ICAN-1 TNF-α | Bax TNF-α | Bcl-xL TNF-α | Bax Cisplatin | IL-8 Cisplatin |
|---|---|---|---|---|---|---|---|
| 45 | ++ | ++ | ++ | ++ | ++ | ++ | + |
| 43 | ++ | ++ | ++ | | | | |
| 24 | ++ | ++ | ++ | | | | |
| 209 | ++ | ++ | ++ | ++ | | | |
| 213 | + | + | + | | | | |
| 33 | ++ | ++ | ++ | | | | |
| 217 | ++ | ++ | ++ | | | | |
| 221 | + | | | | | | |
| 222 | | | | | | | |
| 16 | | | | | | | |

FIG. 11

*In vitro* receptor binding data

| SEQ ID NO | BMPR-II | ALK-3 | ALK-6 |
|---|---|---|---|
| 45 | + | + | - |
| 43 |   | + |   |
| 24 |   | + |   |
| 209 |   | + |   |
| 213 |   | + |   |
| 33 |   | + |   |
| 217 |   | + |   |
| 221 |   | + |   |
| 16 | - | - | - |

FIG. 12

*In vitro* data using the respective cardiomyocyte cell-based assays

| SEQ ID NO | pAkt Starvation | pAkt Doxorubicin | Caspase-3 Doxorubicin | pAkt LPS | Caspase-3 LPS | IL-6 LPS | TNF-α LPS | MCP-1 LPS |
|---|---|---|---|---|---|---|---|---|
| 45 | | ++ | ++ | + | ++ | ++ | + | ++ |
| 217 | ++ | | | | | | | |

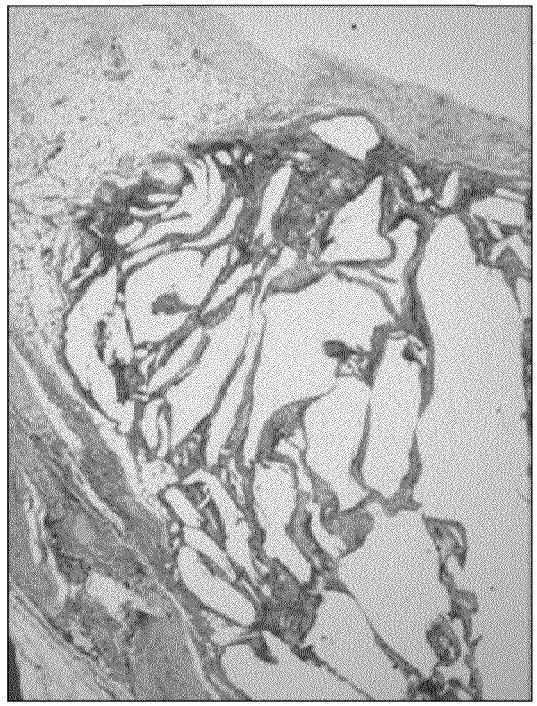
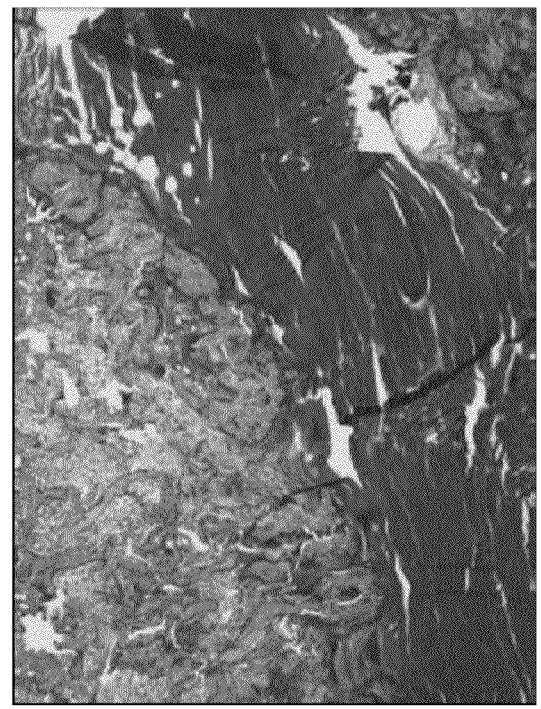

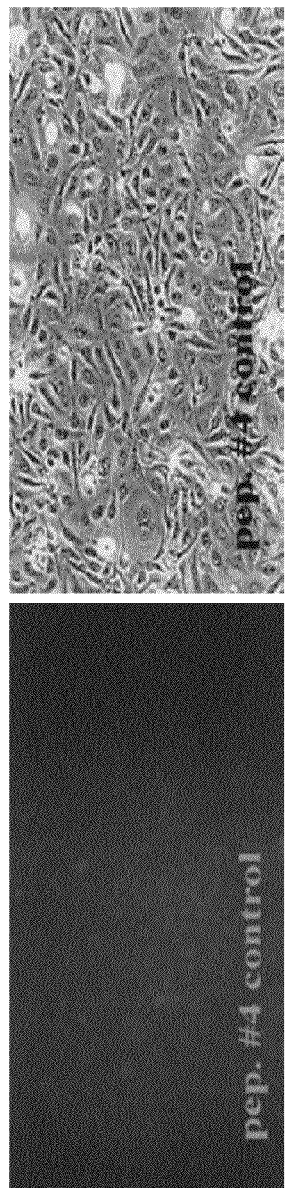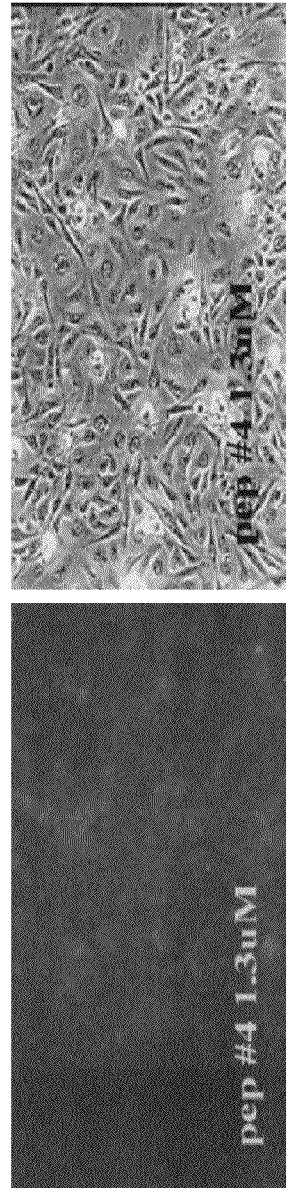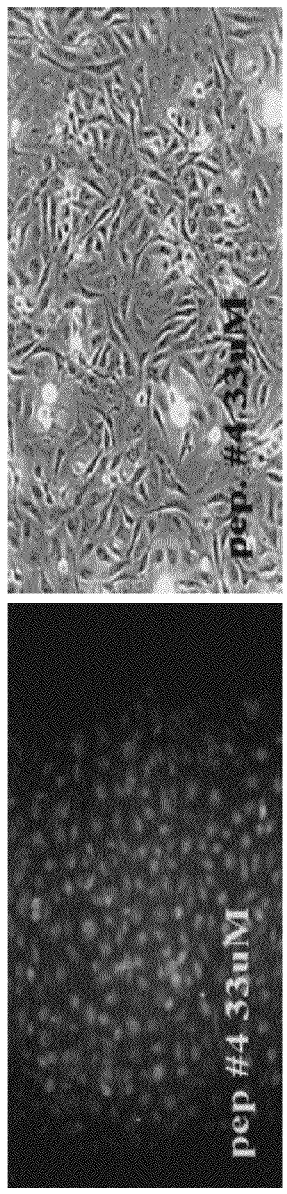
FIG. 15A  SEQ ID NO:45  0.0 μM
FIG. 15B  1.3 μM
FIG. 15C  33.0 μM

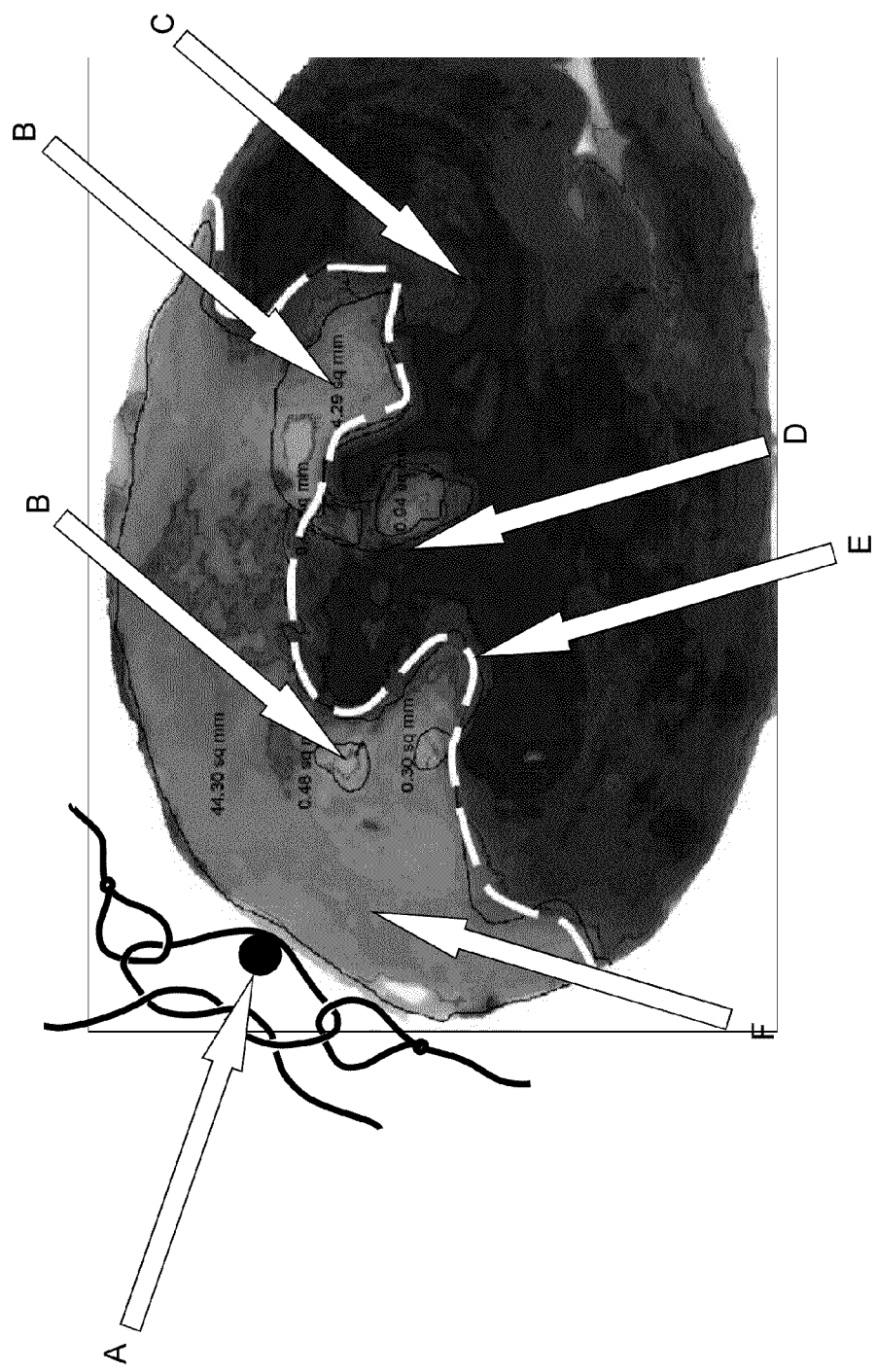

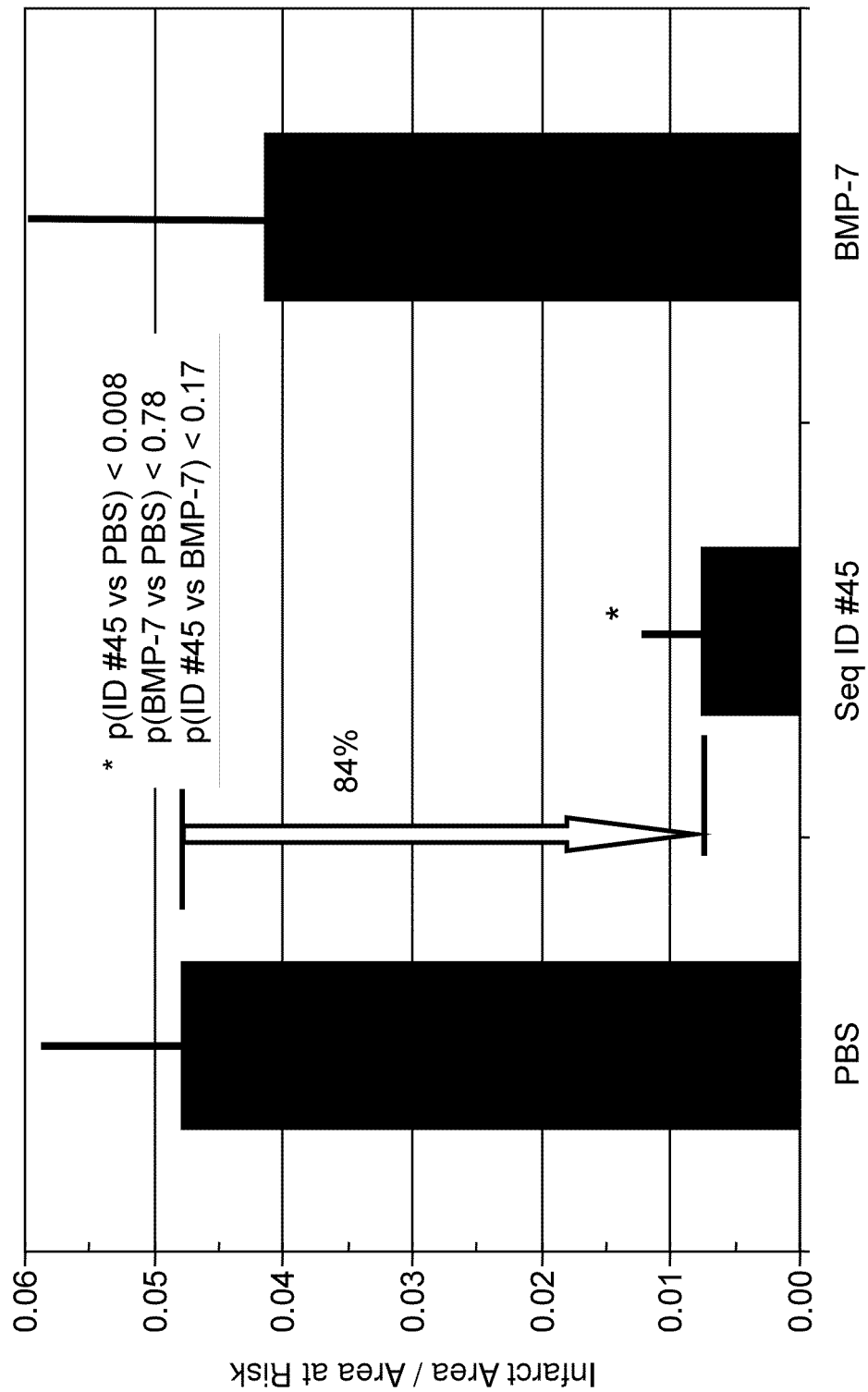

Effect of 2.8 mg/kg SEQ ID #45

SEQ ID #45 Medium Dose = 2.8 mg/kg BW
Day 7

Rat kidney on cisplatin

Control: 5 mg/kg BW Cisplatin
Day 7

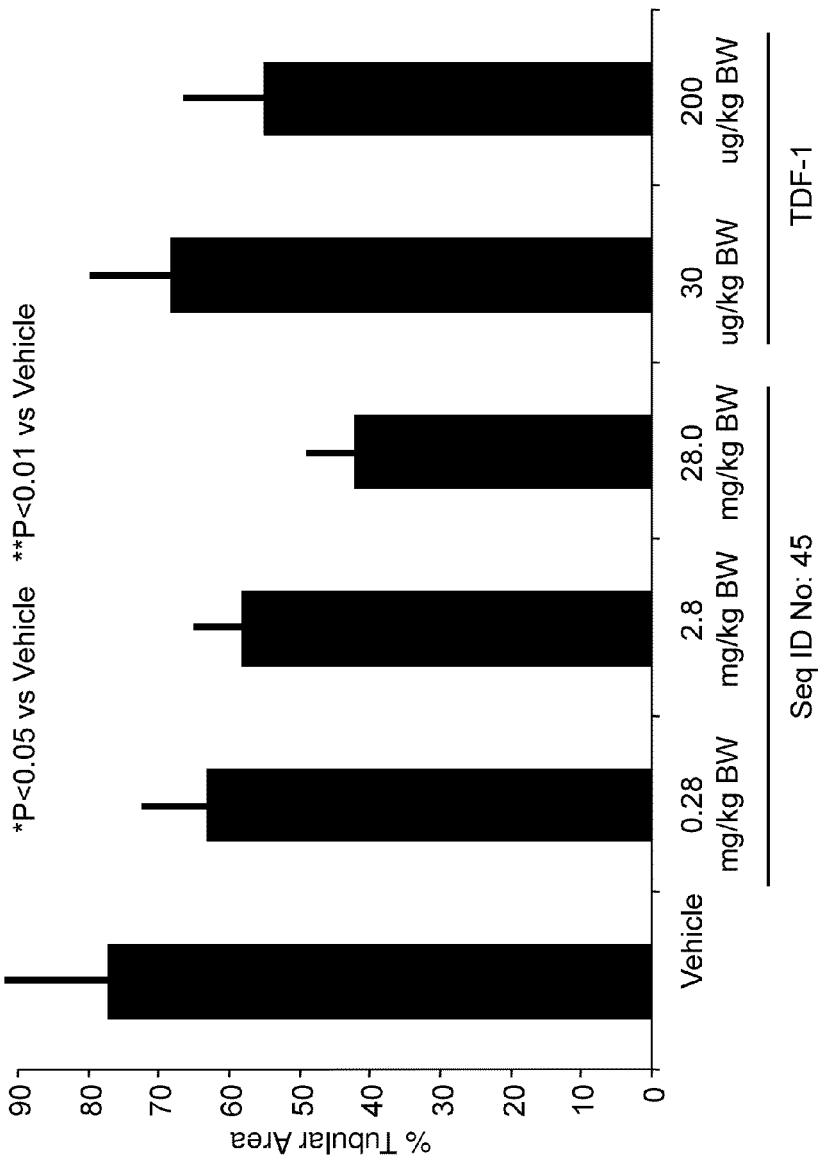

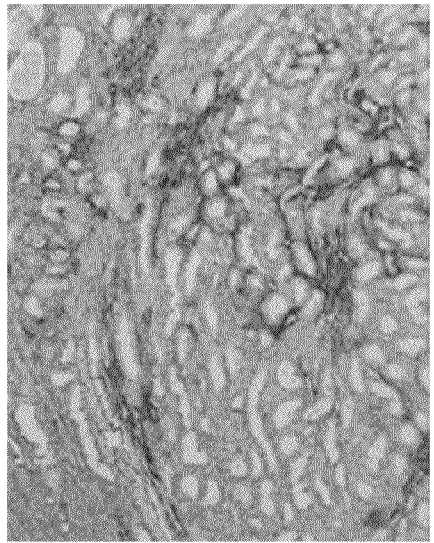
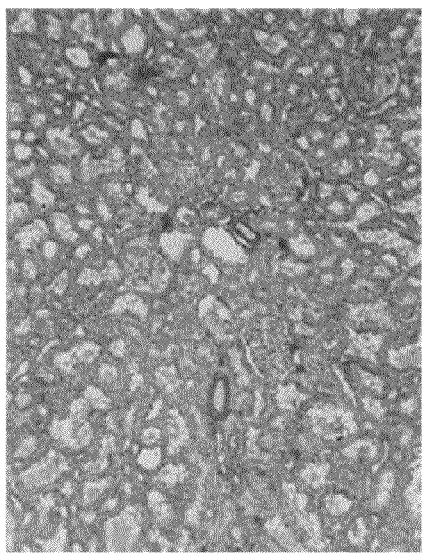
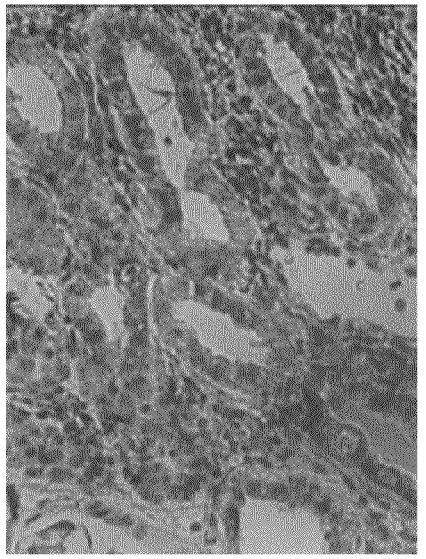
FIG. 22A
FIG. 22B
SEQ ID #45 maintains the expression of vascular smooth muscle in the peri-cellular capillaries & protects regenerative activity (PCNA stain)
SEQ ID #45 & cisplatin
VEHICLE (cisplatin alone)
Smooth Muscle Actin
Proliferating Cell Nuclear Antigen

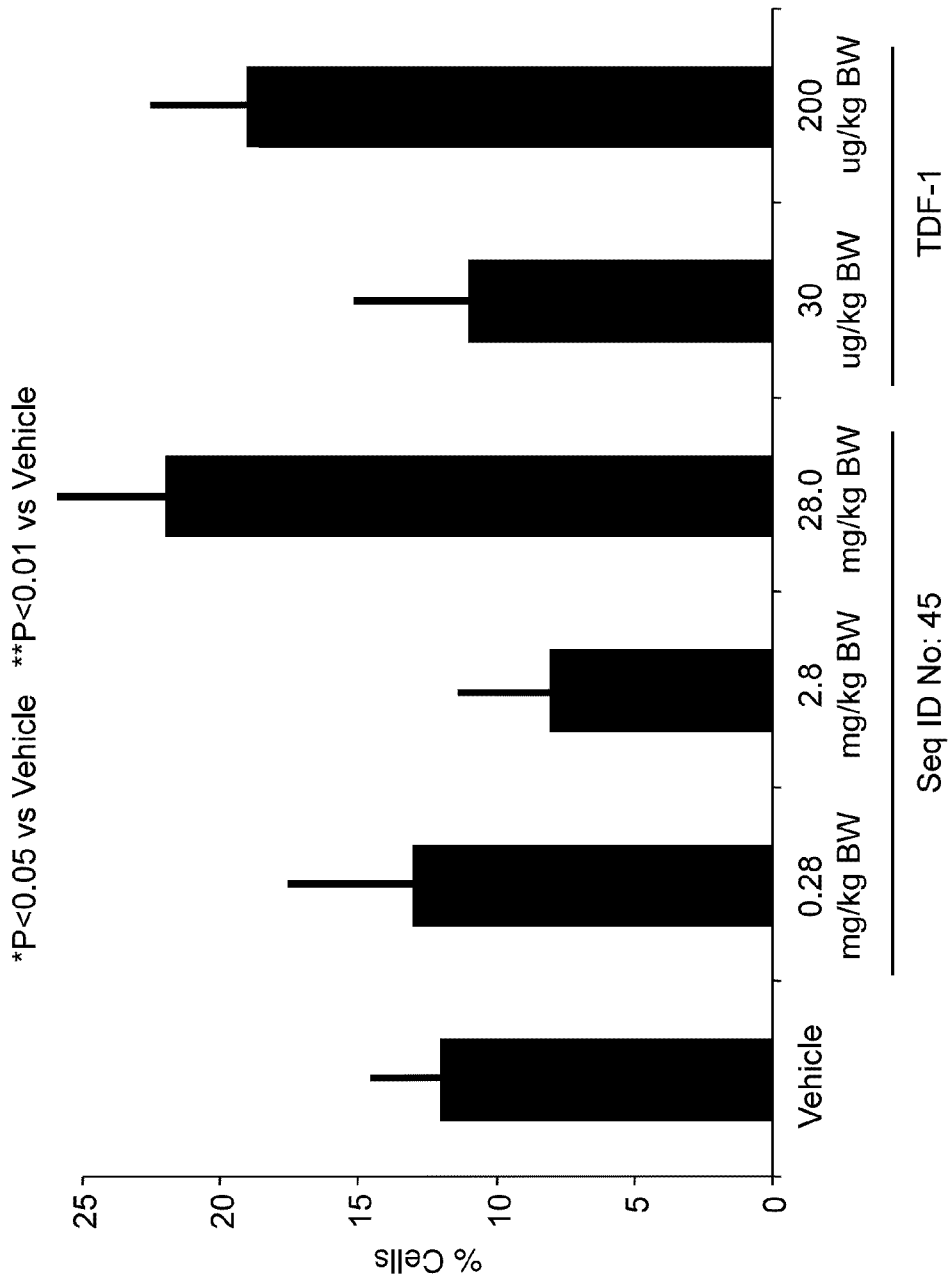

TDF-RELATED COMPOUNDS AND ANALOGS THEREOF

CROSS-REFERENCE TO RELATED APPLICATIONS

This application is a Continuation of application Ser. No. 11/629,558, filed on Feb. 23, 2009, now U.S. Pat. No. 8,410, 246, issued on Apr. 2, 2013, which is a National Stage Application of Application PCT/US2005/021444 filed on Jun. 17, 2005, which claims the benefit of U.S. Provisional Application 60/580,511 filed on Jun. 17, 2004, U.S. Provisional Application 60/608,625 filed on Sep. 10, 2004, U.S. Provisional Application 60/610,054 filed on Sep. 15, 2004, and U.S. Provisional Application 60/618,735 filed on Oct. 14, 2004. The entire contents of each of the aforementioned applications are hereby incorporated by reference.

FIELD OF THE INVENTION

The present invention relates generally to tissue differentiation factor (TDF) analogs. More specifically, the invention relates to structure-based methods and compositions useful in identifying, designing, and producing molecules, which act as functional modulators of TDF-like receptors.

BACKGROUND OF THE INVENTION

Cell differentiation is the central characteristic of tissue morphogenesis, which initiates during embryogenesis, and continues to various degrees throughout the life of an organism in adult tissue repair and regeneration mechanisms. The degree of morphogenesis in adult tissue varies among different tissues and is related, among other things, to the degree of cell turnover in a given tissue.

The cellular and molecular events, which govern the stimulus for differentiation of cells is an area of intensive research. In the medical and veterinary fields, it is anticipated that discovery of the factor or factors which control cell differentiation and tissue morphogenesis will advance significantly the ability to repair and regenerate diseased, injured or damaged mammalian tissues and organs. Particularly useful areas for human and veterinary therapeutics include reconstructive surgery, the treatment of tissue degenerative diseases including, for example, arthritis, emphysema, osteoporosis, cardiomyopathy, cirrhosis, degenerative nerve diseases, inflammatory diseases, and cancer, and in the protection and/or regeneration of tissues, organs and limbs. The terms "morphogenetic" and "morphogenic" are often used interchangeably.

A number of different factors have been isolated in recent years, which appear to play a role in cell differentiation. Recently, a distinct subfamily of the "superfamily" of structurally related polypeptides referred to in the art as the "Transforming Growth Factor-beta (TGF-beta; TGF-β) superfamily of polypeptides" have been identified as tissue morphogens.

The members of this distinct "subfamily" of tissue morphogenic polypeptides share substantial amino acid sequence homology within their morphogenetically active C-terminal domains, including a conserved six or seven cysteine skeleton, and share the in vivo activity of inducing tissue-specific morphogenesis in a variety of organs and tissues. The polypeptides apparently contact and interact with progenitor cells e.g., by binding suitable cell surface molecules, predisposing or otherwise stimulating the cells to proliferate and differentiate in a morphogenetically permissive environment.

Recent studies on cell surface receptor binding of various members of the TGF-beta polypeptide superfamily suggests that the peptides mediate their activity by interaction with two different receptors, referred to as Type I and Type II receptors. The Type I or Type II receptors are both serine/threonine kinases, and share similar structures: an intracellular domain that consists essentially of the kinase, a short, extended hydrophobic sequence sufficient to span the membrane one time, and an extracellular domain characterized by a high concentration of conserved cysteines.

Morphogenic polypeptides are capable of inducing the developmental cascade of cellular and molecular events that culminate in the formation of new organ-specific tissue, including any vascularization, connective tissue formation, and nerve innervation as required by the naturally occurring tissue. The polypeptides have been shown to induce morphogenesis of cartilage and bone, as well as, periodontal tissues, dentin, liver, heart, kidney and neural tissue, including retinal tissue.

These tissue morphogenic polypeptides are recognized in the art as a distinct subfamily of polypeptides different from other members of the TGF-beta superfamily in that they share a high degree of sequence identity in the C-terminal domain and in that the tissue morphogenic polypeptides are able to induce, on their own, the full cascade of events that result in formation of functional tissue rather than merely inducing formation of fibrotic (scar) tissue. Specifically, members of the family of morphogenic polypeptides are capable of all of the following in a morphogenetically permissive environment: stimulating cell proliferation and cell differentiation, and supporting the growth and maintenance of differentiated cells. The morphogenic polypeptides also may act as endocrine, paracrine or autocrine factors.

As a result of their biological activities, significant effort has been directed toward the development of morphogen-based therapeutics for treating injured or diseased mammalian tissue, including, for example, therapeutic compositions for inducing regenerative healing of bone defects such as fractures, as well as therapeutic compositions for preserving or restoring healthy metabolic properties in diseased tissue, e.g., osteopenic bone tissue.

SUMMARY OF THE INVENTION

The present invention relates to compositions having properties similar to TGF-beta superfamily polypeptides, and methods for the prophylactic and therapeutic treatment of a subject having disease states characterized by aberrant levels of TGF-beta-like polypeptides. More particularly, the compositions and methods have bone morphogenetic protein-like properties, and are useful in treating or preventing diseases associated with the same.

In one aspect, the invention includes tissue differentiation factor related polypeptides (TDFRP) compounds having amino acid sequences selected from the group consisting of SEQ ID NOs:1-314, further including polynucleotides encoding the polypeptides of SEQ ID NOs:1-314. Also included are variants, analogs, homologs, or fragments of the polypeptide and polynucleotide sequences, and small molecules related to these. In one embodiment, the TDFRP compounds modulate signal transduction across a membrane of a cell that expresses a tissue differentiation factor receptor (a TDFR), such as, but not limited to, a TGF-beta superfamily receptor. In another embodiment, the invention includes an isolated nucleic acid molecule encoding the TDFRP compounds. In yet another embodiment, the isolated nucleic acid is a vector, and the vector may optionally include a promoter sequence that can be operably linked to the nucleic acid, where the promoter causes expression of the nucleic acid molecule. In one embodiment, the promoter is inducible. In still another embodiment, the vector is transformed into a cell, such as a prokaryotic or eukaryotic cell, preferably a mammalian cell, or more preferably a human cell. In even another embodiment, the vector is a viral vector capable of infecting a mammalian cell and causing expression of a polypeptide of SEQ ID NOs:1-314 in an animal infected with the virus.

In another aspect, the invention includes a pharmaceutical composition having a TDFRP compound with or without a pharmaceutically acceptable carrier.

In yet another aspect, the invention includes an antibody to a TDFRP compound or a fragment thereof that binds immunospecifically to a TDFRP compound. In one embodiment, the antibody is an antibody fragment, such as but not limited to an Fab, (Fab)$_2$, Fv or Fc fragment. In another embodiment, the antibody or fragment thereof is a monoclonal antibody. In even another embodiment, the antibody or fragment thereof is a humanized antibody. In still another embodiment, the invention includes an antibody or antibody fragment immunospecific to SEQ ID NOs:1-314 or at least 6 contiguous amino acid residues of SEQ ID NOs:1-314, with or without a pharmaceutically acceptable carrier. In yet another embodiment, the invention includes a pharmaceutical composition having a polypeptide or the nucleic acid sequence of SEQ ID NOs:1-314, an antibody or antibody fragment, with or without a pharmaceutically-acceptable carrier.

In yet another aspect, the invention includes a method for preparing a TDFRP compound, the method having the steps of culturing a cell containing a nucleic acid encoding SEQ ID NOs:1-314 under conditions that provide for expression of the TDFRP compound; and recovering the expressed TDFRP compound.

In still another aspect, the invention includes a method for determining the presence or amount of the TDFRP compound in a sample, the method having the steps of providing the sample, contacting the sample with an antibody or antibody fragment to SEQ ID NOs:1-314 that binds immunospecifically to the TDFRP compound, and determining the presence or amount of the antibody bound to the TDFRP compound, thereby determining the presence or amount of the TDFRP compound in the sample.

In even another aspect, the invention includes a method for determining the presence or amount of the nucleic acid molecule encoding SEQ ID NOs:1-314 in a sample, the method having the steps of providing the sample, contacting the sample with a nucleic acid probe that hybridizes to the nucleic acid molecule, and determining the presence or amount of the probe hybridized to the nucleic acid molecule, thereby determining the presence or amount of the nucleic acid molecule in the sample.

In another aspect, the invention includes a method of identifying a candidate compound that binds to SEQ ID NOs:1-314, the method having the steps of contacting the compound with the TDFRP compound, and determining whether the candidate compound binds to the TDFRP compound.

In one aspect, the invention includes a method of treating or preventing a tissue differentiation factor-associated disorder, the method comprising administering to a subject in which such treatment or prevention is desired a TDFRP compound in an amount sufficient to treat or prevent the tissue differentiation factor-associated disorder in the subject. In one embodiment, the tissue differentiation factor-associated disorder is selected from the group consisting of a tissue degenerative disease and tissue regeneration. In another embodiment, the tissue degenerative disease is renal disease, heart disease, traumatic brain injury, stroke, atherosclerosis, arthritis, emphysema, osteoporosis, cardiomyopathy, cirrhosis, degenerative nerve disease, Holt-Oram disease, congenital disease, pulmonary disease, eye disease, diabetic nephropathy, degenerative bone disease, periodontal disease, chronic kidney disease, diabetes, cardiovascular disease, inflammatory disease, immune disease, skeletal disease, reproductive disease, hematopoetic disease, or cancer. In another embodiment, the tissue regeneration includes regeneration of muscle (particularly cardiac muscle), dendritic tissue, nerve, kidney, brain, bone, skin, lung, muscle, ovary, testes, heart, spleen, cartilage, nerve, periodontal, dentin, liver, vascular, connective, lymphatic, hematopoetic, or renal tissue. In still another embodiment, the invention includes a method of treating or preventing a tissue differentiation factor-associated disorder, by administering to a subject in which such treatment or prevention is desired the nucleic acid of claim 5 in an amount sufficient to treat or prevent the tissue differentiation factor-associated disorder in the subject. In another embodiment, the invention includes a method of treating or preventing a tissue differentiation factor-associated disorder, by administering to an explant or ex vivo culture a TDFRP compound in an amount sufficient to treat or prevent the tissue differentiation factor-associated disorder. In one embodiment, the subject is a human subject. In another embodiment, the subject is an animal subject.

In one aspect, the invention includes a kit having in one or more containers, a pharmaceutical TDFRP composition and instructions for using the contents therein.

In yet another aspect, the invention includes a method for determining the presence of or predisposition to a disease associated with altered levels of tissue differentiation factor receptor in a first mammalian subject, the method having the steps of providing a test sample from the first mammalian subject; contacting the test sample from the first mammalian subject with a TDFRP compound, detecting the level of compound/tissue differentiation factor receptor complex, quantifying the level of expression of the tissue differentiation factor receptor in the sample from the first mammalian subject; and comparing the amount of the tissue differentiation factor receptor in the sample of step (a) to the amount of the tissue differentiation factor receptor present in a control sample from a second mammalian subject known not to have, or not to be predisposed to, the disease, wherein an alteration in the expression level of the tissue differentiation factor receptor in the first subject as compared to the control sample indicates the presence of or predisposition to the disease.

In yet another aspect, the invention includes a method of treating a pathological state in a mammal, the method comprising administering to the mammal a compound in an amount that is sufficient to alleviate the pathological state, wherein the compound is a compound having an amino acid sequence at least 90% identical to a compound comprising an amino acid sequence including SEQ ID NOs:1-314.

In another aspect, the invention includes a method of treating a pathological state in a mammal, the method comprising administering to the mammal an antibody or fragment thereof immunospecific to SEQ ID NOs:1-314 or at least 6 contiguous amino acids thereof, in an amount sufficient to alleviate the pathological state. In one embodiment, the invention includes a method of treating a tissue differentiation factor-associated disorder in a mammal, the method including administering to the mammal at least one compound which modulates the expression or activity of a TDFRP compound. In yet another embodiment, the tissue differentiation factor-associated disorder is selected from the group consisting of renal disease, traumatic brain injury, stroke, atherosclerosis, arthritis, emphysema, osteoporosis, cardiomyopathy, cirrhosis, degenerative nerve disease, Holt-Oram disease, congenital disease, pulmonary disease, eye disease, diabetic nephropathy, degenerative bone disease, renal disease, periodontal disease, chronic kidney disease, diabetes, atherosclerosis, cardiovascular disease, inflammatory disease, immune disease, skeletal disease, reproductive disease, hematopoetic disease, or cancer. In still another embodiment, the invention includes a compound for use in treating a tissue differentiation factor-associated disorder, wherein the compound is SEQ ID NOs:1-314. In yet another embodiment, the invention include the use of a compound for the manufacture of a medicament for treatment of a tissue differentiation factor-associated disorder, wherein the compound is SEQ ID NOs:1-314.

In another aspect, the invention includes a method of identifying a candidate compound, which binds to a TDFRP compound, the method having the steps of, providing a candidate compound, contacting the candidate compound with the TDFRP compound under conditions where a complex is formed between the test compound and the TDFRP compound, incubating the complex under conditions where co-crystals of the complex form, determining the structural atomic coordinates of the complex by x-ray diffraction, and modeling the structure of the complex to determine the binding of the candidate compound to the TDFRP compound. In one embodiment the invention includes a crystalline preparation of a candidate compound and a TDFRP compound. In another embodiment, the complex is not crystallized but the complex is subjected to nuclear magnetic spectroscopy or mass spectroscopy to determine binding of the complex.

In another aspect, the invention provides a transgenic non-human mammal, for example but not limited to a mouse, having genomically-integrated in non-human mammal cells, a nucleic acid encoding SEQ ID NOs:1-314, having a first sequence segment which is a regulatory region and a second sequence segment which is a polynucleotide sequence encoding a TDFRP compound, wherein the first sequence segment is operably linked to the second sequence segment. In one embodiment, the first segment is a regulatable expression element or elements, which are subject to cell- or tissue-specific regulation. In one embodiment, the invention includes tissue or cells derived or cultured from the non-human transgenic mammal.

In another aspect, the invention provides a coated implantable medical device which, when implanted in to a mammal it prevents or treats a disorder in the mammal. The coating on the implantable medical device can contain an amino acid sequence selected from the group consisting of, SEQ ID NOs:1-314, or polynucleotides encoding SEQ ID NOs:1-314, and variants, analogs, homologs, or fragments thereof.

In another aspect, the invention provides a method of making a device suitable form implantation into a mammal by obtaining an implantable medical device and coating the medical device. The coating on the implantable device can contain an amino acid sequence selected from the group consisting of, SEQ ID NOs:1-314, or polynucleotides encoding SEQ ID NOs:1-314, and variants, analogs, homologs, or fragments thereof.

In another aspect, the invention provides a method of using a device to prevent or treat a disorder in a mammal. The method includes identifying a mammal with a disorder, then obtaining an implantable medical device further having a coating comprised of an amino acid sequence selected from the group consisting of, SEQ ID NOs:1-314, or polynucleotides encoding SEQ ID NOs:1-314, and variants, analogs, homologs, or fragments thereof; and implanting the device into a mammal. In one embodiment, the device is implanted into a mammal with a disorder of the cardiovascular system.

Another aspect of the present invention relates to methods of treating or preventing a tissue differentiation factor-associated disorder or disease, the method comprising administering to a subject in which such treatment or prevention is desired at least one TDFRP compound in combination with one or more therapeutic agents in amounts sufficient to treat or prevent the tissue differentiation factor-associated disorder or disease in the subject. For example, such therapeutic agents include small molecule mimetics for TDF receptors, TDF agonists, TDF antagonists, bone morphogenetic proteins, ACE inhibitors, anti-neoplastic agents, antibiotics, vaccines, immunosuppressive agents, anti-hypertensive agents and mediators of the hedgehog signaling pathway.

BRIEF DESCRIPTION OF THE DRAWINGS

FIG. 2
Smad phosphorylation in vascular endothelial cells due to SEQ ID NO 16, 24, 33, 43, 45, 209, 229.

FIG. 3
In vitro data for the phosphorylation of smad 1/5 in LNCaP human prostate cancer cells in response to compounds SEQ ID NO 16 and 45. SEQ ID NO 16 was designed to be inactive.

FIG. 4
Schematic of the unilateral urinary obstruction (UUO) model.

FIG. 5A: Kidney section of vehicle-treated animal,
FIG. 5B: Kidney section of animal received ip administration of BMP-7 (300 ug/kg/48 hours),
FIG. 5C: Kidney section of animal received oral administration of Thrasos compound (5 mg/kg/24 hours), FIG. 5D. Kidney section of animal received Thrasos compound (5 mg/kg/24 hours). Sac: Day 5. Note that Thrasos compound Administration significantly attenuated progression of tubulointerstitial fibrosis.

FIG. 6A: Kidney section of vehicle-treated animal,
FIG. 6B: Kidney section of animal received ip administration of BMP-7 (300 ug/kg/48 hours),
FIG. 6C: Kidney section of animal received oral administration of Thrasos compound (5 mg/kg/24 hours), FIG. 6D. Kidney section of animal received Thrasos compound (50 mg/kg/24 hours). Sac: Day 7. Note that Thrasos compound administration significantly attenuated progression of tubulointerstitial fibrosis.

FIG. 7A. schematic of the experimental protocol,
FIG. 7B: Kidney section of vehicle-treated animal,
FIG. 7C: Kidney section of animal received ip administration of Thrasos compound (5 mg/kg/24 hr). Sac: After one month treatment. Note that the compound administration effectively reversed renal interstitial fibrosis.

FIG. 8A: Kidney section of vehicle-treated animal,
FIG. 8B: Kidney section of animal received oral administration of compound SEQ ID NO 45 (5 mg/kg/24 hr). Note that the compound significantly attenuated progression of renal fibrosis.

FIG. 9

Influence of compounds SEQ ID NO 16, 33, 45, 217, 221 on chondrogenic differentiation of synovial membrane-derived mesenchymal stem cells leading to increased extracellular matrix deposition as determined by alcian blue staining. SEQ ID NO:16, 33, 45, 217, and 221 correspond to Compounds E, A, C, B, and D, respectively.

FIG. 10

In vitro compound activities in HK-2 cells using assays indicated above the columns

FIG. 11

In vitro compound binding activities for the receptor extra cellular domains indicated in the column headings.

FIG. 12

In vitro compound activities in cardiomyocytes cells using assays indicated above the columns

FIG. 13A-FIG. 13B

Subcutaneous implantation assay in rodents. FIG. 13A: 5 ug of BMP-7+25 mg of demineralized bone matrix (DBM), or Panel B: 10 mg of alginate-coupled SEQ ID 38 compound, is implanted into muscle of each rat. Note that BMP-7+DBM induced ectopic bone formation (FIG. 13A), while Alginate-coupled Thrasos compound failed (FIG. 13B).

FIG. 14A-FIG. 14D

Figure 14A:
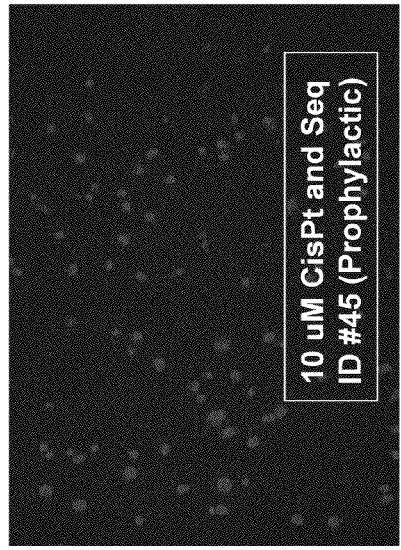
Figure 14C:
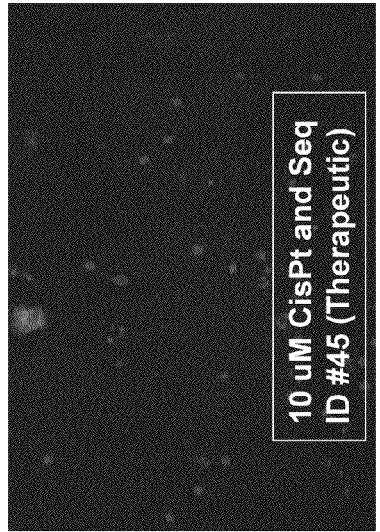
Figure 14B:
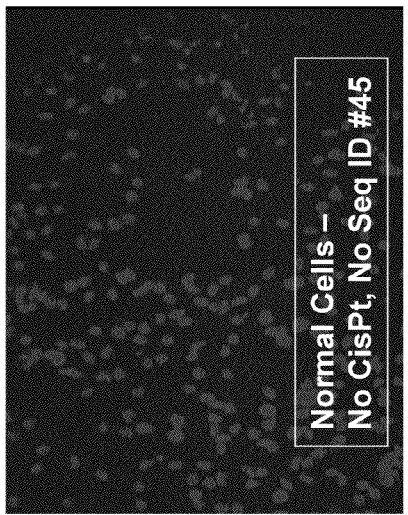
Figure 14D:
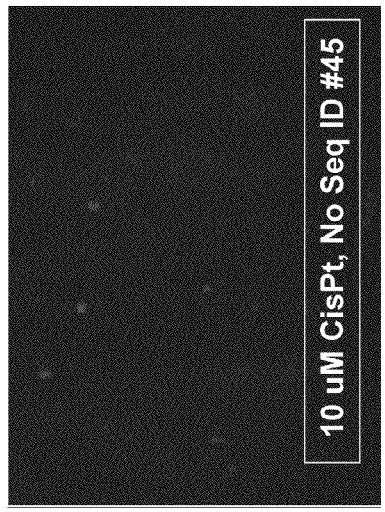

Compound SEQ ID NO 45 inhibits cisplatin-induced apoptosis in HK-2 cells: FIG. 14A) Normal cells—no cisplatin, FIG. 14B) cells with 10 uM cisplatin, FIG. 14C) cells with 10 uM cisplatin and 500 uM compound administered prophylactically, FIG. 14D) cells with 10 uM cisplatin and 500 uM compound administered therapeutically.

FIG. 15A-FIG. 15C

Smad1 Translocation in HK-2 cells due to compound SEQ ID No 45: FIG. 15A) No Compound, FIG. 15B) 1.3 uM compound, FIG. 15C) 33 uM compound.

FIG. 16

Schematic of the LAD occlusion model of myocardial injury: A) Left Anterior Descending Coronary Artery Ligated to create ischemia, B) Infarct Areas (IA), C) The unaffected, perfused region. Dyed blue at sacrifice, D) Ventricular lumen, E) Approximate regional boundary, F) The affected (ischemic) region (AR). Where reperfusion injury leads to apoptosis

FIG. 17A-FIG. 17B

Figure 17B:
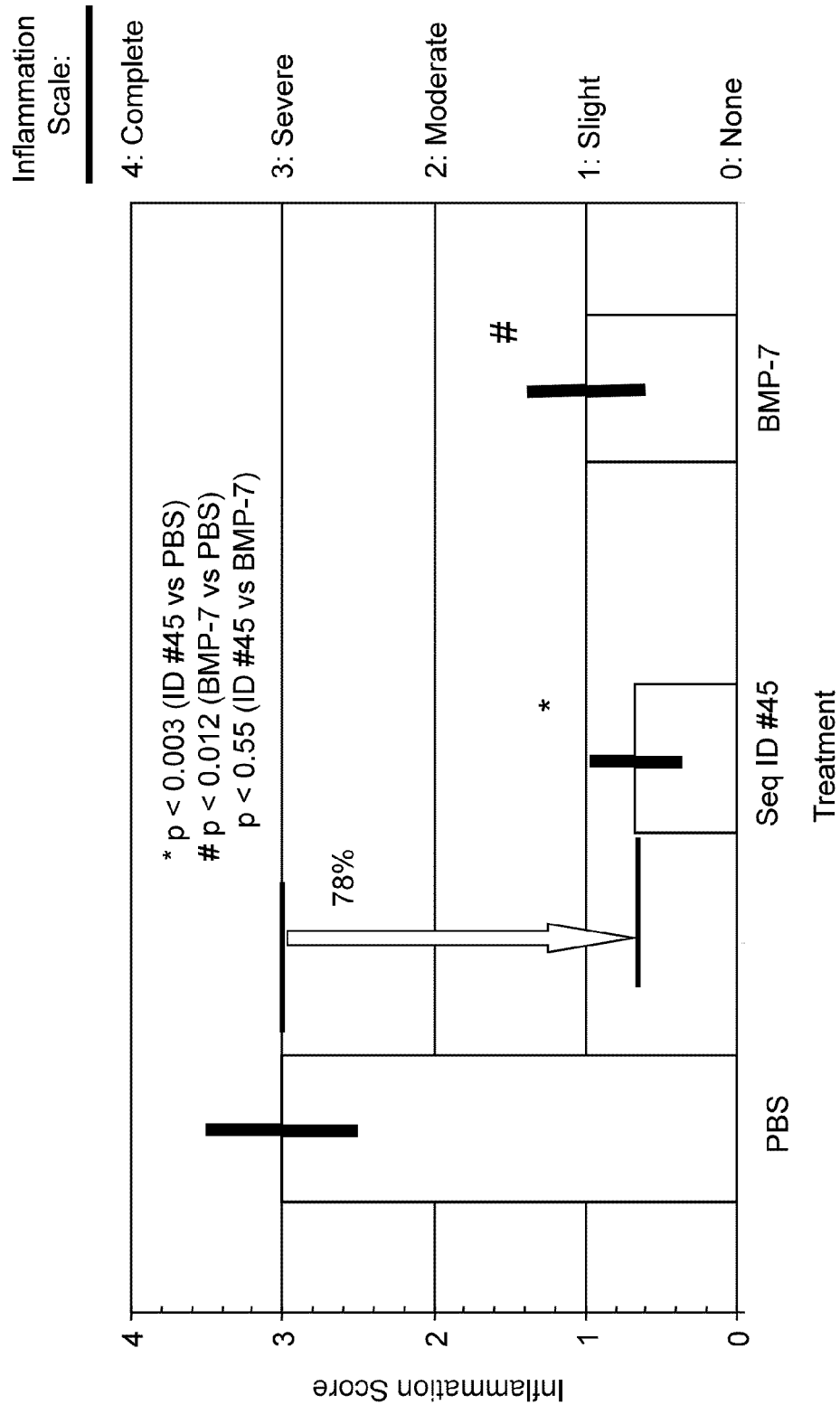

FIG. 17A) Compound SEQ ID NO 45 reduces the necrotic area to area at risk ratio (IA/AR) in the LAD occlusion model of myocardial infarction. FIG. 17B) Compound SEQ ID NO 45 reduces the degree of cardiac inflammation in the LAD occlusion model of myocardial infarction.

FIG. 18

Compound SEQ ID NO 45 reduces the cisplatin-induced level of creatinine in serum: A) rats treated with cisplatin only; rats treated with cisplatin plus compound at dose levels: B) 0.28 mg/kg bw, C) 2.8 mg/kg bw and D) 28 mg/kg bw; rats treated with cisplatin plus rhmBMP-7 at E) 30 ug/kg bw and F) 200 ug/kg bw. Open arrows indicate prophylactic (−2 hours) and therapeutic dosing times; filled arrow indicates cisplatin dosing at time zero.

FIG. 19A-FIG. 19B

Figure 19B:
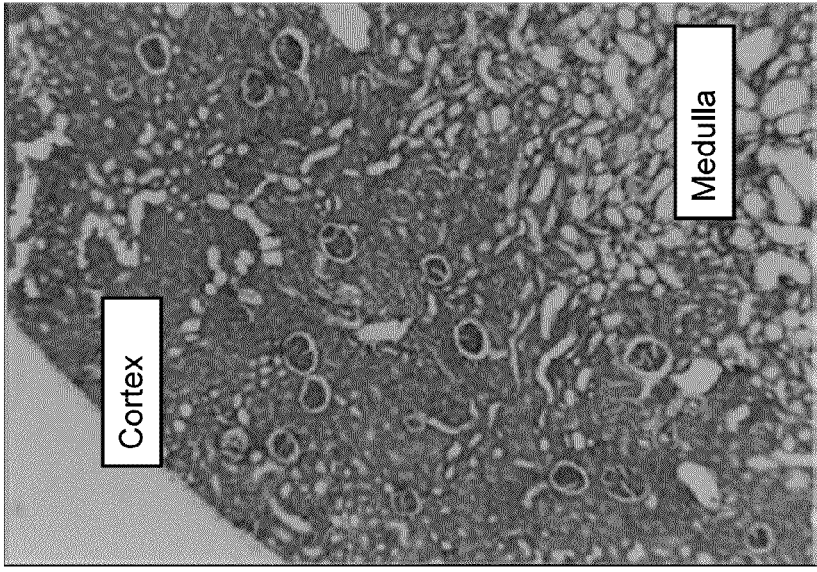
Figure 19A:
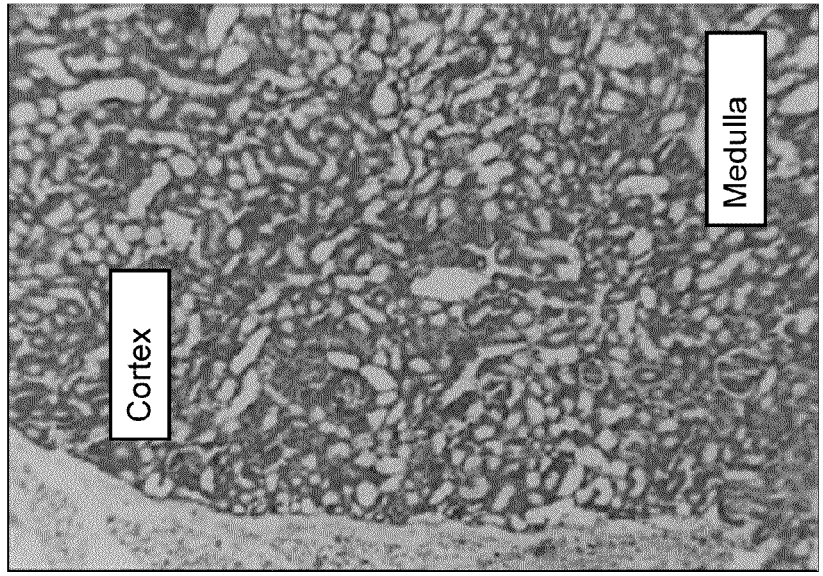

H&E stained kidney sections: FIG. 19A) from a rat treated with cisplatin only, FIG. 19B) from a rat treated with cisplatin and compound SEQ ID NO 45 at 2.8 mg/kg bw.

FIG. 20

Histomorphometry of renal cortex proximal tubule dilation.

FIG. 21A-FIG. 21B

Figures 21A, 21B:
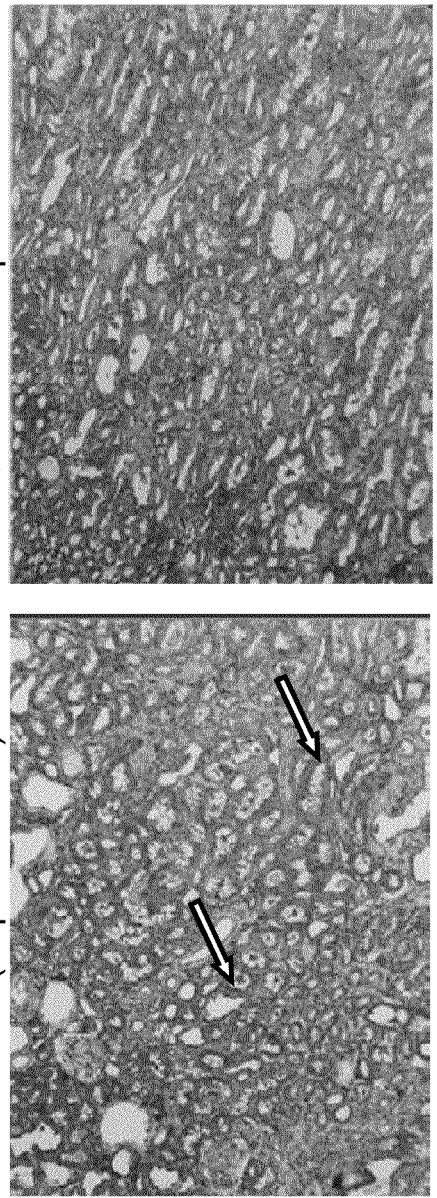

Sections stained with anti-ICAM-1 antibody from a rat the received FIG. 21A) cisplatin only and FIG. 21B) a rat the received cisplatin and compound SEQ ID NO 45

FIG. 22A-FIG. 22B

Differential staining of kidney sections for proliferating cell nuclear antigen (PCNA): FIG. 22A) sections stained with anti-smooth muscle actin antibody from, FIG. 22B) a rat the received cisplatin only and a rat the received cisplatin and compound SEQ ID NO 45.

FIG. 23

Histomorphometry of renal cortex cell proliferation (PCNA stain).

DETAILED DESCRIPTION OF THE INVENTION

Definitions

"Transforming Growth Factor-beta (TGF-beta) superfamily of polypeptides," as used herein, refers to a superfamily of polypeptide factors with pleiotropic functions that is composed of many multifunctional cytokines which includes, but is not limited to, TGF-βs, activins, inhibins, anti-mullerian hormone (AMH), mullerian inhibiting substance (MIS), bone morphogenetic proteins (BMPs), and myostatin. The highly similar TGF-β isoforms TGF-β1, TGF-β2, and TGF-β3 potently inhibit cellular proliferation of many cell types, including those from epithelial origin. Most mesenchymal cells, however, are stimulated in their growth by TGF-β. In addition, TGF-βs strongly induce extracellular matrix synthesis and integrin expression, and modulate immune responses. BMPs, also known as osteogenic proteins (OPs), are potent inducers of bone and cartilage formation and play important developmental roles in the induction of ventral mesoderm, differentiation of neural tissue, and organogenesis. Activins, named after their initial identification as activators of follicle-stimulating hormone (FSH) secretion from pituitary glands, are also known to promote erythropoiesis, mediate dorsal mesoderm induction, and contribute to survival of nerve cells. Several growth factors belonging to the TGF-β superfamily play important roles in embryonic patterning and tissue homeostasis. Their inappropriate functioning has been implicated in several pathological situations like fibrosis, rheumatoid arthritis, and carcinogenesis. The term, tissue differentiation factor (TDF), as used herein, includes, but is not limited to, all members of the TGF-beta superfamily of polypeptides. TGF-beta superfamily polypeptides can be antagonists or agonists of TGF-beta superfamily receptors.

"Transforming Growth Factor-beta (TGF-beta) superfamily receptors," as used herein, refers to polypeptide receptors that mediate the pleiotropic effects of transforming growth factor-β (TGF-β) superfamily polypeptides, as well as fragments, analogs and homologs thereof. Such receptors may include, but are not limited to, distinct combinations of Type I and Type II serine/threonine kinase receptors. The term, tissue differentiation factor receptor (TDF), as used herein, includes, but is not limited to, all members of the TGF-beta superfamily of receptors.

"Aromatic amino acid," as used herein, refers to a hydrophobic amino acid having a side chain containing at least one ring having a conjugated electron system (aromatic group). The aromatic group may be further substituted with substituent groups such as alkyl, alkenyl, alkynyl, hydroxyl, sulfanyl, nitro and amino groups, as well as others. Examples of genetically encoded aromatic amino acids include phenylalanine, tyrosine and tryptophan. Commonly encountered non-genetically encoded aromatic amino acids include phenylglycine, 2-naphthylalanine, beta-2-thienylalanine, 1,2,3,4-tetrahydroisoquinoline-3-carboxylic acid, 4-chlorophenylalanine, 2-fluorophenylalanine, 3-fluorophenylalanine and 4-fluorophenylalanine.

"Aliphatic amino acid," as used herein, refers to an apolar amino acid having a saturated or unsaturated straight chain, branched or cyclic hydrocarbon side chain. Examples of genetically encoded aliphatic amino acids include alanine, leucine, valine and isoleucine. Examples of non-encoded aliphatic amino acids include norleucine (Nle).

"Acidic amino acid," as used herein, refers to a hydrophilic amino acid having a side chain pK value of less than 7. Acidic amino acids typically have negatively charged side chains at physiological pH due to loss of a hydrogen ion. Examples of genetically encoded acidic amino acids include aspartic acid (aspartate) and glutamic acid (glutamate).

"Basic amino acid," as used herein, refers to a hydrophilic amino acid having a side chain pK value of greater than 7. Basic amino acids typically have positively charged side chains at physiological pH due to association with hydronium ion. Examples of genetically encoded basic amino acids include arginine, lysine and histidine. Examples of non-genetically encoded basic amino acids include the non-cyclic amino acids ornithine, 2,3-diaminopropionic acid, 2,4-diaminobutyric acid and homoarginine.

"Polar amino acid," as used herein, refers to a hydrophilic amino acid having a side chain that is uncharged at physiological pH, but which has a bond in which the pair of electrons shared in common by two atoms is held more closely by one of the atoms. Examples of genetically encoded polar amino acids include asparagine and glutamine. Examples of non-genetically encoded polar amino acids include citrulline, N-acetyl lysine and methionine sulfoxide.

As will be appreciated by those having skill in the art, the above classification are not absolute—several amino acids exhibit more than one characteristic property, and can therefore be included in more than one category. For example, tyrosine has both an aromatic ring and a polar hydroxyl group. Thus, tyrosine has dual properties and can be included in both the aromatic and polar categories.

A "subject," as used herein, is preferably a mammal, such as a human, but can also be an animal, e.g., domestic animals (e.g., dogs, cats and the like), farm animals (e.g., cows, sheep, pigs, horses and the like) and laboratory animals (e.g., rats, mice, guinea pigs and the like).

An "effective amount" of a compound, as used herein, is a quantity sufficient to achieve a desired therapeutic and/or prophylactic effect, for example, an amount which results in the prevention of or a decrease in the symptoms associated with a disease that is being treated, e.g., the diseases associated with TGF-beta superfamily polypeptides listed above. The amount of compound administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. Typically, an effective amount of the compounds of the present invention, sufficient for achieving a therapeutic or prophylactic effect, range from about 0.000001 mg per kilogram body weight per day, to about 10,000 mg per kilogram body weight per day. Preferably, the dosage ranges are from about 0.0001 mg per kilogram body weight per day to about 100 mg per kilogram body weight per day. The compounds of the present invention can also be administered in combination with each other, or with one or more additional therapeutic compounds.

An "isolated" or "purified" polypeptide or polypeptide or biologically-active portion thereof is substantially free of cellular material or other contaminating polypeptides from the cell or tissue source from which the tissue differentiation factor-related polypeptide is derived, or substantially free from chemical precursors or other chemicals when chemically synthesized.

"Substantially free of cellular material," as used herein, includes preparations of tissue differentiation factor-related polypeptide in which the polypeptide is separated from cellular components of the cells from which it is isolated or recombinantly-produced. In one embodiment, the language "substantially free of cellular material" includes preparations of tissue differentiation factor-related polypeptides having less than about 30% (by dry weight) of non-tissue differentiation factor-related polypeptides (also referred to herein as a "contaminating polypeptide"), more preferably less than about 20% of non-tissue differentiation factor-related polypeptides, still more preferably less than about 10% of non-tissue differentiation factor-related polypeptides, and most preferably less than about 5% of non-tissue differentiation factor-related polypeptides. When the tissue differentiation factor-related polypeptide or biologically-active portion thereof is recombinantly-produced, it is also preferably substantially free of culture medium, i.e., culture medium represents less than about 20%, more preferably less than about 10%, and most preferably less than about 5% of the volume of the tissue differentiation factor-related polypeptides preparation.

The language "substantially free of chemical precursors or other chemicals," as used herein, includes preparations of tissue differentiation factor-related polypeptides in which the polypeptide is separated from chemical precursors or other chemicals that are involved in the synthesis of the polypeptide. In one embodiment, the language "substantially free of chemical precursors or other chemicals" includes preparations of tissue differentiation factor-related polypeptides having less than about 30% (by dry weight) of chemical precursors or non-tissue differentiation factor-related chemicals, more preferably less than about 20% chemical precursors or non-tissue differentiation factor-related chemicals, still more preferably less than about 10% chemical precursors or non-tissue differentiation factor-related chemicals, and most preferably less than about 5% chemical precursors or non-tissue differentiation factor-related chemicals.

The term "variant," as used herein, refers to a compound that differs from the compound of the present invention, but retains essential properties thereof. A non-limiting example of this is a polynucleotide or polypeptide compound having conservative substitutions with respect to the reference compound, commonly known as degenerate variants. Another non-limiting example of a variant is a compound that is structurally different, but retains the same active domain of the compounds of the present invention. Variants include N-terminal or C-terminal extensions, capped amino acids, modifications of reactive amino acid side chain functional groups, e.g., branching from lysine residues, pegylation, and/or truncations of a polypeptide compound. Generally, variants are overall closely similar, and in many regions, identical to the compounds of the present invention. Accordingly, the variants may contain alterations in the coding regions, non-coding regions, or both.

A "small molecule," as used herein, refers to a composition that has a molecular weight of less than about 5 kDa and more preferably less than about 2 kDa. Small molecules can be, e.g., nucleic acids, peptides, polypeptides, glycopeptides, peptidomimetics, carbohydrates, lipids, lipopolysaccharides, combinations of these, or other organic or inorganic molecules.

The terms "ischemia" or "ischemic episode," as used herein, mean any circumstance that results in a deficient supply of blood or oxygen to a tissue. Thus, a central nervous system ischemic episode results from an insufficiency or interruption in the blood or oxygen supply to any locus of the brain such as, but not limited to, a locus of the cerebrum, cerebellum or brain stem. The spinal cord, which is also a part of the central nervous system, is equally susceptible to ischemia resulting from diminished blood flow or lack of oxygen. An ischemic episode may be caused by a constriction or obstruction of a blood vessel, as occurs in the case of a thrombus or embolus. Alternatively, the ischemic episode may result from any form of compromised cardiac function, including cardiac arrest, as described above. Where the deficiency is sufficiently severe and prolonged, it can lead to disruption of physiologic function, subsequent death of neurons, and necrosis (infarction) of the affected areas. The extent and type of neurologic abnormality resulting from the injury depend on the location and size of the infarct or the focus of ischemia. Where the ischemia is associated with a stroke, it can be either global or focal in extent. Ischemia can occur in other tissues or organs including kidney. Restoration of blood flow or reperfusion leads to a series of cellular responses that are known to cause tissue damage.

DETAILED DESCRIPTION

The TGF-β polypeptide superfamily mediate their activity by interaction with two different receptors, referred to as Type I and Type II receptors (Table 1). As summarized in Table 1, presently, there are seven different Type I activin-like kinase receptors (hereinafter "ALK") known.

TABLE I

| Type I Receptors | Type II Receptors |
|---|---|
| ALK-1 (activin-like kinase receptor; TSR-1) | ActR-IIA |
| ALK-2 (Type I activin receptor; ActR-I) | ActR-IIB |
| ALK-3 (BMP receptor Type I/IA; BMPR-I/IA) | TβR-II |
| ALK-4 (Type IB activin receptor; ActR-IB) | BMPR-II |
| ALK-5 (Type I TGF-β receptor; TβR-I) | AMHR-II |
| ALK-6 (BMP receptor Type IB; BMPR-IB) | |
| ALK-7 | |

Ligand binding of the Type I and Type II receptors results in the phosphorylation and activation of the Type I receptor, which is required for downstream signal cascades. Smad proteins activated by Type I receptors carry signal to the nucleus, and together with other proteins direct transcriptional responses. Type I receptors for activin and TGF-β can only recognize ligand that is bound to the Type II receptor. In contrast, Type II receptors can bind ligand independently of the Type I receptor, but they are unable to signal without the Type I receptor. Specificity in signaling, therefore is determined by a combination of the Type I and Type II receptors (Table 2).

The ligand-binding specificity of ALK receptors are summarized in Table 2. The table cites published literature reports, patents, and patent applications describing ligand binding to ALK receptors. These citations are detailed in the "Reference List," supra. The contents of all references appearing in this application are hereby incorporated herein by reference in their entireties.

TABLE 2

| CATEGORY | LIGAND | ALK-1 | ALK-2 | ALK-3 | ALK-4 | ALK-5 | ALK-6 | ALK-7 |
|---|---|---|---|---|---|---|---|---|
| Activins | Activin | | | | | 25 | | |
| | Activin | | | | 27 | 27 | | |
| | Activin | | | | 101 | | | |
| | Activin | 26 | | | | | | |
| | Activin | | 164 | | 164 | | | |
| | Activin A | | 165 | | 165 | | | |
| | Activin A | | 168 | 168 | 168 | 168 | 168 | 168 |
| | Activin A | | 169 | 169 | 169 | 169 | 169 | 169 |
| | Activin A | | 156 | 156 | 156 | 156 | 156 | 156 |
| | Activin A | | | | 42 | | | |
| | Activin A | | 162 | | 162 | | | |
| | Activin A | 165 | | 165 | | | 165 | |
| | Activin type 1 | | 11 | | 11 | | | |
| | Activin type 1 | | | | | 34 | | |
| Bone Morphogenetic Proteins | BMP-2 | | | 38 | | | | |
| | BMP-2 | | | 92 | | | | |
| | BMP-2 | | | 112 | | | | |
| | BMP-4 | | | 38 | | | | |
| | BMP-4 | | | 59 | | | | |
| | BMP-4 | | | 162 | | | 162 | |
| | BMP-4 | | | 166 | | | 166 | |
| | BMP-4 | | | 159 | | | 159 | |
| | BMP-5 | | | 57 | | | | |
| | BMP-6 | | 6 | 6 | | | 6 | |
| | BMP-6 | | 67 | 67 | | | 67 | |
| | BMP-7 | | 42 | 42 | | | | |
| | BMP-7 | | 11 | 11 | | | 11 | |
| | BMP-7 | | 101 | | | | | |
| | BMP-7 | | | | | | 77 | |
| | BMP-7 | | | | | | 132 | |
| | BMP-7 | | 162 | 162 | | | 162 | |

TABLE 2-continued

| CATEGORY | LIGAND | ALK-1 | ALK-2 | ALK-3 | ALK-4 | ALK-5 | ALK-6 | ALK-7 |
|---|---|---|---|---|---|---|---|---|
| | BMP-7 | | 159 | | | | | |
| | BMP-7 | | 166 | | | | | |
| | BMP-7 | | 167 | | | | | |
| Cartilage-Derived Morphogenic Protein | CDMP-1 | | | 70 | | | 70 | |
| | CDMP-2 | | | 70 | | | 70 | |
| Transforming Growth Factors | TGF-β | 26 | | | | | | |
| | TGF-β | 157 | | | | | | |
| | TGF-β | | | | | 162 | | |
| | TGF-β | | | | | 164 | | |
| | TGF-β-1 | 35 | | | | | | |
| | TGF-β-1 | | | | | 11 | | |
| | TGF-β-1 | 31 | 31 | | | 31 | | |
| | TGF-β-1 | | | | | 42 | | |
| | TGF-β-1 | | | | | 162 | | |
| | TGF-β-1 | 165 | | 165 | | | 165 | |
| | TGF-β-1 | 168 | | 168 | | | 168 | |
| | TGF-β-1 | 169 | | 169 | | | 169 | |
| | TGF-β-1 | 156 | | 156 | | | 156 | |
| | TGF-β-1 | | | | | 157 | | |
| | TGF-β-1 | 28 | 28 | | 28 | | | |
| | TGF-β-1 | | | | 27 | 27 | | |
| | TGF-β-2 | | 46 | | | 46 | | |
| | TGF-β-3 | 35 | | | | | | |
| | TGF-β-3 | | 46 | | | 46 | | |
| | TGF-β-3 | | | | | 157 | | |
| Small Molecule | SB-431542 | | | | 25 | 25 | | |
| Other | Endoglin | 35 | | | | | | |
| | Serum factor | 35 | | | | | | |

Vertebrate Type I receptors can be divided into two different groups according to their sequence homology at the kinase domain and their signaling activities. One group includes activin-like receptor type 5 (hereinafter ALK-5), ALK-4, and ALK-7. The other group includes ALK-1, ALK-2, ALK-3, and ALK-6. The ALK receptors are differentially expressed among tissues and are regulated during embryo development (Table 3).

The tissue and cell expression of ALK receptors is summarized in Table 3. The table cites published literature reports, patents, and patent applications describing the expression of ALK receptors. These citations are detailed in the "Reference List," supra.

TABLE 3

| TISSUE | SPECIES | ALK-1 | ALK-2 | ALK-3 | ALK-4 | ALK-5 | ALK-6 | ALK-7 |
|---|---|---|---|---|---|---|---|---|
| Bone/Cartilage | | | | | | | | |
| Bone | Mouse | | | | | | 149 | |
| Bone Forming Tissue | Rat | | | 130 | | | 130 | |
| Bone fractures | Human | | | 95 | | | 95 | |
| Bone fractures | Rat | | | 120 | | | 120 | |
| Femoral fractures | Rat | | | 143 | | | | |
| Bone Marrow Stromal Cells | Mouse | | | 51 | | | | |
| Bone Medullary Cavity | Mouse | | | 125 | | | | |
| Bone rudiments | Mouse | | 8 | 8 | | | 8 | |
| Bone Tissue | Rat | | 19 | | | | | |
| Calvaria cells | Rat | | | 138 | | | 138 | |
| Calvaria cells | Rat | | 146 | 146 | | | 146 | |
| Calvaria cells | Rat | | 147 | 147 | | | 147 | |
| ROB-C26 Calvarial Osteogenic Cells | Rat | | | 67 | | | 67 | |
| ROB-C26 Calvarial Osteogenic Cells | Rat | | | | | | 132 | |
| Cartilage (bone) | Chicken | | | 155 | | | 155 | |
| Digit Cartilage | Mouse | | | | | | 56 | |
| Chondrocytes | | 116 | 116 | 116 | | | 116 | |
| Chondrocytes | | | | | | | 111 | |

TABLE 3-continued

| TISSUE | SPECIES | ALK-1 | ALK-2 | ALK-3 | ALK-4 | ALK-5 | ALK-6 | ALK-7 |
|---|---|---|---|---|---|---|---|---|
| MC615 Chondrocytes | Mouse | 13 | 13 | 13 | | | | |
| ATDC5 Chondrocytes | Mouse | | | 16 | | | | |
| Sternal Chondrocytes | | | | 68 | | | 68 | |
| MC3T3-E1 Osteoblasts | Mouse | | 67 | 67 | | | | |
| MC3T3-E1 Osteoblasts | | | | 11 | | | | |
| MC3T3-E1 Osteoblasts | Mouse | | 162 | 162 | | | | |
| Osteoblasts | | | 67 | 67 | | | 67 | |
| Osteoblasts | Mouse | | | 85 | | | 85 | |
| Osteoclasts and Osteoblasts | | | | 89 | | | | |
| Osteosarcoma | Rat | | 162 | 162 | | | | |
| Osteosarcoma Cell Lines | | | | | | | 76 | |
| Osteosarcoma Cell Lines | Human | | | 152 | | | 152 | |
| Osteosarcoma Cell MG63 | | | | 152 | | | | |
| Preosteoblastic KS483 | Mouse | | 135 | 135 | 135 | | | |
| Kidney | | | | | | | | |
| Kidney | | 165 | 165 | 165 | 165 | 165 | | |
| Kidney | | 168 | 168 | 168 | 168 | 168 | | |
| Kidney | | 169 | 169 | 169 | 169 | 169 | | |
| Kidney | | 156 | 156 | 156 | 156 | 156 | | |
| Kidney | Rat | | | | | 21 | | |
| Kidney Fibroblast (Expression Study) | Monkey | 4 | | 4 | | 4 | 4 | |
| Kidney Fibroblast (Expression Study) | Monkey | 10 | 10 | 10 | 10 | 10 | 10 | |
| HK-2 Proximal Tubular Cells | Human | | | 93 | | | 93 | |
| Renal | Rats | | | | | 17 | | |
| Renal | Human | | 43 | | | 43 | | |
| A498 Renal Carcinoma | | | | | | 29 | | |
| Metanephros | Mouse | | | 103 | | | | |
| Metanephros | Mouse | | | 104 | | | 104 | |
| Proximal Tubule Epithelial Cells | Human | | 74 | 74 | | | | |
| Liver | | | | | | | | |
| Biliary Adenocarinomas | | | | | | | 7 | |
| Liver | | | 168 | | 168 | 168 | | |
| Liver | | | 169 | | 169 | 169 | | |
| Liver | | | 156 | | 156 | 156 | | |
| Pancreas | | | | | | | | |
| Pancreas | | | | | | | 7 | |
| Pancreas | Human | | | 94 | | | | |
| Pancreas | | | 165 | 165 | 165 | 165 | | |
| Pancreas | | | 168 | 168 | 168 | 168 | | |
| Pancreas | | | 169 | 169 | 169 | 169 | | |
| Pancreas | | | 156 | 156 | 156 | 156 | | |
| Reproductive Tissue | | | | | | | | |
| Uterine Cells | Sheep | | | | | | 148 | |
| Oocytes and granulosa cells | Booroola Sheep | | | | | | 50 | |
| Oocytes and granulosa cells | Booroola Sheep | | | | | | 105 | |
| Ovarian cells | Rat | | | 69 | | | 69 | |
| Chinese Hampster Ovarian Cells | Hamster | | | | 34 | | | |

TABLE 3-continued

| TISSUE | SPECIES | ALK-1 | ALK-2 | ALK-3 | ALK-4 | ALK-5 | ALK-6 | ALK-7 |
|---|---|---|---|---|---|---|---|---|
| Prostate | | | | | | | | |
| Prostate | Human | | | | | | | 158 |
| Prostate cancer cells | Human | | | 83 | | | 83 | |
| Prostate Cells | Rat | | | | 27 | 27 | | |
| Prostate Tumor Cells (Benign) | Human | | | 91 | | | 91 | |
| LNCaP (prostate cancer cell) | Human | 28 | 28 | | | | | |
| LNCaP (prostate cancer cell) | Human | | | 82 | | | 82 | |
| Endocrine Gland | Pig | | | 71 | | | | |
| Oral Cavity | | | | | | | | |
| Dental Pulp | Rat | 133 | 133 | 133 | 133 | 133 | | |
| Dental Pulp and Gingival Fibroblast | Human | | 60 | 60 | | | 60 | |
| Dental Pulp Cells | Bovine | | 134 | 134 | 134 | 134 | | |
| Dental Pulp Cells | Human | | 75 | 75 | | | 75 | |
| Follicle Cells | Mouse | | | 154 | | | | |
| Gingival Fibroblasts | Human | | 79 | 79 | | | 79 | |
| Oral Carcinoma Cells | Human | | | 88 | | | | |
| Periodontal Ligament Cells (PDL) | Rat | | 3 | 3 | | | 3 | |
| Periodontal Ligament Cells (PDL) | Mouse | | | 154 | | | | |
| Cementoblast, Osteoblast, PDL Cells | Rat | | | 98 | | | | |
| Vascular | | | | | | | | |
| Atherosclerotic Aortic Vessels | Human | | | | | 20 | | |
| Blood vessels | Pig | | | | | 47 | | |
| Blood vessels | Rat | | 49 | | | 49 | | |
| Pulmonary blood vessels | Rat | 41 | | | | | | |
| Carotid Artery | Rat | | 46 | | | 46 | | |
| Glomerular Mesaugial Cells | | | 93 | 93 | | | | |
| Erythroleukemic F5-5.fl Cells | Mouse | | | | 36 | 36 | | |
| Vascular Smooth Muscle Cells | | | 1 | 1 | | 1 | 1 | |
| Vascular Smooth Muscle Cells | Rat | | | | | 15 | | |
| Vascular Smooth Muscle Cells | | | | | | 48 | | |
| Muscle | | | | | | | | |
| C2C12 Myoblast/Fibroblast | Mouse | | 2 | 2 | | | 2 | |
| C2C12 Myoblast/Fibroblast | Mouse | 72 | 72 | 72 | | | 72 | |
| C2C12 Myoblast/Fibroblast | Mouse | | 9 | 9 | | 9 | 9 | |
| C2C12 Myoblast/Fibroblast | Mouse | | 67 | 67 | | | | |
| C2C12 Myoblast/Fibroblast | Mouse | | | 54 | | | | |
| C2C12 Myoblast/Fibroblast | Mouse | | | 112 | | | | |
| C2C12 Myoblast/Fibroblast | Mouse | | | 51 | | | | |

TABLE 3-continued

| TISSUE | SPECIES | ALK-1 | ALK-2 | ALK-3 | ALK-4 | ALK-5 | ALK-6 | ALK-7 |
|---|---|---|---|---|---|---|---|---|
| Skeletal Muscle | | 165 | 165 | 165 | 165 | 165 | | |
| Skeletal Muscle | | 168 | 168 | 168 | 168 | 168 | | |
| Skeletal Muscle | | 169 | 169 | 169 | 169 | 169 | | |
| Skeletal Muscle | | 156 | 156 | 156 | 156 | 156 | | |
| Heart | | | | | | | | |
| Heart | | 165 | 165 | 165 | 165 | 165 | | |
| Heart | | 168 | 168 | 168 | 168 | 168 | | |
| Heart | | 169 | 169 | 169 | 169 | 169 | | |
| Heart | | 156 | 156 | 156 | 156 | 156 | | |
| Lung | | | | | | | | |
| Lung | Mouse | | | | | | 5 | |
| Lung | | | | | | | 169 | |
| Lung | | 165 | 165 | | 165 | 165 | | |
| Lung | | 168 | 168 | | 168 | 168 | | |
| Lung | | 169 | 169 | | 169 | 169 | | |
| Lung | | 156 | 156 | | 156 | 156 | | |
| Calu-6 Lung Carcinoma Cells | Human | | | | | | | 158 |
| Embryonic/Placental | | | | | | | | |
| Embryo | Zebrafish | | | | | | 114 | |
| Embryo | Zebrafish | | | 115 | | | | |
| Embryo | Mouse | | | 38 | | | | |
| Embryo | Mouse | | 122 | 122 | | | 122 | |
| Embryo/Reproductive Tract | Mouse | | | | | 22 | | |
| Embryo Cartilage | Chicken | | | 55 | | | 55 | |
| Embryonic Bone Rudiments | | | 77 | 77 | | | 77 | |
| Embryonic Cells | Quail | | | 106 | | | 106 | |
| Embryonic Fibroblast | Mouse | | | 63 | 63 | | | |
| Embryonic Lung | Rat | 32 | | | | 32 | | |
| Embryonic Tissue | Mouse | | | | 5 | | 5 | |
| Embryotic Stem Cells | Mouse | | | | | 24 | | |
| Gastrulation cells | Chicken | | | 109 | | | | |
| Mesenchymal Cells | Mouse | | | 102 | | | 102 | |
| Mesenchymal Cells | Mouse | | | 108 | | | | |
| Neural Crest Cells | | | | 136 | | | | |
| Neural Precursor Cells | | | | 121 | | | 121 | |
| P19 Embryonic Carcinoma Cells | Mouse | | 101 | | 101 | | | |
| Placenta | | 165 | 165 | 165 | 165 | 165 | | |
| Placenta | | 168 | 168 | 168 | 168 | 168 | | |
| Placenta | | 169 | 169 | 169 | 169 | 169 | | |
| Placenta | | 156 | 156 | 156 | 156 | 156 | | |
| Villi and Decidua | | | | | | 170 | | |
| Wolffian Duct and Ureter | | | | | | | 108 | |
| Brain/CNS | | | | | | | | |
| Brain | Rat | | | | 40 | | | |
| Brain | Rat | | 128 | 128 | 128 | | 128 | |
| Brain | Mouse | | | | | | 5 | |
| Brain | | | 165 | | 165 | 165 | | |
| Brain | | | | | | | 169 | |
| Brain | | | 160 | | 160 | | | |
| Brain | | | | | | | | 161 |
| Brain | | | | | | | | 163 |
| Gliobastoma | Human | | 162 | 162 | | | 162 | |
| Glioma | Human | | 142 | 142 | | | 142 | |

TABLE 3-continued

| TISSUE | SPECIES | ALK-1 | ALK-2 | ALK-3 | ALK-4 | ALK-5 | ALK-6 | ALK-7 |
|---|---|---|---|---|---|---|---|---|
| Hippocampal Forming Cells | Sham Rats | | 160 | | 160 | | | |
| Hippocampus | Human | | | | | | | 158 |
| Hypothalamic Nuclei | Human | | | | | | | 158 |
| SVZa Neuronal Progenitor Cells | | | | 64 | | | | |
| Cerebellar Granular Neurons | | | | 107 | | | 107 | |
| Cerebellum | Rat | | | | 27 | 27 | | |
| Rostral Migratory Stream | Rodent | | | 64 | | | | |
| Substantia Nigra | Human | | | | | | | 158 |
| Nervous System | | | | 153 | | | 153 | |

Eye

| Corneal Epithelium and Stromal | Human | | | 151 | | | 151 | |
|---|---|---|---|---|---|---|---|---|
| Ocular Tissues | Rat | 119 | 119 | 119 | | | 119 | |
| Retina | Rat | | 141 | 141 | 141 | | 141 | |
| Retina and Optic Stalk | Chicken | 58 | 58 | 58 | | | | |
| Retina and Ventral Ganglion Cell | Mouse | | | | | | 100 | |

Skin

| AG1518 Foreskin Fibroblasts | Human | | | 162 | | | | |
|---|---|---|---|---|---|---|---|---|
| Foreskin Fibroblasts | Human | | | 11 | | | | |
| Hair Follicle Germ Cells | | | | 59 | | | | |
| Skin cells | | 26 | | | | 26 | | |
| Skin Fibroblasts | Human | | | 66 | | | | |
| Sweat Gland Epithelium | Human | | | 139 | | | 139 | |

Other Tissue/Cells

| Adult Tissues | Mouse | | | 5 | | | | |
|---|---|---|---|---|---|---|---|---|
| Adipose (Fat) Tissue | Rat | | | | 27 | 27 | | |
| Anti-Mullerian Hormone Expressing Tissue | | | | | | | 73 | |
| Endothelial cells | | 35 | | | | | | |
| Endothelial cells | Human/ Mouse | 39 | | | | | | |
| Endothelial HHT2 Cells | Human | 14 | | | | | | |
| Epithelial Ear cells | Chicken | | | | | | 61 | |
| Mv1Lu Epithelial Cells | Mink | | 162 | 162 | 162 | 162 | 162 | |
| NMuMG Mammary Epithelial Cells | Mouse | | 42 | 42 | 42 | 42 | | |
| Ossified Spinal Ligament Tissue | Human | | 150 | 150 | | | 150 | |
| Periosteal Explants | Rabbit | | | 124 | | | 124 | |
| Periosteum-Derived Cells | Rat | | | 78 | | | 78 | |
| Pituitary | Human | | | | | | | 158 |
| Pituitary Tumor Cell GH3 | Rat | | 45 | | | 45 | | |
| Spleen | | | | 169 | | | | |

I. Compositions of the Invention

A. TDFRP Compounds

The present invention provides compounds that are functional analogs of tissue differentiation factors, i.e., compounds that functionally mimic TGF-beta superfamily proteins, for example by acting as TGF-beta superfamily receptor agonists, and preferentially bind to select ALK receptor(s). The present compounds include small molecules, more particularly polypeptides, with the general structure identified herein as SEQ ID NOs:1-314, i.e., TDF-related polypeptides (hereinafter "TDFRP"), as detailed below. In one embodiment, the TDFRP compound binds one ALK receptor with greater binding affinity than the binding affinity to other ALK receptors based on distinct binding sites or properties. In an aspect of this embodiment, the TDFRP compound binds ALK-3 receptor with greater binding affinity than its binding affinity to ALK-6 receptor. In another embodiment, the TDFRP compound binds one ALK receptor with greater binding affinity than the binding affinity to other ALK receptors based on differential affinities. Such compounds are suitable for administration to a subject where it is desirable, for example, to promote the growth and differentiation of cells in one tissue without promoting an undesirable cellular response in the same or another tissue. That is, the more specificity in the design of the TDFRP compound the more likely it will not interfere with related TDFRs (e.g., its specificity to ALK-3 receptors but not ALK-6 receptors, or vice versa). This will minimize potential side-effects due to unwanted interactions with other targets. For example, ALK-3 receptors are more prevalent in kidney tissue, while ALK-6 receptors are more prevalent in bone tissue; the native BMP-7 protein binds to ALK-6 with a higher affinity, and a potential side effect of BMP-7 therapy in kidney disease is osteogenesis. The TDFRP compounds are selected and designed for increased specificity to ALK-3 and lowered affinity to ALK-6 receptors (FIG. 1), thereby reducing undesirable osteogenesis in a subject being treated for kidney disorders or myocardial injury.

TDFRP compounds of the present invention are suitable to promote the growth or differentiation of cells and tissues in the subject, such as kidney cells, mesenchymal cells, extracellular matrix synthesis, integrin expression, bone and cartilage formation, induction of ventral mesoderm, differentiation of neural tissue, to promote organogenesis, to promote erythropoiesis, to induce growth of dorsal mesoderm and nerve cells, to promote tissue homeostasis and to induce immune responses. In contrast, pathological conditions such as fibrosis, rheumatoid arthritis, and carcinogenesis among others, are thought to be the result of excessive tissue differentiation factor-like activity. Accordingly, it is further an object of the invention to provide for compounds that are functional antagonists of TGF-beta superfamily receptors. It is also an object of the invention to provide for compounds that are partial antagonists and partial agonists of TGF-beta superfamily receptors. The compounds of the present invention can be used to treat both acute and chronic renal disease, as well as stroke, myocardial injury and traumatic brain injury.

Accordingly, TDFRP compounds can be used to treat one or more adverse consequences of central nervous system injury that arise from a variety of conditions. The term "stroke" connotes central nervous system injury resulting from sudden and dramatic neurologic deficits associated with, e.g., but not limited to, thrombus, embolus, and systemic hypotension. Other injuries may be caused by hypertension, hypertensive cerebral vascular disease, rupture of an aneurysm, an angioma, blood dyscrasia, cardiac failure, cardiac arrest, cardiogenic shock, kidney failure, septic shock, head trauma, spinal cord trauma, seizure, bleeding from a tumor, or other loss of blood volume or pressure. These injuries lead to disruption of physiologic function, subsequent death of neurons, and necrosis (infarction) of the affected areas.

The TDFRP compounds of the present invention can be useful for treating traumatic injuries to the central nervous system that are caused by mechanical forces, such as a blow to the head. Such traumatic tissue insults may involve, e.g., but not limited to, an abrasion, incision, contusion, puncture, compression. Traumatic injuries to the central nervous system can arise from traumatic contact of a foreign object with any locus of or appurtenant to the mammalian head, neck or vertebral column. Other forms of traumatic injury can arise from constriction or compression of mammalian CNS tissue by an inappropriate accumulation of fluid (e.g., a blockade or dysfunction of normal cerebrospinal fluid or vitreous humor fluid production, turnover or volume regulation, or a subdural or intracranial hematoma or edema). Similarly, traumatic constriction or compression can arise from the presence of a mass of abnormal tissue, such as a metastatic or primary tumor.

The invention further relates to structure-based methods useful in identifying, designing and producing TDFRP compounds, which act as functional modulators of select TGF-beta superfamily receptors.

The TDFRP compounds of the present invention can be useful for treating injuries to tissues caused by infection or other insults. Such tissue insults may involve, e.g., but are not limited to bacterial (e.g. endotoxin-mediated), fungal or viral infections.

Variants, analogs, homologs, or fragments of these TDFRP compounds, such as species homologs, are also included in the present invention, as well as degenerate forms thereof. The TDFRP compounds of the present invention may be capped on the N-terminus, e.g., SEQ ID NO:17, or the C-terminus, e.g., SEQ ID NO:18, or on both the N-terminus and the C-terminus, e.g., SEQ ID NO:19. The TDFRP compounds of the present invention may be pegylated, or modified, e.g., branching, at any amino acid residue containing a reactive side chain, e.g., lysine residue. The TDFRP compounds of the present invention may be linear or cyclized or otherwise constrained. The tail sequence of the TDFRP may vary in length.

The TDFRP compounds can contain natural amino acids, non-natural amino acids, d-amino acids and l-amino acids, and any combinations thereof. In certain embodiments, the compounds of the invention can include commonly encountered amino acids, which are not genetically encoded. These non-genetically encoded amino acids include, but are not limited to, β-alanine (β-Ala) and other omega-amino acids such as 3-aminopropionic acid (Dap), 2,3-diaminopropionic acid (Dpr), 4-aminobutyric acid and so forth; α-aminoisobutyric acid (Aib); ε-aminohexanoic acid (Aha); δ-aminovaleric acid (Ava); N-methylglycine or sarcosine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (hArg); N-acetyl lysine (AcLys); 2,3-diaminobutyric acid (Dab); 2,3-diaminobutyric acid (Dbu); p-aminophenylalanine (Phe(pNH$_2$)); N-methyl valine (MeVal);

homocysteine (hCys) and homoserine (hSer). Non-naturally occurring variants of the TDFRP compounds may be produced by mutagenesis techniques or by direct synthesis. The TDFRP compound of the present invention may be capped on the N-terminus or the C-terminus or on both the N-terminus and the C-terminus. The TDFRP compounds of the present invention may be pegylated, or modified, e.g., branching, at any amino acid residue containing a reactive side chain, e.g., lysine residue. In one aspect of the present invention, the TDFRP compounds of the invention are prodrugs, i.e., the biological activity of the TDFRP compound is altered, e.g., increased, upon contacting a biological system in vivo or in vitro.

In one embodiment, TDFRP is a polypeptide with the general structure shown in SEQ ID NO:1.

$X_1X_2X_3X_4X_5X_6X_7X_8X_9X_{10}X_{11}X_{12}X_{13}X_{14}X_{15}X_{16}X_{17}X_{18}X_{19}X_{20}$ (SEQ ID NO:1), wherein $X_1$-$X_{20}$ vary independently of each other, and wherein X can be any naturally occurring or non-naturally occurring amino acid and wherein up to 17 amino acids may be absent. In an aspect of this embodiment, the amino acids that are absent may be contiguous or discontiguous. In another embodiment, TDFRP is a polypeptide with the general structure shown in SEQ ID NO:1, wherein $X_1$-$X_{20}$ vary independently of each other, and wherein X can be any naturally occurring amino acid or non-naturally occurring amino acid; and wherein the polypeptide includes at least two Cys residues, and wherein up to 17 amino acids may be absent. In an aspect of this embodiment, the amino acids that are absent may be contiguous or discontiguous.

In another embodiment, TDFRP is a polypeptide with the general structure shown in SEQ ID NO:2.

$CX_2X_3X_4X_5X_6X_7X_8X_9X_{10}CX_{12}X_{13}X_{14}X_{15}X_{16}$ (SEQ ID NO:2), wherein $X_2$-$X_{10}$ along with $X_{12}$-$X_{16}$ vary independently of each other, and wherein $X_2$ is Tyr, Ile, any aromatic amino acid, any aliphatic amino acid or any polar amino acid; wherein $X_3$ is Phe, Val, any aromatic amino acid, or any aliphatic amino acid; wherein $X_4$ is Asp or any acidic amino acid; wherein $X_5$ is Asp, Glu or any acidic amino acid; wherein $X_6$ is Ser, Asn or any polar amino acid; wherein $X_7$ is Ser or any polar amino acid; wherein $X_8$ is Asn, Gln or any polar amino acid; wherein $X_9$ is Val or any aliphatic amino acid; wherein $X_{10}$ is Ile, Val, Leu or any aliphatic amino acid; wherein $X_{12}$ is Lys or any basic amino acid; wherein $X_{13}$ is Lys or any basic amino acid; wherein $X_{14}$ is Tyr or any polar amino acid; wherein $X_{15}$ is Arg or any basic amino acid; and wherein $X_{16}$ is Ser or any polar amino acid.

Representative TM-RP sequences based on, for example, but not limited to, permutations of SEQ ID NO:2 are identified herein as SEQ ID NOs:3-254, and are described below Tables 4-9.

The present compounds include small molecules, more particularly polypeptides, identified herein as SEQ ID NOs: 3-38, summarized in Table 4. Variants, analogs, homologs, or fragments of these compounds, such as species homologs, are also included in the present invention, as well as degenerate forms thereof.

The compounds can contain single, double, triple or other multiple amino acid substitutions at any amino acid within the sequences disclosed as SEQ ID NO:3-38. Substitutions can contain natural amino acids, non-natural amino acids, d-amino acids and l-amino acids, and any combinations thereof. The compounds can be fragments of SEQ ID NO:3-38, for example from about at least 3 amino acids in length.

TABLE 4

| Sequence | SEQ ID NO: |
|---|---|
| CKKHELYVSFRDLGWQDWIIAPEGYAAYYCEQ | 3 |
| CELYVSFRDLGWQDWIIAPEGYAAYC | 4 |
| CFRDLGWQDWIIAPC | 5 |
| ECRDLGWQDWC | 6 |
| CRDLGWQDWIIAPC | 7 |
| CLNAISVLYFDDSSNVILKKYRNMVVRC | 8 |
| CFDDSSNVCLKKYRS | 9 |
| CFDDSSNVICKKYRS | 10 |
| CYFDDSSNVCLKKYRS | 11 |
| CAFPLNSYMNATNHAIVQTLVHFINPETVPKC | 12 |
| CLNSYMNATNHAC | 13 |
| CFINPETVPKC | 14 |
| CLFDDSSNVICKKYRS | 15 |
| CIVNSSDDFLCKKYRS | 16 |
| AcNH-CYFDDSSNVIC | 17 |
| CYFDDSSNVIC-NH2 | 18 |
| AcNH-CYFDDSSNVIC-NH2 | 19 |
| CYFDDSSNVICKK | 20 |
| CYFDDSSNVICK | 21 |
| CFINPETVC | 22 |
| CYFDDSSNVICKKYKS | 23 |
| CYFDDSSNVICKRYRS | 24 |
| CYFDDSSNVICRKYRS | 25 |
| CYLDENEKVVCKNYQS | 26 |
| CYLDEYDKVVCKNYQS | 27 |
| ISVCYFDDSSNVICKKYRS | 28 |
| CYFDDSSNVIC | 29 |
| CYLDDSSNVICKKYRS | 30 |
| CYLDDSSNVLCKKYRS | 31 |
| CYFEDSSNVICKKYRS | 32 |
| CYFDDSSNVLCKKYRS-NH2 | 33 |
| CYLDEDSSKVLCKNYRS-NH2 | 34 |
| CYFDESSKVLCKKYRS-NH2 | 35 |
| CYFDDSSNVLCKKYRSGSGGGC-NH2 | 36 |
| CGGGSGSCYFDDSSNVLCKKYRS-NH2 | 37 |
| CYFDDSSNVICKKYRS | 38 |

Representative compounds the same length as SEQ ID NO:38 with single, double, or triple amino acid substitutions include, but are not limited to, the following amino acid sequences summarized in Table 5. SEQ ID NOs:1-37 are not exhaustively illustrated, but can be similarly modified as described.

TABLE 5

| Sequence | SEQ ID NO: |
| --- | --- |
| CIFDDSSNVICKKYRS | 39 |
| CYVDDSSNVICKKYRS | 40 |
| CYFDESSNVICKKYRS | 41 |
| CYFDDNSNVICKKYRS | 42 |
| CYFDDSSQVICKKYRS | 43 |
| CYFDDSSNVVCKKYRS | 44 |
| CYFDDSSNVLCKKYRS | 45 |
| CIVDDSSNVICKKYRS | 46 |
| CIFDESSNVICKKYRS | 47 |
| CIFDDNSNVICKKYRS | 48 |
| CIFDDSSQVICKKYRS | 49 |
| CIFDDSSNVVCKKYRS | 50 |
| CIFDDSSNVLCKKYRS | 51 |
| CYVDESSNVICKKYRS | 52 |
| CYVDDNSNVICKKYRS | 53 |
| CYVDDSSQVICKKYRS | 54 |
| CYVDDSSNVVCKKYRS | 55 |
| CYVDDSSNVLCKKYRS | 56 |
| CYFDENSNVICKKYRS | 57 |
| CYFDESSQVICKKYRS | 58 |
| CYFDESSNVVCKKYRS | 59 |
| CYFDESSNVLCKKYRS | 60 |
| CYFDDNSQVICKKYRS | 61 |
| CYFDDNSNVVCKKYRS | 62 |
| CYFDDNSNVLCKKYRS | 63 |
| CYFDDSSQVVCKKYRS | 64 |
| CYFDDSSQVLCKKYRS | 65 |
| CIVDESSNVICKKYRS | 66 |
| CIVDDNSNVICKKYRS | 67 |
| CIVDDSSQVICKKYRS | 68 |
| CIVDDSSNVVCKKYRS | 69 |
| CIVDDSSNVLCKKYRS | 70 |
| CIFDENSNVICKKYRS | 71 |
| CIFDESSQVICKKYRS | 72 |
| CIFDESSNVVCKKYRS | 73 |
| CIFDESSNVLCKKYRS | 74 |

TABLE 5-continued

| Sequence | SEQ ID NO: |
| --- | --- |
| CIFDDNSQVICKKYRS | 75 |
| CIFDDNSNVVCKKYRS | 76 |
| CIFDDNSNVLCKKYRS | 77 |
| CIFDDSSQVVCKKYRS | 78 |
| CIFDDSSQVLCKKYRS | 79 |
| CYVDENSNVICKKYRS | 80 |
| CYVDESSQVICKKYRS | 81 |
| CYVDESSNVVCKKYRS | 82 |
| CYVDESSNVLCKKYRS | 83 |
| CYVDDNSQVICKKYRS | 84 |
| CYVDDNSNVVCKKYRS | 85 |
| CYVDDNSNVLCKKYRS | 86 |
| CYVDDSSQVVCKKYRS | 87 |
| CYVDDSSQVLCKKYRS | 88 |
| CYFDENSQVICKKYRS | 89 |
| CYFDENSNVVCKKYRS | 90 |
| CYFDENSNVLCKKYRS | 91 |
| CYFDESSQVVCKKYRS | 92 |
| CYFDESSQVLCKKYRS | 93 |
| CYFDDNSQVVCKKYRS | 94 |
| CYFDDNSQVLCKKYRS | 95 |
| CIVDENSNVICKKYRS | 96 |
| CIVDESSQVICKKYRS | 97 |
| CIVDESSNVVCKKYRS | 98 |
| CIVDESSNVLCKKYRS | 99 |
| CIVDDNSQVICKKYRS | 100 |
| CIVDDNSNVVCKKYRS | 101 |
| CIVDDNSNVLCKKYRS | 102 |
| CIVDDSSQVVCKKYRS | 103 |
| CIVDDSSQVLCKKYRS | 104 |
| CIFDENSQVICKKYRS | 105 |
| CIFDENSNVVCKKYRS | 106 |
| CIFDENSNVLCKKYRS | 107 |
| CIFDESSQVVCKKYRS | 108 |
| CIFDESSQVLCKKYRS | 109 |
| CIFDDNSQVVCKKYRS | 110 |
| CIFDDNSQVLCKKYRS | 111 |
| CYVDENSQVICKKYRS | 112 |
| CYVDENSNVVCKKYRS | 113 |

TABLE 5-continued

| Sequence | SEQ ID NO: |
|---|---|
| CYVDENSNVLCKKYRS | 114 |
| CYVDESSQVVCKKYRS | 115 |
| CYVDESSQVLCKKYRS | 116 |
| CYVDDNSQVVCKKYRS | 117 |
| CYVDDNSQVLCKKYRS | 118 |
| CYFDENSQVVCKKYRS | 119 |
| CYFDENSQVLCKKYRS | 120 |
| CIVDENSQVICKKYRS | 121 |
| CIVDENSNVVCKKYRS | 122 |
| CIVDENSNVLCKKYRS | 123 |
| CIFDENSQVVCKKYRS | 124 |
| CIFDENSQVLCKKYRS | 125 |
| CYVDENSQVVCKKYRS | 126 |
| CYVDENSQVLCCKYRS | 127 |
| CIVDENSQVVCKKYRS | 128 |
| CIVDENSQVLCKKYRS | 129 |
| CYFDDSSKVICKKYRS | 130 |
| CYLDDSSNVICKKYRN | 131 |
| CYFDDSSKVVCKKYRS | 132 |
| CYLDDSSNVVCKKYRS | 133 |
| CYFDDSSKVLCKKYRS | 134 |
| CYLDDSSNVLCKKYRN | 135 |
| CYFDDNSKVICKKYRS | 136 |
| CYFDESSKVICKKYRS | 137 |
| CYLDDSSKVICKKYRS | 138 |
| CYLDDNSNVICKKYRS | 139 |
| CYLDESSNVICKKYRS | 140 |
| CYLDDSSQVICKKYRS | 141 |
| CYFDDNSKVVCKKYRS | 142 |
| CYFDESSKVVCKKYRS | 143 |
| CYLDDSSKVVCKKYRS | 144 |
| CYFDDNSKVLCKKYRS | 145 |
| CYFDESSKVLCKKYRS | 146 |
| CYLDDSSKVLCKKYRS | 147 |
| CYLDESSSKVICKKYRS | 148 |
| CYFDENSKVICKKYRS | 149 |
| CYLDDNSKVICKKYRS | 150 |
| CYLDESSQVICKKYRS | 151 |

Representative fragments of SEQ ID NO:38 (again, selected for illustrative purposes) are summarized in Table 6. Notably, the sequence fragments provided in Table 6 include fragments all having 11 amino acids, but smaller or larger fragments, for example from about 3 or more amino acids are included in the scope of the invention.

TABLE 6

| Sequence | SEQ ID NO: |
|---|---|
| CYFDDSSNVVC | 152 |
| CYFDDSSNVLC | 153 |
| CYFDDSSKVIC | 154 |
| CYFDDNSNVIC | 155 |
| CYFDESSNVIC | 156 |
| CYFDDSSQVIC | 157 |
| CYLDDSSNVIC | 158 |

The present compounds also include small molecules, more particularly peptides, identified in part in Table 7. Variants, analogs, homologs, or fragments of these compounds, such as species homologs, are also included in the present invention, as well as degenerate forms thereof.

TABLE 7

| Sequence | SEQ ID NO: |
|---|---|
| CYLDDNSKVVCKKYR | 159 |
| CYLDDNSNVICKKYR | 160 |
| CYLEDNSNVTCKKYR | 161 |
| CYLEENSNVVCKKYR | 162 |
| CYLDDNSKVTCKKYR | 163 |
| CYLEENSQVICKKYR | 164 |
| CYLEDNSQVVCKKYR | 165 |
| CYLDDNSNFICKKYR | 166 |
| CYLDENSKVVCKKYR | 167 |
| CWLDENSNVVCKKYR | 168 |
| CYLEENSNVICKKYR | 169 |
| CYLEDNSNVVCKKYR | 170 |
| CYLDENSKVICKKYR | 171 |
| CYLDENSQVTCKKYR | 172 |
| CYLEDNSNVICKKYR | 173 |
| CYLDDNSKVICKKYR | 174 |
| CYLDENSNVTCKKYR | 175 |
| CYLDDNSQVTCKKYR | 176 |
| CYLDENSQVVCKKYR | 177 |
| CYLDDNSNVTCKKYR | 178 |
| CYLDENSNVVCKKYR | 179 |
| CYLDENSQVICKKYR | 180 |

TABLE 7-continued

| Sequence | SEQ ID NO: |
|---|---|
| CYLDENSNVICKKYR | 181 |
| CYLDDNSNVVCKKYR | 182 |
| CYLEDNSQVICKKYR | 183 |
| CYLDENSNVTCKKWR | 184 |
| CYLDDNSNVTCKKWR | 185 |
| CYLDENSNVVCKKWR | 186 |
| CYLDDNSNVVCKKWR | 187 |
| CYLDDNSQVTCKKWR | 188 |
| CYLDENSQVVCKKWR | 189 |
| CYLDENSNVVCKQYR | 190 |
| CYLDDNSNVTCKQYR | 191 |
| CYLDDNSQVVCKKWR | 192 |
| CYLDDNSNVVCKNYR | 193 |
| CYLDDNSNVVCKQYR | 194 |
| CYLDENSQVICKQYR | 195 |
| CYADENSNVVCKKWR | 196 |
| CYADDNSNVTCKKWR | 197 |
| CYLDDNSQVICKNYR | 198 |
| CYLDDNSQVVCKQYR | 199 |
| CYLDDNSQVICKQYR | 200 |
| CYADDNSNVVCKKWR | 201 |
| CYLDENDNVCKKWR | 202 |
| CYLDDNDNVTCKKWR | 203 |
| CYADDNSQVVCKKWR | 204 |
| CYADDNSNVVCKQYR | 205 |
| CYLDDNDNVVCKKWR | 206 |
| CYLDDNSNIICKKWR | 207 |

The present compounds also include small molecules, more particularly peptides, identified in part in Table 8. Variants, analogs, homologs, or fragments of these compounds, such as species homologs, are also included in the present invention, as well as degenerate forms thereof.

TABLE 8

| Sequence | SEQ ID NO: |
|---|---|
| CYFDDSNNVLCKKYRS | 208 |
| CYFDDSSSVLCKKYRS | 209 |
| CYFNDSSNVLCKKYRS | 210 |
| CHFDDSSNVLCKKYRS | 211 |
| CYFDDSSNVLCKKYHS | 212 |
| CYFDDSSNVLCKKYRN | 213 |
| CYFDDSSNVLCKKHRS | 214 |
| CYFNDSSQVLCKKHRS | 215 |
| CYWDDSSNVLCKKYRS | 216 |
| CYYDDSSNVLCKKYRS | 217 |
| CYFDDSSQVLCKRYRS | 218 |
| CYYDDSSQVLCKRYRS | 219 |
| CYFNDSSDVLCKKYRS | 220 |
| CYFNDSSQVLCKRYRS | 221 |
| CYYDDSSNVLCKRYRS-NH2 | 222 |
| CYFDDSSNVLCKKYR | 223 |
| CYFDDSSNVLCKKY | 224 |
| KKYRS | 225 |
| KRYRS | 226 |
| CYFDDSSNCLIKKYRS | 227 |
| CYFDDSSNCLLKKYRS | 228 |
| CYFNDSSNCLLKKYRS | 229 |
| CYFDNSSNCLLKKYRS | 230 |
| CYFNNSSNCLLKKYRS | 231 |
| CYFDDSSQCLLKKYRS | 232 |
| CYYDDSSNCLLKKYRS | 233 |
| CYFDDSTNCLLKKYRS | 234 |
| CYFDDSSSCLLKKYRS | 235 |
| CYFDDSSNCALKKYRS | 236 |
| CYFDDSSNCLLKRYRS | 237 |
| CYFDDSSNCLLKKYRN | 238 |
| CYFDDSSNCLLKKYR | 239 |
| CYFDDSSNCLAKKYRS | 240 |
| CYFDDSSNCLLKKY | 241 |
| CYFDDSSNCLLKKYRS-NH2 | 242 |
| CYFDDSSNVNluCKKYRS | 243 |
| CYFDDSSNVAbuCKKYRS | 244 |
| CYFDDSSNVLCSRYKK | 245 |
| CLVNSSDDFYCKKYRS | 246 |
| KKYRSCLVNSSDDFYC | 247 |
| SRYKKCYFDDSSNVLC | 248 |
| SRYKKCLVNSSDDFYC | 249 |

The present compounds also include small molecules, more particularly peptides, identified in part in Table 9. Variants, analogs, homologs, or fragments of these compounds, such as species homologs, are also included in the present invention, as well as degenerate forms thereof.

TABLE 9

```
   O=C————————————————————————NH                                                              250
   |                            |
   CH2                          CH2
   |                            |
NH2—CH——C-Tyr-Phe-Asp-Asp-Ser-Ser-Asn-Val-Leu-NH——CH——C-Lys-Lys-Tyr-Arg-Ser-OH
        ||                          ||
        O                           O

NH—————————————————————————C=O                                                             251
   |                            |
   CH2                          CH2
   |                            |
NH2—CH——C-Tyr-Phe-Asp-Asp-Ser-Ser-Asn-Val-Leu-NH——CH——C-Lys-Lys-Tyr-Arg-Ser-OH
        ||                          ||
        O                           O

O=C————————————————————————NH                                                              252
   |                            |
   CH2                          CH2
   |                            |
   CH2—C-Tyr-Phe-Asp-Asp-Ser-Ser-Asn-Val-Leu-NH——CH——C-Lys-Lys-Tyr-Arg-Ser-NH2
        ||                          ||
        O                           O

NH—————————————————————————C=O                                                             253
   |                            |
   CH2                          CH2
   |                            |
NH2—CH——C-Tyr-Phe-Asp-Asp-Ser-Ser-Asn-Val-Leu-NH——CH——C-Lys-Lys-Tyr-Arg-Ser-NH2
        ||                          ||
        O                           O

NH—————————————————————————C=O                                                             254
   |                            |
   CH2                          CH2
   |                            |
   CH2—C-Tyr-Phe-Asp-Asp-Ser-Ser-Asn-Val-Leu-NH——CH——C-Lys-Lys-Tyr-Arg-Ser-OH
        ||                          ||
        O                           O
```

In one preferred embodiment, the peptides will comprise a core sequence of amino acids $CX_2X_3X_4X_5X_6X_7X_8X_9X_{10}CX_{12}X_{13}X_{14}X_{15}X_{16}$ (SEQ ID NO:255), wherein $X_2$ is Tyr, Phe, Met, Ser, any alicyclic amino acid, or any aromatic amino acid; wherein $X_3$ is Tyr, Phe, Met, Ser, any alicyclic amino acid, or any aromatic amino acid; wherein $X_4$ is Asp, Asn, Glu, Gln, Ser, or any beta-carbonyl amino acid; wherein $X_5$ is Asp, Asn, Glu, Gln, Ser, or any beta-carbonyl amino acid; wherein $X_6$ is Ser, Thr, Cys, Met, His, or any beta-heteroatom amino acid; wherein $X_7$ is Ser, Thr, Cys, Met, His, or any beta-heteroatom amino acid; wherein $X_8$ is Asp, Asn, Glu, Gln, Ser, Thr, Met, His, or any polar amino acid; wherein $X_9$ is Val, Ile, Thr, Leu, Ala, Gly, Met, Phe, or any nonpolar amino acid; wherein $X_{10}$ is Ile, Leu, Ala, Gly, Val, Met, Ser, Phe, or any nonpolar amino acid; wherein $X_{12}$ is Lys, Arg, His, Trp, or any basic amino acid; wherein $X_{13}$ is Lys, Arg, His, Trp, or any basic amino acid; wherein $X_{14}$ is Tyr, Phe, His, Trp, or any aromatic amino acid; wherein $X_{15}$ is Arg, Lys, His, Trp, or any basic amino acid; and wherein $X_{16}$ is Ser, Thr, Asp, Asn, Glu, Gln, any polar amino acid, or is absent.

In one preferred embodiment, the peptides will comprise a core sequence of amino acids $CX_2X_3DDSX_7X_8X_9X_{10}CKX_{13}X_{14}RX_{16}$ (SEQ ID NO:256), wherein $X_2$ is Tyr, Phe, Met, Ser, any alicyclic amino acid, or any aromatic amino acid; wherein $X_3$ is Tyr, Phe, Met, Ser, any alicyclic amino acid, or any aromatic amino acid; wherein $X_7$ is Ser, Thr, Cys, Met, His, or any beta-heteroatom amino acid; wherein $X_8$ is Asp, Asn, Glu, Gln, Ser, Thr, Met, His, or any polar amino acid; wherein $X_9$ is Val, Ile, Thr, Leu, Ala, Gly, Met, Phe, or any nonpolar amino acid; wherein $X_{10}$ is Ile, Leu, Ala, Gly, Val, Met, Ser, Phe, or any nonpolar amino acid; wherein $X_{13}$ is Lys, Arg, His, Trp, or any basic amino acid; wherein $X_{14}$ is Tyr, Phe, His, Trp, or any aromatic amino acid; and wherein $X_{16}$ is Ser, Thr, Asp, Asn, Glu, Gln, any polar amino acid, or is absent.

In one preferred embodiment, the peptides will comprise a core sequence of amino acids $CX_2X_3NDSX_7X_8X_9X_{10}CKX_{13}X_{14}RX_{16}$ (SEQ ID NO:257), wherein $X_2$ is Tyr, Phe, Met, Ser, any alicyclic amino acid, or any aromatic amino acid; wherein $X_3$ is Tyr, Phe, Met, Ser, any alicyclic amino acid, or any aromatic amino acid; wherein $X_7$ is Ser, Thr, Cys, Met, His, or any beta-heteroatom amino acid; wherein $X_8$ is Asp, Asn, Glu, Gln, Ser, Thr, Met, His, or any polar amino acid; wherein $X_9$ is Val, Ile, Thr, Leu, Ala, Gly, Met, Phe, or any nonpolar amino acid; wherein $X_{10}$ is Ile, Leu, Ala, Gly, Val, Met, Ser, Phe, or any nonpolar amino acid; wherein $X_{13}$ is Lys, Arg, His, Trp, or any basic amino acid; wherein $X_{14}$ is Tyr, Phe, His, Trp, or any aromatic amino acid; and wherein $X_{16}$ is Ser, Thr, Asp, Asn, Glu, Gln, any polar amino acid, or is absent.

In one preferred embodiment, the peptides will comprise a core sequence of amino acids $CX_2X_3DNSX_7X_8X_9X_{10}CKX_{13}X_{14}RX_{16}$ (SEQ ID NO:258), wherein $X_2$ is Tyr, Phe, Met, Ser, any alicyclic amino acid, or any aromatic amino acid; wherein $X_3$ is Tyr, Phe, Met, Ser, any alicyclic amino acid, or any aromatic amino acid; wherein $X_7$ is Ser, Thr, Cys, Met, His, or any beta-heteroatom amino acid; wherein $X_8$ is Asp, Asn, Glu, Gln, Ser, Thr, Met, His, or any polar amino acid; wherein $X_9$ is Val, Ile, Thr, Leu, Ala, Gly, Met, Phe, or any nonpolar amino acid; wherein $X_{10}$ is Ile, Leu, Ala, Gly, Val, Met, Ser, Phe, or any nonpolar amino acid; wherein $X_{13}$ is Lys, Arg, His, Trp, or any basic amino acid; wherein $X_{14}$ is Tyr, Phe, His, Trp, or any aromatic amino acid; and wherein $X_{16}$ is Ser, Thr, Asp, Asn, Glu, Gln, any polar amino acid, or is absent.

In one preferred embodiment, the peptides will comprise a core sequence of amino acids $CX_2X_3NNSX_7X_8X_9X_{10}CKX_{13}X_{14}RX_{16}$ (SEQ ID NO:259), wherein $X_2$ is Tyr, Phe, Met, Ser, any alicyclic amino acid, or any aromatic amino acid; wherein $X_3$ is Tyr, Phe, Met, Ser, any alicyclic amino acid, or any aromatic amino acid; wherein $X_7$ is Ser, Thr, Cys, Met, His, or any beta-heteroatom amino acid; wherein $X_8$ is Asp, Asn, Glu, Gln, Ser, Thr, Met, His, or any polar amino acid; wherein $X_9$ is Val, Ile, Thr, Leu, Ala, Gly, Met, Phe, or any nonpolar amino acid; wherein $X_{10}$ is Ile, Leu, Ala, Gly, Val, Met, Ser, Phe, or any nonpolar amino acid; wherein $X_{13}$ is Lys, Arg, His, Trp, or any basic amino acid; wherein $X_{14}$ is Tyr, Phe, His, Trp, or any aromatic amino acid; and wherein $X_{16}$ is Ser, Thr, Asp, Asn, Glu, Gln, any polar amino acid, or is absent.

In one preferred embodiment, the peptides will comprise a core sequence of amino acids $CYX_3DDSX_7X_8X_9X_{10}CKX_{13}YRX_{16}$ (SEQ ID NO:260), wherein $X_3$ is Tyr, Phe, Met, Ser, any alicyclic amino acid, or any aromatic amino acid; wherein $X_7$ is Ser, Thr, Cys, Met, His, or any beta-heteroatom amino acid; wherein $X_8$ is Asp, Asn, Glu, Gln, Ser, Thr, Met, His, or any polar amino acid; wherein $X_9$ is Val, Ile, Thr, Leu, Ala, Gly, Met, Phe, or any nonpolar amino acid; wherein $X_{10}$ is Ile, Leu, Ala, Gly, Val, Met, Ser, Phe, or any nonpolar amino acid; wherein $X_{13}$ is Lys, Arg, His, Trp, or any basic amino acid; and wherein $X_{16}$ is Ser, Thr, Asp, Asn, Glu, Gln, any polar amino acid, or is absent.

In one preferred embodiment, the peptides will comprise a core sequence of amino acids $CYX_3NDSX_7X_8X_9X_{10}CKX_{13}YRX_{16}$ (SEQ ID NO:261), wherein $X_3$ is Tyr, Phe, Met, Ser, any alicyclic amino acid, or any aromatic amino acid; wherein $X_7$ is Ser, Thr, Cys, Met, His, or any beta-heteroatom amino acid; wherein $X_8$ is Asp, Asn, Glu, Gln, Ser, Thr, Met, His, or any polar amino acid; wherein $X_9$ is Val, Ile, Thr, Leu, Ala, Gly, Met, Phe, or any nonpolar amino acid; wherein $X_{10}$ is Ile, Leu, Ala, Gly, Val, Met, Ser, Phe, or any nonpolar amino acid; wherein $X_{13}$ is Lys, Arg, His, Trp, or any basic amino acid; and wherein $X_{16}$ is Ser, Thr, Asp, Asn, Glu, Gln, any polar amino acid, or is absent.

In one preferred embodiment, the peptides will comprise a core sequence of amino acids $CYX_3DNSX_7X_8X_9X_{10}CKX_{13}YRX_{16}$ (SEQ ID NO:262), wherein $X_3$ is Tyr, Phe, Met, Ser, any alicyclic amino acid, or any aromatic amino acid; wherein $X_7$ is Ser, Thr, Cys, Met, His, or any beta-heteroatom amino acid; wherein $X_8$ is Asp, Asn, Glu, Gln, Ser, Thr, Met, His, or any polar amino acid; wherein $X_9$ is Val, Ile, Thr, Leu, Ala, Gly, Met, Phe, or any nonpolar amino acid; wherein $X_{10}$ is Ile, Leu, Ala, Gly, Val, Met, Ser, Phe, or any nonpolar amino acid; wherein $X_{13}$ is Lys, Arg, His, Trp, or any basic amino acid; and wherein $X_{16}$ is Ser, Thr, Asp, Asn, Glu, Gln, any polar amino acid, or is absent.

In one preferred embodiment, the peptides will comprise a core sequence of amino acids $CYX_3NNSX_7X_8X_9X_{10}CKX_{13}YRX_{16}$ (SEQ ID NO:263), wherein $X_3$ is Tyr, Phe, Met, Ser, any alicyclic amino acid, or any aromatic amino acid; wherein $X_7$ is Ser, Thr, Cys, Met, His, or any beta-heteroatom amino acid; wherein $X_8$ is Asp, Asn, Glu, Gln, Ser, Thr, Met, His, or any polar amino acid; wherein $X_9$ is Val, Ile, Thr, Leu, Ala, Gly, Met, Phe, or any nonpolar amino acid; wherein $X_{10}$ is Ile, Leu, Ala, Gly, Val, Met, Ser, Phe, or any nonpolar amino acid; wherein $X_{13}$ is Lys, Arg, His, Trp, or any basic amino acid; and wherein $X_{16}$ is Ser, Thr, Asp, Asn, Glu, Gln, any polar amino acid, or is absent.

In one preferred embodiment, the peptides will comprise a core sequence of amino acids $CX_2X_3DDSSX_8X_9X_{10}CKX_{13}X_{14}RX_{16}$ (SEQ ID NO:264), wherein $X_2$ is Tyr, Phe, Met, Ser, any alicyclic amino acid, or any aromatic amino acid; wherein $X_3$ is Tyr, Phe, Met, Ser, any alicyclic amino acid, or any aromatic amino acid; wherein $X_8$ is Asp, Asn, Glu, Gln, Ser, Thr, Met, His, or any polar amino acid; wherein $X_9$ is Val, Ile, Thr, Leu, Ala, Gly, Met, Phe, or any nonpolar amino acid; wherein $X_{10}$ is Ile, Leu, Ala, Gly, Val, Met, Ser, Phe, or any nonpolar amino acid; wherein $X_{13}$ is Lys, Arg, His, Trp, or any basic amino acid; wherein $X_{14}$ is Tyr, Phe, His, Trp, or any aromatic amino acid; and wherein $X_{16}$ is Ser, Thr, Asp, Asn, Glu, Gln, any polar amino acid, or is absent.

In one preferred embodiment, the peptides will comprise a core sequence of amino acids $CX_2X_3NDSSX_8X_9X_{10}CKX_{13}X_{14}RX_{16}$ (SEQ ID NO:265), wherein $X_2$ is Tyr, Phe, Met, Ser, any alicyclic amino acid, or any aromatic amino acid; wherein $X_3$ is Tyr, Phe, Met, Ser, any alicyclic amino acid, or any aromatic amino acid; wherein $X_8$ is Asp, Asn, Glu, Gln, Ser, Thr, Met, His, or any polar amino acid; wherein $X_9$ is Val, Ile, Thr, Leu, Ala, Gly, Met, Phe, or any nonpolar amino acid; wherein $X_{10}$ is Ile, Leu, Ala, Gly, Val, Met, Ser, Phe, or any nonpolar amino acid; wherein $X_{13}$ is Lys, Arg, His, Trp, or any basic amino acid; wherein $X_{14}$ is Tyr, Phe, His, Trp, or any aromatic amino acid; and wherein $X_{16}$ is Ser, Thr, Asp, Asn, Glu, Gln, any polar amino acid, or is absent.

In one preferred embodiment, the peptides will comprise a core sequence of amino acids $CX_2X_3DNSSX_8X_9X_{10}CKX_{13}X_{14}RX_{16}$ (SEQ ID NO:266), wherein $X_2$ is Tyr, Phe, Met, Ser, any alicyclic amino acid, or any aromatic amino acid; wherein $X_3$ is Tyr, Phe, Met, Ser, any alicyclic amino acid, or any aromatic amino acid; wherein $X_8$ is Asp, Asn, Glu, Gln, Ser, Thr, Met, His, or any polar amino acid; wherein $X_9$ is Val, Ile, Thr, Leu, Ala, Gly, Met, Phe, or any nonpolar amino acid; wherein $X_{10}$ is Ile, Leu, Ala, Gly, Val, Met, Ser, Phe, or any nonpolar amino acid; wherein $X_{13}$ is Lys, Arg, His, Trp, or any basic amino acid; wherein $X_{14}$ is Tyr, Phe, His, Trp, or any aromatic amino acid; and wherein $X_{16}$ is Ser, Thr, Asp, Asn, Glu, Gln, any polar amino acid, or is absent.

In one preferred embodiment, the peptides will comprise a core sequence of amino acids $CX_2X_3NNSSX_8X_9X_{10}CKX_{13}X_{14}RX_{16}$ (SEQ ID NO:267), wherein $X_2$ is Tyr, Phe, Met, Ser, any alicyclic amino acid, or any aromatic amino acid; wherein $X_3$ is Tyr, Phe, Met, Ser, any alicyclic amino acid, or any aromatic amino acid; wherein $X_8$ is Asp, Asn, Glu, Gln, Ser, Thr, Met, His, or any polar amino acid; wherein $X_9$ is Val, Ile, Thr, Leu, Ala, Gly, Met, Phe, or any nonpolar amino acid; wherein $X_{10}$ is Ile, Leu, Ala, Gly, Val, Met, Ser, Phe, or any nonpolar amino acid; wherein $X_{13}$ is Lys, Arg, His, Trp, or any basic amino acid; wherein $X_{14}$ is Tyr, Phe, His, Trp, or any aromatic amino acid; and wherein $X_{16}$ is Ser, Thr, Asp, Asn, Glu, Gln, any polar amino acid, or is absent.

In one preferred embodiment, the peptides will comprise a core sequence of amino acids CYX$_3$DDSSX$_8$X$_9$X$_{10}$CKX$_{13}$YRX$_{16}$ (SEQ ID NO:268), wherein X$_3$ is Tyr, Phe, Met, Ser, any alicyclic amino acid, or any aromatic amino acid; wherein X$_8$ is Asp, Asn, Glu, Gln, Ser, Thr, Met, His, or any polar amino acid; wherein X$_9$ is Val, Ile, Thr, Leu, Ala, Gly, Met, Phe, or any nonpolar amino acid; wherein X$_{10}$ is Ile, Leu, Ala, Gly, Val, Met, Ser, Phe, or any nonpolar amino acid; wherein X$_{13}$ is Lys, Arg, His, Trp, or any basic amino acid; and wherein X$_{16}$ is Ser, Thr, Asp, Asn, Glu, Gln, any polar amino acid, or is absent.

In one preferred embodiment, the peptides will comprise a core sequence of amino acids CYX$_3$NDSSX$_8$X$_9$X$_{10}$CKX$_{13}$YRX$_{16}$ (SEQ ID NO:269), wherein X$_3$ is Tyr, Phe, Met, Ser, any alicyclic amino acid, or any aromatic amino acid; wherein X$_8$ is Asp, Asn, Glu, Gln, Ser, Thr, Met, His, or any polar amino acid; wherein X$_9$ is Val, Ile, Thr, Leu, Ala, Gly, Met, Phe, or any nonpolar amino acid; wherein X$_{10}$ is Ile, Leu, Ala, Gly, Val, Met, Ser, Phe, or any nonpolar amino acid; wherein X$_{13}$ is Lys, Arg, His, Trp, or any basic amino acid; and wherein X$_{16}$ is Ser, Thr, Asp, Asn, Glu, Gln, any polar amino acid, or is absent.

In one preferred embodiment, the peptides will comprise a core sequence of amino acids CYX$_3$DNSSX$_8$X$_9$X$_{10}$CKX$_{13}$YRX$_{16}$ (SEQ ID NO:270), wherein X$_3$ is Tyr, Phe, Met, Ser, any alicyclic amino acid, or any aromatic amino acid; wherein X$_8$ is Asp, Asn, Glu, Gln, Ser, Thr, Met, His, or any polar amino acid; wherein X$_9$ is Val, Ile, Thr, Leu, Ala, Gly, Met, Phe, or any nonpolar amino acid; wherein X$_{10}$ is Ile, Leu, Ala, Gly, Val, Met, Ser, Phe, or any nonpolar amino acid; wherein X$_{13}$ is Lys, Arg, His, Trp, or any basic amino acid; and wherein X$_{16}$ is Ser, Thr, Asp, Asn, Glu, Gln, any polar amino acid, or is absent.

In one preferred embodiment, the peptides will comprise a core sequence of amino acids CYX$_3$NNSSX$_8$X$_9$X$_{10}$CKX$_{13}$YRX$_{16}$ (SEQ ID NO:271), wherein X$_3$ is Tyr, Phe, Met, Ser, any alicyclic amino acid, or any aromatic amino acid; wherein X$_8$ is Asp, Asn, Glu, Gln, Ser, Thr, Met, His, or any polar amino acid; wherein X$_9$ is Val, Ile, Thr, Leu, Ala, Gly, Met, Phe, or any nonpolar amino acid; wherein X$_{10}$ is Ile, Leu, Ala, Gly, Val, Met, Ser, Phe, or any nonpolar amino acid; wherein X$_{13}$ is Lys, Arg, His, Trp, or any basic amino acid; and wherein X$_{16}$ is Ser, Thr, Asp, Asn, Glu, Gln, any polar amino acid, or is absent.

In a more preferred embodiment, the peptides will comprise a core sequence of amino acids CX$_2$X$_3$X$_4$X$_5$X$_6$X$_7$X$_8$X$_9$X$_{10}$CX$_{12}$X$_{13}$X$_{14}$X$_{15}$X$_{16}$ (SEQ ID NO:272), wherein X$_2$ is Tyr, Phe, or any aromatic amino acid; wherein X$_3$ is Tyr, Phe, or any aromatic amino acid; wherein X$_4$ is Asp, Asn, or any beta-carbonyl amino acid; wherein X$_5$ is Asp, Asn, or any beta-carbonyl amino acid; wherein X$_6$ is Ser, Thr, or any beta-heteroatom amino acid; wherein X$_7$ is Ser, Thr, or any beta-heteroatom amino acid; wherein X$_8$ is Asn, Gln, Ser, Thr, or any polar amino acid; wherein X$_9$ is Val, Ile, Leu, Ala, or any nonpolar amino acid; wherein X$_{10}$ is Ile, Leu, Ala, Gly, or any nonpolar amino acid; wherein X$_{12}$ is Lys, Arg, or any basic amino acid; wherein X$_{13}$ is Lys, Arg, or any basic amino acid; wherein X$_{14}$ is Tyr, Phe, or any aromatic amino acid; wherein X$_{15}$ is Arg, Lys, or any basic amino acid; and wherein X$_{16}$ is Ser, Thr, Asn, Gln, any polar amino acid, or is absent.

In a more preferred embodiment, the peptides will comprise a core sequence of amino acids CX$_2$X$_3$DDSX$_7$X$_8$X$_9$X$_{10}$CKX$_{13}$X$_{14}$RX$_{16}$ (SEQ ID NO:273), wherein X$_2$ is Tyr, Phe, or any aromatic amino acid; wherein X$_3$ is Tyr, Phe, or any aromatic amino acid; wherein X$_7$ is Ser, Thr, or any beta-heteroatom amino acid; wherein X$_8$ is Asn, Gln, Ser, Thr, or any polar amino acid; wherein X$_9$ is Val, Ile, Leu, Ala, or any nonpolar amino acid; wherein X$_{10}$ is Ile, Leu, Ala, Gly, or any nonpolar amino acid; wherein X$_{13}$ is Lys, Arg, or any basic amino acid; wherein X$_{14}$ is Tyr, Phe, or any aromatic amino acid; and wherein X$_{16}$ is Ser, Thr, Asn, Gln, any polar amino acid, or is absent.

In a more preferred embodiment, the peptides will comprise a core sequence of amino acids CX$_2$X$_3$NDSX$_7$X$_8$X$_9$X$_{10}$CKX$_{13}$X$_{14}$RX$_{16}$ (SEQ ID NO:274), wherein X$_2$ is Tyr, Phe, or any aromatic amino acid; wherein X$_3$ is Tyr, Phe, or any aromatic amino acid; wherein X$_7$ is Ser, Thr, or any beta-heteroatom amino acid; wherein X$_8$ is Asn, Gln, Ser, Thr, or any polar amino acid; wherein X$_9$ is Val, Ile, Leu, Ala, or any nonpolar amino acid; wherein X$_{10}$ is Ile, Leu, Ala, Gly, or any nonpolar amino acid; wherein X$_{13}$ is Lys, Arg, or any basic amino acid; wherein X$_{14}$ is Tyr, Phe, or any aromatic amino acid; and wherein X$_{16}$ is Ser, Thr, Asn, Gln, any polar amino acid, or is absent.

In a more preferred embodiment, the peptides will comprise a core sequence of amino acids CX$_2$X$_3$DNSX$_7$X$_8$X$_9$X$_{10}$CKX$_{13}$X$_{14}$RX$_{16}$ (SEQ ID NO:275), wherein X$_2$ is Tyr, Phe, or any aromatic amino acid; wherein X$_3$ is Tyr, Phe, or any aromatic amino acid; wherein X$_7$ is Ser, Thr, or any beta-heteroatom amino acid; wherein X$_8$ is Asn, Gln, Ser, Thr, or any polar amino acid; wherein X$_9$ is Val, Ile, Leu, Ala, or any nonpolar amino acid; wherein X$_{10}$ is Ile, Leu, Ala, Gly, or any nonpolar amino acid; wherein X$_{13}$ is Lys, Arg, or any basic amino acid; wherein X$_{14}$ is Tyr, Phe, or any aromatic amino acid; and wherein X$_{16}$ is Ser, Thr, Asn, Gln, any polar amino acid, or is absent.

In a more preferred embodiment, the peptides will comprise a core sequence of amino acids CX$_2$X$_3$NNSX$_7$X$_8$X$_9$X$_{10}$CKX$_{13}$X$_{14}$RX$_{16}$ (SEQ ID NO:276), wherein X$_2$ is Tyr, Phe, or any aromatic amino acid; wherein X$_3$ is Tyr, Phe, or any aromatic amino acid; wherein X$_7$ is Ser, Thr, or any beta-heteroatom amino acid; wherein X$_8$ is Asn, Gln, Ser, Thr, or any polar amino acid; wherein X$_9$ is Val, Ile, Leu, Ala, or any nonpolar amino acid; wherein X$_{10}$ is Ile, Leu, Ala, Gly, or any nonpolar amino acid; wherein X$_{13}$ is Lys, Arg, or any basic amino acid; wherein X$_{14}$ is Tyr, Phe, or any aromatic amino acid; and wherein X$_{16}$ is Ser, Thr, Asn, Gln, any polar amino acid, or is absent.

In a more preferred embodiment, the peptides will comprise a core sequence of amino acids CYX$_3$DDSX$_7$X$_8$X$_9$X$_{10}$CKX$_{13}$YRX$_{16}$ (SEQ ID NO:277), wherein X$_3$ is Tyr, Phe, or any aromatic amino acid; wherein X$_7$ is Ser, Thr, or any beta-heteroatom amino acid; wherein X$_8$ is Asn, Gln, Ser, Thr, or any polar amino acid; wherein X$_9$ is Val, Ile, Leu, Ala, or any nonpolar amino acid; wherein X$_{10}$ is Ile, Leu, Ala, Gly, or any nonpolar amino acid; wherein X$_{13}$ is Lys, Arg, or any basic amino acid; and wherein X$_{16}$ is Ser, Thr, Asn, Gln, any polar amino acid, or is absent.

In a more preferred embodiment, the peptides will comprise a core sequence of amino acids CYX$_3$NDSX$_7$X$_8$X$_9$X$_{10}$CKX$_{13}$YRX$_{16}$ (SEQ ID NO:278), wherein X$_3$ is Tyr, Phe, or any aromatic amino acid; wherein X$_7$ is Ser, Thr, or any beta-heteroatom amino acid; wherein X$_8$ is Asn, Gln, Ser, Thr, or any polar amino acid; wherein X$_9$ is Val, Ile, Leu, Ala, or any nonpolar amino acid; wherein X$_{10}$ is Ile, Leu, Ala, Gly, or any nonpolar amino acid; wherein X$_{13}$ is Lys, Arg, or any basic amino acid; and wherein X$_{16}$ is Ser, Thr, Asn, Gln, any polar amino acid, or is absent.

In a more preferred embodiment, the peptides will comprise a core sequence of amino acids CYX$_3$DNSX$_7$X$_8$X$_9$X$_{10}$CKX$_{13}$YRX$_{16}$ (SEQ ID NO:279), wherein X$_3$ is Tyr, Phe, or any aromatic amino acid; wherein X$_7$ is Ser, Thr, or any beta-heteroatom amino acid; wherein X$_8$ is Asn, Gln, Ser, Thr, or any polar amino acid; wherein X$_9$ is Val, Ile, Leu, Ala, or any nonpolar amino acid; wherein X$_{10}$ is Ile, Leu, Ala, Gly, or any nonpolar amino acid; wherein $X_{13}$ is Lys, Arg, or any basic amino acid; and wherein $X_{16}$ is Ser, Thr, Asn, Gln, any polar amino acid, or is absent.

In a more preferred embodiment, the peptides will comprise a core sequence of amino acids $CYX_3NNSX_7X_8X_9X_{10}CKX_{13}YRX_{16}$ (SEQ ID NO:280), wherein $X_3$ is Tyr, Phe, or any aromatic amino acid; wherein $X_7$ is Ser, Thr, or any beta-heteroatom amino acid; wherein $X_8$ is Asn, Gln, Ser, Thr, or any polar amino acid; wherein $X_9$ is Val, Ile, Leu, Ala, or any nonpolar amino acid; wherein $X_{10}$ is Ile, Leu, Ala, Gly, or any nonpolar amino acid; wherein $X_{13}$ is Lys, Arg, or any basic amino acid; and wherein $X_{16}$ is Ser, Thr, Asn, Gln, any polar amino acid, or is absent.

In a more preferred embodiment, the peptides will comprise a core sequence of amino acids $CX_2X_3DDSSX_8X_9X_{10}CKX_{13}X_{14}RX_{16}$ (SEQ ID NO:281), wherein $X_2$ is Tyr, Phe, or any aromatic amino acid; wherein $X_3$ is Tyr, Phe, or any aromatic amino acid; wherein $X_8$ is Asn, Gln, Ser, Thr, or any polar amino acid; wherein $X_9$ is Val, Ile, Leu, Ala, or any nonpolar amino acid; wherein $X_{10}$ is Ile, Leu, Ala, Gly, or any nonpolar amino acid; wherein $X_{13}$ is Lys, Arg, or any basic amino acid; wherein $X_{14}$ is Tyr, Phe, or any aromatic amino acid; and wherein $X_{16}$ is Ser, Thr, Asn, Gln, any polar amino acid, or is absent.

In a more preferred embodiment, the peptides will comprise a core sequence of amino acids $CX_2X_3NDSSX_8X_9X_{10}CKX_{13}X_{14}RX_{16}$ (SEQ ID NO:282), wherein $X_2$ is Tyr, Phe, or any aromatic amino acid; wherein $X_3$ is Tyr, Phe, or any aromatic amino acid; wherein $X_8$ is Asn, Gln, Ser, Thr, or any polar amino acid; wherein $X_9$ is Val, Ile, Leu, Ala, or any nonpolar amino acid; wherein $X_{10}$ is Ile, Leu, Ala, Gly, or any nonpolar amino acid; wherein $X_{13}$ is Lys, Arg, or any basic amino acid; wherein $X_{14}$ is Tyr, Phe, or any aromatic amino acid; and wherein $X_{16}$ is Ser, Thr, Asn, Gln, any polar amino acid, or is absent.

In a more preferred embodiment, the peptides will comprise a core sequence of amino acids $CX_2X_3DNSSX_8X_9X_{10}CKX_{13}X_{14}RX_{16}$ (SEQ ID NO:283), wherein $X_2$ is Tyr, Phe, or any aromatic amino acid; wherein $X_3$ is Tyr, Phe, or any aromatic amino acid; wherein $X_8$ is Asn, Gln, Ser, Thr, or any polar amino acid; wherein $X_9$ is Val, Ile, Leu, Ala, or any nonpolar amino acid; wherein $X_{10}$ is Ile, Leu, Ala, Gly, or any nonpolar amino acid; wherein $X_{13}$ is Lys, Arg, or any basic amino acid; wherein $X_{14}$ is Tyr, Phe, or any aromatic amino acid; and wherein $X_{16}$ is Ser, Thr, Asn, Gln, any polar amino acid, or is absent.

In a more preferred embodiment, the peptides will comprise a core sequence of amino acids $CX_2X_3NNSSX_8X_9X_{10}CKX_{13}X_{14}RX_{16}$ (SEQ ID NO:284), wherein $X_2$ is Tyr, Phe, or any aromatic amino acid; wherein $X_3$ is Tyr, Phe, or any aromatic amino acid; wherein $X_8$ is Asn, Gln, Ser, Thr, or any polar amino acid; wherein $X_9$ is Val, Ile, Leu, Ala, or any nonpolar amino acid; wherein $X_{10}$ is Ile, Leu, Ala, Gly, or any nonpolar amino acid; wherein $X_{13}$ is Lys, Arg, or any basic amino acid; wherein $X_{14}$ is Tyr, Phe, or any aromatic amino acid; and wherein $X_{16}$ is Ser, Thr, Asn, Gln, any polar amino acid, or is absent.

In a more preferred embodiment, the peptides will comprise a core sequence of amino acids $CYX_3DDSSX_8X_9X_{10}CKX_{13}YRX_{16}$ (SEQ ID NO:285), wherein $X_3$ is Tyr, Phe, or any aromatic amino acid; wherein $X_8$ is Asn, Gln, Ser, Thr, or any polar amino acid; wherein $X_9$ is Val, Ile, Leu, Ala, or any nonpolar amino acid; wherein $X_{10}$ is Ile, Leu, Ala, Gly, or any nonpolar amino acid; wherein $X_{13}$ is Lys, Arg, or any basic amino acid; and wherein $X_{16}$ is Ser, Thr, Asn, Gln, any polar amino acid, or is absent.

In a more preferred embodiment, the peptides will comprise a core sequence of amino acids $CYX_3NDSSX_8X_9X_{10}CKX_{13}YRX_{16}$ (SEQ ID NO:286), wherein $X_3$ is Tyr, Phe, or any aromatic amino acid; wherein $X_8$ is Asn, Gln, Ser, Thr, or any polar amino acid; wherein $X_9$ is Val, Ile, Leu, Ala, or any nonpolar amino acid; wherein $X_{10}$ is Ile, Leu, Ala, Gly, or any nonpolar amino acid; wherein $X_{13}$ is Lys, Arg, or any basic amino acid; and wherein $X_{16}$ is Ser, Thr, Asn, Gln, any polar amino acid, or is absent.

In a more preferred embodiment, the peptides will comprise a core sequence of amino acids $CYX_3DNSSX_8X_9X_{10}CKX_{13}YRX_{16}$ (SEQ ID NO:287), wherein $X_3$ is Tyr, Phe, or any aromatic amino acid; wherein $X_8$ is Asn, Gln, Ser, Thr, or any polar amino acid; wherein $X_9$ is Val, Ile, Leu, Ala, or any nonpolar amino acid; wherein $X_{10}$ is Ile, Leu, Ala, Gly, or any nonpolar amino acid; wherein $X_{13}$ is Lys, Arg, or any basic amino acid; and wherein $X_{16}$ is Ser, Thr, Asn, Gln, any polar amino acid, or is absent.

In a more preferred embodiment, the peptides will comprise a core sequence of amino acids $CYX_3NNSSX_8X_9X_{10}CKX_{13}YRX_{16}$ (SEQ ID NO:288), wherein $X_3$ is Tyr, Phe, or any aromatic amino acid; wherein $X_8$ is Asn, Gln, Ser, Thr, or any polar amino acid; wherein $X_9$ is Val, Ile, Leu, Ala, or any nonpolar amino acid; wherein $X_{10}$ is Ile, Leu, Ala, Gly, or any nonpolar amino acid; wherein $X_{13}$ is Lys, Arg, or any basic amino acid; and wherein $X_{16}$ is Ser, Thr, Asn, Gln, any polar amino acid, or is absent.

In an especially preferred embodiment, the peptides will comprise a core sequence of amino acids $CX_2X_3X_4X_5X_6X_7X_8X_9X_{10}CX_{12}X_{13}X_{14}X_{15}X_{16}$ (SEQ ID NO:289), wherein $X_2$ is Tyr, or Phe; wherein $X_3$ is Phe, or Tyr; wherein $X_4$ is Asp, or Asn; wherein $X_5$ is Asp, or Asn; wherein $X_6$ is Ser, or Thr; wherein $X_7$ is Ser, or Thr; wherein $X_8$ is Asn, Gln, Ser, or Thr; wherein $X_9$ is Val, Ile, Leu, or Ala; wherein $X_{10}$ is Ile, Leu, Ala, or Gly; wherein $X_{12}$ is Lys, or Arg; wherein $X_{13}$ is Lys, or Arg; wherein $X_{14}$ is Tyr, or Phe; wherein $X_{15}$ is Arg, or Lys; and wherein $X_{16}$ is Ser, Thr, Asn, Gln, or is absent.

In an especially preferred embodiment, the peptides will comprise a core sequence of amino acids $CX_2X_3DDSX_7X_8X_9X_{10}CKX_{13}X_{14}RX_{16}$ (SEQ ID NO:290), wherein $X_2$ is Tyr, or Phe; wherein $X_3$ is Phe, or Tyr; wherein $X_7$ is Ser, or Thr; wherein $X_8$ is Asn, Gln, Ser, or Thr; wherein $X_9$ is Val, Ile, Leu, or Ala; wherein $X_{10}$ is Ile, Leu, Ala, or Gly; wherein $X_{13}$ is Lys, or Arg; wherein $X_{14}$ is Tyr, or Phe; and wherein $X_{16}$ is Ser, Thr, Asn, Gln, or is absent.

In an especially preferred embodiment, the peptides will comprise a core sequence of amino acids $CX_2X_3NDSX_7X_8X_9X_{10}CKX_{13}X_{14}RX_{16}$ (SEQ ID NO:291), wherein $X_2$ is Tyr, or Phe; wherein $X_3$ is Phe, or Tyr; wherein $X_7$ is Ser, or Thr; wherein $X_8$ is Asn, Gln, Ser, or Thr; wherein $X_9$ is Val, Ile, Leu, or Ala; wherein $X_{10}$ is Ile, Leu, Ala, or Gly; wherein $X_{13}$ is Lys, or Arg; wherein $X_{14}$ is Tyr, or Phe; and wherein $X_{16}$ is Ser, Thr, Asn, Gln, or is absent.

In an especially preferred embodiment, the peptides will comprise a core sequence of amino acids $CX_2X_3DNSX_7X_8X_9X_{10}CKX_{13}X_{14}RX_{16}$ (SEQ ID NO:292), wherein $X_2$ is Tyr, or Phe; wherein $X_3$ is Phe, or Tyr; wherein $X_7$ is Ser, or Thr; wherein $X_8$ is Asn, Gln, Ser, or Thr; wherein $X_9$ is Val, Ile, Leu, or Ala; wherein $X_{10}$ is Ile, Leu, Ala, or Gly; wherein $X_{13}$ is Lys, or Arg; wherein $X_{14}$ is Tyr, or Phe; and wherein $X_{16}$ is Ser, Thr, Asn, Gln, or is absent.

In an especially preferred embodiment, the peptides will comprise a core sequence of amino acids $CX_2X_3NNSX_7X_8X_9X_{10}CKX_{13}X_{14}RX_{16}$ (SEQ ID NO:293), wherein $X_2$ is Tyr, or Phe; wherein $X_3$ is Phe, or Tyr; wherein $X_7$ is Ser, or Thr; wherein $X_8$ is Asn, Gln, Ser, or Thr; wherein $X_9$ is Val, Ile, Leu, or Ala; wherein $X_{10}$ is Ile, Leu, Ala, or Gly; wherein $X_{13}$ is Lys, or Arg; wherein $X_{14}$ is Tyr, or Phe; and wherein $X_{16}$ is Ser, Thr, Asn, Gln, or is absent.

In an especially preferred embodiment, the peptides will comprise a core sequence of amino acids $CYX_3DDSX_7X_8X_9X_{10}CKX_{13}YRX_{16}$ (SEQ ID NO:294), wherein $X_3$ is Phe, or Tyr; wherein $X_7$ is Ser, or Thr; wherein $X_8$ is Asn, Gln, Ser, or Thr; wherein $X_9$ is Val, Ile, Leu, or Ala; wherein $X_{10}$ is Ile, Leu, Ala, or Gly; wherein $X_{13}$ is Lys, or Arg; and wherein $X_{16}$ is Ser, Thr, Asn, Gln, or is absent.

In an especially preferred embodiment, the peptides will comprise a core sequence of amino acids $CYX_3NDSX_7X_8X_9X_{10}CKX_{13}YRX_{16}$ (SEQ ID NO:295), wherein $X_3$ is Phe, or Tyr; wherein $X_7$ is Ser, or Thr; wherein $X_8$ is Asn, Gln, Ser, or Thr; wherein $X_9$ is Val, Ile, Leu, or Ala; wherein $X_{10}$ is Ile, Leu, Ala, or Gly; wherein $X_{13}$ is Lys, or Arg; and wherein $X_{16}$ is Ser, Thr, Asn, Gln, or is absent.

In an especially preferred embodiment, the peptides will comprise a core sequence of amino acids $CYX_3DNSX_7X_8X_9X_{10}CKX_{13}YRX_{16}$ (SEQ ID NO:296), wherein $X_3$ is Phe, or Tyr; wherein $X_7$ is Ser, or Thr; wherein $X_8$ is Asn, Gln, Ser, or Thr; wherein $X_9$ is Val, Ile, Leu, or Ala; wherein $X_{10}$ is Ile, Leu, Ala, or Gly; wherein $X_{13}$ is Lys, or Arg; and wherein $X_{16}$ is Ser, Thr, Asn, Gln, or is absent.

In an especially preferred embodiment, the peptides will comprise a core sequence of amino acids $CYX_3NNSX_7X_8X_9X_{10}CKX_{13}YRX_{16}$ (SEQ ID NO:297), wherein $X_3$ is Phe, or Tyr; wherein $X_7$ is Ser, or Thr; wherein $X_8$ is Asn, Gln, Ser, or Thr; wherein $X_9$ is Val, Ile, Leu, or Ala; wherein $X_{10}$ is Ile, Leu, Ala, or Gly; wherein $X_{13}$ is Lys, or Arg; and wherein $X_{16}$ is Ser, Thr, Asn, Gln, or is absent.

In an especially preferred embodiment, the peptides will comprise a core sequence of amino acids $CX_2X_3DDSSX_8X_9X_{10}CKX_{13}X_{14}RX_{16}$ (SEQ ID NO:298), wherein $X_2$ is Tyr, or Phe; wherein $X_3$ is Phe, or Tyr; wherein $X_8$ is Asn, Gln, Ser, or Thr; wherein $X_9$ is Val, Ile, Leu, or Ala; wherein $X_{10}$ is Ile, Leu, Ala, or Gly; wherein $X_{13}$ is Lys, or Arg; wherein $X_{14}$ is Tyr, or Phe; and wherein $X_{16}$ is Ser, Thr, Asn, Gln, or is absent.

In an especially preferred embodiment, the peptides will comprise a core sequence of amino acids $CX_2X_3NDSSX_8X_9X_{10}CKX_{13}X_{14}RX_{16}$ (SEQ ID NO:299), wherein $X_2$ is Tyr, or Phe; wherein $X_3$ is Phe, or Tyr; wherein $X_8$ is Asn, Gln, Ser, or Thr; wherein $X_9$ is Val, Ile, Leu, or Ala; wherein $X_{10}$ is Ile, Leu, Ala, or Gly; wherein $X_{13}$ is Lys, or Arg; wherein $X_{14}$ is Tyr, or Phe; and wherein $X_{16}$ is Ser, Thr, Asn, Gln, or is absent.

In an especially preferred embodiment, the peptides will comprise a core sequence of amino acids $CX_2X_3DNSSX_8X_9X_{10}CKX_{13}X_{14}RX_{16}$ (SEQ ID NO:300), wherein $X_2$ is Tyr, or Phe; wherein $X_3$ is Phe, or Tyr; wherein $X_8$ is Asn, Gln, Ser, or Thr; wherein $X_9$ is Val, Ile, Leu, or Ala; wherein $X_{10}$ is Ile, Leu, Ala, or Gly; wherein $X_{13}$ is Lys, or Arg; wherein $X_{14}$ is Tyr, or Phe; and wherein $X_{16}$ is Ser, Thr, Asn, Gln, or is absent.

In an especially preferred embodiment, the peptides will comprise a core sequence of amino acids $CX_2X_3NNSSX_8X_9X_{10}CKX_{13}X_{14}RX_{16}$ (SEQ ID NO:301), wherein $X_2$ is Tyr, or Phe; wherein $X_3$ is Phe, or Tyr; wherein $X_8$ is Asn, Gln, Ser, or Thr; wherein $X_9$ is Val, Ile, Leu, or Ala; wherein $X_{10}$ is Ile, Leu, Ala, or Gly; wherein $X_{13}$ is Lys, or Arg; wherein $X_{14}$ is Tyr, or Phe; and wherein $X_{16}$ is Ser, Thr, Asn, Gln, or is absent.

In an especially preferred embodiment, the peptides will comprise a core sequence of amino acids $CYX_3DDSSX_8X_9X_{10}CKX_{13}YRX_{16}$ (SEQ ID NO:302), wherein $X_3$ is Phe, or Tyr; wherein $X_8$ is Asn, Gln, Ser, or Thr; wherein $X_9$ is Val, Ile, Leu, or Ala; wherein $X_{10}$ is Ile, Leu, Ala, or Gly; wherein $X_{13}$ is Lys, or Arg; and wherein $X_{16}$ is Ser, Thr, Asn, Gln, or is absent.

In an especially preferred embodiment, the peptides will comprise a core sequence of amino acids $CYX_3NDSSX_8X_9X_{10}CKX_{13}YRX_{16}$ (SEQ ID NO:303), wherein $X_3$ is Phe, or Tyr; wherein $X_8$ is Asn, Gln, Ser, or Thr; wherein $X_9$ is Val, Ile, Leu, or Ala; wherein $X_{10}$ is Ile, Leu, Ala, or Gly; wherein $X_{13}$ is Lys, or Arg; and wherein $X_{16}$ is Ser, Thr, Asn, Gln, or is absent.

In an especially preferred embodiment, the peptides will comprise a core sequence of amino acids $CYX_3DNSSX_8X_9X_{10}CKX_{13}YRX_{16}$ (SEQ ID NO:304), wherein $X_3$ is Phe, or Tyr; wherein $X_8$ is Asn, Gln, Ser, or Thr; wherein $X_9$ is Val, Ile, Leu, or Ala; wherein $X_{10}$ is Ile, Leu, Ala, or Gly; wherein $X_{13}$ is Lys, or Arg; and wherein $X_{16}$ is Ser, Thr, Asn, Gln, or is absent.

In an especially preferred embodiment, the peptides will comprise a core sequence of amino acids $CYX_3NNSSX_8X_9X_{10}CKX_{13}YRX_{16}$ (SEQ ID NO:305), wherein $X_3$ is Phe, or Tyr; wherein $X_8$ is Asn, Gln, Ser, or Thr; wherein $X_9$ is Val, Ile, Leu, or Ala; wherein $X_{10}$ is Ile, Leu, Ala, or Gly; wherein $X_{13}$ is Lys, or Arg; and wherein $X_{16}$ is Ser, Thr, Asn, Gln, or is absent.

Particularly preferred peptides include but are not limited to, the following:

```
CYFDDSSNVICKRYRS        (SEQ ID NO: 24)

CYFDDSSNVLCKKYRS-NH2    (SEQ ID NO: 33)

CYFDDSSQVICKKYRS        (SEQ ID NO: 43)

CYFDDSSNVLCKKYRS        (SEQ ID NO: 45)

CYFDDSSSVLCKKYRS        (SEQ ID NO: 209)

CYFDDSSNVLCKKYRN        (SEQ ID NO: 213)

CYYDDSSNVLCKKYRS        (SEQ ID NO: 217)

CYFNDSSQVLCKRYRS        (SEQ ID NO: 221)

CYYDDSSNVLCKRYRS-NH2    (SEQ ID NO: 222)

CYFDDSSNVLCKKYR         (SEQ ID NO: 223)
```

Multidomain TDFRP Compounds

The present invention provides compounds that are functional analogs of tissue differentiation factors, i.e., compounds that functionally mimic TGF-beta superfamily proteins, for example by acting as TGF-beta superfamily receptor agonists. Such compounds are suitable for administration to a subject or to isolated tissues where it is desirable, for example, to promote the growth or differentiation of cells and tissues in the subject or tissue, such as kidney cells, stem cells, mesenchymal cells, extracellular matrix synthesis, integrin expression, bone and cartilage formation, induction of ventral mesoderm, differentiation of neural tissue, to promote organogenesis, to promote erythropoiesis, to induce growth of dorsal mesoderm and nerve cells, to promote tissue homeostasis and to induce or modulate immune responses. In contrast, pathological conditions such as fibrosis, rheumatoid arthritis, and carcinogenesis among others, are thought to be the result of excessive tissue differentiation factor-like activity. Accordingly, it is further an object of the invention to provide for compounds that are functional antagonists of TGF-beta superfamily receptors. It is also an object of the invention to provide for compounds that are partial antagonists and partial agonists of TGF-beta superfamily receptors. The compounds of the present invention can be used to treat both acute and chronic renal disease, as well as stroke and traumatic brain injury among other conditions.

The invention further relates to structure-based methods useful in identifying, designing and producing compounds, which act as functional modulators of TGF-beta superfamily receptors and/or their signaling pathways.

The compounds of the present invention contain multiple TDF-related polypeptides (i.e., multiple domain TDF-related polypeptide compounds, hereinafter "TDFRP") with the general structure shown below:

TDFRP1-linker-TDFRP2

Where a first TDFRP domain (TDFRP1, i.e., TDF-related polypeptide 1) is covalently linked via the C-terminus, N-terminus, or any position with a functionalizable side group, e.g., lysine or aspartic acid to a linker molecule, which, in turn, is covalently linked to the N-terminus of a second TDFRP domain (TDFRP2).

The TDRFP domains are compounds that include small molecules, more particularly polypeptides identified herein, i.e., TDF-related polypeptides (TDFRP), summarized in Tables 4-9. Variants, analogs, homologs, or fragments of these compounds, such as species homologs, are also included in the present invention, as well as degenerate forms thereof.

A first domain is linked to a second domain through a linker. The term "linker," as used herein, refers to an element capable of providing appropriate spacing or structural rigidity, or structural orientation, alone, or in combination, to a first and a second domain, e.g., TDFRP1 and TDFRP2, such that the biological activity of the TDFRP is preserved. For example, linkers may include, but are not limited to, a diamino alkane, a dicarboxylic acid, an amino carboxylic acid alkane, an amino acid sequence, e.g., glycine polypeptide, a disulfide linkage, a helical or sheet-like structural element or an alkyl chain. In one aspect, the linker is not inert, e.g., chemically or enzymatically cleavable in vivo or in vitro. In another aspect, the linker is inert, i.e., substantially unreactive in vivo or in vitro, e.g., is not chemically or enzymatically degraded. Examples of inert groups which can serve as linking groups include aliphatic chains such as alkyl, alkenyl and alkynyl groups (e.g., C1-C20), cycloalkyl rings (e.g., C3-C10), aryl groups (carbocyclic aryl groups such as 1-naphthyl, 2-naphthyl, 1-anthracyl and 2-anthracyl and heteroaryl group such as N-imidazolyl, 2-imidazole, 2-thienyl, 3-thienyl, 2-furanyl, 3-furanyl, 2-pyridyl, 3-pyridyl, 4-pyridyl, 2-pyrimidy, 4-pyrimidyl, 2-pyranyl, 3-pyranyl, 3-pyrazolyl, 4-pyrazolyl, 5-pyrazolyl, 2-pyrazinyl, 2-thiazole, 4-thiazole, 5-thiazole, 2-oxazolyl, 4-oxazolyl, 5-oxazolyl, 2-benzothienyl, 3-benzothienyl, 2-benzofuranyl, 3-benzofuranyl, 2-indolyl, 3-indolyl, 2-quinolinyl, 3-quinolinyl, 2-benzothiazole, 2-benzooxazole, 2-benzimidazole, 2-quinolinyl, 3-quinolinyl, 1-isoquinolinyl, 3-quinolinyl, 1-isoindolyl, and 3-isoindolyl), non-aromatic heterocyclic groups (e.g., 2-tetrahydrofuranyl, 3-tetrahydrofuranyl, 2-tetrahyrothiophenyl, 3-tetrahyrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl and 4-thiazolidinyl) and aliphatic groups in which one, two or three methylenes have been replaced with —O—, —S—, —NH—, —$SO_2$—, —SO— or —$SO_2$NH—.

The present compounds include small molecules, more particularly TDFRP compound domains, with the general structure identified herein, as detailed below. The TDFRP compound domains disclosed herein may be present in a TDFRP compound in any combination or orientation. Variants, analogs, homologs, or fragments of these TDFRP compound domains, such as species homologs, are also included in the present invention, as well as degenerate forms thereof. The TDFRP compound domains of the present invention may capped on the N-terminus, or the C-terminus, or on both the N-terminus and the C-terminus. The TDFRP compounds of the present invention may be pegylated, or modified, e.g., branching, at any amino acid residue containing a reactive side chain, e.g., lysine residue, or chemically reactive group on the linker. The TDFRP compound of the present invention may be linear or cyclized. The tail sequence of the TDFRP or TDFRP domains may vary in length. In one aspect of the present invention, the TDFRP compounds of the invention are prodrugs, i.e., the biological activity of the TDFRP compound, is altered, e.g., increased, upon contacting a biological system in vivo or in vitro.

The TDFRP compounds can contain natural amino acids, non-natural amino acids, d-amino acids and l-amino acids, and any combinations thereof. In certain embodiments, the compounds of the invention can include commonly encountered amino acids, which are not genetically encoded. These non-genetically encoded amino acids include, but are not limited to, β-alanine (β-Ala) and other omega-amino acids such as 3-aminopropionic acid (Dap), 2,3-diaminopropionic acid (Dpr), 4-aminobutyric acid and so forth; α-aminoisobutyric acid (Aib); ε-aminohexanoic acid (Aha); δ-aminovaleric acid (Ava); N-methylglycine or sarcosine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (hArg); N-acetyl lysine (AcLys); 2,3-diaminobutyric acid (Dab); 2,3-diaminobutyric acid (Dbu); p-aminophenylalanine (Phe(p$NH_2$)); N-methyl valine (MeVal); homocysteine (hCys) and homoserine (hSer). Non-naturally occurring variants of the compounds may be produced by mutagenesis techniques or by direct synthesis.

In one embodiment, TDFRP compound domain is a polypeptide with the general structure shown in SEQ ID NO:1.

$X_1X_2X_3X_4X_5X_6X_7X_8X_9X_{10}X_{11}X_{12}X_{13}X_{14}X_{15}X_{16}X_{17}X_{18}X_{19}X_{20}$ (SEQ ID NO:1), wherein $X_1$-$X_{20}$ vary independently of each other, and wherein X can be any naturally occurring or non-naturally occurring amino acid and wherein up to 17 amino acids may be absent. In an aspect of this embodiment, the amino acids that are absent may be contiguous or discontiguous. In another embodiment, TDFRP compound domain is a polypeptide with the general structure shown in SEQ ID NO:1, wherein $X_1$-$X_{20}$ vary independently of each other, and wherein X can be any naturally occurring amino acid or non-naturally occurring amino acid; and wherein the polypeptide includes at least two Cys residues, and wherein up to 17 amino acids may be absent. In an aspect of this embodiment, the amino acids that are absent may be contiguous or discontiguous.

In another embodiment, TDFRP compound domain is a polypeptide with the general structure shown in SEQ ID NO:2.

$CX_2X_3X_4X_5X_6X_7X_8X_9X_{10}CX_{12}X_{13}X_{14}X_{15}X_{16}$ (SEQ ID NO:2), wherein $X_2$-$X_{10}$ along with $X_{12}$-$X_{16}$ vary independently of each other, and wherein $X_2$ is Tyr, Ile, any aromatic amino acid, any aliphatic amino acid or any polar amino acid; wherein $X_3$ is Phe, Val, any aromatic amino acid, or any aliphatic amino acid; wherein $X_4$ is Asp or any acidic amino acid; wherein $X_5$ is Asp, Glu or any acidic amino acid; wherein $X_6$ is Ser, Asn or any polar amino acid; wherein $X_7$ is Ser or any polar amino acid; wherein $X_8$ is Asn, Gln or any polar amino acid; wherein $X_9$ is Val or any aliphatic amino acid; wherein $X_{10}$ is Ile, Val, Leu or any aliphatic amino acid; wherein $X_{12}$ is Lys or any basic amino acid; wherein $X_{13}$ is Lys or any basic amino acid; wherein $X_{14}$ is Tyr or any polar amino acid; wherein $X_{15}$ is Arg or any basic amino acid; and wherein $X_{16}$ is Ser or any polar amino acid.

The present compounds include small molecules, more particularly peptides, summarized in part in Table 4. Variants, analogs, homologs, or fragments of these compounds, such as species homologs, are also included in the present invention, as well as degenerate forms thereof.

The compounds can contain single, double, triple or other multiple amino acid substitutions at any amino acid within the sequences disclosed. Substitutions can contain natural amino acids, non-natural amino acids, d-amino acids and l-amino acids, and any combinations thereof. The compounds can be fragments, for example from about at least 3 amino acids in length. Additional representative compounds include ECRDLGWQDQC (SEQ ID NO: 306), ACFDDSSNVICKKYRS (SEQ ID NO: 307), and SRYKKCYFDDSSNVIC (SEQ ID NO: 308).

Representative TDFRP compound domains with single, double, or triple amino acid substitutions include, but are not limited to, the following amino acid sequences summarized in Table 5. These are not exhaustively illustrated, but can be similarly modified as described.

Representative fragments are summarized in Table 6. Notably, the sequence fragments provided in Table 6 include fragments all having 11 amino acids, but smaller or larger fragments, for example from about 3 or more amino acids are included in the scope of the invention.

TDFRP domains also include small molecules, more particularly peptides, are summarized in Table 7. Variants, analogs, homologs, or fragments of these compounds, such as species homologs, are also included in the present invention, as well as degenerate forms thereof.

TDFRP domains also include small molecules, more particularly peptides, identified in part in Table 8. Variants, analogs, homologs, or fragments of these compounds, such as species homologs, are also included in the present invention, as well as degenerate forms thereof.

The present compounds also include small molecules, more particularly peptides, identified in part in Table 9. Variants, analogs, homologs, or fragments of these compounds, such as species homologs, are also included in the present invention, as well as degenerate forms thereof.

Representative TDFRP compounds, provided by the present invention are summarized in Table 10.

TABLE 10

| Sequence | SEQ ID NOS |
|---|---|
| ECRDLGWQDQC-linker-CFDDSSNVICKKYRS | 309 and 557 |
| ECRDLGWQDQC-linker-ACFDDSSNVICKKYRS | 310 and 558 |
| CYFDDSSNVIC-linker-CYFDDSSNVICKKYRS | 311 and 559 |
| SRYKKCYFDDSSNVIC-linker-CYFDDSSNVIC | 312 and 560 |
| CFRDLGWQDWIIAPC-linker-CFRDLGWQDWIIAPC | 313 and 561 |
| ECRDLGWQDWC-linker-CFRDLGWQDWIIAPC | 314 and 562 |

In one preferred embodiment, the peptides will comprise a core sequence of amino acids $CX_2X_3X_4X_5X_6X_7X_8X_9X_{10}CX_{12}X_{13}X_{14}X_{15}X_{16}$ (SEQ ID NO:255), wherein $X_2$ is Tyr, Phe, Met, Ser, any alicyclic amino acid, or any aromatic amino acid; wherein $X_3$ is Tyr, Phe, Met, Ser, any alicyclic amino acid, or any aromatic amino acid; wherein $X_4$ is Asp, Asn, Glu, Gln, Ser, or any beta-carbonyl amino acid; wherein $X_5$ is Asp, Asn, Glu, Gln, Ser, or any beta-carbonyl amino acid; wherein $X_6$ is Ser, Thr, Cys, Met, His, or any beta-heteroatom amino acid; wherein $X_7$ is Ser, Thr, Cys, Met, His, or any beta-heteroatom amino acid; wherein $X_8$ is Asp, Asn, Glu, Gln, Ser, Thr, Met, His, or any polar amino acid; wherein $X_9$ is Val, Ile, Thr, Leu, Ala, Gly, Met, Phe, or any nonpolar amino acid; wherein $X_{10}$ is Ile, Leu, Ala, Gly, Val, Met, Ser, Phe, or any nonpolar amino acid; wherein $X_{12}$ is Lys, Arg, His, Trp, or any basic amino acid; wherein $X_{13}$ is Lys, Arg, His, Trp, or any basic amino acid; wherein $X_{14}$ is Tyr, Phe, His, Trp, or any aromatic amino acid; wherein $X_{15}$ is Arg, Lys, His, Trp, or any basic amino acid; and wherein $X_{16}$ is Ser, Thr, Asp, Asn, Glu, Gln, any polar amino acid, or is absent.

In one preferred embodiment, the peptides will comprise a core sequence of amino acids $CX_2X_3DDSX_7X_8X_9X_{10}CKX_{13}X_{14}RX_{16}$ (SEQ ID NO:256), wherein $X_2$ is Tyr, Phe, Met, Ser, any alicyclic amino acid, or any aromatic amino acid; wherein $X_3$ is Tyr, Phe, Met, Ser, any alicyclic amino acid, or any aromatic amino acid; wherein $X_7$ is Ser, Thr, Cys, Met, His, or any beta-heteroatom amino acid; wherein $X_8$ is Asp, Asn, Glu, Gln, Ser, Thr, Met, His, or any polar amino acid; wherein $X_9$ is Val, Ile, Thr, Leu, Ala, Gly, Met, Phe, or any nonpolar amino acid; wherein $X_{10}$ is Ile, Leu, Ala, Gly, Val, Met, Ser, Phe, or any nonpolar amino acid; wherein $X_{13}$ is Lys, Arg, His, Trp, or any basic amino acid; wherein $X_{14}$ is Tyr, Phe, His, Trp, or any aromatic amino acid; and wherein $X_{16}$ is Ser, Thr, Asp, Asn, Glu, Gln, any polar amino acid, or is absent.

In one preferred embodiment, the peptides will comprise a core sequence of amino acids $CX_2X_3NDSX_7X_8X_9X_{10}CKX_{13}X_{14}RX_{16}$ (SEQ ID NO:257), wherein $X_2$ is Tyr, Phe, Met, Ser, any alicyclic amino acid, or any aromatic amino acid; wherein $X_3$ is Tyr, Phe, Met, Ser, any alicyclic amino acid, or any aromatic amino acid; wherein $X_7$ is Ser, Thr, Cys, Met, His, or any beta-heteroatom amino acid; wherein $X_8$ is Asp, Asn, Glu, Gln, Ser, Thr, Met, His, or any polar amino acid; wherein $X_9$ is Val, Ile, Thr, Leu, Ala, Gly, Met, Phe, or any nonpolar amino acid; wherein $X_{10}$ is Ile, Leu, Ala, Gly, Val, Met, Ser, Phe, or any nonpolar amino acid; wherein $X_{13}$ is Lys, Arg, His, Trp, or any basic amino acid; wherein $X_{14}$ is Tyr, Phe, His, Trp, or any aromatic amino acid; and wherein $X_{16}$ is Ser, Thr, Asp, Asn, Glu, Gln, any polar amino acid, or is absent.

In one preferred embodiment, the peptides will comprise a core sequence of amino acids CX$_2$X$_3$DNSX$_7$X$_8$X$_9$X$_{10}$CKX$_{13}$X$_{14}$RX$_{16}$ (SEQ ID NO:258), wherein X$_2$ is Tyr, Phe, Met, Ser, any alicyclic amino acid, or any aromatic amino acid; wherein X$_3$ is Tyr, Phe, Met, Ser, any alicyclic amino acid, or any aromatic amino acid; wherein X$_7$ is Ser, Thr, Cys, Met, His, or any beta-heteroatom amino acid; wherein X$_8$ is Asp, Asn, Glu, Gln, Ser, Thr, Met, His, or any polar amino acid; wherein X$_9$ is Val, Ile, Thr, Leu, Ala, Gly, Met, Phe, or any nonpolar amino acid; wherein X$_{10}$ is Ile, Leu, Ala, Gly, Val, Met, Ser, Phe, or any nonpolar amino acid; wherein X$_{13}$ is Lys, Arg, His, Trp, or any basic amino acid; wherein X$_{14}$ is Tyr, Phe, His, Trp, or any aromatic amino acid; and wherein X$_{16}$ is Ser, Thr, Asp, Asn, Glu, Gln, any polar amino acid, or is absent.

In one preferred embodiment, the peptides will comprise a core sequence of amino acids CX$_2$X$_3$NNSX$_7$X$_8$X$_9$X$_{10}$CKX$_{13}$X$_{14}$RX$_{16}$ (SEQ ID NO:259), wherein X$_2$ is Tyr, Phe, Met, Ser, any alicyclic amino acid, or any aromatic amino acid; wherein X$_3$ is Tyr, Phe, Met, Ser, any alicyclic amino acid, or any aromatic amino acid; wherein X$_7$ is Ser, Thr, Cys, Met, His, or any beta-heteroatom amino acid; wherein X$_8$ is Asp, Asn, Glu, Gln, Ser, Thr, Met, His, or any polar amino acid; wherein X$_9$ is Val, Ile, Thr, Leu, Ala, Gly, Met, Phe, or any nonpolar amino acid; wherein X$_{10}$ is Ile, Leu, Ala, Gly, Val, Met, Ser, Phe, or any nonpolar amino acid; wherein X$_{13}$ is Lys, Arg, His, Trp, or any basic amino acid; wherein X$_{14}$ is Tyr, Phe, His, Trp, or any aromatic amino acid; and wherein X$_{16}$ is Ser, Thr, Asp, Asn, Glu, Gln, any polar amino acid, or is absent.

In one preferred embodiment, the peptides will comprise a core sequence of amino acids CYX$_3$DDSX$_7$X$_8$X$_9$X$_{10}$CKX$_{13}$YRX$_{16}$ (SEQ ID NO:260), wherein X$_3$ is Tyr, Phe, Met, Ser, any alicyclic amino acid, or any aromatic amino acid; wherein X$_7$ is Ser, Thr, Cys, Met, His, or any beta-heteroatom amino acid; wherein X$_8$ is Asp, Asn, Glu, Gln, Ser, Thr, Met, His, or any polar amino acid; wherein X$_9$ is Val, Ile, Thr, Leu, Ala, Gly, Met, Phe, or any nonpolar amino acid; wherein X$_{10}$ is Ile, Leu, Ala, Gly, Val, Met, Ser, Phe, or any nonpolar amino acid; wherein X$_{13}$ is Lys, Arg, His, Trp, or any basic amino acid; and wherein X$_{16}$ is Ser, Thr, Asp, Asn, Glu, Gln, any polar amino acid, or is absent.

In one preferred embodiment, the peptides will comprise a core sequence of amino acids CYX$_3$NDSX$_7$X$_8$X$_9$X$_{10}$CKX$_{13}$YRX$_{16}$ (SEQ ID NO:261), wherein X$_3$ is Tyr, Phe, Met, Ser, any alicyclic amino acid, or any aromatic amino acid; wherein X$_7$ is Ser, Thr, Cys, Met, His, or any beta-heteroatom amino acid; wherein X$_8$ is Asp, Asn, Glu, Gln, Ser, Thr, Met, His, or any polar amino acid; wherein X$_9$ is Val, Ile, Thr, Leu, Ala, Gly, Met, Phe, or any nonpolar amino acid; wherein X$_{10}$ is Ile, Leu, Ala, Gly, Val, Met, Ser, Phe, or any nonpolar amino acid; wherein X$_{13}$ is Lys, Arg, His, Trp, or any basic amino acid; and wherein X$_{16}$ is Ser, Thr, Asp, Asn, Glu, Gln, any polar amino acid, or is absent.

In one preferred embodiment, the peptides will comprise a core sequence of amino acids CYX$_3$DNSX$_7$X$_8$X$_9$X$_{10}$CKX$_{13}$YRX$_{16}$ (SEQ ID NO:262), wherein X$_3$ is Tyr, Phe, Met, Ser, any alicyclic amino acid, or any aromatic amino acid; wherein X$_7$ is Ser, Thr, Cys, Met, His, or any beta-heteroatom amino acid; wherein X$_8$ is Asp, Asn, Glu, Gln, Ser, Thr, Met, His, or any polar amino acid; wherein X$_9$ is Val, Ile, Thr, Leu, Ala, Gly, Met, Phe, or any nonpolar amino acid; wherein X$_{10}$ is Ile, Leu, Ala, Gly, Val, Met, Ser, Phe, or any nonpolar amino acid; wherein X$_{13}$ is Lys, Arg, His, Trp, or any basic amino acid; and wherein X$_{16}$ is Ser, Thr, Asp, Asn, Glu, Gln, any polar amino acid, or is absent.

In one preferred embodiment, the peptides will comprise a core sequence of amino acids CYX$_3$NNSX$_7$X$_8$X$_9$X$_{10}$CKX$_{13}$YRX$_{16}$ (SEQ ID NO:263), wherein X$_3$ is Tyr, Phe, Met, Ser, any alicyclic amino acid, or any aromatic amino acid; wherein X$_7$ is Ser, Thr, Cys, Met, His, or any beta-heteroatom amino acid; wherein X$_8$ is Asp, Asn, Glu, Gln, Ser, Thr, Met, His, or any polar amino acid; wherein X$_9$ is Val, Ile, Thr, Leu, Ala, Gly, Met, Phe, or any nonpolar amino acid; wherein X$_{10}$ is Ile, Leu, Ala, Gly, Val, Met, Ser, Phe, or any nonpolar amino acid; wherein X$_{13}$ is Lys, Arg, His, Trp, or any basic amino acid; and wherein X$_{16}$ is Ser, Thr, Asp, Asn, Glu, Gln, any polar amino acid, or is absent.

In one preferred embodiment, the peptides will comprise a core sequence of amino acids CX$_2$X$_3$DDSSX$_8$X$_9$X$_{10}$CKX$_{13}$X$_{14}$RX$_{16}$ (SEQ ID NO:264), wherein X$_2$ is Tyr, Phe, Met, Ser, any alicyclic amino acid, or any aromatic amino acid; wherein X$_3$ is Tyr, Phe, Met, Ser, any alicyclic amino acid, or any aromatic amino acid; wherein X$_8$ is Asp, Asn, Glu, Gln, Ser, Thr, Met, His, or any polar amino acid; wherein X$_9$ is Val, Ile, Thr, Leu, Ala, Gly, Met, Phe, or any nonpolar amino acid; wherein X$_{10}$ is Ile, Leu, Ala, Gly, Val, Met, Ser, Phe, or any nonpolar amino acid; wherein X$_{13}$ is Lys, Arg, His, Trp, or any basic amino acid; wherein X$_{14}$ is Tyr, Phe, His, Trp, or any aromatic amino acid; and wherein X$_{16}$ is Ser, Thr, Asp, Asn, Glu, Gln, any polar amino acid, or is absent.

In one preferred embodiment, the peptides will comprise a core sequence of amino acids CX$_2$X$_3$NDSSX$_8$X$_9$X$_{10}$CKX$_{13}$X$_{14}$RX$_{16}$ (SEQ ID NO:265), wherein X$_2$ is Tyr, Phe, Met, Ser, any alicyclic amino acid, or any aromatic amino acid; wherein X$_3$ is Tyr, Phe, Met, Ser, any alicyclic amino acid, or any aromatic amino acid; wherein X$_8$ is Asp, Asn, Glu, Gln, Ser, Thr, Met, His, or any polar amino acid; wherein X$_9$ is Val, Ile, Thr, Leu, Ala, Gly, Met, Phe, or any nonpolar amino acid; wherein X$_{10}$ is Ile, Leu, Ala, Gly, Val, Met, Ser, Phe, or any nonpolar amino acid; wherein X$_{13}$ is Lys, Arg, His, Trp, or any basic amino acid; wherein X$_{14}$ is Tyr, Phe, His, Trp, or any aromatic amino acid; and wherein X$_{16}$ is Ser, Thr, Asp, Asn, Glu, Gln, any polar amino acid, or is absent.

In one preferred embodiment, the peptides will comprise a core sequence of amino acids CX$_2$X$_3$DNSSX$_8$X$_9$X$_{10}$CKX$_{13}$X$_{14}$RX$_{16}$ (SEQ ID NO:266), wherein X$_2$ is Tyr, Phe, Met, Ser, any alicyclic amino acid, or any aromatic amino acid; wherein X$_3$ is Tyr, Phe, Met, Ser, any alicyclic amino acid, or any aromatic amino acid; wherein X$_8$ is Asp, Asn, Glu, Gln, Ser, Thr, Met, His, or any polar amino acid; wherein X$_9$ is Val, Ile, Thr, Leu, Ala, Gly, Met, Phe, or any nonpolar amino acid; wherein X$_{10}$ is Ile, Leu, Ala, Gly, Val, Met, Ser, Phe, or any nonpolar amino acid; wherein X$_{13}$ is Lys, Arg, His, Trp, or any basic amino acid; wherein X$_{14}$ is Tyr, Phe, His, Trp, or any aromatic amino acid; and wherein X$_{16}$ is Ser, Thr, Asp, Asn, Glu, Gln, any polar amino acid, or is absent.

In one preferred embodiment, the peptides will comprise a core sequence of amino acids CX$_2$X$_3$NNSSX$_8$X$_9$X$_{10}$CKX$_{13}$X$_{14}$RX$_{16}$ (SEQ ID NO:267), wherein X$_2$ is Tyr, Phe, Met, Ser, any alicyclic amino acid, or any aromatic amino acid; wherein X$_3$ is Tyr, Phe, Met, Ser, any alicyclic amino acid, or any aromatic amino acid; wherein X$_8$ is Asp, Asn, Glu, Gln, Ser, Thr, Met, His, or any polar amino acid; wherein X$_9$ is Val, Ile, Thr, Leu, Ala, Gly, Met, Phe, or any nonpolar amino acid; wherein X$_{10}$ is Ile, Leu, Ala, Gly, Val, Met, Ser, Phe, or any nonpolar amino acid; wherein X$_{13}$ is Lys, Arg, His, Trp, or any basic amino acid; wherein $X_{14}$ is Tyr, Phe, His, Trp, or any aromatic amino acid; and wherein $X_{16}$ is Ser, Thr, Asp, Asn, Glu, Gln, any polar amino acid, or is absent.

In one preferred embodiment, the peptides will comprise a core sequence of amino acids $CYX_3DDSSX_8X_9X_{10}CKX_{13}YRX_{16}$ (SEQ ID NO:268), wherein $X_3$ is Tyr, Phe, Met, Ser, any alicyclic amino acid, or any aromatic amino acid; wherein $X_8$ is Asp, Asn, Glu, Gln, Ser, Thr, Met, His, or any polar amino acid; wherein $X_9$ is Val, Ile, Thr, Leu, Ala, Gly, Met, Phe, or any nonpolar amino acid; wherein $X_{10}$ is Ile, Leu, Ala, Gly, Val, Met, Ser, Phe, or any nonpolar amino acid; wherein $X_{13}$ is Lys, Arg, His, Trp, or any basic amino acid; and wherein $X_{16}$ is Ser, Thr, Asp, Asn, Glu, Gln, any polar amino acid, or is absent.

In one preferred embodiment, the peptides will comprise a core sequence of amino acids $CYX_3NDSSX_8X_9X_{10}CKX_{13}YRX_{16}$ (SEQ ID NO:269), wherein $X_3$ is Tyr, Phe, Met, Ser, any alicyclic amino acid, or any aromatic amino acid; wherein $X_8$ is Asp, Asn, Glu, Gln, Ser, Thr, Met, His, or any polar amino acid; wherein $X_9$ is Val, Ile, Thr, Leu, Ala, Gly, Met, Phe, or any nonpolar amino acid; wherein $X_{10}$ is Ile, Leu, Ala, Gly, Val, Met, Ser, Phe, or any nonpolar amino acid; wherein $X_{13}$ is Lys, Arg, His, Trp, or any basic amino acid; and wherein $X_{16}$ is Ser, Thr, Asp, Asn, Glu, Gln, any polar amino acid, or is absent.

In one preferred embodiment, the peptides will comprise a core sequence of amino acids $CYX_3DNSSX_8X_9X_{10}CKX_{13}YRX_{16}$ (SEQ ID NO:270), wherein $X_3$ is Tyr, Phe, Met, Ser, any alicyclic amino acid, or any aromatic amino acid; wherein $X_8$ is Asp, Asn, Glu, Gln, Ser, Thr, Met, His, or any polar amino acid; wherein $X_9$ is Val, Ile, Thr, Leu, Ala, Gly, Met, Phe, or any nonpolar amino acid; wherein $X_{10}$ is Ile, Leu, Ala, Gly, Val, Met, Ser, Phe, or any nonpolar amino acid; wherein $X_{13}$ is Lys, Arg, His, Trp, or any basic amino acid; and wherein $X_{16}$ is Ser, Thr, Asp, Asn, Glu, Gln, any polar amino acid, or is absent.

In one preferred embodiment, the peptides will comprise a core sequence of amino acids $CYX_3NNSSX_8X_9X_{10}CKX_{13}YRX_{16}$ (SEQ ID NO:271), wherein $X_3$ is Tyr, Phe, Met, Ser, any alicyclic amino acid, or any aromatic amino acid; wherein $X_8$ is Asp, Asn, Glu, Gln, Ser, Thr, Met, His, or any polar amino acid; wherein $X_9$ is Val, Ile, Thr, Leu, Ala, Gly, Met, Phe, or any nonpolar amino acid; wherein $X_{10}$ is Ile, Leu, Ala, Gly, Val, Met, Ser, Phe, or any nonpolar amino acid; wherein $X_{13}$ is Lys, Arg, His, Trp, or any basic amino acid; and wherein $X_{16}$ is Ser, Thr, Asp, Asn, Glu, Gln, any polar amino acid, or is absent.

In a more preferred embodiment, the peptides will comprise a core sequence of amino acids $CX_2X_3X_4X_5X_6X_7X_8X_9X_{10}CX_{12}X_{13}X_{14}X_{15}X_{16}$ (SEQ ID NO:272), wherein $X_2$ is Tyr, Phe, or any aromatic amino acid; wherein $X_3$ is Tyr, Phe, or any aromatic amino acid; wherein $X_4$ is Asp, Asn, or any beta-carbonyl amino acid; wherein $X_5$ is Asp, Asn, or any beta-carbonyl amino acid; wherein $X_6$ is Ser, Thr, or any beta-heteroatom amino acid; wherein $X_7$ is Ser, Thr, or any beta-heteroatom amino acid; wherein $X_8$ is Asn, Gln, Ser, Thr, or any polar amino acid; wherein $X_9$ is Val, Ile, Leu, Ala, or any nonpolar amino acid; wherein $X_{10}$ is Ile, Leu, Ala, Gly, or any nonpolar amino acid; wherein $X_{12}$ is Lys, Arg, or any basic amino acid; wherein $X_{13}$ is Lys, Arg, or any basic amino acid; wherein $X_{14}$ is Tyr, Phe, or any aromatic amino acid; wherein $X_{15}$ is Arg, Lys, or any basic amino acid; and wherein $X_{16}$ is Ser, Thr, Asn, Gln, any polar amino acid, or is absent.

In a more preferred embodiment, the peptides will comprise a core sequence of amino acids $CX_2X_3DDSX_7X_8X_9X_{10}CKX_{13}X_{14}RX_{16}$ (SEQ ID NO:273), wherein $X_2$ is Tyr, Phe, or any aromatic amino acid; wherein $X_3$ is Tyr, Phe, or any aromatic amino acid; wherein $X_7$ is Ser, Thr, or any beta-heteroatom amino acid; wherein $X_8$ is Asn, Gln, Ser, Thr, or any polar amino acid; wherein $X_9$ is Val, Ile, Leu, Ala, or any nonpolar amino acid; wherein $X_{10}$ is Ile, Leu, Ala, Gly, or any nonpolar amino acid; wherein $X_{13}$ is Lys, Arg, or any basic amino acid; wherein $X_{14}$ is Tyr, Phe, or any aromatic amino acid; and wherein $X_{16}$ is Ser, Thr, Asn, Gln, any polar amino acid, or is absent.

In a more preferred embodiment, the peptides will comprise a core sequence of amino acids $CX_2X_3NDSX_7X_8X_9X_{10}CKX_{13}X_{14}RX_{16}$ (SEQ ID NO:274), wherein $X_2$ is Tyr, Phe, or any aromatic amino acid; wherein $X_3$ is Tyr, Phe, or any aromatic amino acid; wherein $X_7$ is Ser, Thr, or any beta-heteroatom amino acid; wherein $X_8$ is Asn, Gln, Ser, Thr, or any polar amino acid; wherein $X_9$ is Val, Ile, Leu, Ala, or any nonpolar amino acid; wherein $X_{10}$ is Ile, Leu, Ala, Gly, or any nonpolar amino acid; wherein $X_{13}$ is Lys, Arg, or any basic amino acid; wherein $X_{14}$ is Tyr, Phe, or any aromatic amino acid; and wherein $X_{16}$ is Ser, Thr, Asn, Gln, any polar amino acid, or is absent.

In a more preferred embodiment, the peptides will comprise a core sequence of amino acids $CX_2X_3DNSX_7X_8X_9X_{10}CKX_{13}X_{14}RX_{16}$ (SEQ ID NO:275), wherein $X_2$ is Tyr, Phe, or any aromatic amino acid; wherein $X_3$ is Tyr, Phe, or any aromatic amino acid; wherein $X_7$ is Ser, Thr, or any beta-heteroatom amino acid; wherein $X_8$ is Asn, Gln, Ser, Thr, or any polar amino acid; wherein $X_9$ is Val, Ile, Leu, Ala, or any nonpolar amino acid; wherein $X_{10}$ is Ile, Leu, Ala, Gly, or any nonpolar amino acid; wherein $X_{13}$ is Lys, Arg, or any basic amino acid; wherein $X_{14}$ is Tyr, Phe, or any aromatic amino acid; and wherein $X_{16}$ is Ser, Thr, Asn, Gln, any polar amino acid, or is absent.

In a more preferred embodiment, the peptides will comprise a core sequence of amino acids $CX_2X_3NNSX_7X_8X_9X_{10}CKX_{13}X_{14}RX_{16}$ (SEQ ID NO:276), wherein $X_2$ is Tyr, Phe, or any aromatic amino acid; wherein $X_3$ is Tyr, Phe, or any aromatic amino acid; wherein $X_7$ is Ser, Thr, or any beta-heteroatom amino acid; wherein $X_8$ is Asn, Gln, Ser, Thr, or any polar amino acid; wherein $X_9$ is Val, Ile, Leu, Ala, or any nonpolar amino acid; wherein $X_{10}$ is Ile, Leu, Ala, Gly, or any nonpolar amino acid; wherein $X_{13}$ is Lys, Arg, or any basic amino acid; wherein $X_{14}$ is Tyr, Phe, or any aromatic amino acid; and wherein $X_{16}$ is Ser, Thr, Asn, Gln, any polar amino acid, or is absent.

In a more preferred embodiment, the peptides will comprise a core sequence of amino acids $CYX_3DDSX_7X_8X_9X_{10}CKX_{13}YRX_{16}$ (SEQ ID NO:277), wherein $X_3$ is Tyr, Phe, or any aromatic amino acid; wherein $X_7$ is Ser, Thr, or any beta-heteroatom amino acid; wherein $X_8$ is Asn, Gln, Ser, Thr, or any polar amino acid; wherein $X_9$ is Val, Ile, Leu, Ala, or any nonpolar amino acid; wherein $X_{10}$ is Ile, Leu, Ala, Gly, or any nonpolar amino acid; wherein $X_{13}$ is Lys, Arg, or any basic amino acid; and wherein $X_{16}$ is Ser, Thr, Asn, Gln, any polar amino acid, or is absent.

In a more preferred embodiment, the peptides will comprise a core sequence of amino acids $CYX_3NDSX_7X_8X_9X_{10}CKX_{13}YRX_{16}$ (SEQ ID NO:278), wherein $X_3$ is Tyr, Phe, or any aromatic amino acid; wherein $X_7$ is Ser, Thr, or any beta-heteroatom amino acid; wherein $X_8$ is Asn, Gln, Ser, Thr, or any polar amino acid; wherein $X_9$ is Val, Ile, Leu, Ala, or any nonpolar amino acid; wherein $X_{10}$ is Ile, Leu, Ala, Gly, or any nonpolar amino acid; wherein $X_{13}$ is Lys, Arg, or any basic amino acid; and wherein $X_{16}$ is Ser, Thr, Asn, Gln, any polar amino acid, or is absent.

In a more preferred embodiment, the peptides will comprise a core sequence of amino acids CYX$_3$DNSX$_7$X$_8$X$_9$X$_{10}$CKX$_{13}$YRX$_{16}$ (SEQ ID NO:279), wherein X$_3$ is Tyr, Phe, or any aromatic amino acid; wherein X$_7$ is Ser, Thr, or any beta-heteroatom amino acid; wherein X$_8$ is Asn, Gln, Ser, Thr, or any polar amino acid; wherein X$_9$ is Val, Ile, Leu, Ala, or any nonpolar amino acid; wherein X$_{10}$ is Ile, Leu, Ala, Gly, or any nonpolar amino acid; wherein X$_{13}$ is Lys, Arg, or any basic amino acid; and wherein X$_{16}$ is Ser, Thr, Asn, Gln, any polar amino acid, or is absent.

In a more preferred embodiment, the peptides will comprise a core sequence of amino acids CYX$_3$NNSX$_7$X$_8$X$_9$X$_{10}$CKX$_{13}$YRX$_{16}$ (SEQ ID NO:280), wherein X$_3$ is Tyr, Phe, or any aromatic amino acid; wherein X$_7$ is Ser, Thr, or any beta-heteroatom amino acid; wherein X$_8$ is Asn, Gln, Ser, Thr, or any polar amino acid; wherein X$_9$ is Val, Ile, Leu, Ala, or any nonpolar amino acid; wherein X$_{10}$ is Ile, Leu, Ala, Gly, or any nonpolar amino acid; wherein X$_{13}$ is Lys, Arg, or any basic amino acid; and wherein X$_{16}$ is Ser, Thr, Asn, Gln, any polar amino acid, or is absent.

In a more preferred embodiment, the peptides will comprise a core sequence of amino acids CX$_2$X$_3$DDSSX$_8$X$_9$X$_{10}$CKX$_{13}$X$_{14}$RX$_{16}$ (SEQ ID NO:281), wherein X$_2$ is Tyr, Phe, or any aromatic amino acid; wherein X$_3$ is Tyr, Phe, or any aromatic amino acid; wherein X$_8$ is Asn, Gln, Ser, Thr, or any polar amino acid; wherein X$_9$ is Val, Ile, Leu, Ala, or any nonpolar amino acid; wherein X$_{10}$ is Ile, Leu, Ala, Gly, or any nonpolar amino acid; wherein X$_{13}$ is Lys, Arg, or any basic amino acid; wherein X$_{14}$ is Tyr, Phe, or any aromatic amino acid; and wherein X$_{16}$ is Ser, Thr, Asn, Gln, any polar amino acid, or is absent.

In a more preferred embodiment, the peptides will comprise a core sequence of amino acids CX$_2$X$_3$NDSSX$_8$X$_9$X$_{10}$CKX$_{13}$X$_{14}$RX$_{16}$ (SEQ ID NO:282), wherein X$_2$ is Tyr, Phe, or any aromatic amino acid; wherein X$_3$ is Tyr, Phe, or any aromatic amino acid; wherein X$_8$ is Asn, Gln, Ser, Thr, or any polar amino acid; wherein X$_9$ is Val, Ile, Leu, Ala, or any nonpolar amino acid; wherein X$_{10}$ is Ile, Leu, Ala, Gly, or any nonpolar amino acid; wherein X$_{13}$ is Lys, Arg, or any basic amino acid; wherein X$_{14}$ is Tyr, Phe, or any aromatic amino acid; and wherein X$_{16}$ is Ser, Thr, Asn, Gln, any polar amino acid, or is absent.

In a more preferred embodiment, the peptides will comprise a core sequence of amino acids CX$_2$X$_3$DNSSX$_8$X$_9$X$_{10}$CKX$_{13}$X$_{14}$RX$_{16}$ (SEQ ID NO:283), wherein X$_2$ is Tyr, Phe, or any aromatic amino acid; wherein X$_3$ is Tyr, Phe, or any aromatic amino acid; wherein X$_8$ is Asn, Gln, Ser, Thr, or any polar amino acid; wherein X$_9$ is Val, Ile, Leu, Ala, or any nonpolar amino acid; wherein X$_{10}$ is Ile, Leu, Ala, Gly, or any nonpolar amino acid; wherein X$_{13}$ is Lys, Arg, or any basic amino acid; wherein X$_{14}$ is Tyr, Phe, or any aromatic amino acid; and wherein X$_{16}$ is Ser, Thr, Asn, Gln, any polar amino acid, or is absent.

In a more preferred embodiment, the peptides will comprise a core sequence of amino acids CX$_2$X$_3$NNSSX$_8$X$_9$X$_{10}$CKX$_{13}$X$_{14}$RX$_{16}$ (SEQ ID NO:284), wherein X$_2$ is Tyr, Phe, or any aromatic amino acid; wherein X$_3$ is Tyr, Phe, or any aromatic amino acid; wherein X$_8$ is Asn, Gln, Ser, Thr, or any polar amino acid; wherein X$_9$ is Val, Ile, Leu, Ala, or any nonpolar amino acid; wherein X$_{10}$ is Ile, Leu, Ala, Gly, or any nonpolar amino acid; wherein X$_{13}$ is Lys, Arg, or any basic amino acid; wherein X$_{14}$ is Tyr, Phe, or any aromatic amino acid; and wherein X$_{16}$ is Ser, Thr, Asn, Gln, any polar amino acid, or is absent.

In a more preferred embodiment, the peptides will comprise a core sequence of amino acids CYX$_3$DDSSX$_8$X$_9$X$_{10}$CKX$_{13}$YRX$_{16}$ (SEQ ID NO:285), wherein X$_3$ is Tyr, Phe, or any aromatic amino acid; wherein X$_8$ is Asn, Gln, Ser, Thr, or any polar amino acid; wherein X$_9$ is Val, Ile, Leu, Ala, or any nonpolar amino acid; wherein X$_{10}$ is Ile, Leu, Ala, Gly, or any nonpolar amino acid; wherein X$_{13}$ is Lys, Arg, or any basic amino acid; and wherein X$_{16}$ is Ser, Thr, Asn, Gln, any polar amino acid, or is absent.

In a more preferred embodiment, the peptides will comprise a core sequence of amino acids CYX$_3$NDSSX$_8$X$_9$X$_{10}$CKX$_{13}$YRX$_{16}$ (SEQ ID NO:286), wherein X$_3$ is Tyr, Phe, or any aromatic amino acid; wherein X$_8$ is Asn, Gln, Ser, Thr, or any polar amino acid; wherein X$_9$ is Val, Ile, Leu, Ala, or any nonpolar amino acid; wherein X$_{10}$ is Ile, Leu, Ala, Gly, or any nonpolar amino acid; wherein X$_{13}$ is Lys, Arg, or any basic amino acid; and wherein X$_{16}$ is Ser, Thr, Asn, Gln, any polar amino acid, or is absent.

In a more preferred embodiment, the peptides will comprise a core sequence of amino acids CYX$_3$DNSSX$_8$X$_9$X$_{10}$CKX$_{13}$YRX$_{16}$ (SEQ ID NO:287), wherein X$_3$ is Tyr, Phe, or any aromatic amino acid; wherein X$_8$ is Asn, Gln, Ser, Thr, or any polar amino acid; wherein X$_9$ is Val, Ile, Leu, Ala, or any nonpolar amino acid; wherein X$_{10}$ is Ile, Leu, Ala, Gly, or any nonpolar amino acid; wherein X$_{13}$ is Lys, Arg, or any basic amino acid; and wherein X$_{16}$ is Ser, Thr, Asn, Gln, any polar amino acid, or is absent.

In a more preferred embodiment, the peptides will comprise a core sequence of amino acids CYX$_3$NNSSX$_8$X$_9$X$_{10}$CKX$_{13}$YRX$_{16}$ (SEQ ID NO:288), wherein X$_3$ is Tyr, Phe, or any aromatic amino acid; wherein X$_8$ is Asn, Gln, Ser, Thr, or any polar amino acid; wherein X$_9$ is Val, Ile, Leu, Ala, or any nonpolar amino acid; wherein X$_{10}$ is Ile, Leu, Ala, Gly, or any nonpolar amino acid; wherein X$_{13}$ is Lys, Arg, or any basic amino acid; and wherein X$_{16}$ is Ser, Thr, Asn, Gln, any polar amino acid, or is absent.

In an especially preferred embodiment, the peptides will comprise a core sequence of amino acids CX$_2$X$_3$X$_4$X$_5$X$_6$X$_7$X$_8$X$_9$X$_{10}$CX$_{12}$X$_{13}$X$_{14}$X$_{15}$X$_{16}$ (SEQ ID NO:289), wherein X$_2$ is Tyr, or Phe; wherein X$_3$ is Phe, or Tyr; wherein X$_4$ is Asp, or Asn; wherein X$_5$ is Asp, or Asn; wherein X$_6$ is Ser, or Thr; wherein X$_7$ is Ser, or Thr; wherein X$_8$ is Asn, Gln, Ser, or Thr; wherein X$_9$ is Val, Ile, Leu, or Ala; wherein X$_{10}$ is Ile, Leu, Ala, or Gly; wherein X$_{12}$ is Lys, or Arg; wherein X$_{13}$ is Lys, or Arg; wherein X$_{14}$ is Tyr, or Phe; wherein X$_{15}$ is Arg, or Lys; and wherein X$_{16}$ is Ser, Thr, Asn, Gln, or is absent.

In an especially preferred embodiment, the peptides will comprise a core sequence of amino acids CX$_2$X$_3$DDSX$_7$X$_8$X$_9$X$_{10}$CKX$_{13}$X$_{14}$RX$_{16}$ (SEQ ID NO:290), wherein X$_2$ is Tyr, or Phe; wherein X$_3$ is Phe, or Tyr; wherein X$_7$ is Ser, or Thr; wherein X$_8$ is Asn, Gln, Ser, or Thr; wherein X$_9$ is Val, Ile, Leu, or Ala; wherein X$_{10}$ is Ile, Leu, Ala, or Gly; wherein X$_{13}$ is Lys, or Arg; wherein X$_{14}$ is Tyr, or Phe; and wherein X$_{16}$ is Ser, Thr, Asn, Gln, or is absent.

In an especially preferred embodiment, the peptides will comprise a core sequence of amino acids CX$_2$X$_3$NDSX$_7$X$_8$X$_9$X$_{10}$CKX$_{13}$X$_{14}$RX$_{16}$ (SEQ ID NO:291), wherein X$_2$ is Tyr, or Phe; wherein X$_3$ is Phe, or Tyr; wherein X$_7$ is Ser, or Thr; wherein X$_8$ is Asn, Gln, Ser, or Thr; wherein X$_9$ is Val, Ile, Leu, or Ala; wherein X$_{10}$ is Ile, Leu, Ala, or Gly; wherein X$_{13}$ is Lys, or Arg; wherein X$_{14}$ is Tyr, or Phe; and wherein X$_{16}$ is Ser, Thr, Asn, Gln, or is absent.

In an especially preferred embodiment, the peptides will comprise a core sequence of amino acids CX$_2$X$_3$DNSX$_7$X$_8$X$_9$X$_{10}$CKX$_{13}$X$_{14}$RX$_{16}$ (SEQ ID NO:292), wherein X$_2$ is Tyr, or Phe; wherein X$_3$ is Phe, or Tyr; wherein X$_7$ is Ser, or Thr; wherein X$_8$ is Asn, Gln, Ser, or Thr; wherein X$_9$ is Val, Ile, Leu, or Ala; wherein X$_{10}$ is Ile, Leu, Ala, or Gly; wherein X$_{13}$ is Lys, or Arg; wherein X$_{14}$ is Tyr, or Phe; and wherein X$_{16}$ is Ser, Thr, Asn, Gln, or is absent.

In an especially preferred embodiment, the peptides will comprise a core sequence of amino acids $CX_2X_3NNSX_7X_8X_9X_{10}CKX_{13}X_{14}RX_{16}$ (SEQ ID NO:293), wherein $X_2$ is Tyr, or Phe; wherein $X_3$ is Phe, or Tyr; wherein $X_7$ is Ser, or Thr; wherein $X_8$ is Asn, Gln, Ser, or Thr; wherein $X_9$ is Val, Ile, Leu, or Ala; wherein $X_{10}$ is Ile, Leu, Ala, or Gly; wherein $X_{13}$ is Lys, or Arg; wherein $X_{14}$ is Tyr, or Phe; and wherein $X_{16}$ is Ser, Thr, Asn, Gln, or is absent.

In an especially preferred embodiment, the peptides will comprise a core sequence of amino acids $CYX_3DDSX_7X_8X_9X_{10}CKX_{13}YRX_{16}$ (SEQ ID NO:294), wherein $X_3$ is Phe, or Tyr; wherein $X_7$ is Ser, or Thr; wherein $X_8$ is Asn, Gln, Ser, or Thr; wherein $X_9$ is Val, Ile, Leu, or Ala; wherein $X_{10}$ is Ile, Leu, Ala, or Gly; wherein $X_{13}$ is Lys, or Arg; and wherein $X_{16}$ is Ser, Thr, Asn, Gln, or is absent.

In an especially preferred embodiment, the peptides will comprise a core sequence of amino acids $CYX_3NDSX_7X_8X_9X_{10}CKX_{13}YRX_{16}$ (SEQ ID NO:295), wherein $X_3$ is Phe, or Tyr; wherein $X_7$ is Ser, or Thr; wherein $X_8$ is Asn, Gln, Ser, or Thr; wherein $X_9$ is Val, Ile, Leu, or Ala; wherein $X_{10}$ is Ile, Leu, Ala, or Gly; wherein $X_{13}$ is Lys, or Arg; and wherein $X_{16}$ is Ser, Thr, Asn, Gln, or is absent.

In an especially preferred embodiment, the peptides will comprise a core sequence of amino acids $CYX_3DNSX_7X_8X_9X_{10}CKX_{13}YRX_{16}$ (SEQ ID NO:296), wherein $X_3$ is Phe, or Tyr; wherein $X_7$ is Ser, or Thr; wherein $X_8$ is Asn, Gln, Ser, or Thr; wherein $X_9$ is Val, Ile, Leu, or Ala; wherein $X_{10}$ is Ile, Leu, Ala, or Gly; wherein $X_{13}$ is Lys, or Arg; and wherein $X_{16}$ is Ser, Thr, Asn, Gln, or is absent.

In an especially preferred embodiment, the peptides will comprise a core sequence of amino acids $CYX_3NNSX_7X_8X_9X_{10}CKX_{13}YRX_{16}$ (SEQ ID NO:297), wherein $X_3$ is Phe, or Tyr; wherein $X_7$ is Ser, or Thr; wherein $X_8$ is Asn, Gln, Ser, or Thr; wherein $X_9$ is Val, Ile, Leu, or Ala; wherein $X_{10}$ is Ile, Leu, Ala, or Gly; wherein $X_{13}$ is Lys, or Arg; and wherein $X_{16}$ is Ser, Thr, Asn, Gln, or is absent.

In an especially preferred embodiment, the peptides will comprise a core sequence of amino acids $CX_2X_3DDSSX_8X_9X_{10}CKX_{13}X_{14}RX_{16}$ (SEQ ID NO:298), wherein $X_2$ is Tyr, or Phe; wherein $X_3$ is Phe, or Tyr; wherein $X_8$ is Asn, Gln, Ser, or Thr; wherein $X_9$ is Val, Ile, Leu, or Ala; wherein $X_{10}$ is Ile, Leu, Ala, or Gly; wherein $X_{13}$ is Lys, or Arg; wherein $X_{14}$ is Tyr, or Phe; and wherein $X_{16}$ is Ser, Thr, Asn, Gln, or is absent.

In an especially preferred embodiment, the peptides will comprise a core sequence of amino acids $CX_2X_3NDSSX_8X_9X_{10}CKX_{13}X_{14}RX_{16}$ (SEQ ID NO:299), wherein $X_2$ is Tyr, or Phe; wherein $X_3$ is Phe, or Tyr; wherein $X_8$ is Asn, Gln, Ser, or Thr; wherein $X_9$ is Val, Ile, Leu, or Ala; wherein $X_{10}$ is Ile, Leu, Ala, or Gly; wherein $X_{13}$ is Lys, or Arg; wherein $X_{14}$ is Tyr, or Phe; and wherein $X_{16}$ is Ser, Thr, Asn, Gln, or is absent.

In an especially preferred embodiment, the peptides will comprise a core sequence of amino acids $CX_2X_3DNSSX_8X_9X_{10}CKX_{13}X_{14}RX_{16}$ (SEQ ID NO:300), wherein $X_2$ is Tyr, or Phe; wherein $X_3$ is Phe, or Tyr; wherein $X_8$ is Asn, Gln, Ser, or Thr; wherein $X_9$ is Val, Ile, Leu, or Ala; wherein $X_{10}$ is Ile, Leu, Ala, or Gly; wherein $X_{13}$ is Lys, or Arg; wherein $X_{14}$ is Tyr, or Phe; and wherein $X_{16}$ is Ser, Thr, Asn, Gln, or is absent.

In an especially preferred embodiment, the peptides will comprise a core sequence of amino acids $CX_2X_3NNSSX_8X_9X_{10}CKX_{13}X_{14}RX_{16}$ (SEQ ID NO:301), wherein $X_2$ is Tyr, or Phe; wherein $X_3$ is Phe, or Tyr; wherein $X_8$ is Asn, Gln, Ser, or Thr; wherein $X_9$ is Val, Ile, Leu, or Ala; wherein $X_{10}$ is Ile, Leu, Ala, or Gly; wherein $X_{13}$ is Lys, or Arg; wherein $X_{14}$ is Tyr, or Phe; and wherein $X_{16}$ is Ser, Thr, Asn, Gln, or is absent.

In an especially preferred embodiment, the peptides will comprise a core sequence of amino acids $CYX_3DDSSX_8X_9X_{10}CKX_{13}YRX_{16}$ (SEQ ID NO:302), wherein $X_3$ is Phe, or Tyr; wherein $X_8$ is Asn, Gln, Ser, or Thr; wherein $X_9$ is Val, Ile, Leu, or Ala; wherein $X_{10}$ is Ile, Leu, Ala, or Gly; wherein $X_{13}$ is Lys, or Arg; and wherein $X_{16}$ is Ser, Thr, Asn, Gln, or is absent.

In an especially preferred embodiment, the peptides will comprise a core sequence of amino acids $CYX_3NDSSX_8X_9X_{10}CKX_{13}YRX_{16}$ (SEQ ID NO:303), wherein $X_3$ is Phe, or Tyr; wherein $X_8$ is Asn, Gln, Ser, or Thr; wherein $X_9$ is Val, Ile, Leu, or Ala; wherein $X_{10}$ is Ile, Leu, Ala, or Gly; wherein $X_{13}$ is Lys, or Arg; and wherein $X_{16}$ is Ser, Thr, Asn, Gln, or is absent.

In an especially preferred embodiment, the peptides will comprise a core sequence of amino acids $CYX_3DNSSX_8X_9X_{10}CKX_{13}YRX_{16}$ (SEQ ID NO:304), wherein $X_3$ is Phe, or Tyr; wherein $X_8$ is Asn, Gln, Ser, or Thr; wherein $X_9$ is Val, Ile, Leu, or Ala; wherein $X_{10}$ is Ile, Leu, Ala, or Gly; wherein $X_{13}$ is Lys, or Arg; and wherein $X_{16}$ is Ser, Thr, Asn, Gln, or is absent.

In an especially preferred embodiment, the peptides will comprise a core sequence of amino acids $CYX_3NNSSX_8X_9X_{10}CKX_{13}YRX_{16}$ (SEQ ID NO:305), wherein $X_3$ is Phe, or Tyr; wherein $X_8$ is Asn, Gln, Ser, or Thr; wherein $X_9$ is Val, Ile, Leu, or Ala; wherein $X_{10}$ is Ile, Leu, Ala, or Gly; wherein $X_{13}$ is Lys, or Arg; and wherein $X_{16}$ is Ser, Thr, Asn, Gln, or is absent.

Particularly preferred peptides include but are not limited to, the following:

```
                            (SEQ ID NO: 24)
CYFDDSSNVICKRYRS (SEQ ID NO: 33)
CYFDDSSNVLCKKYRS-NH2

(SEQ ID NO: 43)
CYFDDSSQVICKKYRS (SEQ ID NO: 45)
CYFDDSSNVLCKKYRS (SEQ ID NO: 209)
CYFDDSSSVLCKKYRS (SEQ ID NO: 213)
CYFDDSSNVLCKKYRN (SEQ ID NO: 217)
CYYDDSSNVLCKKYRS (SEQ ID NO: 221)
CYFNDSSQVLCKRYRS (SEQ ID NO: 222)
CYYDDSSNVLCKRYRS-NH2

(SEQ ID NO: 223)
CYFDDSSNVLCKKYR
```

In one embodiment, a TDFRP compound includes an analog or homolog of SEQ ID NOs:1-314. Compounds of the present invention include those with homology to SEQ ID NOs:1-314, for example, preferably 50% or greater amino acid identity, more preferably 75% or greater amino acid identity, and even more preferably 90% or greater amino acid identity.

Sequence identity can be measured using sequence analysis software (Sequence Analysis Software Package of the Genetics Computer Group, University of Wisconsin Biotechnology Center, 1710 University Avenue, Madison, Wis. 53705), with the default parameters therein.

In the case of polypeptide sequences, which are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine. Thus, included in the invention are peptides having mutated sequences such that they remain homologous, e.g., in sequence, in structure, in function, and in antigenic character or other function, with a polypeptide having the corresponding parent sequence. Such mutations can, for example, be mutations involving conservative amino acid changes, e.g., changes between amino acids of broadly similar molecular properties. For example, interchanges within the aliphatic group alanine, valine, leucine and isoleucine can be considered as conservative. Sometimes substitution of glycine for one of these can also be considered conservative. Other conservative interchanges include those within the aliphatic group aspartate and glutamate; within the amide group asparagine and glutamine; within the hydroxyl group serine and threonine; within the aromatic group phenylalanine, tyrosine and tryptophan; within the basic group lysine, arginine and histidine; and within the sulfur-containing group methionine and cysteine. Sometimes substitution within the group methionine and leucine can also be considered conservative. Preferred conservative substitution groups are aspartate-glutamate; asparagine-glutamine; valine-leucine-isoleucine; alanine-valine; phenylalanine-tyrosine; and lysine-arginine.

The invention also provides for compounds having altered sequences including insertions such that the overall amino acid sequence is lengthened, while the compound still retains the appropriate TDF agonist or antagonist properties. Additionally, altered sequences may include random or designed internal deletions that truncate the overall amino acid sequence of the compound, however the compound still retains its TDF-like functional properties. In certain embodiments, one or more amino acid residues within SEQ ID NOs: 1-314 are replaced with other amino acid residues having physical and/or chemical properties similar to the residues they are replacing. Preferably, conservative amino acid substitutions are those wherein an amino acid is replaced with another amino acid encompassed within the same designated class, as will be described more thoroughly below. Insertions, deletions, and substitutions are appropriate where they do not abrogate the functional properties of the compound. Functionality of the altered compound can be assayed according to the in vitro and in vivo assays described below that are designed to assess the TDF-like properties of the altered compound.

The amino acid residues of SEQ ID NOs:1-314, analogs or homologs of SEQ ID NOs:1-314 include genetically-encoded 1-amino acids, naturally occurring non-genetically encoded 1-amino acids, synthetic d-amino acids, or d-enantiomers of all of the above.

B. TDFRP Nucleic Acid Sequences

The compounds of the present invention include one or more polynucleotides encoding SEQ ID NOs:1-314, including degenerate variants thereof. Accordingly, nucleic acid sequences capable of hybridizing at low stringency with any nucleic acid sequences encoding SEQ ID NOs:1-314 are considered to be within the scope of the invention. For example, for a nucleic acid sequence of about 20-40 bases, a typical prehybridization, hybridization, and wash protocol is as follows: (1) prehybridization: incubate nitrocellulose filters containing the denatured target DNA for 3-4 hours at 55° C. in 5×Denhardt's solution, 6×SSC (20×SSC consists of 175 g NaCl, 88.2 g sodium citrate in 800 ml $H_2O$ adjusted to pH. 7.0 with 10 N NaOH), 0.1% SDS, and 100 µg/ml denatured salmon sperm DNA, (2) hybridization: incubate filters in prehybridization solution plus probe at 42° C. for 14-48 hours, (3) wash; three 15 minutes washes in 6×SSC and 0.1% SDS at room temperature, followed by a final 1-1.5 minutes wash in 6×SSC and 0.1% SDS at 55° C. Other equivalent procedures, e.g., employing organic solvents such as formamide, are well known in the art. Standard stringency conditions are well characterized in standard molecular biology cloning texts. See, for example Molecular Cloning A Laboratory Manual, $2^{nd}$ Ed., ed., Sambrook, Fritsch, and Maniatis (Cold Spring Harbor Laboratory Press: 1989); DNA Cloning, Volumes I and II (D. N. Glovered., 1985); Oligonucleotide synthesis (M. J. Gait ed., 1984); Nucleic Acid Hybridization (B. D. Hames & S. J. Higgins eds, 1984).

The invention also encompasses allelic variants of the same, that is, naturally-occurring alternative forms of the isolated polynucleotides that encode polypeptides that are identical, homologous or related to those encoded by the polynucleotides. Alternatively, non-naturally occurring variants may be produced by mutagenesis techniques or by direct synthesis techniques well known in the art.

C. TDFRP Recombinant Expression Vectors

Another aspect of the invention includes vectors containing one or more nucleic acid sequences encoding a TDFRP compound. For recombinant expression of one or more the polypeptides of the invention, the nucleic acid containing all or a portion of the nucleotide sequence encoding the polypeptide is inserted into an appropriate cloning vector, or an expression vector (i.e., a vector that contains the necessary elements for the transcription and translation of the inserted polypeptide coding sequence) by recombinant DNA techniques well known in the art and as detailed below.

In general, expression vectors useful in recombinant DNA techniques are often in the form of plasmids. In the present specification, "plasmid" and "vector" can be used interchangeably as the plasmid is the most commonly used form of vector. However, the invention is intended to include such other forms of expression vectors that are not technically plasmids, such as viral vectors (e.g., replication defective retroviruses, adenoviruses and adeno-associated viruses), which serve equivalent functions. Such viral vectors permit infection of a subject and expression in that subject of a compound.

The recombinant expression vectors of the invention comprise a nucleic acid encoding a compound with TDF-like properties in a form suitable for expression of the nucleic acid in a host cell, which means that the recombinant expression vectors include one or more regulatory sequences, selected on the basis of the host cells to be used for expression that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to include promoters, enhancers and other expression control elements (e.g., polyadenylation signals). Such regulatory sequences are described, for example, in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides, encoded by nucleic acids as described herein (e.g., TDFRP compounds and TDFRP-derived fusion polypeptides, etc.).

D. TDFRP-Expressing Host Cells

Another aspect of the invention pertains to TDFRP-expressing host cells, which contain a nucleic acid encoding one or more TDFRP compounds. The recombinant expression vectors of the invention can be designed for expression of TDFRP compounds in prokaryotic or eukaryotic cells. For example, TDFRP compounds can be expressed in bacterial cells such as *Escherichia coli*, insect cells (using baculovirus expression vectors), fungal cells, e.g., yeast, yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Expression of polypeptides in prokaryotes is most often carried out in *Escherichia coli* with vectors containing constitutive or inducible promoters directing the expression of either fusion or non-fusion polypeptides. Fusion vectors add a number of amino acids to a polypeptide encoded therein, usually to the amino terminus of the recombinant polypeptide. Such fusion vectors typically serve three purposes: (i) to increase expression of recombinant polypeptide; (ii) to increase the solubility of the recombinant polypeptide; and (iii) to aid in the purification of the recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin and enterokinase. Typical fusion expression vectors include pGEX (Pharmacia Biotech Inc; Smith and Johnson, 1988. Gene 67: 31-40), pMAL (New England Biolabs, Beverly, Mass.) and pRIT5 (Pharmacia, Piscataway, N.J.) that fuse glutathione S-transferase (GST), maltose E binding polypeptide, or polypeptide A, respectively, to the target recombinant polypeptide.

Examples of suitable inducible non-fusion *E. coli* expression vectors include pTrc (Amrann et al., (1988) Gene 69:301-315) and pET 11d (Studier et al., GENE EXPRESSION TECHNOLOGY: METHODS IN ENZYMOLOGY 185, Academic Press, San Diego, Calif. (1990) 60-89).

One strategy to maximize recombinant polypeptide expression in *E. coli* is to express the polypeptide in host bacteria with an impaired capacity to proteolytically cleave the recombinant polypeptide. See, e.g., Gottesman, GENE EXPRESSION TECHNOLOGY: METHODS IN ENZYMOLOGY 185, Academic Press, San Diego, Calif. (1990) 119-128. Another strategy is to alter the nucleic acid sequence of the nucleic acid to be inserted into an expression vector so that the individual codons for each amino acid are those preferentially utilized in the expression host, e.g., *E. coli* (see, e.g., Wada, et al., 1992. Nucl. Acids Res. 20: 2111-2118). Such alteration of nucleic acid sequences of the invention can be carried out by standard DNA synthesis techniques.

In another embodiment, the TDFRP expression vector is a yeast expression vector. Examples of vectors for expression in yeast *Saccharomyces cerivisae* include pYepSec1 (Baldari, et al., 1987. EMBO J. 6: 229-234), pMFa (Kurjan and Herskowitz, 1982. Cell 30: 933-943), pJRY88 (Schultz et al., 1987. Gene 54: 113-123), pYES2 (Invitrogen Corporation, San Diego, Calif.), and picZ (Invitrogen Corp, San Diego, Calif.). Alternatively, TDFRP can be expressed in insect cells using baculovirus expression vectors. Baculovirus vectors available for expression of polypeptides in cultured insect cells (e.g., SF9 cells) include the pAc series (Smith, et al., 1983. Mol. Cell. Biol. 3: 2156-2165) and the pVL series (Lucklow and Summers, 1989. Virology 170: 31-39).

In yet another embodiment, a nucleic acid of the invention is expressed in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBO J. 8: 729-733) and immunoglobulins (Banerji, et al., 1983. Cell 33: 729-740; Queen and Baltimore, 1983. Cell 33: 741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. Science 249: 374-379) and the α-fetoprotein promoter (Campes and Tilghman, 1989. Genes Dev. 3: 537-546).

The invention further provides a recombinant expression vector comprising a DNA molecule of the invention cloned into the expression vector in an antisense orientation. That is, the DNA molecule is operatively-linked to a regulatory sequence in a manner that allows for expression (by transcription of the DNA molecule) of an RNA molecule that is antisense to a TDRFP mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see, e.g., Weintraub, et al., "Antisense RNA as a molecular tool for genetic analysis," Reviews-Trends in Genetics, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, TDFRP can be expressed in bacterial cells such as E. coli, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding TDFRP or can be introduced on a separate vector. Cells stably transfected with the introduced nucleic acid can be identified by drug selection (e.g., cells that have incorporated the selectable marker gene will survive, while the other cells die).

A host cell that includes a compound of the invention, such as a prokaryotic or eukaryotic host cell in culture, can be used to produce (i.e., express) recombinant TDFRP. In one embodiment, the method comprises culturing the host cell of invention (into which a recombinant expression vector encoding TDFRP has been introduced) in a suitable medium such that TDFRP is produced. In another embodiment, the method further comprises the step of isolating TDFRP from the medium or the host cell. Purification of recombinant polypeptides is well-known in the art and include ion-exchange purification techniques, or affinity purification techniques, for example with an antibody to the compound. Methods of creating antibodies to the compounds of the present invention are discussed below.

E. TDFRP-Derived Chimeric and Fusion Polypeptides

The invention also provides for compounds that are TDFRP-derived chimeric or fusion polypeptides. As used herein, a TDFRP-derived "chimeric polypeptide" or "fusion polypeptide" comprises a TDFRP operatively-linked to a polypeptide having an amino acid sequence corresponding to a polypeptide that is not substantially homologous to the TDFRP, e.g., a polypeptide that is different from the TDFRP and that is derived from the same or a different organism (i.e., non-TDFRP). Within a TDFRP-derived fusion polypeptide, the TDFRP can correspond to all or a portion of a TDFRP. In one embodiment, a TDFRP-derived fusion polypeptide comprises at least one biologically-active portion of a TDFRP, for example a fragment of SEQ ID NOs:1-314. In another embodiment, a TDFRP-derived fusion polypeptide comprises at least two biologically-active portions of a TDFRP. In yet another embodiment, a TDFRP-derived fusion polypeptide comprises at least three biologically-active portions of a TDFRP polypeptide. Within the fusion polypeptide, the term "operatively-linked" is intended to indicate that the TDFRP polypeptide and the non-TDFRP polypeptide are fused in-frame with one another. The non-TDFRP polypeptide can be fused to the N-terminus or C-terminus of the TDFRP.

In one embodiment, the fusion polypeptide is a GST-TDFRP fusion polypeptide in which the TDFRP sequences are fused to the N- or C-terminus of the GST (glutathione S-transferase) sequences. Such fusion polypeptides can facilitate the purification of recombinant TDFRP by affinity means.

In another embodiment, the fusion polypeptide is a TDFRP polypeptide containing a heterologous signal sequence at its N-terminus. In certain host cells (e.g., mammalian host cells), expression and/or secretion of TDFRP can be increased through use of a heterologous signal sequence.

In yet another embodiment, the fusion polypeptide is a TDFRP-immunoglobulin fusion polypeptide in which the TDFRP sequences are fused to sequences derived from a member of the immunoglobulin superfamily. The TDFRP-immunoglobulin fusion polypeptides of the invention can be incorporated into pharmaceutical compositions and administered to a subject to inhibit an interaction between a TDF and a TDF receptor polypeptide on the surface of a cell, to thereby suppress TDF-mediated signal transduction in vivo. The TDFRP-immunoglobulin fusion polypeptides can be used to affect the bioavailability of a TDFRP, for example to target the compound to a particular cell or tissue having the requisite antigen Inhibition of the TDF/TDF receptor interaction can be useful therapeutically for both the treatment of proliferative and differentiative disorders, as well as modulating (e.g., promoting or inhibiting) cell survival. Moreover, the TDFRP-immunoglobulin fusion polypeptides of the invention can be used as immunogens to produce anti-TDFRP antibodies in a subject, to purify TDFRP ligands, and in screening assays to identify molecules that inhibit the interaction of TDF with a TDF ligand.

F. TDFRP1-Linker-TDFRP2

The compounds of the present invention contain multiple TDF-related polypeptides (i.e., multiple domain TDF-related polypeptide compounds, hereinafter "TDFRP") with the general structure shown below:

Where a first TDFRP domain (TDFRP1, i.e., TDF-related polypeptide 1) is covalently linked via the C-terminus, N-terminus, or any position with a functionalizable side group, e.g., lysine or aspartic acid to a linker molecule, which, in turn, is covalently linked to the N-terminus of a second TDFRP domain (TDFRP2).

The TDRFP domains are compounds that include small molecules, more particularly polypeptides identified herein, i.e., TDF-related polypeptides (TDFRP), summarized in Tables 1b-4-b. Variants, analogs, homologs, or fragments of these compounds, such as species homologs, are also included in the present invention, as well as degenerate forms thereof.

A first domain is linked to a second domain through a linker. The term "linker," as used herein, refers to an element capable of providing appropriate spacing or structural rigidity, or structural orientation, alone, or in combination, to a first and a second domain, e.g., TDFRP1 and TDFRP2, such that the biological activity of the TDFRP is preserved. For example, linkers may include, but are not limited to, a diamino alkane, a dicarboxylic acid, an amino carboxylic acid alkane, an amino acid sequence, e.g., glycine polypeptide, a disulfide linkage, a helical or sheet-like structural element or an alkyl chain. In one aspect the linker is not inert, e.g., chemically or enzymatically cleavable in vivo or in vitro. In another aspect the linker is inert, i.e., substantially unreactive in vivo or in vitro, e.g., is not chemically or enzymatically degraded. Examples of inert groups which can serve as linking groups include aliphatic chains such as alkyl, alkenyl and alkynyl groups (e.g., C1-C20), cycloalkyl rings (e.g., C3-C10), aryl groups (carbocyclic aryl groups such as 1-naphthyl, 2-naphthyl, 1-anthracyl and 2-anthracyl and heteroaryl group such as N-imidazolyl, 2-imidazole, 2-thienyl, 3-thienyl, 2-furanyl, 3-furanyl, 2-pyridyl, 3-pyridyl, 4-pyridyl, 2-pyrimidy, 4-pyrimidyl, 2-pyranyl, 3-pyranyl, 3-pyrazolyl, 4-pyrazolyl, 5-pyrazolyl, 2-pyrazinyl, 2-thiazole, 4-thiazole, 5-thiazole, 2-oxazolyl, 4-oxazolyl, 5-oxazolyl, 2-benzothienyl, 3-benzothienyl, 2-benzofuranyl, 3-benzofuranyl, 2-indolyl, 3-indolyl, 2-quinolinyl, 3-quinolinyl, 2-benzothiazole, 2-benzooxazole, 2-benzimidazole, 2-quinolinyl, 3-quinolinyl, 1-isoquinolinyl, 3-quinolinyl, 1-isoindolyl, and 3-isoindolyl), non-aromatic heterocyclic groups (e.g., 2-tetrahydrofuranyl, 3-tetrahydrofuranyl, 2-tetrahyrothiophenyl, 3-tetrahyrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl and 4-thiazolidinyl) and aliphatic groups in which one, two or three methylenes have been replaced with —O—, —S—, —NH—, —SO$_2$—, —SO— or —SO$_2$NH—.

The present compounds include small molecules, more particularly TDFRP compound domains, with the general structure identified herein, as detailed below. The TDFRP compound domains disclosed herein may be present in an TDFRP compound in any combination or orientation. Variants, analogs, homologs, or fragments of these TDFRP compound domains, such as species homologs, are also included in the present invention, as well as degenerate forms thereof. The TDFRP compound domains of the present invention may capped on the N-terminus, or the C-terminus, or on both the N-terminus and the C-terminus. The TDFRP compounds of the present invention may be pegylated, or modified, e.g., branching, at any amino acid residue containing a reactive side chain, e.g., lysine residue, or chemically reactive group on the linker. The TDFRP compound of the present invention may be linear or cyclized. The tail sequence of the TDFRP or TDFRP domains may vary in length. In one aspect of the present invention, the TDFRP compounds of the invention are prodrugs, i.e., the biological activity of the TDFRP compound is altered, e.g., increased, upon contacting a biological system in vivo or in vitro.

The TDFRP compounds can contain natural amino acids, non-natural amino acids, d-amino acids and 1-amino acids, and any combinations thereof. In certain embodiments, the compounds of the invention can include commonly encountered amino acids which are not genetically encoded. These non-genetically encoded amino acids include, but are not limited to, β-alanine (β-Ala) and other omega-amino acids such as 3-aminopropionic acid (Dap), 2,3-diaminopropionic acid (Dpr), 4-aminobutyric acid and so forth; α-aminoisobutyric acid (Aib); ε-aminohexanoic acid (Aha); δ-aminovaleric acid (Ava); N-methylglycine or sarcosine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (hArg); N-acetyl lysine (AcLys); 2,3-diaminobutyric acid (Dab); 2,3-diaminobutyric acid (Dbu); p-aminophenylalanine (Phe(pNH$_2$)); N-methyl valine (MeVal); homocysteine (hCys) and homoserine (hSer). Non-naturally occurring variants of the compounds may be produced by mutagenesis techniques or by direct synthesis.

II. Preparation of TDRPs

A. Peptide Synthesis of TDFRP Compounds

In one embodiment, a TDFRP compound can be synthesized chemically using standard peptide synthesis techniques, e.g., solid-phase or solution-phase peptide synthesis. That is, the compounds disclosed as SEQ ID NOs:1-314 are chemically synthesized, for example, on a solid support or in solution using compositions and methods well known in the art, see, e.g., Fields, G. B. (1997) Solid-Phase Peptide Synthesis. Academic Press, San Diego.

The TDFRP compound may be prepared by either Fmoc (base labile protecting group) or -Boc (acid labile a-amino protecting group) peptide synthesis. Following synthesis, TDFRP compound can then be rendered substantially free of chemical precursors or other chemicals by an appropriate purification scheme using standard polypeptide purification techniques for example, ion exchange chromatography, affinity chromatography, reverse-phase HPLC, e.g., using columns such as C-18, C-8, and C-4, size exclusion chromatography, chromatography based on hydrophobic interactions, or other polypeptide purification method.

B. Production of TDFRP Compound Using Recombinant DNA Techniques

In another embodiment, TDFRP compounds are produced by recombinant DNA techniques, for example, overexpression of the compounds in bacteria, yeast, baculovirus or eukaryotic cells yields sufficient quantities of the compounds. Purification of the compounds from heterogeneous mixtures of materials, e.g., reaction mixtures or cellular lysates or other crude fractions, is accomplished by methods well known in the art, for example, ion exchange chromatography, affinity chromatography or other polypeptide purification methods. These can be facilitated by expressing the compounds described by SEQ ID NOs:1-314 as fusions to a cleavable or otherwise inert epitope or sequence. The choice of an expression system, as well as, methods of purification are well known to skilled artisans.

The polynucleotides provided by the present invention can be used to express recombinant compounds for analysis, characterization or therapeutic use; as markers for tissues in which the corresponding compound is preferentially expressed (either constitutively or at a particular stage of tissue differentiation or development or in disease states).

For recombinant expression of one or more the compounds of the invention, the nucleic acid containing all or a portion of the nucleotide sequence encoding the peptide may be inserted into an appropriate expression vector (i.e., a vector that contains the necessary elements for the transcription and translation of the inserted peptide coding sequence). In some embodiments, the regulatory elements are heterologous (i.e., not the native gene promoter). Alternately, the necessary transcriptional and translational signals may also be supplied by the native promoter for the genes and/or their flanking regions.

A variety of host-vector systems may be utilized to express the peptide coding sequence(s). These include, but are not limited to: (i) mammalian cell systems that are infected with vaccinia virus, adenovirus, and the like; (ii) insect cell systems infected with baculovirus and the like; (iii) yeast containing yeast vectors or (iv) bacteria transformed with bacteriophage, DNA, plasmid DNA, or cosmid DNA. Depending upon the host-vector system utilized, any one of a number of suitable transcription and translation elements may be used.

Promoter/enhancer sequences within expression vectors may utilize plant, animal, insect, or fungus regulatory sequences, as provided in the invention. For example, promoter/enhancer elements from yeast and other fungi can be used (e.g., the GAL4 promoter, the alcohol dehydrogenase promoter, the phosphoglycerol kinase promoter, the alkaline phosphatase promoter). Alternatively, or in addition, they may include animal transcriptional control regions, e.g., (i) the insulin gene control region active within pancreatic cells (see, e.g., Hanahan, et al., 1985. Nature 315: 115-122); (ii) the immunoglobulin gene control region active within lymphoid cells (see, e.g., Grosschedl, et al., 1984. Cell 38: 647-658); (iii) the albumin gene control region active within liver (see, e.g., Pinckert, et al., 1987. Genes and Dev 1: 268-276; (iv) the myelin basic polypeptide gene control region active within brain oligodendrocyte cells (see, e.g., Readhead, et al., 1987. Cell 48: 703-712); and (v) the gonadotropin-releasing hormone gene control region active within the hypothalamus (see, e.g., Mason, et al., 1986. Science 234: 1372-1378), and the like.

Expression vectors or their derivatives include, e.g. human or animal viruses (e.g., vaccinia virus or adenovirus); insect viruses (e.g., baculovirus); yeast vectors; bacteriophage vectors (e.g., lambda phage); plasmid vectors and cosmid vectors.

A host cell strain may be selected that modulates the expression of inserted sequences of interest, or modifies or processes expressed peptides encoded by the sequences in the specific manner desired. In addition, expression from certain promoters may be enhanced in the presence of certain inducers in a selected host strain; thus facilitating control of the expression of a genetically-engineered compounds. Moreover, different host cells possess characteristic and specific mechanisms for the translational and post-translational processing and modification (e.g., glycosylation, phosphorylation, and the like) of expressed peptides. Appropriate cell lines or host systems may thus be chosen to ensure the desired modification and processing of the foreign peptide is achieved. For example, peptide expression within a bacterial system can be used to produce an unglycosylated core peptide; whereas expression within mammalian cells ensures "native" glycosylation of a heterologous peptide.

C. Preparation of TDFRP-Derived Chimeric or Fusion Polypeptide Compounds

A TDFRP-derived chimeric or fusion polypeptide compound of the invention can be produced by standard recombinant DNA techniques known in the art. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, e.g., Ausubel, et al. (eds.) CURRENT PROTOCOLS IN MOLECULAR BIOLOGY, John Wiley & Sons, 1992). Moreover, many expression vectors are commercially available that already encode a fusion moiety (e.g., a GST polypeptide). A TDFRP-encoding nucleic acid can be cloned into such an expression vector such that the fusion moiety is linked in-frame to the TDFRP encoding nucleic acid sequence.

D. Preparation of TDFRP Compound Libraries

In addition, libraries of fragments of the nucleic acid sequences encoding TDFRP compounds can be used to generate a population of TDFRP fragments for screening and subsequent selection of variants of a TDFRP compound. In one embodiment, a library of coding sequence fragments can be generated by treating a double stranded PCR fragment of a nucleic acid sequence encoding TDFRP compound with a nuclease under conditions wherein nicking occurs only about once per molecule, denaturing the double stranded DNA, renaturing the DNA to form double-stranded DNA that can include sense/antisense pairs from different nicked products, removing single stranded portions from reformed duplexes by treatment with S1 nuclease, and ligating the resulting fragment library into an expression vector. By this method, expression libraries can be derived which encode N-terminal, C-terminal, and internal fragments of various sizes of the TDFRP compounds.

Various techniques are known in the art for screening gene products of combinatorial libraries made by point mutations or truncation, and for screening cDNA libraries for gene products having a selected property. Such techniques are adaptable for rapid screening of the DNA libraries generated by the combinatorial mutagenesis of TDFRP compound. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify TDFRP compound variants. See, e.g., Arkin and Yourvan, 1992. Proc. Natl. Acad. Sci. USA 89: 7811-7815; Delgrave, et al., 1993. Polypeptide Engineering 6:327-331.

A library of TDRFP compounds can be produced by phage display. Known phage display or other nucleotide expression systems may be exploited to produce simultaneously a large number of TDFRP candidate constructs. The pool of candidate constructs subsequently may be screened for binding specificity using, for example, a chromatography column comprising surface immobilized receptors, salt gradient elution to select for, and to concentrate high binding candidates, and in vitro assays to determine whether or not particular isolated candidates agonize the activity of the template superfamily member. Identification of a useful construct is followed by production of cell lines expressing commercially useful quantities of the construct for laboratory use and ultimately for producing therapeutically useful drugs. It is contemplated also that preferred single-chain constructs, once identified and characterized by the recombinant DNA methodologies described above, may be produced by standard peptide synthesis methodologies.

Alternatively, a library of synthetic DNA constructs can be prepared simultaneously for example, by the assembly of synthetic nucleotide sequences that differ in nucleotide composition in a preselected region. For example, it is contemplated that during production of a construct based upon a specific TGF-beta superfamily member, the artisan may choose appropriate finger and heel regions for such a superfamily member. Once the appropriate finger and heel regions have been selected, the artisan then may produce synthetic DNA encoding these regions, which subsequently may be connected by linker sequences encoding polypeptide linkers. For example, if a plurality of DNA molecules encoding different linker sequences are included into a ligation reaction containing DNA molecules encoding finger and heel sequences, by judicious choice of appropriate restriction sites and reaction conditions, the artisan may produce a library of DNA constructs wherein each of the DNA constructs encode finger and heel regions but connected by different linker sequences. The resulting DNAs then are ligated into a suitable expression vehicle, i.e., a plasmid useful in the preparation of a phage display library, transfected into a host cell, and the polypeptides encoded by the synthetic DNAs expressed to generate a pool of candidate compounds. The pool of candidate compounds subsequently can be screened to identify lead compounds having binding affinity and/or selectivity for a pre-selected receptor.

Screening may be performed by passing a solution comprising the candidate compounds through a chromatography column containing surface immobilized receptor. Then lead compounds with the desired binding specificity are eluted, for example by means of a salt gradient and/or a concentration gradient of the template TGF-beta superfamily member. Nucleotide sequences encoding the lead compounds subsequently may be isolated and characterized. Once the appropriate nucleotide sequences of the lead compounds have been identified, the lead compounds subsequently may be produced, either by conventional recombinant DNA or peptide synthesis methodologies, in quantities sufficient to test whether the particular construct mimics the activity of the template TGF-beta superfamily member. (Amberg et al. (1993) "SurfZAP Vector: Linking Phenotype to Genotype for Phagemid Display Libraries," Strategies in Molecular Biology 6: 2-6.; Lowman et al. (1991) "Selecting High-Affinity Binding Proteins by Monovalent Phage Display," Biochemistry 30: 10832-10838; Marks et al. (1992) "Molecular Evolution of Proteins on Filamentous Phage," Journal of Biological Chemistry 267: 16007-16010; McCafferty et al. (1990) "Phage Antibodies: Filamentous Phage Displaying Antibody Variable Domains," Nature: 348: 552-554).

It is appreciated, however, that a library of DNA constructs encoding a plurality of sequences may be produced simultaneously by standard recombinant DNA methodologies, such as the ones, described above, For example, the skilled artisan by the use of cassette mutagenesis or oligonucleotide directed mutagenesis may produce, for example, a series of DNA constructs each of which contain different DNA sequences within a predefined location, e.g., within a DNA cassette encoding a linker sequence. The resulting library of DNA constructs subsequently may be expressed, for example, in a phage display library and any protein construct that binds to a specific receptor may be isolated by affinity purification, e.g., using a chromatographic column comprising surface immobilized receptor. Once molecules that bind the preselected receptor have been isolated, their binding and agonist properties may be modulated using the binding and activity assays described herein.

When recombinant DNA methodologies are used, it is necessary to establish and maintain a physical connection between the polypeptide of interest and the nucleic acid encoding it. A system useful in the practice of this aspect of the invention includes, for example, phage display methodologies wherein the peptide of interest is immobilized on the surface of the phage as a fusion with a phage coat protein, see for example, Scott et al. (1990) Science 249: 386-390; Parmely et al. (1988) Gene 73: 305-318; Devlin et al., (1990) Science 249: 404-406; McCafferty et al. (1990) Nature 348: 552-554; Marks et al. (1992) J. Biol. Chem. 267:16007-16010; Lowman et al. (1991) Biochem. 30:10832-10838; Wells et al. supra; Amberg et al. in Strategies in Molecular Biology 6:2-4; and the Recombinant Phage Antibody System instruction manual from Pharmacia, P-L Biochemicals.

Briefly, the DNAs encoding candidate constructs are expressed on the surface of phage particles, typically as N-terminal fusions to a phage minor coat protein. In a typical experiment, it is contemplated that nucleotides encoding specific portions of the synthetic gene, e.g., those encoding linker sequences, may be randomized so as to produce a library of nucleic acid sequences encoding constructs that have random amino acid sequences in that region. Once a library of DNA molecules encoding selected constructs has been produced, the DNAs are ligated into the phage genome at a position adjacent to the gene encoding a minor coat protein. The resulting DNAs are packaged, amplified in a host cell, and expressed to produce recombinant phage particles having on their cell surface minor coat proteins fused to the protein of interest. The recombinant phage particles that express selected constructs having the desired binding affinity and/or specificity for a receptor of interest subsequently are isolated by several rounds of affinity enrichment followed by phage growth. By using these approaches, single phage particles expressing polypeptides having specific biological properties may be isolated routinely from phage libraries comprising more than 10.sup.6-10.sup.8 phage particles.

Affinity enrichment may, for example, be performed by passing a solution comprising recombinant phage particles through a chromatography column that comprises surface immobilized receptor under conditions which permit selected constructs expressed on the surface of recombinant phage particles to bind to the receptor. Then, the column is washed to remove residual and/or non-specifically bound phage, and phage expressing the conformationally active constructs are eluted by specific desorption, for example, by addition of excess of the template TGF-beta superfamily member, or by non-specific desorption, for example, using pH, polarity-reducing agents or chaotropic salts. The highest binding particles may be eluted using concentration gradient of the desorption-inducing reagent wherein the highest binding particles elute at higher concentrations of the reagent. The highest binding particles, once eluted are re-amplified, and the nucleic acid encoding the morphon of interest isolated and sequenced. Once the DNA sequence, and therefore the nucleic acid sequence of the highest binding morphons, has been determined, then the refinement process may be repeated, for example, by mutagenesis of another portion of the molecule, until morphon molecules having a preferred binding activity have been produced. The resulting constructs subsequently may be assayed for biological activity using in vivo or in vitro assays that have been developed for each of the template TGF-beta superfamily members identified to date.

Following the identification of useful constructs, the constructs may be produced in commercially useful quantities, for example, by producing cell lines that express the construct of interest or by producing synthetic peptides defining the appropriate amino acid sequence. It is appreciated, however, that conventional methodologies for producing the appropriate cell lines and for producing synthetic peptides are well known and thoroughly documented in the art, and so are not discussed in detail herein.

A library of TDFRP variant compounds can also be produced by, for example, enzymatically ligating a mixture of synthetic oligonucleotides into gene sequences such that a degenerate set of potential TDFRP compound sequences are expressible as individual polypeptides, or alternatively, as a set of larger fusion polypeptides (e.g., for phage display) containing the set of TDFRP compound sequences therein. There are a variety of methods that can be used to produce libraries of potential TDFRP variant compounds from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential TDFRP compound sequences. Methods for synthesizing degenerate oligonucleotides are well-known within the art. See, e.g., Narang, 1983. Tetrahedron 39: 3; Itakura, et al., 1984. Annu. Rev. Biochem. 53: 323; Itakura, et al., 1984. Science 198: 1056; Ike, et al., 1983. Nucl. Acids Res. 11:477.

E. Anti-TDFRP Compound Antibodies

The invention provides compounds including polypeptides and polypeptide fragments suitable for use as immunogens to raise anti-TDFRP compound antibodies. The compounds can be used to raise whole antibodies and antibody fragments, such as Fv, Fab or $(Fab)_2$, that bind immunospecifically to any of the TDFRP compounds of the invention, including bispecific or other multivalent antibodies.

An isolated TDFRP polypeptide compound, or a portion or fragment thereof, can be used as an immunogen to generate antibodies that bind to TDFRP compound or TDF polypeptides using standard techniques for polyclonal and monoclonal antibody preparation. The full-length TFD polypeptides can be used or, alternatively, the invention provides for the use of compounds including TDFRP compounds or TDFRP fragments as immunogens. The TDFRP compound comprises at least 4 amino acid residues of the amino acid sequence shown in SEQ ID NOs:1-314, and encompasses an epitope of TDFRP compound such that an antibody raised against the peptide forms a specific immune complex with TDF polypeptide or TDFRP compound. Preferably, the antigenic peptide comprises at least 5, 8, 10, 15, 20, or 30 amino acid residues. Longer antigenic peptides are sometimes preferable over shorter antigenic peptides, depending on use and according to methods well known to those skilled in the art.

In certain embodiments of the invention, at least one epitope encompassed by the antigenic peptide is a region of TDF polypeptide that is located on the surface of the polypeptide (e.g., a hydrophilic region). As a means for targeting antibody production, hydropathy plots showing regions of hydrophilicity and hydrophobicity can be generated by any method well known in the art, including, for example, the Kyte Doolittle or the Hopp Woods methods, either with or without Fourier transformation (see, e.g., Hopp and Woods, 1981. Proc. Nat. Acad. Sci. USA 78: 3824-3828; Kyte and Doolittle, 1982. J. Mol. Biol. 157: 105-142, each incorporated herein by reference in their entirety).

As disclosed herein, TDFRP compounds or derivatives thereof, can be utilized as immunogens in the generation of antibodies that immunospecifically-bind these polypeptide components. In a specific embodiment, antibodies to human TDFRP polypeptides are disclosed. Various procedures known within the art can be used for the production of polyclonal or monoclonal antibodies to a TDFRP compound sequence of SEQ ID NOs:1-314, or a derivative, fragment, analog or homolog thereof. Some of these polypeptides are discussed below.

For the production of polyclonal antibodies, various suitable host animals (e.g., rabbit, goat, mouse or other mammal) can be immunized by injection with the native polypeptide, or a synthetic variant thereof, or a derivative of the foregoing. An appropriate immunogenic preparation can contain, for example, recombinantly-expressed TDFRP compound or a chemically-synthesized TDFRP compound. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), human adjuvants such as Bacille Calmette-Guerin and *Corynebacterium parvum*, or similar immunostimulatory compounds. If desired, the antibody molecules directed against TDF or TDFRP compound can be isolated from the mammal (e.g., from the blood) and further purified by well-known techniques, such as polypeptide A chromatography to obtain the IgG fraction.

For preparation of monoclonal antibodies directed towards a particular TDFRP compound, or derivatives, fragments, analogs or homologs thereof, any technique that provides for the production of antibody molecules by continuous cell line culture can be utilized. Such techniques include, but are not limited to, the hybridoma technique (see, e.g., Kohler & Milstein, 1975. Nature 256: 495-497); the trioma technique; the human B-cell hybridoma technique (see, e.g., Kozbor, et al., 1983. Immunol. Today 4: 72) and the EBV hybridoma technique to produce human monoclonal antibodies (see, e.g., Cole, et al., 1985. In: MONOCLONAL ANTIBODIES AND CANCER THERAPY, Alan R. Liss, Inc., pp. 77-96). Human monoclonal antibodies can be utilized in the practice of the invention and can be produced by using human hybridomas (see, e.g., Cote, et al., 1983. Proc Natl Acad Sci USA 80: 2026-2030) or by transforming human B-cells with Epstein Barr Virus in vitro (see, e.g., Cole, et al., 1985. In: MONOCLONAL ANTIBODIES AND CANCER THERAPY, Alan R. Liss, Inc., pp. 77-96). Each of the above citations is incorporated herein by reference in their entirety. Synthetic dendromeric trees can be added a reactive amino acid side chains, e.g., lysine to enhance the immunogenic properties of TDFRP compounds. Also, CPG-dinucleotide technique can be used to enhance the immunogenic properties of TDFRP compounds. According to the invention, techniques can be adapted for the production of single-chain antibodies specific to a TDFRP compound (see, e.g., U.S. Pat. No. 4,946,778). In addition, methods can be adapted for the construction of Fab expression libraries (see, e.g., Huse, et al., 1989. Science 246:

1275-1281) to allow rapid and effective identification of monoclonal Fab fragments with the desired specificity for a TDFRP compound, e.g., a polypeptide or derivatives, fragments, analogs or homologs thereof. Non-human antibodies can be "humanized" by techniques well known in the art. See, e.g., U.S. Pat. No. 5,225,539. Antibody fragments that contain the idiotypes to a TDFRP compound can be produced by techniques known in the art including, but not limited to: (i) an F(ab')$_2$ fragment produced by pepsin digestion of an antibody molecule; (ii) an Fab fragment generated by reducing the disulfide bridges of an F(ab')$_2$ fragment; (iii) an Fab fragment generated by the treatment of the antibody molecule with papain and a reducing compound; and (iv) Fv fragments.

Additionally, recombinant anti-TDFRP compound antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in International Application No. PCT/US86/02269; European Patent Application No. 184,187; European Patent Application No. 171,496; European Patent Application No. 173,494; PCT International Publication No. WO 86/01533; U.S. Pat. Nos. 4,816,567; 5,225, 539; European Patent Application No. 125,023; Better, et al., 1988. Science 240: 1041-1043; Liu, et al., 1987. Proc. Natl. Acad. Sci. USA 84: 3439-3443; Liu, et al., 1987. J. Immunol. 139: 3521-3526; Sun, et al., 1987. Proc. Natl. Acad. Sci. USA 84: 214-218; Nishimura, et al., 1987. Cancer Res. 47: 999-1005; Wood, et al., 1985. Nature 314:446-449; Shaw, et al., 1988. J. Natl. Cancer Inst. 80: 1553-1559); Morrison (1985) Science 229:1202-1207; Oi, et al. (1986) BioTechniques 4:214; Jones, et al., 1986. Nature 321: 552-525; Verhoeyan, et al., 1988. Science 239: 1534; and Beidler, et al., 1988. J. Immunol. 141: 4053-4060. Each of the above citations are incorporated herein by reference in their entirety.

In one embodiment, methods for the screening of antibodies that possess the desired specificity to the TDFRP compounds include, but are not limited to, enzyme-linked immunosorbent assay (ELISA) and other immunologically-mediated techniques known within the art. In a specific embodiment, selection of antibodies that are specific to a particular domain of a TDFRP compound is facilitated by generation of hybridomas that bind to the fragment of a TDFRP compound possessing such a domain. Thus, antibodies that are specific for a desired domain within a TDFRP compound, or derivatives, fragments, analogs or homologs thereof, are also provided herein.

Anti-TDFRP compound antibodies can be used in methods known within the art relating to the localization and/or quantitation of a TDF polypeptide or TDFRP compound (e.g., for use in measuring levels of the TDF polypeptide or TDFRP compound within appropriate physiological samples, for use in diagnostic methods, for use in imaging the polypeptide, and the like). In a given embodiment, antibodies for TDFRP compounds, or derivatives, fragments, analogs or homologs thereof that contain the antibody derived binding domain, are utilized as pharmacologically-active compounds (hereinafter "Therapeutics").

An anti-TDFRP compound antibody (e.g., monoclonal antibody) can be used to isolate a TDFRP compound or TDF polypeptide by standard techniques, such as affinity chromatography or immunoprecipitation. An anti-TDFRP compound antibody can facilitate the purification of natural TDF polypeptide from cells and of recombinantly-produced TDFRP compound expressed in host cells. Moreover, an anti-TDFRP compound antibody can be used to detect TDF polypeptide or TDFRP compounds (e.g., in a cellular lysate or cell supernatant) in order to evaluate the abundance and pattern of expression of the TDF polypeptide or TDFRP compound. Anti-TDFRP compound antibodies can be used diagnostically to monitor polypeptide levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{32}$P, $^{125}$I, $^{131}$I, $^{35}$S, $^{33}$P, $^{14}$C, $^{13}$C, or $^3$H.

III. Measuring the Binding or Biological Activity of TDFRP Compounds

A. TDF Agonists and Antagonists

TDFRP compounds can function as either TDF receptor agonists (i.e., mimetics) or as TDF receptor antagonists, as well as to the TDF, itself. An agonist of the TDFR (or TDF) can retain substantially the same, or a subset of, the biological activities of the naturally occurring form of the TDF polypeptide. An antagonist of the TDFRP compound (or TDF) can inhibit one or more of the activities of the naturally occurring form of the TDF polypeptide by, for example, competitively binding to a downstream or upstream member of a cellular signaling cascade, which includes the TDF receptor polypeptide. Thus, specific biological effects can be elicited by treatment with a variant of limited function. In one embodiment, treatment of a subject with a variant having a subset of the biological activities of the naturally occurring form of the polypeptide has fewer side effects in a subject relative to treatment with the naturally occurring form of the TDF polypeptide. For example, ALK-3 receptors are more prevalent in kidney tissue, while ALK-6 receptors are more prevalent in bone tissue; the native BMP-7 protein binds to ALK-6 with a higher affinity, and a potential side effect of BMP-7 therapy in kidney disease is osteogenesis. It is an object of the present invention to provide TDFRP compound that preferentially binds one ALK receptor compared with the binding affinity of the TDFRP compound for other ALK receptors, thereby reducing undesirable cellular response, e.g., side effects such as, but not limited to, cellular response in non-target tissue. In a preferred embodiment, TDFRP compounds are selected and designed for increased specificity to ALK-3 and lowered affinity to ALK-6 receptors, thereby reducing undesirable osteogenesis in a subject being treated for kidney disorders. In another embodiment, the TDFRP compound may preferentially signal through specific ALK receptors by targeting the compounds to the desired tissues or cell populations.

Accordingly, the compounds disclosed as SEQ ID NOs:1-314 are used as agonists or antagonists of TDF polypeptides or TDF receptors, and are used, for example, to modulate signal transduction across a cell membrane of a cell expressing, e.g., TDF Type I or TDF Type II receptors. Modulation of signal transduction in such cells appears to occur as a result of specific binding interaction of the compounds disclosed as SEQ ID NOs:1-314 with one or more cell surface receptors, including co-receptors (i.e. DRAGON molecules and related family members). Specific interaction means binding of the compounds to a TDF receptor with an equilibrium dissociation constant greater than $10^6$ M$^{-1}$. A cell surface bound membrane structure also may enhance the specificity of the binding interaction. Extracellular molecules may modulate the specificity and activity of compound interaction with the TDF receptors. Variants of the TDFRP compounds that function as either TDF agonists (i.e., mimetics) or as TDFRP antagonists can be identified by screening libraries of mutants (e.g., truncation mutants) of the TDFRP compound for TDF agonist or antagonist activity.

B. Measurement of TDFRP Binding

In one embodiment a TDFRP binding assay refers to a competitive assay format wherein a TDF receptor, its macromolecular ligand and a TDFRP are mixed under conditions suitable for binding between the TDF receptor and the ligand and assessing the amount of binding between the TDF receptor and its ligand. The amount of binding is compared with a suitable control, which can be the amount of binding in the absence of the TDFRP, the amount of the binding in the presence of a known inhibitor, or both. The amount of binding can be assessed by any suitable method. Binding assay methods include, for example, ELISA, radioreceptor binding assays, scintillation proximity assays, cell surface receptor binding assays, fluorescence energy transfer assays, liquid chromatography, membrane filtration assays, and the like.

In a typical ligand/receptor binding assay useful in the practice of this invention, purified peptides having a known, quantifiable affinity for a pre-selected receptor (see, for example, Ten Dijke et al. (1994) Science 264:101-103, the disclosure of which is incorporated herein by reference) is labeled with a detectable moiety, for example, a radiolabel, a chromogenic label, or a fluorogenic label. Aliquots of purified receptor, receptor binding domain fragments, or cells expressing the receptor of interest on their surface are incubated with labeled peptide in the presence of various concentrations of the unlabeled peptide. The relative binding affinity of the peptide may be measured by quantitating the ability of the candidate (unlabeled peptide) to inhibit the binding of labeled peptide with the receptor. In performing the assay, fixed concentrations of the receptor and the peptide are incubated in the presence and absence of unlabeled peptide. Sensitivity may be increased by pre-incubating the receptor with the TDFRP analog before adding labeled peptide. After the labeled competitor has been added, sufficient time is allowed for adequate competitor binding, and then free and bound labeled peptide are separated from one another, and one or the other measured. Labels useful in the practice of the screening procedures include radioactive labels (e.g., $^{125}$I, $^{131}$I, $^{111}$In or $^{77}$Br), chromogenic labels, spectroscopic labels (such as those disclosed in Haughland (1994) "Handbook of Fluorescent and Research Chemicals 5 ed." by Molecular Probes, Inc., Eugene, Oreg.), or conjugated enzymes having high turnover rates, for example, horseradish peroxidase, alkaline phosphatase, or beta-galactosidase, used in combination with chemiluminescent or fluorogenic substrates. Maximum binding signal is the signal measured in the presence of the native ligand, but without TDFRP present in the assay mixture. Background signal is the binding signal measured without the native ligand.

In a typical compound/receptor binding assay useful in the practice of this invention, purified reference compounds having a known, quantifiable affinity for a pre-selected receptor are labeled with a detectable moiety, for example, a radiolabel, a chromogenic label, or a fluorogenic label (see, for example, Ten Dijke et al. (1994) Science 264:101-103, the disclosure of which is incorporated herein by reference). Aliquots of purified receptor, receptor binding domain fragments, or cells expressing the receptor of interest on their surface are incubated with labeled compounds in the presence of various concentrations of the unlabeled compounds.

Typically, the relative binding affinity of the peptide may be measured by quantitating the ability of the candidate (unlabeled peptide) to inhibit the binding of labeled peptide with the receptor. In performing the assay, fixed concentrations of the receptor and the peptide are incubated in the presence and absence of unlabeled peptide. Sensitivity may be increased by pre-incubating the receptor with the TDFRP compound before adding labeled peptide. After the labeled competitor has been added, sufficient time is allowed for adequate competitor binding, and then free and bound labeled peptide are separated from one another, and one or the other measured. Labels useful in the practice of the screening procedures include radioactive labels (e.g., $^{125}$I, $^{131}$I, $^{51}$Cr, $^{111}$In or $^{77}$Br), chromogenic labels, spectroscopic labels (such as those disclosed in Haughland (1994) "Handbook of Fluorescent and Research Chemicals 5 ed." by Molecular Probes, Inc., Eugene, Oreg.), or conjugated enzymes having high turnover rates, for example, horseradish peroxidase, alkaline phosphatase, or beta-galactosidase, used in combination with chemiluminescent or fluorogenic substrates.

In another embodiment, a TDFRP binding assay refers to mixing a TDFRP binding ligand and a TDFRP compound under conditions suitable for binding between the TDFRP binding ligand and the TDFRP compound and assessing the degree of binding between the TDFRP binding ligand and the TDFRP compound, for example, measuring the dissociation constant and deriving the equilibrium binding constant through Scatchard or non-linear regression analysis. The amount of binding is compared with a suitable control the amount of the binding in the presence of a known inhibitor, or both. The amount of binding can be assessed by any suitable method. Binding assay methods include, for example, ELISA, radioreceptor binding assays, scintillation proximity assays, cell surface receptor binding assays, fluorescence energy transfer assays, liquid chromatography, membrane filtration assays, and the like.

Biophysical assays for the direct measurement of TDFRP binding to TDFRP-binding ligands are, for example, nuclear magnetic resonance, fluorescence, fluorescence polarization, surface plasmon resonance (BIACORE chips) and the like. TDFRP binding ligands, include, but are not limited to, TDF receptor, anti-TDFRP antibody, lipids, small molecules, and nucleic acids, e.g., DNA and RNA. Specific binding is determined by standard assays known in the art, for example, radioligand binding assays, ELISA, FRET, immunoprecipitation, SPR, NMR (2D-NMR), mass spectroscopy and the like. Co-crystals of the TDFRP compounds and TDFRP binding ligands, for example, but not limited to, TDF receptor, anti-TDFRP antibody, lipids, small molecules, and nucleic acids, e.g., DNA and RNA, are also provided by the present invention as a method of determining molecular interactions. Conditions suitable for binding between the TDFRP ligand and a TDFRP compound will depend on the compound and its ligand and can be readily determined by one of ordinary skill in the art. Further, the methods disclosed in references summarized in Tables 2 and 3 are useful for the measurement of ligand binding to ALK receptors. These methods are useful in identifying ALK receptor-selective TDFRP compounds of the present invention.

C. Measurement of TDFRP Biological Activity

The biological activity, namely the agonist or antagonist properties of TDF polypeptides or TDFRP compounds can be characterized using any conventional in vivo and in vitro assays that have been developed to measure the biological activity of the TDFRP compound, a TDF polypeptide or a TDF signaling pathway component. Specific in vivo assays for testing the efficacy of a compound or analog, e.g., TDFRP compound, in an application to repair or regenerate damaged bone, liver, kidney, or nerve tissue, periodontal tissue, including cementum and/or periodontal ligament, gastrointestinal and renal tissues, and immune-cell mediated damages tissues are disclosed in publicly available documents, which include, for example, EP 0575,555; WO93/04692; WO93/05751; WO/06399; WO94/03200; WO94/06449; and WO94/06420, as well as, the references summarized in Table 2 and Table 3, each incorporated herein by reference in their entireties. Example 2 illustrates in vitro functional assays for TDFRPs. Example 3 illustrates in vivo functional assays for TDF or TDFRP compounds.

IV. TDFRP Transgenic Animals

In still another embodiment, a transgenic animal, e.g., a mammal having a nucleic acid encoding a TDFRP compound is provided. The host cells of the invention can also be used to produce non-human transgenic animals. For example, in one embodiment, a host cell of the invention is a fertilized oocyte or an embryonic stem cell into which TDFRP polypeptide-coding sequences have been introduced. Such host cells can then be used to create non-human transgenic animals in which exogenous TDFRP sequences have been introduced into their genome or homologous recombinant animals in which endogenous TDFRP sequences have been altered. Such animals are useful for studying the function and/or activity of TDFRP polypeptide and for identifying and/or evaluating modulators of TDFRP polypeptide activity.

A transgenic animal of the invention can be created by introducing a TDFRP-encoding nucleic acid into the male pronuclei of a fertilized oocyte (e.g., by microinjection, retroviral infection) and allowing the oocyte to develop in a pseudopregnant female foster animal. The TDFRP cDNA sequences of can be introduced as a transgene into the genome of a non-human animal. Intronic sequences and polyadenylation signals can also be included in the transgene to increase the efficiency of expression of the transgene. A tissue-specific regulatory sequence(s) can be operably-linked to the TDFRP transgene to direct expression of TDFRP polypeptide to particular cells. Methods for generating transgenic animals via embryo manipulation and microinjection, particularly animals such as mice, have become conventional in the art and are described, for example, in U.S. Pat. Nos. 4,736,866; 4,870,009; and 4,873,191; and Hogan, 1986. In: MANIPULATING THE MOUSE EMBRYO, Cold Spring Harbor Laboratory Press, Cold Spring Harbor, N.Y. Similar methods are used for production of other transgenic animals. A transgenic founder animal can be identified based upon the presence of the TDFRP transgene in its genome and/or expression of TDFRP mRNA in tissues or cells of the animals. A transgenic founder animal can then be used to breed additional animals carrying the transgene. Moreover, transgenic animals carrying a transgene-encoding TDFRP polypeptide can further be bred to other transgenic animals carrying other transgenes.

In the homologous recombination vector, the TDFRP gene is flanked at its 5'- and 3'-termini by additional nucleic acid to allow for homologous recombination to occur between the exogenous TDFRP gene carried by the vector and an endogenous gene in an embryonic stem cell. The additional flanking nucleic acid is of sufficient length for successful homologous recombination with the endogenous gene. Typically, several kilobases of flanking DNA (both at the 5'- and 3'-termini) are included in the vector. See, e.g., Thomas, et al., 1987. Cell 51: 503 for a description of homologous recombination vectors. The vector is then introduced into an embryonic stem cell line (e.g., by electroporation) and cells in which the introduced TDFRP gene has homologously-recombined with an endogenous gene are selected. See, e.g., Li, et al., 1992. Cell 69: 915.

The selected cells are then injected into a blastocyst of an animal (e.g., a mouse) to form aggregation chimeras. See, e.g., Bradley, 1987. In: TERATOCARCINOMAS AND EMBRYONIC STEM CELLS: A PRACTICAL APPROACH, Robertson, ed. IRL, Oxford, pp. 113-152. A chimeric embryo can then be implanted into a suitable pseudopregnant female foster animal and the embryo brought to term. Progeny harboring the homologously-recombined DNA in their germ cells can be used to breed animals in which all cells of the animal contain the homologously-recombined DNA by germline transmission of the transgene. Methods for constructing homologous recombination vectors and homologous recombinant animals are described further in Bradley, 1991. Curr. Opin. Biotechnol. 2: 823-829; PCT International Publication Nos.: WO 90/11354; WO 91/01140; WO 92/0968; and WO 93/04169.

In another embodiment, transgenic non-human animals can be produced that contain selected systems that allow for regulated expression of the TRFRP transgene. One example of such a system is the cre/loxP recombinase system of bacteriophage P1. For a description of the cre/loxP recombinase system, See, e.g., Lakso, et al., 1992. Proc. Natl. Acad. Sci. USA 89: 6232-6236. Another example of a recombinase system is the FLP recombinase system of *Saccharomyces cerevisiae*. See, O'Gorman, et al., 1991. Science 251:1351-4255. If a cre/loxP recombinase system is used to regulate expression of the transgene, animals containing transgenes encoding both the Cre recombinase and a selected polypeptide are required. Such animals can be provided through the construction of "double" transgenic animals, e.g., by mating two transgenic animals, one containing a transgene encoding a selected polypeptide and the other containing a transgene encoding a recombinase.

Clones of the non-human transgenic animals described herein can also be produced according to the methods described in Wilmut, et al., 1997. Nature 385: 810-813. In brief, a cell (e.g., a somatic cell) from the transgenic animal can be isolated and induced to exit the growth cycle and enter G0 phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell (e.g., the somatic cell) is isolated.

V. Pharmaceutical Compositions

The TDFRP-encoding nucleic acid molecules, TDFRP compounds, and anti-TDFRP compound antibodies (also referred to herein as "active compounds") of the invention, and derivatives, fragments, analogs and homologs thereof, can be incorporated into pharmaceutical compositions suitable for administration. Such compositions typically comprise the nucleic acid molecule, polypeptide, or antibody with or without a pharmaceutically acceptable carrier. As used herein, "pharmaceutically acceptable carrier" is intended to include any and all solvents, dispersion media, coatings, antibacterial and antifungal compounds, isotonic and absorption delaying compounds, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, Ringer's solutions, dextrose solution, and 5% human serum albumin Liposomes and non-aqueous vehicles such as fixed oils may also be used. The use of such media and compounds for pharmaceutically active substances is well known in the art. Except insofar as any conventional media or compound is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal compounds, for example, parabens, chlorobutanol, phenol, ascorbic acid, thimerosal, and the like. In many cases, it will be preferable to include isotonic compounds, for example, sugars, polyalcohols such as manitol, sorbitol, sodium chloride in the composition. Prolonged absorption of the injectable compositions can be brought about by including in the composition a compound, which delays absorption, for example, aluminum monostearate and gelatin.

Sterile injectable solutions can be prepared by incorporating the active compound (e.g., a TDFRP compound or anti-TDFRP compound antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared as pharmaceutical compositions in the form of suppositories (e.g., with conventional suppository bases such as cocoa butter and other glycerides) or retention enemas for rectal delivery. The compounds can be prepared for use in conditioning or treatment of ex vivo explants or implants.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen, et al., 1994. Proc. Natl. Acad. Sci. USA 91: 3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system. The pharmaceutical compositions can be included in a container, pack, or dispenser together with instructions for administration.

VI. Screening and Detection Methods

The compounds of the invention can be used to express TDFRP compounds (e.g., via a recombinant expression vector in a host cell in gene therapy applications), to detect TDFRP mRNA (e.g., in a biological sample) or a genetic lesion in a TDFRP gene, and to modulate TDFRP compound activity, as described further, below. In addition, the TDFRP polypeptides can be used to screen drugs or compounds that modulate the TDF polypeptide or TDFRP compound activity or expression as well as to treat disorders characterized by insufficient or excessive production of TDF polypeptides or production of TDF polypeptide forms that have decreased or aberrant activity compared to TDF wild-type polypeptide. In addition, the anti-TDFRP compound antibodies of the invention can be used to detect and isolate TDF or TDFRP compounds and modulate their activity. Accordingly, the present invention further includes novel compounds identified by the screening assays described herein and uses thereof for treatments as described, supra.

VII. Screening Assays

The invention provides for methods for identifying modulators, i.e., candidate or test compounds or compounds (e.g., peptides, peptidomimetics, small molecules or other drugs) that bind to TDFRP compound or TDF polypeptides or have a stimulatory or inhibitory effect on, e.g., TDFRP compound or TDF polypeptide expression or activity (also referred to herein as "screening assays"). The invention also includes compounds identified in the screening assays described herein.

In one embodiment, the invention includes assays for screening candidate or test compounds, which bind to or modulate the activity TDFRP compound or TDF polypeptides or biologically-active portions thereof. The compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. See, e.g., Lam, 1997. Anticancer Drug Design 12: 145.

Libraries of chemical and/or biological mixtures, such as fungal, bacterial, or algal extracts, are known in the art and can be screened with any of the assays described as well as those known to skilled artisans. Examples of methods for the synthesis of molecular libraries can be found in the scientific literature, for example in: DeWitt, et al., 1993. Proc. Natl. Acad. Sci. U.S.A. 90: 6909; Erb, et al., 1994. Proc. Natl. Acad. Sci. U.S.A. 91: 11422; Zuckermann, et al., 1994. J. Med. Chem. 37: 2678; Cho, et al., 1993. Science 261: 1303; Carrell, et al., 1994. Angew. Chem. Int. Ed. Engl. 33: 2059; Carell, et al., 1994. Angew. Chem. Int. Ed. Engl. 33: 2061; and Gallop, et al., 1994. J. Med. Chem. 37: 1233.

Libraries of compounds can be presented in solution (e.g., Houghten, 1992. Biotechniques 13: 412-421), or on beads (Lam, 1991. Nature 354: 82-84), on chips (Fodor, 1993. Nature 364: 555-556), bacteria (Ladner, U.S. Pat. No. 5,223,409), spores (Ladner, U.S. Pat. No. 5,233,409), plasmids (Cull, et al., 1992. Proc. Natl. Acad. Sci. USA 89: 1865-1869) or on phage (Scott and Smith, 1990. Science 249: 386-390; Devlin, 1990. Science 249: 404-406; Cwirla, et al., 1990. Proc. Natl. Acad. Sci. U.S.A. 87: 6378-6382; Felici, 1991. J. Mol. Biol. 222: 301-310; Ladner, U.S. Pat. No. 5,233,409.).

Determining the ability of a compound to modulate the activity of a TDFRP polypeptide can be accomplished, for example, by determining the ability of the TDFRP compound to bind to or interact with a TDFRP compound target molecule. A target molecule is a molecule that a TDFRP compound binds to or interacts with, for example, a molecule on the surface of a cell which expresses a TDFRP interacting polypeptide, a molecule on the surface of a second cell, a molecule in the extracellular milieu, a molecule associated with the internal surface of a cell membrane or a cytoplasmic molecule. A TDFRP compound target molecule can be a non-TDFRP compound molecule or a TDFRP polypeptide or polypeptide of the invention. In one embodiment, a TDFRP compound target molecule is a component of a signal transduction pathway that facilitates transduction of an extracellular signal (e.g., a signal generated by binding of a compound to a membrane-bound TDF receptor molecule) through the cell membrane and into the cell. The target, for example, can be a second intracellular polypeptide that has catalytic activity or a polypeptide that facilitates the association of downstream signaling molecules with TDF receptor polypeptide. The compounds of the present invention either agonize or antagonize such interactions and the resultant biological responses, measured by the assays described.

Determining the ability of the TDFRP compound to bind to or interact with a TDFRP compound target molecule can be accomplished by one of the methods described above for determining direct binding. In one embodiment, determining the ability of the TDFRP compound to bind to or interact with a TDFRP compound target molecule can be accomplished by determining the activity of the target molecule. For example, the activity of the target molecule can be determined by detecting induction of a cellular second messenger of the target (i.e., intracellular $Ca^{2+}$, diacylglycerol, IP3, etc.), detecting catalytic/enzymatic activity of the target and appropriate substrate, detecting the induction of a reporter gene (comprising a TDFRP-responsive regulatory element operatively linked to a nucleic acid encoding a detectable marker, e.g., luciferase), or detecting a cellular response, for example, cell survival, cellular differentiation, or cell proliferation.

In yet another embodiment, an assay of the invention is a cell-free assay comprising contacting a TDFRP compound or biologically-active portion thereof with a test compound and determining the ability of the test compound to bind to the TDFRP compound or biologically-active portion thereof. Binding of the test compound to the TDFRP compound can be determined either directly or indirectly as described above. In one such embodiment, the assay comprises contacting the TDFRP compound or biologically-active portion thereof with a known compound which binds TDFRP to form an assay mixture, contacting the assay mixture with a test compound, and determining the ability of the test compound to interact with a TDFRP compound, wherein determining the ability of the test compound to interact with a TDFRP compound comprises determining the ability of the test compound to preferentially bind to TDFRP or biologically-active portion thereof as compared to the known compound.

In still another embodiment, an assay is a cell-free assay comprising contacting TDFRP compound or biologically-active portion thereof with a test compound and determining the ability of the test compound to modulate (e.g. stimulate or inhibit) the activity of the TDFRP compound or biologically-active portion thereof. Determining the ability of the test compound to modulate the activity of TDFRP can be accomplished, for example, by determining the ability of the TDFRP compound to bind to a TDFRP compound target molecule by one of the methods described above for determining direct binding. In an alternative embodiment, determining the ability of the test compound to modulate the activity of TDFRP compound can be accomplished by determining the ability of the TDFRP compound to further modulate a TDFRP compound target molecule. For example, the catalytic/enzymatic activity of the target molecule on an appropriate substrate can be determined as described, supra.

In yet another embodiment, the cell-free assay comprises contacting the TDFRP compound or biologically-active portion thereof with a known compound which binds TDFRP compound to form an assay mixture, contacting the assay mixture with a test compound, and determining the ability of the test compound to interact with a TDFRP compound, wherein determining the ability of the test compound to interact with a TDFRP compound comprises determining the ability of the TDFRP compound to preferentially bind to or modulate the activity of a TDFRP compound target molecule.

In more than one embodiment of the above assay methods of the invention, it can be desirable to immobilize either TDFRP compound or its target molecule to facilitate separation of complexed from uncomplexed forms of one or both of the polypeptides, as well as to accommodate automation of the assay. Binding of a test compound to TDFRP compound, or interaction of TDFRP compound with a target molecule in the presence and absence of a candidate compound, can be accomplished in any vessel suitable for containing the reactants. Examples of such vessels include microtiter plates, test tubes, and micro-centrifuge tubes. In one embodiment, a fusion polypeptide can be provided that adds a domain that allows one or both of the polypeptides to be bound to a matrix. For example, GST-TDFRP fusion polypeptides or GST-target fusion polypeptides can be adsorbed onto glutathione sepharose beads (Sigma Chemical, St. Louis, Mo.) or glutathione derivatized microtiter plates, that are then combined with the test compound or the test compound and either the non-adsorbed target polypeptide or TDFRP compound, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described, supra. Alternatively, the complexes can be dissociated from the matrix, and the level of TDFRP compound binding or activity determined using standard techniques.

Other techniques for immobilizing polypeptides on matrices can also be used in the screening assays of the invention. For example, either the TDFRP compound or its target molecule can be immobilized utilizing conjugation of biotin and streptavidin. Biotinylated TDFRP compound or target molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, antibodies reactive with TDFRP compound or target molecules, but which do not interfere with binding of the TDFRP compound to its target molecule, can be derivatized to the wells of the plate, and unbound target or TDFRP compound trapped in the wells by antibody conjugation. Methods for detecting such complexes, in addition to those described above for the GST-immobilized complexes, include immunodetection of complexes using antibodies reactive with the TDFRP compound or target molecule, as well as enzyme-linked assays that rely on detecting an enzymatic activity associated with the TDFRP compound or target molecule.

In another embodiment, modulators of TDFRP compound expression are identified in a method wherein a cell is contacted with a candidate compound and the expression of TDFRP mRNA or polypeptide in the cell is determined. The level of expression of TDFRP mRNA or polypeptide in the presence of the candidate compound is compared to the level of expression of TDFRP mRNA or polypeptide in the absence of the candidate compound. The candidate compound can then be identified as a modulator of TDFRP mRNA or polypeptide expression based upon this comparison. For example, when expression of TDFRP mRNA or polypeptide is greater (i.e., statistically significantly greater) in the presence of the candidate compound than in its absence, the candidate compound is identified as a stimulator of TDFRP mRNA or polypeptide expression. Alternatively, when expression of TDFRP mRNA or polypeptide is less (statistically significantly less) in the presence of the candidate compound than in its absence, the candidate compound is identified as an inhibitor of TDFRP mRNA or polypeptide expression. The level of TDFRP mRNA or polypeptide expression in the cells can be determined by methods described herein for detecting TDFRP mRNA or polypeptide.

In yet another aspect of the invention, the TDFRP compounds can be used as "bait polypeptides" in a two-hybrid assay or three hybrid assay (see, e.g., U.S. Pat. No. 5,283,317; Zervos, et al., 1993. Cell 72: 223-232; Madura, et al., 1993. J. Biol. Chem. 268: 12046-12054; Bartel, et al., 1993. Biotechniques 14: 920-924; Iwabuchi, et al., 1993. Oncogene 8: 1693-1696; and Brent WO 94/10300), to identify other molecules, e.g., polypeptides, that bind to or interact with TDFRP ("TDFRP-binding molecules" or "TDFRP-bp") and modulate TDFRP activity. Such TDFRP-binding molecules are also likely to be involved in the propagation of signals by the TDFRP compounds as, for example, upstream or downstream elements of a TDF pathway.

The two-hybrid system is based on the modular nature of most transcription factors, which consist of separable DNA-binding and activation domains. Briefly, the assay utilizes two different DNA constructs. In one construct, the gene that codes for TDFRP compound is fused to a gene encoding the DNA binding domain of a known transcription factor (e.g., GAL-4). In the other construct, a DNA sequence, from a library of DNA sequences, that encodes an unidentified polypeptide ("prey" or "sample") is fused to a gene that codes for the activation domain of the known transcription factor. If the "bait" and the "prey" polypeptides are able to interact, in vivo, forming a TDFRP-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the polypeptide, which interacts with TDFRP compound.

In still another embodiment, a system comprising structural information relating to the TDFRP compound atomic coordinates can be obtained by biophysical techniques, e.g., x-ray diffraction. Binding between a TDFRP compound and a compound can be assessed by x-ray diffraction to determine the x-ray crystal structure of the TDFRP compound complexes, e.g., target polypeptide/drug complex. Alternatively; NMR may be used to analyze the change in chemical shifts observed after a compound binds with the TDFRP compound. Such approaches may be used to screen for compounds based on their binding interactions with TDFRP compounds.

The invention further pertains to TDFRP compounds identified by the aforementioned screening assays and uses thereof for treatments as described herein.

VIII. Detection Assays

A. Detection of TDFRP Expression

An exemplary method for detecting the presence or absence of TDFRP compound in a biological sample involves obtaining a biological sample from a test subject and contacting the biological sample with a compound or a compound capable of detecting TDFRP compound or nucleic acid (e.g., mRNA, genomic DNA) that encodes TDFRP compound such that the presence of TDFRP compound is detected in the biological sample. A compound for detecting TDFRP mRNA or genomic DNA is a labeled nucleic acid probe capable of hybridizing to TDFRP mRNA or genomic DNA. The nucleic acid probe can be, for example, a full-length TDFRP nucleic acid or a portion thereof, such as an oligonucleotide of at least 5, 15, 30, 50, 100, 250 or 500 nucleotides in length and sufficient to specifically hybridize under stringent conditions to TDFRP mRNA or genomic DNA. Other suitable probes for use in the diagnostic assays of the invention are described herein.

An example of a compound for detecting a TDFRP compound is an antibody raised against SEQ ID NOs:1-314, capable of binding to the TDFRP compound, preferably an antibody with a detectable label. Antibodies can be polyclonal, or more preferably, monoclonal. An intact antibody, or a fragment thereof (e.g., Fab or F(ab)$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another compound that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. That is, the detection method of the invention can be used to detect TDFRP mRNA, polypeptide, or genomic DNA in a biological sample in vitro as well as in vivo. For example, in vitro techniques for detection of TDFRP mRNA include RT-PCR, Northern hybridizations and in situ hybridizations. In vitro techniques for detection of TDFRP compound include enzyme linked immunosorbent assays (ELISAs), Western blots, immunoprecipitations, and immunofluorescence. In vitro techniques for detection of TDFRP genomic DNA include Southern hybridizations. Furthermore, in vivo techniques for detection of TDFRP compound include introducing into a subject a labeled anti-TDFRP antibody. For example, the antibody can be labeled with a radioactive marker whose presence and location in a subject can be detected by standard imaging techniques. In one embodiment, the biological sample contains polypeptide molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or compound capable of detecting TDFRP compound, mRNA, or genomic DNA, such that the presence of TDFRP compound, mRNA or genomic DNA is detected in the biological sample, and comparing the presence of TDFRP compound, mRNA or genomic DNA in the control sample with the presence of TDFRP compound, mRNA or genomic DNA in the test sample.

The invention also encompasses kits for detecting the presence of TDFRP compound in a biological sample. For example, the kit can comprise: a labeled compound or compound capable of detecting TDFRP compound or mRNA in a biological sample; means for determining the amount of TDFRP compound in the sample; and means for comparing the amount of TDFRP compound in the sample with a standard. The compound or compound can be packaged in a suitable container. The kit can further comprise instructions for using the kit to detect TDFRP compound or nucleic acid.

B. Predictive Medicine

The invention also pertains to the field of predictive medicine in which diagnostic assays, prognostic assays, pharmacogenomics, and monitoring clinical trials are used for prognostic (predictive) purposes to treat prophylactically a subject. Accordingly, one aspect of the invention relates to diagnostic assays for determining TDFRP compound target molecule expression as well as TDFRP compound target molecule activity, in the context of a biological sample (e.g., blood, serum, cells, tissue) to thereby determine whether an individual is afflicted with a disease or disorder, or is at risk of developing a disorder, associated with aberrant TDFRP compound target molecule expression or activity.

The invention also provides for prognostic (or predictive) assays for determining whether an individual is at risk of developing a disorder associated with TDFRP compound target molecule expression or activity. Such assays can be used for prognostic or predictive purpose to thereby prophylactically treat an individual prior to the onset of a disorder characterized by or associated with a TDFRP compound target polypeptide. Furthermore, the methods of the present invention can also be used to assess whether an individual expresses a TDFRP compound target molecule or a polymorphic form of the target polypeptide in instances where a TDFRP compound of the present invention has greater affinity for the TDFRP compound target molecule for its polymorphic form (or vice versa).

The levels of certain polypeptides in a particular tissue (or in the blood) of a subject may be indicative of the toxicity, efficacy, rate of clearance, or rate of metabolism of a given drug when administered to the subject. The methods described herein can also be used to determine the levels of such polypeptide(s) in subjects to aid in predicting the response of such subjects to these drugs. Another aspect of the invention provides methods for determining TDFRP compound activity in an individual to thereby select appropriate therapeutic or prophylactic compounds for that individual (referred to herein as "pharmacogenomics"). Pharmacogenomics allows for the selection of compounds (e.g., drugs) for therapeutic or prophylactic treatment of an individual based on the genotype of the individual (e.g., the genotype of the individual examined to determine the ability of the individual to respond to a particular compound.)

C. Prognostic Assays

The binding of a TDFRP compound to a TDFRP compound target molecule, e.g., TDF receptor, can be utilized to identify a subject having or at risk of developing a disorder associated with TDFRP compound target molecule expression or activity (which are described above). Alternatively, the prognostic assays can be utilized to identify a subject having or at risk for developing the disease or disorder. Thus, the invention provides a method for identifying a disease or disorder associated with aberrant TDFRP compound target expression or activity in which a test sample is obtained from a subject and TDFRP compound binding or activity is detected, wherein the presence of an alteration of TDFRP compound binding or activity is diagnostic for a subject having or at risk of developing a disease or disorder associated with aberrant TDFRP compound target expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered a compound (e.g., an agonist, antagonist, peptidomimetic, polypeptide, peptide, nucleic acid, small molecule, or other drug candidate) to treat a TDF-associated disease or disorder associated with aberrant TDFRP compound target expression or activity. For example, such methods can be used to determine whether a subject can be effectively treated with a compound for a TDF-associated disorder. Thus, the invention provides methods for determining whether a subject can be effectively treated with a compound for a disorder associated with aberrant TDFRP compound target expression or activity in which a test sample is obtained and TDFRP compound target is detected using TDFRP compound (e.g., wherein the presence of TDFRP compound target molecule is diagnostic for a subject that can be administered the compound to treat a disorder associated with aberrant TDFRP compound target molecule expression or activity).

The level of the TDFRP compound target molecule in a blood or tissue sample obtained from a subject is determined and compared with the level found in a blood sample or a sample from the same tissue type obtained from an individual who is free of the disease. An overabundance (or underabundance) of the TDFRP compound target molecule in the sample obtained from the subject suspected of having the TDF-associated disease compared with the sample obtained from the healthy subject is indicative of the TDF-associated disease in the subject being tested. Further testing may be required to make a positive diagnosis.

There are a number of diseases in which the degree of overexpression (or underexpression) of certain TDFRP compound target molecules, referred to herein as "prognostic polypeptides", is known to be indicative of whether a subject with the disease is likely to respond to a particular type of therapy or treatment. Thus, the method of detecting a TDFRP compound target molecule in a sample can be used as a method of prognosis, e.g., to evaluate the likelihood that the subject will respond to the therapy or treatment. The level of the relevant prognostic polypeptide in a suitable tissue or blood sample from the subject is determined and compared with a suitable control, e.g., the level in subjects with the same disease but who have responded favorably to the treatment. The degree to which the prognostic polypeptide is overexpressed (or underexpressed) in the sample compared with the control may be predictive of likelihood that the subject will not respond favorably to the treatment or therapy. The greater the overexpression (or underexpression) relative to the control, the less likely the subject will respond to the treatment. There are a number of diseases in which the degree of overexpression (or underexpression) of certain target polypeptides, referred to herein as "predictive polypeptides", is known to be indicative of whether a subject will develop a disease.

Thus, the method of detecting a TDFRP compound target molecule in a sample can be used as a method of predicting whether a subject will develop a disease. The level of the relevant predictive polypeptide in a suitable tissue or blood sample from a subject at risk of developing the disease is determined and compared with a suitable control, e.g., the level in subjects who are not at risk of developing the disease. The degree to which the predictive polypeptide is overexpressed (or underexpressed) in the sample compared with the control may be predictive of likelihood that the subject will develop the disease. The greater the overexpression (or underexpression) relative to the control, the more likely the subject will development the disease.

The methods described herein can be performed, for example, by utilizing pre-packaged diagnostic kits comprising at least one probe reagent, e.g., TDFRP compound described herein, which can be conveniently used, e.g., in clinical settings to diagnose patients exhibiting symptoms or family history of a disease or illness involving a TDFRP compound target molecule. Furthermore, any cell type or tissue in which TDFRP compound target molecule is expressed can be utilized in the prognostic assays described herein.

IX. Methods of Treatment

The invention provides for both prophylactic and therapeutic methods of treating a subject at risk of (or susceptible to) a disorder or having a disorder associated with aberrant TDF polypeptide or TDFRP compound target molecule expression or activity. TDF and TDFRP compound target molecules, such as TDF receptors, play a role in cell differentiation. Cell differentiation is the central characteristic of tissue morphogenesis. Tissue morphogenesis is a process involved in adult tissue repair and regeneration mechanisms. The degree of morphogenesis in adult tissue varies among different tissues and is related, among other things, to the degree of cell turnover in a given tissue.

The bone morphogenetic proteins are members of the transforming growth factor-beta superfamily. Ozkaynak et al. (EMBO J. 9: 2085-2093, 1990) purified a novel bovine osteogenic protein homolog, which they termed 'osteogenic protein-1' (OP-1; a.k.a., BMP-7). The authors used peptide sequences to clone the human genomic and cDNA clones of OP-1, later named BMP-7. The BMP-7 cDNAs predicted a 431-amino acid polypeptide that includes a secretory signal sequence. The TDFRP compounds described herein are structural mimetics of the biologically active regions of bone morphogenic proteins, for example, but not limited to, BMP-7 (OP-1), and related peptides. Biologically active regions include, for example, the Finger 1 and Finger 2 regions of BMP-7. Groppe et al. (Nature 420: 636-642, 2002) reported the crystal structure of the antagonist Noggin (602991) bound to BMP-7.

TDFRP compounds are useful to treat diseases and disorders that are amenable to treatment with BMP polypeptides. The references summarized in Table 2 and Table 3, as well as the following references (incorporated herein in their entireties) describe in vitro and in vivo assays for determining the efficacy of TDF polypeptides, e.g., BMP-7, or derivatives, in the prophylaxis and treatment of various disease states. These assays are appropriate for determining the biological activity of the TDFRP compounds disclosed herein. As such the TDFRP compounds of the invention are useful to alter, e.g., inhibit or accelerate, the ability to repair and regenerate diseased or damaged tissues and organs, as well as, to treat TDF-associated disorders. Particularly useful areas for TDFRP-based human and veterinary therapeutics include reconstructive surgery, the treatment of tissue degenerative diseases including, for example, renal disease, brain trauma, stroke, atherosclerosis, arthritis, emphysema, osteoporosis, cardiomyopathy, cirrhosis, degenerative nerve diseases, inflammatory diseases, and cancer, and in the regeneration of tissues, organs and limbs. The TDFRP compounds of the invention can also be used to promote or inhibit the growth and differentiation of muscle, bone, skin, epithelial, heart, nerve, endocrine, vessel, cartilage, periodontal, liver, retinal, and connective tissue, or any tissue where functional TDRFP compound target molecules are expressed. Accordingly, diseases associated with aberrant TDF polypeptide or TDFRP compound target molecule expression include viral infections, cancer, healing, neurodegenerative disorders, e.g., Alzheimer's Disease, Parkinson's Disorder, immune disorders, and bone disorders. For example, TDFRP-based therapeutic compositions are useful to induce regenerative healing of bone defects such as fractures, as well as, to preserve or restoring healthy metabolic properties in diseased tissue, e.g., osteopenic bone tissue.

Marker et al. (Genomics 28: 576-580, 1995) studied the distribution of BMP-7 transcripts at various anatomical sites disrupted by Holt-Oram syndrome (142900) mutations. They found BMP-7 expression in all structures that are altered in Holt-Oram patients, including the heart, proximal and distal forelimb, clavicle, and scapula, as well as other unaffected tissues.

Solursh et al. (Biochem. Biophys. Res. Commun 218: 438-443, 1996) examined developmental and temporal expression of OP-1 by hybridization with histologic sections of rat embryos during a 3-day period comprising the primitive streak stages to early limb bud stages. OP-1 expression was detected in the neuroepithelium of the optic vesicle at day E11.5 and was limited to the presumptive neural retina and developing lens placode. From E12.5-E13.5, they found expression in the neural retina, lens, and developing cornea.

You and Kruse (Invest. Ophthal. Vis. Sci. 43: 72-81, 2002) studied corneal myofibroblast differentiation and signal transduction induced by the TGF-β family members activin A and BMP-7. They found that activin A induced phosphorylation of SMAD2, and BMP-7 induced SMAD1, both of which were inhibited by follistatin. The TGF-β proteins have different functions in the cornea.

TDFRP compounds can be used in the prophylaxis or treatment of coronary atherosclerosis (FIG. 2). Induction of BMPs and subsequent inhibition of vascular smooth muscle cell growth and/or induction of vascular bone formation can contribute to the mechanisms by which statins increase plaque stability in patients with coronary atherosclerosis (Emmanuele et al., Biochem Biophys Res Commun. 2003 Feb. 28; 302(1):67-72). Further, studies by Davies et al., (J Am Soc Nephrol. 2003 June; 14(6):1559-67) are consistent with BMP-7 deficiency as a pathophysiologic factor in chronic renal failure, and demonstrate its efficacy as a potential treatment of vascular calcification. Example 3 illustrates in vivo functional assays for TDFRP compounds as a potential treatment for chronic renal failure.

TDFRP compounds can be used to treat cancer, e.g., breast cancer and prostate cancer (FIG. 3). Schwalbe et al., (Int J. Oncol. 2003 July; 23(1):89-95) analyzed normal breast tissue and tumor tissue samples from 170 invasive ductal carcinomas of the breast by immunohistochemistry. BMP-7 expression was observed in normal breast tissue in the end buds, but not in the ductus lactiferus. BMP-7 protein was detected in all 170 tumor samples. The expression of BMP-7 was highly correlated with estrogen receptor levels (p</=0.01) and progesterone receptor levels (p</=0.01), which are important markers for breast cancer prognosis and therapy. Further, Masuda et al., (Prostate. 2003 Mar. 1; 54(4):268-74) demonstrated increased expression of bone morphogenetic protein-7 in bone metastatic prostate cancer.

TDFRP compounds can be used to treat renal dysfunction, disease and injury, e.g. ureteral obstruction, acute and chronic renal failure, renal fibrosis, and diabetic nephropathy. (Klar, S., J. Nephrol. 2003 March-April; 16(2):179-85) demonstrated that BMP-7 treatment significantly decreased renal injury in a rat model of ureteral obstruction (UUO), when treatment was initiated at the time of injury. Subsequent studies suggested that BMP-7 treatment also attenuated renal fibrosis when administered after renal fibrosis had begun. This treatment protocol was also found to increase significantly renal function from the levels measured in the vehicle-treated group. BMP-7 also partially reversed the diabetic nephropathy induced in rats by a single dose of Streptozotocin. It restored glomerular filtration rate (GFR), decreased the excretion of protein, and restored histology towards normal. TDFRP can be used in the prophylaxis or treatment of renal disease, e.g., chronic renal failure (FIG. 4-FIG. 8B). Studies by Klahr et al., (Kidney Int Suppl. 2002 May; (80):23-6) indicate that administration of BMP-7 maintains and restores renal function and structure in animals with ureteral obstruction and diabetic nephropathy.

Figure 7A:
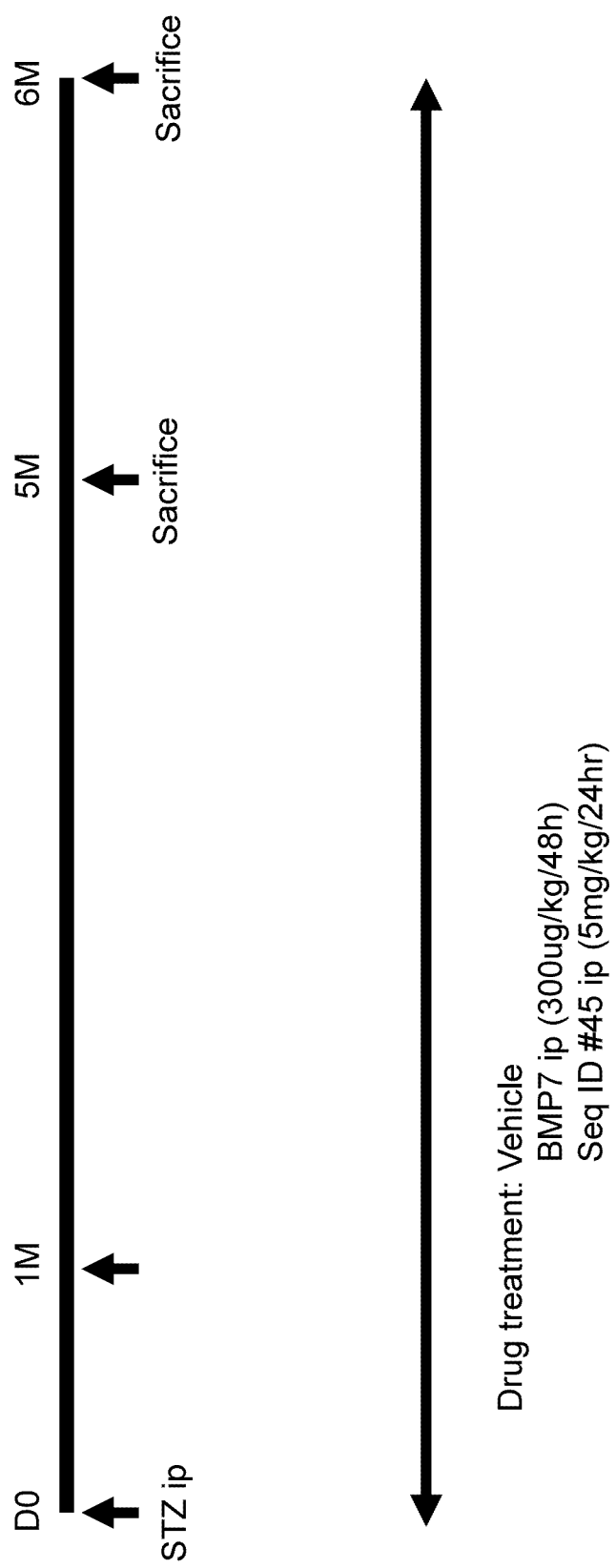
FIG. 7A-FIG. 7C
Reversal of interstitial fibrosis by Thrasos compound SEQ ID NO 45 in a CD1 mouse model of streptozotocin (STZ)-induced diabetic nephropathy.
Figure 7C:
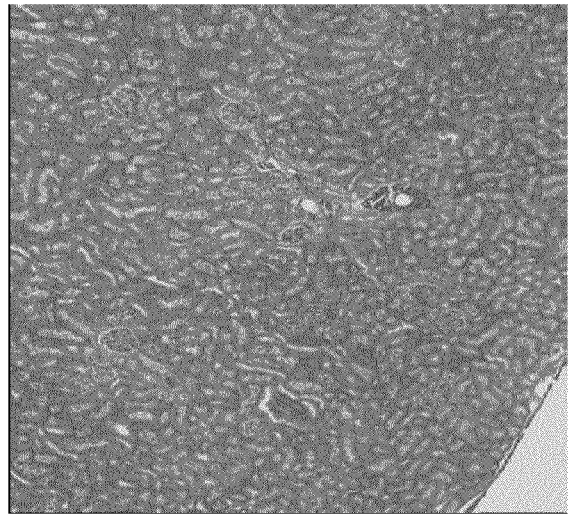
Figure 7B:
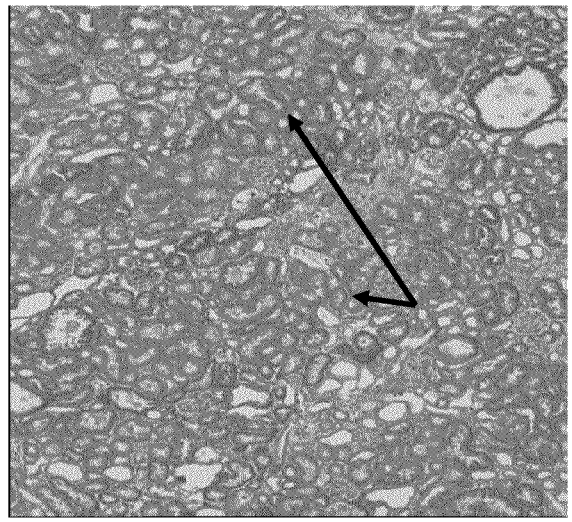
Figure 8A:
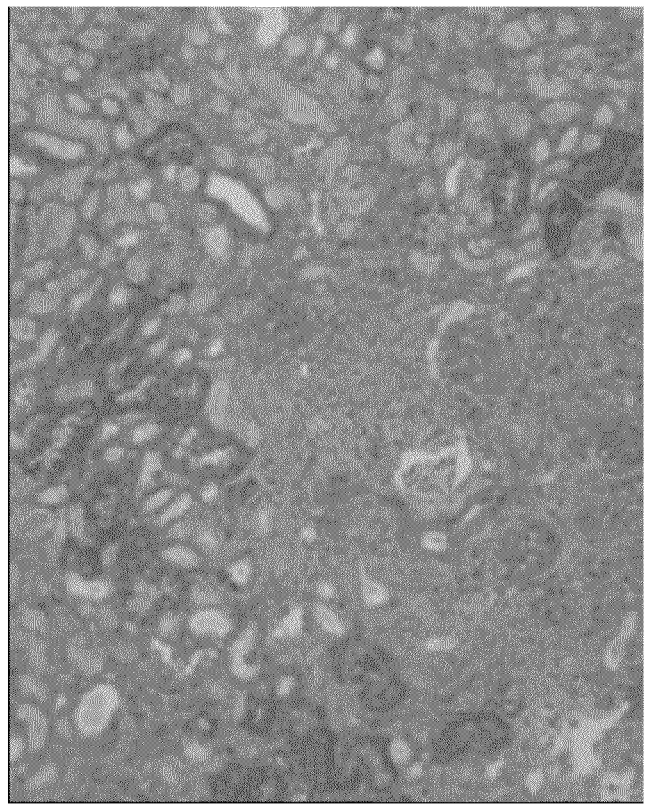
FIG. 8A-FIG. 8B
Attenuation of renal fibrosis progression by Thrasos compound in a mouse model of nephrotoxic serum nephritis.
Figure 8B:
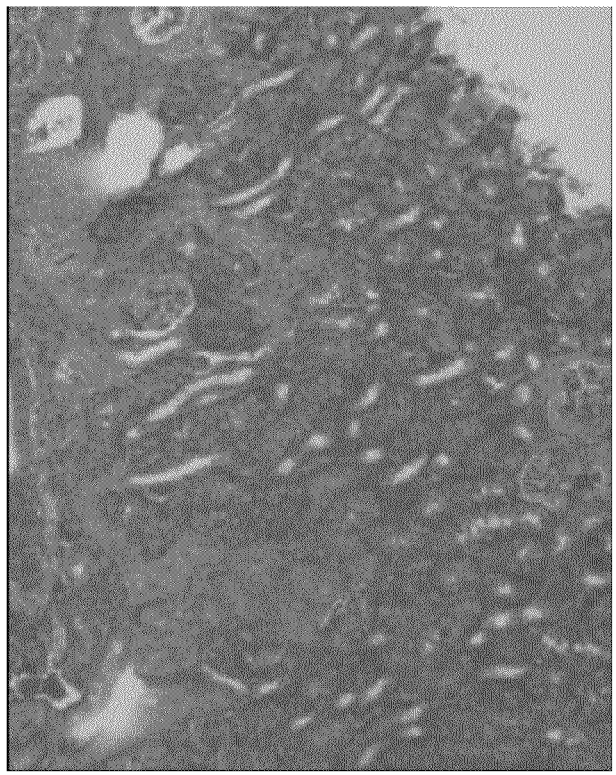

TDFRP compounds can be used in the prophylaxis or treatment of diabetic nephropathy (FIG. 7A-FIG. 7C). Wang et al., (Kidney Int. 2003 June; 63(6):2037-49) have shown that BMP-7 partially reversed diabetic-induced kidney hypertrophy, restoring GFR, urine albumin excretion, and glomerular histology toward normal. Restoration of BMP-7 expression was associated with a successful repair reaction and a reversal of the ill-fated injury response.

TDFRP compounds can be used in the prophylaxis or treatment of renal fibrosis (FIG. 7A-FIG. 7C). Exogenous administration of recombinant human bone morphogenetic protein (BMP)-7 was recently shown to ameliorate renal glomerular and interstitial fibrosis in rodents with experimental renal diseases (Wang and Hirschberg, Am J Physiol Renal Physiol. 2003 May; 284(5):F1006-13).

TDFRP compounds can be used to facilitate tissue repair. Grande et al., (J Bone Joint Surg Am. 2003; 85-A Suppl 2:111-6) demonstrated that the addition of either the BMP-7 or the Shh gene significantly enhanced the quality of the repair tissue, resulting in a much smoother surface and more hyaline-appearing cartilage. There was, however, a noticeable difference in the persistence of the cartilage phase between the group that received the Shh gene and the group that received the BMP-7 gene, with the subchondral compartment in the latter group seeming to remodel with bone much faster TDFRP compounds can be used to in the prophylaxis or treatment of diseases of the oral cavity, e.g., by affecting direct capping of bioactive molecules, or inducing the formation of reparative dentin and coronal or radicular pulp mineralization (Goldberg et al., Am J. Dent. 2003 February; 16(1): 66-76). Further, TDFRP can be used in the prophylaxis or treatment of periodontal disease. Osseous lesions treated by Ad-BMP-7 gene delivery demonstrated rapid chrondrogenesis, with subsequent osteogenesis, cementogenesis and predictable bridging of the periodontal bone defects. These results demonstrate successful evidence of periodontal tissue engineering using ex vivo gene transfer of BMPs and offers a new approach for repairing periodontal defects (Jin et al., J. Periodontol. 2003 February; 74(2):202-13). TDFRP compounds can be used in the prophylaxis or treatment of traumatic brain injury, e.g., stroke, see, e.g., Cairns and Finkelstein, Phys Med Rehabil Clin N Am. 2003 February; 14(1 Suppl):S135-42). Intravenous administration of BMP-7 after ischemia improves motor function in stroke rats (Chang et al., Stroke. 2003 February; 34(2):558-64) and the TDFRP compounds may protect against or repair reperfusion injury. Further, Chang et al., (Neuropharmacology 2002 September; 43(3):418-26) have demonstrated that bone morphogenetic proteins are involved in fetal kidney tissue transplantation-induced neuroprotection in stroke rats. Rehabilitation after cell-based cartilage repair can be prolonged, leading to decreased patient productivity and quality of life by treating a subject with TDFRP compounds. Implantation of genetically modified chondrocytes expressing BMP-7 accelerates the appearance of hyaline-like repair tissue in experimental cartilage defects and that might be important cartilage homeostasis (Hidaka et al., J Orthop Res. 2003 July; 21(4):573-83). The synovium is a thin tissue lining the nonarticular surfaces of diarthrodial joints. Synovial tissues contain various types of cells, including type A cells, macrophage lineage cells and type B cells, which are specialized synovial fibroblasts. It is now widely recognized that synovial tissues are involved primarily in the pathogenesis of arthritic joint disorders by producing matrix-degenerating enzymes and proinflammatory cytokines. Accumulated evidence suggest that TGF-beta super family members play an essential role in bone and cartilage development. Wozney and co-workers (Wozney, J. M. (1989) Prog. Growth factor Res. 1:267-280) reported that bone morphogenetic proteins (BMPs) induce early cartilage formation. Recently it has been shown that ALK3 signaling that mediates BMP action has both stimulatory and regulatory roles in chondrogenesis to induce the chondrogenic differentiation of synovial fibroblastic cells (Seto et al (2004) J. Clin. Invest. 113:718-726). Thrasos compounds that bind to ALK3, a type I receptor for BMP, are therefore analyzed to examine if they induce chondrogenic differentiation leading to extra cellular matrix deposition in synovial membrane-derived mesenchymal stem cells. Of the compounds SEQ ID NO:16, 33, 45, 217 and 221 tested, compounds SEQ ID NO 221 and 16 significantly increased the deposition of the extracellular matrix. TDFRP compounds have been examined in chondrogenesis ex vivo and cell culture assays that may have relevance in osteoarthritis applications, cartilage repair, protection, and/or homeostasis (FIG. 9).

TDFRP compounds can be used in bone tissue engineering. Lu et al., (Biochem Biophys Res Commun. 2003 Jun. 13; 305(4):882-90 have shown the efficacy of a BMP-polymer matrix in inducing the expression of the osteoblastic phenotype by muscle-derived cells and present a new paradigm for bone tissue engineering. TDFRP compounds may be used in bone transplantation (Rees and Haddad, Hosp Med. 2003 April; 64(4):205-9). TDFRP can also be used to promote bone healing. Maniscalco et al., (Acta Biomed Ateneo Parmense. 2002; 73(1-2):27-33) verify the therapeutic potential of this BMP-7 protein in fresh tibial closed fractures, using BMP-7 associated with osteosynthesis by means of a monolateral external fixator. Moreover, TDFRP compounds can be used in the regeneration of bone tissue, e.g., reconstructive surgery of the hip. Cook et al., (J. Arthroplasty. 2001 December; 16(8 Suppl 1):88-94) demonstrated that the use of BMP-7 in conjunction with morcellized cancellous bone and cortical strut allograft in preclinical models dramatically improved the biologic activity of the graft, resulting in greater and earlier new bone formation and graft incorporation. The clinical use of BMP-7 in hip reconstructive procedures also resulted in greater and earlier new bone formation in the more challenging biologic environment compared with allograft bone alone.

TDFRP compounds can be used to treat skeletal defects e.g., acquired and congenital skeletal defects arise from trauma and developmental abnormalities as well as ablative cancer surgery. Rutherford et al., (Drug News Perspect. 2003 January-February; 16(1):5-10) discusses recent advances in bone morphogenetic protein 7 ex vivo gene therapy for localized skeletal regeneration address these limitations.

TDFRP compounds can be used in the prophylaxis or treatment of disorders of haematopoiesis. Studies by Detmer and Walker (Cytokine. 2002 Jan. 7; 17(1):36-42) indicate that individual BMPs form part of the complement of cytokines regulating the development of haematopoietic progenitors, and in particular, point to a role for BMP-4 in the control of definitive, as well as embryonic erythropoiesis. TDFRP compounds have been demonstrated to modulate cytokine production in various cell populations (e.g. HK-2 cell lines, cardiomyocytes, kidney tissues), repair kidney damage and/or protect kidneys from injury, which may affect the regulation and production of hematopoietic progenitor cells and growth factors (FIG. 10).

TDFRP compounds can be used in the treatment of reproductive disorders, e.g., sterility. Zhao et al., (Dev Biol. 2001 Dec. 1; 240(1):212-22) demonstrated that mutation in BMP-7 exacerbates the phenotype of BMP-8a mutants in spermatogenesis and epididymis. These indicate that, similar to BMP-8a, BMP-7 plays a role in both the maintenance of spermatogenesis and epididymal function and it further suggests that BMP-8 and BMP-7 signal through the same or similar receptors in these two systems.

X. Disease and Disorders

Diseases and disorders that are characterized by increased (relative to a subject not suffering from the disease or disorder) levels or biological activity of TDF polypeptides or TDFRP compound target molecules can be treated with TDFRP-based therapeutic compounds that antagonize (i.e., reduce or inhibit) activity, which can be administered in a therapeutic or prophylactic manner. Therapeutic compounds that can be utilized include, but are not limited to: (i) an aforementioned TDFRP compound, or analogs, derivatives, fragments or homologs thereof; (ii) anti-TDFRP compound antibodies to an aforementioned peptide; (iii) nucleic acids encoding TDFRP compound; (iv) administration of antisense nucleic acid and nucleic acids that are "dysfunctional" (i.e., due to a heterologous insertion within the coding sequences of coding sequences to a TDFRP compound) that are utilized to "knockout" endogenous function of TDFRP compound by homologous recombination (see, e.g., Capecchi, 1989. Science 244: 1288-1292); or (v) modulators (i.e., inhibitors, agonists and antagonists, including additional peptide mimetic of the invention or antibodies specific to a peptide of the invention) that alter the interaction between an aforementioned compound and its binding partner.

Diseases and disorders that are characterized by decreased (relative to a subject not suffering from the disease or disorder) levels or biological activity of TDF or TDFRP compound target molecule can be treated with TDFRP-based therapeutic compounds that increase (i.e., are agonists to) TDF activity. Therapeutics that upregulate activity can be administered in a therapeutic or prophylactic manner. Therapeutics that can be utilized include, but are not limited to, TDFRP compound or analogs, derivatives, fragments or homologs thereof; or an agonist that increases bioavailability.

Increased or decreased levels can be readily detected by quantifying TDF-induced peptides and/or RNA, by obtaining a patient tissue sample (e.g., from biopsy tissue) and assaying it in vitro for RNA or peptide levels, structure and/or activity of the expressed peptides (or mRNAs of an aforementioned peptide). Methods that are well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, and the like).

A. Prophylactic Methods

In one aspect, the invention provides a method for preventing, in a subject, a disease or condition associated with an aberrant TDF polypeptide or TDFRP compound target molecule expression or activity, by administering to the subject a TDFRP compound or TDFRP compound mimetic that modulates TDF polypeptide or TDFRP compound target molecule expression or at least one TDF polypeptide or TDFRP compound target molecule activity.

Subjects at risk for a disease that is caused or contributed to by aberrant TDF polypeptide or TDFRP compound target molecule expression or activity can be identified by, for example, any or a combination of diagnostic or prognostic assays as described herein. Administration of a prophylactic compound can occur prior to the manifestation of symptoms characteristic of the aberrancy, such that a disease or disorder is prevented or, alternatively, delayed in its progression. Depending upon the type of aberrancy, for example, a TDFRP compound, TDFRP compound mimetic, or anti-TDFRP compound antibody, which acts as a TDF agonist or TDF antagonist compound can be used for treating the subject. The appropriate compound can be determined based on screening assays described herein.

B. Therapeutic Methods

Another aspect of the invention includes methods of modulating TDF polypeptides or TDFRP compound target molecule expression or activity in a subject for therapeutic purposes. The modulatory method of the invention involves contacting a cell with a compound of the present invention, that modulates one or more of the activities of the TDF polypeptide or TDFRP compound target molecule activity associated with the cell. A compound that modulates a TDF polypeptide or TDFRP compound target molecule activity is described herein, such as a nucleic acid or a polypeptide, a naturally-occurring cognate ligand of a TDFRP compound, a TDFRP compound, an anti-TDFRP compound antibody, a TDFRP compound mimetic, or a small molecule. In one embodiment, the compound stimulates one or more TDF polypeptide or TDFRP compound target molecule activity. Examples of such stimulatory compounds include a TDFRP compound and a nucleic acid molecule encoding TDFRP compound that has been introduced into the cell. In another embodiment, the compound inhibits one or more TDF polypeptide or TDFRP compound target molecule activity, e.g., anti-TDFRP compound antibodies. These modulatory methods can be performed in vitro (e.g., by culturing the cell with the compound) or, alternatively, in vivo (e.g., by administering the compound to a subject). As such, the invention provides methods of treating an individual afflicted with a TDF-associated disease or disorder characterized by aberrant expression or activity of a TDF polypeptide or TDFRP compound target molecule or nucleic acid molecules encoding them. In one embodiment, the method involves administering a compound (e.g., a compound identified by a screening assay described herein), or combination of compounds that modulates (e.g., up-regulates or down-regulates) TDF polypeptide or TDFRP compound target molecule expression or activity. In another embodiment, the method involves administering a TDFRP compound or nucleic acid molecule encoding TDFRP as therapy to compensate for reduced or aberrant TDF polypeptide or TDFRP compound target molecule expression or activity.

Stimulation of TDF polypeptide or TDFRP compound target molecule activity is desirable in situations in which TDF polypeptide or TDFRP compound target molecule is abnormally downregulated and/or in which increased TDF activity is likely to have a beneficial effect. One example of such a situation is where a subject has a disorder characterized by aberrant cell proliferation and/or differentiation (e.g., fibrosis).

C. Determination of the Biological Effect of the TDFRP-Based Therapeutic

In various embodiments of the invention, suitable in vitro or in vivo assays are performed to determine the effect of a specific TDFRP-based therapeutic and whether its administration is indicated for treatment of the affected tissue in a subject.

In various specific embodiments, in vitro assays can be performed with representative cells of the type(s) involved in the patient's disorder, to determine if a given TDFRP-based therapeutic exerts the desired effect upon the cell type(s). Compounds for use in therapy can be tested in suitable animal model systems including, but not limited to rats, mice, chicken, cows, monkeys, rabbits, and the like, prior to testing in human subjects. Similarly, for in vivo testing, any of the animal model system known in the art can be used prior to administration to human subjects.

D. Prophylactic and Therapeutic Uses of the Compositions of the Invention

The TDFRP compounds of the present invention are useful in potential prophylactic and therapeutic applications implicated in a variety of disorders in a subject including, but not limited to: those involving development, differentiation, and activation of bone cells; in diseases or pathologies of cells in blood circulation such as red blood cells and platelets; various immunological disorders and/or pathologies; autoimmune and inflammatory diseases; cardiovascular diseases; metabolic diseases; reproductive diseases, renal diseases, diabetes, brain trauma, cancer growth and metastasis; viral infections, cancer therapy, periodontal disease; tissue regeneration; acute lymphoblastic leukemia; gliomas; neurologic diseases; neurodegenerative disorders; Alzheimer's disease; Parkinson's disorder; and hematopoietic disorders, see also, infra, Methods of Treatment.

As an example, a cDNA encoding the TDFRP compound can be useful in gene therapy, and the TDFRP compound can be useful when administered to a subject in need thereof. By way of non-limiting example, the compositions of the invention will have efficacy for treatment of patients suffering from the above-mentioned disorders.

Both the novel nucleic acid encoding the TDFRP compound, and the TDFRP compound, or fragments thereof, may also be useful in diagnostic applications. A further use is as an anti-bacterial molecule (i.e., some peptides have been found to possess anti-bacterial properties). These materials are further useful in the generation of antibodies, which immuno-specifically-bind to the novel substances of the invention for use in therapeutic or diagnostic methods where a TGF-beta superfamily polypeptide is overexpressed or underexpressed in a subject.

EXAMPLES

The following examples are intended to be non-limiting illustrations of certain embodiments of the present invention. All references cited are hereby incorporated herein by reference in their entireties.

Example 1

Systems and Methods for Structure-Based Rational Drug Design

The TDFRP compounds described above are structural mimetics of bone morphogenic proteins, for example but not limited to BMP-7 (OP-1) and BMP-2, more particularly structural mimetics of the biologically active regions of these proteins (e.g., finger 1, finger 2 and the like). For a description of the crystallization conditions, methods for obtaining and interpreting the resultant crystal structures, and discussions on the biologically active regions of these proteins based on structural models, see, Griffith et al., Proc Natl Acad Sci USA. 1996 Jan. 23; 93(2):878-83 and Scheufler et al., J Mol. Biol. 1999 Mar. 19; 287(1):103-15, each incorporated by reference.

The present TDFRP compounds were designed and refined, in part, based on structural models such as x-ray crystallography and nuclear magnetic resonance, and the following references (all incorporated herein in there entirety) are suitable models for the crystallization, preparation and structural analysis of the TDFRP compounds disclosed herein. Methods of structure-based drug design using crystalline polypeptides are described in at least U.S. Pat. Nos. 6,329,184 and 6,403,330 both to Uppenberg. Methods for using x-ray topography and diffractometry to improve protein crystal growth are described in U.S. Pat. No. 6,468,346 to Arnowitz, et al. Methods and apparatus for automatically selecting Bragg reflections, and systems for automatically determining crystallographic orientation are described by U.S. Pat. No. 6,198,796 to Yokoyama, et al. Methods for the preparation and labeling of proteins for NMR with $^{13}C$, $^{15}N$, and $^2H$ for structural determinations is described in U.S. Pat. No. 6,376,253 to Anderson, et al. NMR spectroscopy of large or complex proteins is described in U.S. Pat. No. 6,198,281 to Wand, et al. Use of nuclear magnetic resonance to design ligands to target biomolecules is described in U.S. Pat. No. 5,989,827 to Fesik, et al.

The process of rational drug design of bone morphogenetic protein mimetics with nuclear magnetic resonance includes the steps of identifying a candidate TDFRP compound that is a potential ligand to the target molecule (such as a TDF receptor) using two-dimensional $^{15}N/^1H$ NMR correlation spectroscopy; b) forming a binary complex by binding the candidate TDFRP compound to the target molecule, c) determining the three dimensional structure of the binary complex and thus the spatial orientation of the candidate TDFRP compound on the target molecule. The process of rational drug design of bone morphogenetic protein mimetics with x-ray crystallography is accomplished in a similar manner, but structural data is first obtained by forming crystals of the candidate TDFRP compound that is a potential ligand to the target molecule (or co-crystals of the complex), and obtaining a data set of the atomic reflections after x-ray irradiation. These techniques are known to those skilled in the art in view of the teachings provided herein.

Refinements to the candidate TDFRP compound are then made to increase the affinity of the candidate TDFRP compound for the target molecule. Refinements include constraining and cyclizing the TDFRP compound or incorporation of non-classical amino acids that induce conformational constraints. A constrained, cyclic or rigidized TDFRP compound may be prepared synthetically, provided that in at least two positions in the sequence of the TDFRP compound, an amino acid or amino acid analog is inserted that provides a chemical functional group capable of crosslinking to constrain, cyclize or rigidize the TDFRP compound after treatment to form the crosslink. Cyclization will be favored when a turn-inducing amino acid is incorporated. Examples of amino acids capable of crosslinking a TDFRP compound are cysteine to form disulfides, aspartic acid to form a lactone or a lactam, and a chelator such as gamma.-carboxyl-glutamic acid (Gla) (Bachem) to chelate a transition metal and form a cross-link. Protected gamma.-carboxyl glutamic acid may be prepared by modifying the synthesis described by Zee-Cheng and Olson (Biophys. Biochem. Res. Commun., 94:1128-1132 (1980)). A TDFRP compound in which the peptide sequence comprises at least two amino acids capable of crosslinking may be treated, e.g., by oxidation of cysteine residues to form a disulfide or addition of a meal ion to form a chelate, so as to crosslink the peptide and form a constrained, cyclic or rigidized TDFRP compound.

The present invention provides strategies to systematically prepare cross-links. For example, if four cysteine residues are incorporated in the peptide sequence, different protecting groups may be used (see, Hiskey, in The Peptides: Analysis, Synthesis, Biology, Vol. 3, Gross and Meienhofer, eds., Academic Press: New York, pp. 137-167 (1981); Ponsanti et al., Tetrahedron, 46:8255-8266 (1990)). The first pair of cysteines may be deprotected and oxidized, then the second set may be deprotected and oxidized. In this way a defined set of disulfide cross-links may be formed. Alternatively, a pair of cysteines and a pair of chelating amino acid analogs may be incorporated so that the cross-links are of a different chemical nature.

Non-classical amino acids may be incorporated in the TDFRP compound in order to introduce particular conformational motifs, for example but not limited to 1,2,3,4-tetrahydroisoquinoline-3-carboxylate (Kazmierski et al., J. Am. Chem. Soc., 113:2275-2283 (1991)); (2S,3S)-methyl-phenylalanine, (2S,3R)-methyl-phenylalanine, (2R,3S)-methyl-phenylalanine and (2R,3R)-methyl-phenylalanine (Kazmierski and Hruby, Tetrahedron Lett. (1991)); 2-aminotetrahydronaphthalene-2-carboxylic acid (Landis, Ph.D. Thesis, University of Arizona (1989)); hydroxy-1,2,3, 4-tetrahydroisoquinoline-3-carboxylate (Miyake et al., J. Takeda Res. Labs, 43:53-76 (1989)); beta-carboline (D and L) (Kazmierski, Ph.D. Thesis, University of Arizona (1988)); HIC (histidine isoquinoline carboxylic acid) (Zechel et al., Int. J. Pep. Protein Res., 43 (1991)); and HIC (histidine cyclic urea) Amino acid analogs and peptidomimetics may be incorporated into a peptide to induce or favor specific secondary structures, including but not limited to: LL-Acp-(LL-3-amino-2-propenidone-6-carboxylic acid), a beta-turn inducing dipeptide analog (Kemp et al., J. Org. Chem. 50:5834-5838 (1985)); beta-sheet inducing analogs (Kemp et al., Tetrahedron Lett. 29:5081-5082 (1988)); beta-turn including analogs (Kemp et al., Tetrahedron Lett., 29:5057-5060 (1988)); helix inducing analogs (Kemp et al., Tetrahedron Lett., 29:4935-4938 (1988)); gamma-turn inducing analogs (Kemp et al., J. Org. Chem. 54:109:115 (1989)); and analogs provided by the following references: Nagai and Sato, Tetrahedron Lett., 26:647; 14 650 (1985); DiMaio et al., J. Chem. Soc. Perkin Trans. p. 1687 (1989); also a Gly-Ala turn analog (Kahn et al., Tetrahedron Lett., 30:2317 (1989)); amide bond isoetere (Jones et al., Tetrahedron Lett., 29:3853-3856 (1988)) tretazol (Zabrocki et al., J. Am. Chem. Soc. 110: 5875-5880 (1988)); DTC (Samanen et al., Int. J. Protein Pep. Res., 35:501:509 (1990)); and analogs taught in Olson et al., J. Am. Chem. Sci., 112:323-333 (1990) and Garvey et al., J. Org. Chem., 56:436 (1990). Conformationally restricted mimetics of beta turns and beta bulges, and peptides containing them, are described in U.S. Pat. No. 5,440,013, issued Aug. 8, 1995 to Kahn.

Once the three-dimensional structure of a TDFRP compound (or a refinement of the same) is determined, its therapeutic potential (as an antagonist or agonist) can be examined through the use of computer modeling using a docking program such as GRAM, DOCK, or AUTODOCK. Computer programs that can be used to aid in solving the three-dimensional structure of the TDFRP compound and binding complexes thereof include QUANTA, CHARMM, INSIGHT, SYBYL, MACROMODE, and ICM, MOLMOL, RASMOL, AND GRASP (Kraulis, J. Appl. Crystallogr. 24:946-950 (1991)). Most if not all of these programs and others as well can be also obtained from the World Wide Web through the Internet. The rational design of TDFRP compounds can include computer fitting of potential agents to the TDFRP compound to ascertain how well the shape and the chemical structure of the modified TDFRP compound will complement or interfere with the interaction between the TDFRP compound and its ligand. Computer programs can also be employed to estimate the attraction, repulsion, and steric hindrance of the potential therapeutic TDFRP compound to the TDFR binding site, for example. Generally the tighter the fit (e.g., the lower the steric hindrance, and/or the greater the attractive force) the more potent the potential therapeutic TDFRP compound will be since these properties are consistent with a tighter binding constraint. Furthermore, the more specificity in the design of the TDFRP compound the more likely it will not interfere with related TDFRs (e.g., its specificity to ALK3 receptors but not ALK6 receptors or vice versa). This will minimize potential side-effects due to unwanted interactions with other targets. For example, ALK3 receptors are more prevalent in kidney tissue, while ALK6 receptors are more prevalent in bone tissue; the native BMP-7 protein binds to ALK6 with a higher affinity, and a potential side effect of BMP-7 therapy in kidney disease is osteogenesis. The TDFRP compounds can be selected and designed for increased specificity to ALK3 and lowered affinity to ALK6 receptors, thereby reducing undesirable osteogenesis in a subject being treated for kidney disorders.

Initially a potential therapeutic TDFRP compound can be obtained by screening a random peptide library produced by recombinant bacteriophage for example, (Scott and Smith, Science, 249:386-390 (1990); Cwirla et al., Proc. Natl. Acad. Sci., 87:6378-6382 (1990); Devlin et al., Science, 249:404-406 (1990)) or a chemical library. A candidate therapeutic TDFRP compound selected in this manner is then systematically modified by computer modeling programs until one or more promising potential therapeutic TDFRP compounds are identified. Such analysis has been shown to be effective in the development of HIV protease inhibitors (Lam et al., Science 263:380-384 (1994); Wlodawer et al., Ann. Rev. Biochem. 62:543-585 (1993); Appelt, Perspectives in Drug Discovery and Design 1:23-48 (1993); Erickson, Perspectives in Drug Discovery and Design 1:109-128 (1993)). A computer-based method for classifying and producing analogs of TDF-1, can be found at PCT Publication WO/02/37313 to Keck, and is directly relevant to the selection of TDFRP compounds as described herein.

Such computer modeling allows the selection of a finite number of rational chemical modifications, as opposed to the countless number of essentially random chemical modifications that could be made, any of which any one might lead to a useful drug. Each chemical modification requires additional chemical steps, which while being reasonable for the synthesis of a finite number of compounds, quickly becomes overwhelming if all possible modifications needed to be synthesized. Thus through the use of the three-dimensional structural analysis disclosed herein and computer modeling, a large number of these candidate TDFRP compounds can be rapidly screened, and a few likely candidate therapeutic TDFRP compounds can be determined without the laborious synthesis of untold numbers of TDFRP compounds.

The candidate therapeutic TDFRP compounds can then be tested in any standard binding assay (including in high throughput binding assays) for its ability to bind to a TDFRP or fragment thereof. Alternatively the potential drug can be tested for its ability to modulate (either inhibit or stimulate) the biological activity of a TDFRP. When a suitable potential drug is identified, a second structural analysis can optionally be performed on the binding complex formed between the ligand and the candidate therapeutic TDFRP compound. For all of the screening assays described herein further refinements to the structure of the candidate TDFRP therapeutic compound will generally be necessary and can be made by the successive iterations of any and/or all of the steps provided by the particular drug screening assay, including further structural analysis by x-ray crystallography or NMR, for example.

Example 2

In Vitro Assays for Biological Activity

A. Radioligand Receptor Binding Assays for ALK-3, ALK-6 and BMPR-2:

General protocol: These assays are based on competition between $^{125}$I-labeled TDF-1 (BMP-7 or OP-1) and candidate TDFRP compounds or unlabeled TDF-1 for binding to respective receptors (ALK-3, ALK-6 or BMPR-2). In brief, the procedure involves immobilization of receptor on 96 well Removawell plates, blocking the wells with 3% BSA in PBS and subsequently washing the wells. Increasing concentrations of unlabeled TDF-1 or TDFRP compounds or control (unlabeled TDF-1) prepared in binding buffer are then added. Incubate plate for 1 hour at room temperature, and then add a fixed amount of $^{125}$I-labeled TDF-1 (250,000 to 350,000 cpm) to the wells and further incubate in cold (4° C.) for 20 hours. Aspirate the contents of the wells and wash the wells four times with a wash buffer, and count the receptor bound $^{125}$I-labeled TDF-1 in an auto gamma counter.

Figure 1:
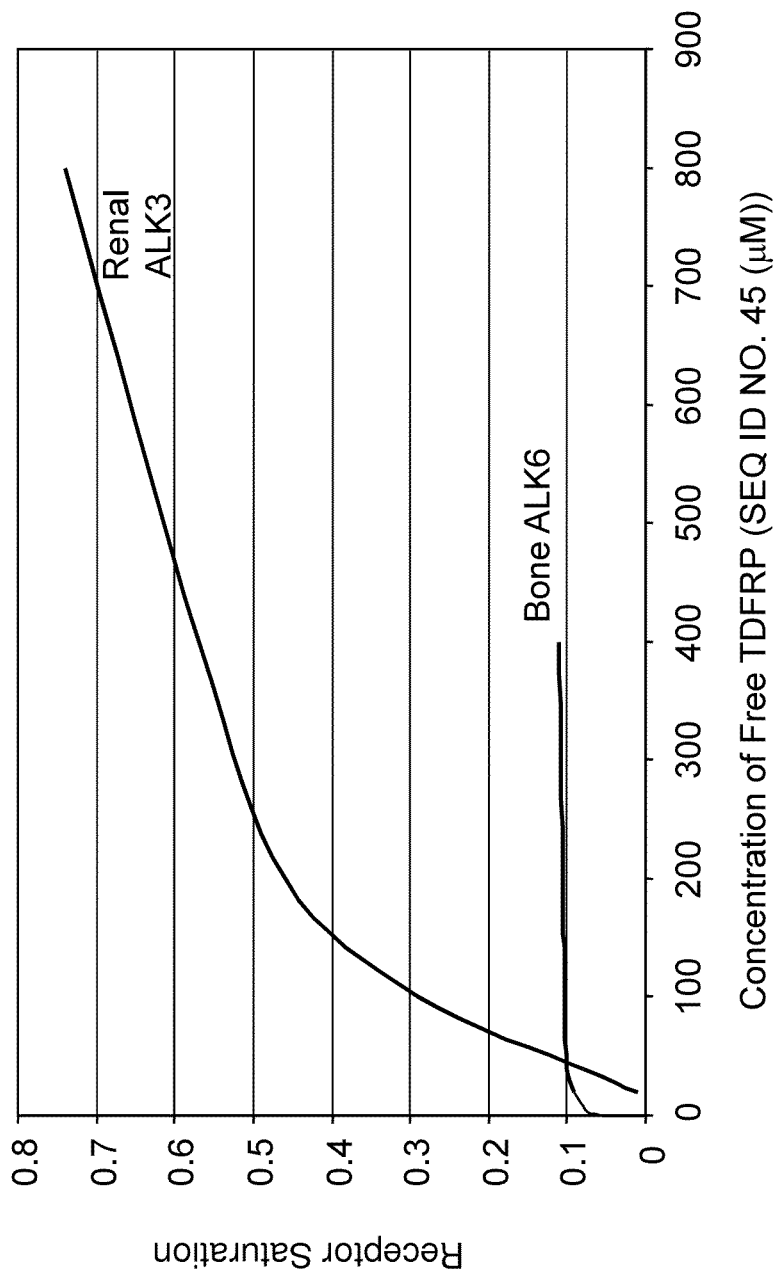
FIG. 1
TDFRP compound differential binding to Type I receptors. TDFRP compound (SEQ ID NO 45) selectively binds to ALK-3 when compared to ALK-6.
Figure 5B:
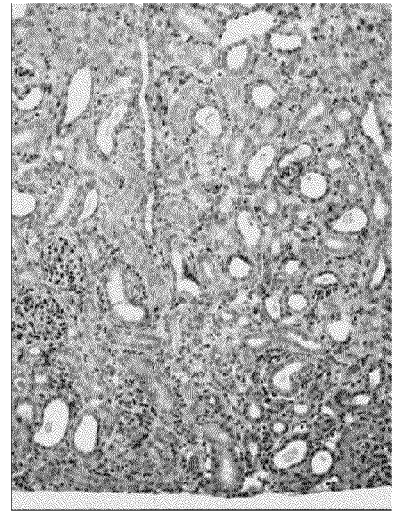
FIG. 5A-FIG. 5D
Reversal of chronic renal injury by Thrasos compound or BMP-7 in a mouse model of unilateral ureteral obstruction.
Figure 5D:
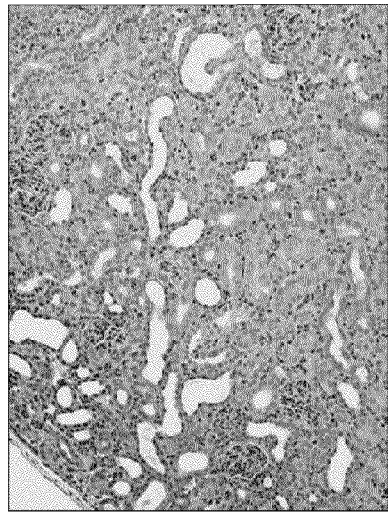
Figure 5A:
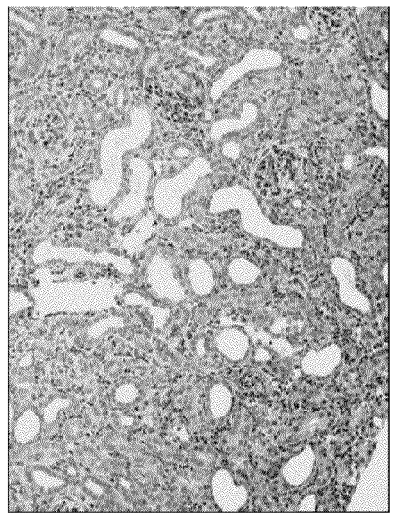
Figure 5C:
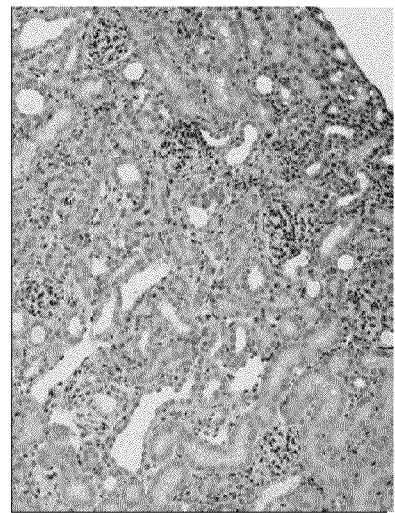
Figure 6B:
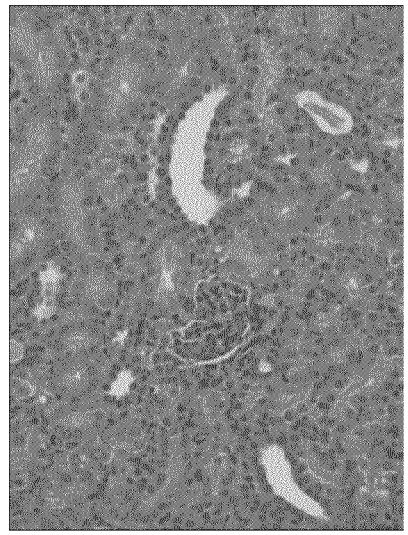
FIG. 6A-FIG. 6D
Reversal of chronic renal injury by Thrasos compound or BMP-7 in a mouse model of unilateral ureteral obstruction.
Figure 6D:
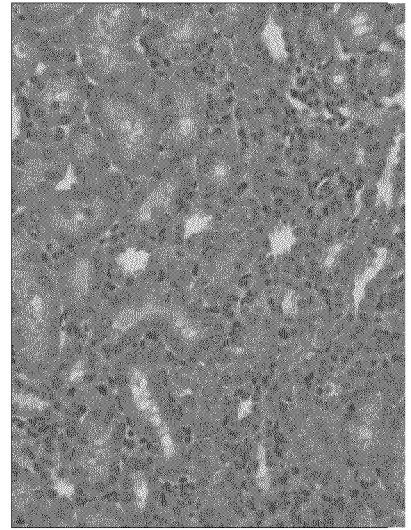
Figure 6A:
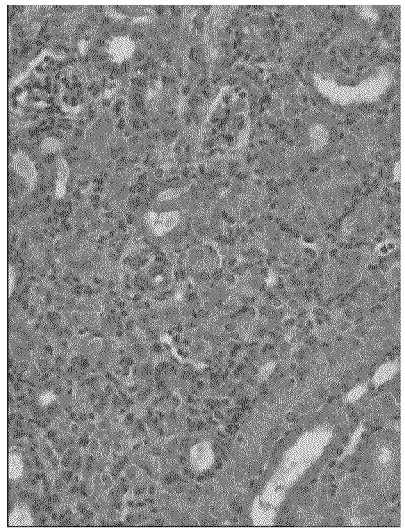
Figure 6C:
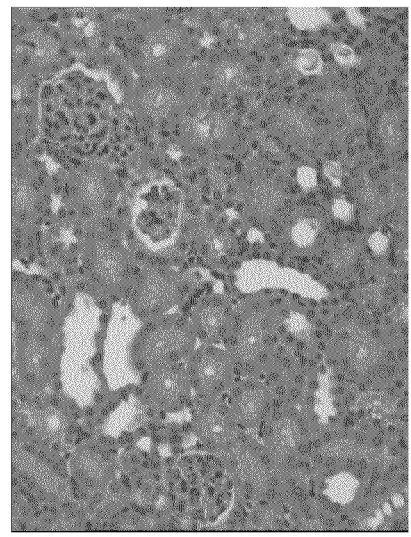

Using this procedure, TDFRP compound binding to select ALK receptors are assessed. Accordingly, TDFRP compounds that preferentially bind select ALK receptors can be identified. For example, TDFRP compounds that preferentially bind to ALK-3 receptor compared with binding to other ALK receptors, e.g., ALK-6 (FIG. 1 and FIG. 11).

B. Rat Osteosarcoma (ROS) Cell-Based Alkaline Phosphatase Assay

BMP interactions with Type I and Type II receptors can induce alkaline phosphatase activity, a marker for osteoblast activity, in ROS cells. An assay procedure as described earlier (Maliakal, J.C., Asahina, I., Hauschka, P. V., and Sampath, T. K. (1994) Growth factors 11, 227-234) was used to determine the biological activities of TDFRP compounds. In a typical experiment, rat osteosarcoma (17/2.8) cells are plated in 96 well plates ($3.0 \times 10^4$ cells/well) and incubated overnight at 37 C in 5-6% $CO_2$ incubator. The next day, healthy and confluent cells are treated with increasing concentrations of BMP-7 standard (1-10,000 ng/ml) served as positive control or TDFRP compounds (0.02-200 uM) prepared in medium containing 1% FBS and incubated for 2 days at 37 C in 5-6% $CO_2$ incubator. The cellular content of alkaline phosphatase activity is determined by the method of Reddi and Huggins (Reddi, A. H., and Huggins, C. B (1972) Proc. Natl. Acad. Sci. USA 69, 1601-1605). Enzyme estimations are performed in 96 well plates. Following removal of culture medium, cells are washed with pre-warmed PBS (150 ul) and incubated in 100 ul of pre-warmed 1% Triton X-100 for 30 minutes at 37 C. Plates are centrifuged for 10 minutes at full speed, and recovered samples (15 ul) are assayed for enzyme activity by adding 90 ul p-nitrophenyl phosphate (Sigma) as a substrate in 0.05 M glycine-NaOH buffer, pH 9.3 and incubating for 20 minutes at 37 C. The reaction is stopped by adding 75 ul of 0.2 N NaOH/well and absorbance at 405/490 nm is measured on a Dynatech MR 700 plate reader. Results are expressed as relative activities compared to a BMP-7 standard. TDFRP compounds (SEQ ID numbers 15-21, 23-33, 41-43, 45, 65, 130, 208-219, 221) did not induce alkaline phosphatase activity in ROS cell assays.

C. Subcutaneous Implant Assay for Bone Induction

BMP-7 induces bone formation in the rat when implanted subcutaneously by a procedure described in (Sampath, T. K., Maliakal, J. C., Hauschka, P. V. et al. (1992) J. Bio. Chem. 267, 20352-20362). This assay is used to assess the bone induction capacity of TDFRP compounds. 25 mg of demineralized bone matrix is added to BMP-7 (concentration series), in 150 ul of 50% acetonitrile, 0.15% TFA, mixed, and then lyophilized as a positive control for bone induction activity. Demineralized bone matrix alone is used as negative control. TDFRP compounds are covalently coupled to alginate hydrogel, using carbodiimide reaction. 10 mg of alginate-coupled compound is implanted into muscle of each rat. Implants are removed on day 14 for evaluation Implants are fixed in Bouin's solution, embedded in JB4 plastic medium, cut into 1 um sections, and stained by toluidine blue for histological examination. Select TDFRP compounds do not display bone inductive activities in this assay (FIG. 13A-FIG. 13B)

D. HK-2 Cell Culture and Determination of Cytokine and Adhesion Molecule Production The immortalized PTEC-derived HK-2 (Human Kidney-2) cells (ATCC number CRL-2190) were grown in serum-free keratinocyte medium (GIBCO number 17005-042) supplemented with epidermal growth factor (EGF: 5 ng/mL) and bovine pituitary extract (40 ug/mL) for 48 hours as described previously (Ryan et al (1994) Kidney International 45:48-57). Cells were transferred to 24-well plates at a density of $3 \times 10^5$ cells per well. After 24 hours, cells were incubated with fresh medium containing TNF-alpha (5 ng/mL) for 20 hours. Controls received medium alone. Then cells were washed twice with fresh culture medium and further incubated with culture medium alone (medium control, and TNF control wells) or TDF-1 at three different concentrations (40, 200 or 1000 ng/mL) or TDFRP compounds at three different concentrations (4, 20 or 100 uM) for sixty hours. During incubation, cells were kept in a 5% $CO_2$ humid atmosphere at 37° C. At the end of the incubation, the media were removed and stored frozen until assayed. The concentrations of IL-6, IL-8 and sICAM-1 in culture supernatants were measured by specific ELISA (FIG. 10).

E. ELISA for IL-6

The capture antibody is diluted to the working concentration in PBS, pH 7.4 without carrier protein. 61 uL of stock antibody (360 ug/mL) is added to 10.939 mL of PBS, and gently vortexed. A 96 well microplate (Immulon 4 HBX) is coated with 100 uL per well of the diluted capture antibody. The plate is sealed and incubated overnight in cold (4° C.). (PBS: 8.1 mM $Na_2HPO_4$, 1.5 mM $KH_2PO_4$, 137 mM NaCl, 2.7 mM KCl, pH 7.4, 0.2 um filtered). The wells are emptied and washed three times, each time using 340 uL of wash buffer per well. (wash buffer: PBS, pH 7.4 containing 0.05% Tween-20).

Blocking buffer is prepared (35 mL per plate) by adding 0.35 grams of BSA and 1.75 grams of sucrose to 35 mL of PBS, pH 7.4, and mixed gently. 300 uL of blocking buffer is added to each well and incubated for a minimum of 1 hour at room temperature. The wells are emptied and washed three times, each time using 340 uL of wash buffer per well.

An 8 point standard curve is prepared using 2-fold serial dilutions in reagent diluent. Recombinant IL-6, 70 ng/mL is diluted to an initial concentration of 2400 ng/mL in reagent diluent and then further diluted to a working range, 1200, 600, 300, 150, 75, 37.5, 18.75 and 9.375 ng/mL using reagent diluent. (reagent diluent is prepared with 0.4 grams of BSA in 40 mL of PBS, pH 7.4 and gently vortexed). 24 uL of each sample (from HK-2 cell cultures) is diluted with 376 uL of reagent diluent. 100 uL of standard or sample is added per well, sealed and incubated overnight in cold (4° C.). Wells are washed three times, each time using 340 uL of wash buffer per well. 61 uL of stock detection antibody (0.1-10 ug/mL) are added to 10.939 mL in reagent diluent and vortexed. 100 uL of working dilution of detection antibody are added to each well. The plate is sealed and incubated for 2 hours at room temperature. Wells are washed three times, each time using 340 uL of wash buffer per well. Streptavidin-HRP, 11 mL per plate is prepared in reagent diluent. 55 uL of stock solution (#890803, R&D Systems) is added to 10.945 mL of reagent diluent and gently vortexed. 100 uL of working dilution of streptavidin-HRP is added to each well. The plate is sealed and incubated for 20 minutes at room temperature. Wells are washed three times, each time using 340 ul of wash buffer per well. 5.5 mL of color reagent A ($H_2O_2$) is mixed with 5.5 mL of color reagent B (Tetramethylbenzidine) (#DY999, R&D Systems). 100 uL of substrate solution is added to each well. The plate is covered and incubated for 20 minutes at room temperature. 50 uL of stop solution (2 N $H_2SO_4$) is added to each well. The optical density of each well is determined immediately using a microplate reader (Dynex Revelation 4.22) set to 450 nm and a wavelength correction at 550 nm F. ELISA for IL-8

The protocol for IL-8 ELISA is similar to the IL-6 methods described above with the following modifications: no sucrose is included in the blocking buffer, 200 uL samples are used and the working range is 4000 pg/mL down to 31.25 pg/mL.

G. ELISA for ICAM-1

The capture antibody is diluted to the working concentration in PBS, pH 7.4 without carrier protein. 61 uL of stock antibody (720 ug/mL) is added to 10.939 mL of PBS, and vortexed. A 96 well microplate (Immulon 4 HBX) is coated with 100 uL per well of the diluted capture antibody. The plate is sealed and incubated overnight in cold (4° C.). (PBS: 8.1 mM $Na_2HPO_4$, 1.5 mM $KH_2PO_4$, 137 mM NaCl, 2.7 mM KCl, pH 7.4, 0.2 um filtered). Wells are washed three times, each time using 340 uL of wash buffer per well (wash buffer: PBS, pH 7.4 containing 0.05% Tween-20). Blocking buffer (35 mL per plate) is prepared by adding 0.35 grams of BSA and 1.75 grams of sucrose to 35 mL of PBS, pH 7.4. 300 uL of blocking buffer is added to each well and incubated for a minimum of 1 hour at room temperature. Wells are washed three times, each time using 340 uL of wash buffer per well. An 8-point standard curve is prepared using 2-fold serial dilutions in reagent diluent. Recombinant sICAM-1, 55 ng/mL is used as a stock standard and diluted to an initial concentration of 2000 ng/mL in reagent diluent and to a working range of: 1000, 500, 250, 125, 62.5, 31.25, 15.625 and 7.813 ng/mL using reagent diluent. 160 uL of each sample medium is diluted (from HK-2 cell cultures) with 240 uL of reagent diluent. 100 uL of standard or sample is added per well, the plate is sealed and incubated overnight in cold (4° C.). Wells are washed three times, each time using 340 uL of wash buffer per well. 61 uL of stock detection antibody (18 ug/mL) is added to 10.939 mL in reagent diluent and gently vortexed. 100 uL of working dilution of detection antibody is added to each well. The plate is sealed and incubated for 2 hours at room temperature. Wells are washed three times, each time using 340 uL of wash buffer per well. 55 uL of stock solution Streptavidin-HRP (#890803, R&D Systems) is added to 10.945 mL of reagent diluent and gently vortexed. 100 uL of working dilution of streptavidin-HRP is added to each well. The plate is sealed and incubated for 20 minutes at room temperature. Wells are washed three times, each time using 340 ul of wash buffer per well. 5.5 mL of color reagent A substrate ($H_2O_2$) is mixed with 5.5 mL of color reagent B (Tetramethylbenzidine) (#DY999, R&D Systems). 100 uL of substrate solution is added to each well. The plate is covered and incubated for 20 minutes at room temperature. 50 uL of stop solution (2 N $H_2SO_4$) is added to each well. The optical density of each well is determined immediately using a microplate reader. (Dynex Revelation 4.22) set to 450 nm and a wavelength correction at 550 nm H. Apoptosis Detection Using Annexin V Immunostaining Apoptosis and cell viability are quantified using Annexin V-FITC and propidium iodide staining of HK-2 cells following cisplatin treatment Immortalized PTEC-derived HK-2 cells (ATCC number CRL-2190) are cultured in serum-free keratinocyte medium (GIBCO number 17005-042) supplemented with EGF and BPE for 48 hours (Ryan et al. 1994 Kidney Int 45:48-57). Medium is aspirated and cells are washed with PBS and incubated in the dark for 15 min at room temperature with 10 μl of media binding agent and 1.25 μl of FITC conjugated AnnexinV. Propidium iodide (10 μl) is added, and samples are analyzed immediately. Quantification of Annexin V-FITC and propidium iodide signals is performed by fluorescence microscopy (Axiovert 135; Carl Zeiss). Phase contrast images are observed using transmitted light. Apoptotic cells show cytoplasmic staining and viable cells remain unstained (FIG. 14A-FIG. 14D).

I. ELISA for Bax

The capture antibody is diluted to a working concentration (200 ul of PBS added to a stock of 360 ug/ml) in PBS, pH 7.4 without carrier protein. 61.2 uL is added of stock antibody (360 ug/mL) to 10.939 mL of PBS, and gently vortexed. A 96 well microplate (Immulon 4 HBX) is coated with 100 uL per well of the diluted capture antibody. The plate is sealed and incubated overnight in cold (4° C.). (PBS: 8.1 mM $Na_2HPO_4$, 1.5 mM $KH_2PO_4$, 137 mM NaCl, 2.7 mM KCl, pH 7.4, 0.2 uM filtered). Wells are washed three times, each time using 300 uL of wash buffer per well. (Wash buffer: PBS, pH 7.4 containing 0.05% Tween-20). Blocking buffer (1% BSA, 5% Sucrose in PBS pH 7.2-7.4), is added to 0.35 grams of BSA and 1.75 grams of sucrose to 35 mL of PBS, pH 7.4, and mixed. 300 uL of blocking buffer is added to each well and incubated for 2 hours at room temperature. Wells are washed three times, each time using 300 uL of Wash buffer per well. An 8 point standard curve is generated using 2-fold serial dilutions in diluent (1 mM EDTA, 0.005% Tween20, 0.5% TritonX-100 in PBS pH 7.2-7.4). Recombinant Bax (270 ng/mL) is diluted to an initial concentration of 20 ng/mL in diluent and to a working range of: 10, 5, 2.5, 1.25, 0.625, 0.3125 and 0.1562 ng/mL using diluent. 100 uL of standard or sample is added per well, sealed and incubated overnight at 4° C. Wells are washed three times, each time using 300 uL of Wash buffer per well. 100 uL of working dilution of detection antibody (11 mL per plate) is added to each well, sealed and incubated for 2 hours at room temperature. Wells are washed three times, each time using 300 uL of Wash buffer per well. 55 uL of stock solution Streptavidin-HRP (#890803, R&D Systems) are added to 10.945 mL of diluent and gently vortexed. 100 uL of working dilution of streptavidin-HRP is added to each well, sealed and incubated for 20 minutes at room temperature. Wells are washed three times, each time using 300 uL of Wash buffer per well. Fresh substrate solution (11 mL per plate) is prepared. 5.5 mL of color reagent A ($H_2O_2$) is mixed with 5.5 mL of color reagent B (Tetramethylbenzidine) (#DY999, R&D Systems). 100 uL of Substrate solution is added to each well, covered and incubated for 20 minutes at room temperature. 50 uL of Stop solution (2 N $H_2SO_4$) is added to each well. The optical density of each well is determined immediately using a microplate reader set to 450 nm and a wavelength correction at 544 nm (FIG. 10).

I. Cardiomyocyte Cell Culture and Determination of Cytokine, Apoptosis Activities Primary neonatal rat cardiomyocytes (Cell Applications) are cultured in cardiomyocyte culture medium with 10% growth supplement (Cell Applications) for 24 hours at 37° C., 5% $CO_2$. Cells are starved of growth supplement for 12 hours followed by treatment with either Doxorubicin (333 nM) or Lipopolysaccharide (LPS) (100 ng/ml) for 24 h or 12 h respectively. Controls receive medium alone. Cells are incubated with culture medium alone or BMP-7 (143 nM) or TDFRP compounds at 4 different concentrations (4, 20, 100, 500 uM) for 24-60 h. Cells are kept in a 5% $CO_2$ humid atmosphere at 37° C. At the end of incubation, conditioned media is removed and Akt phosphorylation at Serine 473 or Caspase-3 enzyme activity are assayed per manufacturer's protocols (Cell Signaling Technology or Calbiochem respectively). The concentration of rat IL-6 in culture supernatants are measured by specific ELISAs as described above (FIG. 12).

J. Protocol to Detect Akt S473 Phosphorylation

The anti-apoptotic activity of TDFRP compounds is assayed using the increased phosphorylation of Akt as a marker of cardiomyocyte cell survival following treatment with doxorubicin. Primary neonatal rat cardiomyocytes (Cell Applications) are cultured in medium with 10% growth supplement (Cell Applications) for 24 hours at 37° C., 5% $CO_2$. Cells are starved of growth supplement for 12 hours, followed by treatment with Doxorubicin (333 nM) for 24 h. Controls receive medium alone. Cells are incubated with culture medium alone, BMP-7 (143 nM) or TDFRP compounds at 4 different concentrations (4, 20, 100, 500 uM) for 60 h to detect Akt phosphorylation at Serine 473 (Cell Signaling Technology). Cell lysates are prepared in manufacturer's lysis buffer (10×) diluted 1:10 in Milli-Q water, and PMSF is added to final concentration of 1 mM. 200 ul ice-cold lysis buffer is used per well of 12-well plate. Cells are incubated for 10 min at 4° C. and cell lysates are obtained by removing supernatant from wells and clarifying by centrifugation at 10,000 rpm, 10 min at 4° C. 100 ul of each dilution is added to the microwell strips (Cell Signaling Technology), sealed and incubated overnight at 4° C. Wells are washed four times with 300 ul of 1× Wash buffer. 100 ul Detection antibody per well is added and incubated 1 h at 37° C. 100 ul HRP-linked secondary antibody is added per well and incubated 30 min at 37° C. 100 ul TMB substrate is added per well and incubated for 30 min at room temperature in the dark. The reaction is stopped and absorabance is read at 450 nM with a microplate reader (FIG. 12).

K Protocol to Detect Caspase-3 Activity

The anti-apoptotic activity of TDFRP compounds is determined by examining the ability to downregulate Caspase-3 activity that is induced by doxorubicin or LPS treatment of cardiomyocytes. Caspase-3 activity serves as an apoptosis marker. Cell lysates are prepared in manufacturer's lysis buffer. 200 ul ice-cold lysis buffer is used per well of 12-well plate. Cells are incubated for 10 min at 4° C. and lysates are obtained by removing supernatant from wells and centrifuging at 10,000 rpm for 10 min at 4° C. 50 ul of assay buffer (Calbiochem) is added to each well and 40 ul of lysate is added and mixed. 10 ul of Caspase-3 substrate is added per well and absorbance is read at 405 nM in a microtiter plate reader (FIG. 12).

L. Smad Phosphorylation

Phosphorylation and nuclear translocation of Smads occurs following the activation of Type I and Type II receptors and subsequent signal transduction to intracellular Smad targets. Phosphorylation and nuclear translocation of R-Smad in HK-2 cells by TDFRP compounds is assayed by immunofluorescent microscopy methods, using anti-phospho Smad 1/5 antibodies according to the procedure of H Aoki, M Fujii, T Imamura, K Yagi, K Takehara, M Kato and K Miyazono. J. of Cell Sci. 114, 1483-1489, 2001) and by Western blot analysis (FIG. 15A-FIG. 15C).

HK2, human proximal tubule cells are incubated in culture medium alone or exposed TDFRP or control compounds for one hour ten minutes at 37 degree C. BMP-7 served as a positive control in the assay. Each well is rinsed with 1 mL prewarmed medium. 1 mL per well of cold Acetone/Methanol mix (1:1) is added and incubated for 2 minutes at room temperature to fix the cells. Wells are washed with 1 mL of cold PBS and blocked with 1 mL blocking buffer (3% BSA, 1% goat serum in PBS) for 7 minutes. Wells are aspirated without disturbing the cells, and 500 uL/well primary antibody is added (anti-phospho-Smad 1) at 0.056 ug/mL concentration in 3% BSA in PBS (no goat serum). Cells are incubated overnight at 4 degrees C. FITC labeled secondary antibody is diluted 1:10 in 1.5% goat serum in PBS and 500 uL/well of secondary antibody is added and incubated at room temperature for 40 minutes in the dark. Wells are washed twice each time with 1 mL of PBS and cells are observed with a fluorescent microscope.

For detection of Smad phosphorylation by Western analysis, LNCaP (prostate cancer cells) or EC (vascular endothelial cells) in culture medium are exposed to varying concentrations of TDFRP or control compounds. BMP-7 served as a positive control. Cells are lysed in RIPA lysis buffer (50 mM Tris-HCl at pH 8.0, 150 mM NaCl, 1% NP-40, 0.5% sodium deoxycholate, 0.1% SDS) containing 1 mM PMSF, 1 mM sodium orthovanadate, and 10 ug/mL proteinase inhibitor cocktail. Lysates are incubated on ice for 15 minutes, centrifuged, and transferred supernatant to a clean tube. 50 to 100 ug is used for analysis by SDS-PAGE. Resolved proteins are electrotransfered onto PVDF membrane. The blot is blocked by incubating in 3% non-fat dry milk prepared in PBS at room temperature for 1 hour with constant slow agitation. The blot is incubated with 1-2 ug/mL of primary antibody (rabbit anti-phospho-Smad 1) prepared in PBS-milk, overnight with agitation at 4 degree C., washed twice with PBS, and incubated with secondary antibody (anti rabbit HRP conjugated IgG, 1:3000 dilution) at room temperature for 2 hours with agitation. After washing in PBS-0.05% Tween 20 for 5 minutes and rinsing, Smad phosphorylation is detected via an HRP reaction according to manufacturer's instructions (FIG. 3).

M. In Vitro Assays to Assess Tumor Suppression

Prostate cancer is one of the most common cancers in men. Several lines of evidence have suggested that bone morphogenetic protein (BMP) inhibits the proliferation of androgen-sensitive (LNCaP) and androgen-insensitive (PC-3, DU-145) human prostate cancer cells. Moreover, it has been shown that BMP signals inhibit the growth and the proliferation of human prostate tumor cells by upregulating the cyclin-dependent kinase inhibitor (CDKI) p21 (CIP1/WAF1) and decreasing the activity of Cdk2, leading to hypophosphorylation of Rb proteins. TDFRP compounds have been screened in in vitro prostate and bladder cancer bioassays to assess growth inhibitory activity of the compounds. $^3$H-thymidine incorporation is used as a marker for cell proliferation activity in human prostate and bladder cancer cell lines. Cisplatin inhibits $^3$H-thymidine incorporation, indicating a tumor-growth suppressive activity of cisplatin in both human prostate and bladder cancer cells. TDFRP compounds are assayed in these cancer cells for the ability to induce receptor-regulated Smad 1/5 phosphorylation in a dose-dependent manner (FIG. 3).

Example 3

In Vivo Assays to Measure Biological Activity of TDFRP Compounds

I. In Vivo Investigation of Compound SEQ ID #45 Efficacy in the Treatment of Myocardial Injury Following Ischemia The efficacy of compound SEQ ID #45 in ameliorating the effects of myocardial ischemia was investigated in the rat after ligation of the coronary artery. Twenty-four unmanipulated rats, sorted into two large groups by initial body weight (>300 g pre-surgery) were evaluated. Fourteen rats underwent surgery on week, 12 rats underwent surgery on week 2 and rats were sorted into 3 treatment groups: Group 1, PBS; Group 2, positive control TDF-1; Group 3, test article SEQ ID #45 (see Table X).

TABLE X

THR 04-02: Target Number of Animals for Each Treatment Group

| Group # | Test Compound | Group Size | Dose/Route |
|---|---|---|---|
| 1 | Vehicle (neg. control) | N = 5 | Equal volume i.v. |
| 2 | TDF-1 (pos. control) | N = 3 | 160 µg/kg i.v. <5 ml/kg |
| 3 | SEQ ID # 45 (Test article) | N = 5 | 10 mg/kg i.v. <5 ml/kg |

Three days prior to surgery, a serum sample was collected from the tail vein of each rat (pre-bleed). On the day of surgery, each rat was administered compound intravenously 2 hr prior to surgery. Surgery was performed sequentially after intubation and ventilation with 0.5% isofluorane anesthetic.

Lead II ECG was monitored throughout the surgery. A thoracotomy was performed and the main left coronary artery was occluded for 20 min using a snare technique (FIG. 16). Successful occlusion of the artery was confirmed by ST elevation in lead II ECG within the first 5 minutes of ligation, and by frequent ventricular arrhythmia after 10 minutes of ligation. The snare was released to restore blood flow. The original suture loop was left in place for subsequent re-occlusion on Day 7. After initiation of reperfusion, the chest cavity was closed with 2 layers of suture. Rats were weaned from the ventilator and observed until fully conscious and mobile. Antibiotic (QD) and analgesic (Q8D) were provided. Additional serum samples were collected 6, 24, 72 and 120 hours post occlusion. Additional compound, positive control or vehicle treatments were delivered by intravenous injection in the tail vein at 24, 72 and 120 hours post occlusion.

On Day 7, each rat was anesthetized (ketamine:xyline), the chest cavity re-opened and a terminal blood sample (1 ml) was withdrawn from the abdominal vein. Gross pathology (i.e. inflammation) was noted and graded on a 4 point inflammation scale: 0=no inflammation, 1=slight, 2=moderate, 3=severe and 4=complete pericarditis. The left coronary artery was then re-occluded using the existing stitch and a concentrated solution of Evans Blue dye in saline (20 mg/ml; 0.5 ml/rat) was injected into the heart apex to stain the non-ischemic cardiac tissue blue. The heart was then arrested by injection of a saturated solution of potassium chloride into the right ventricle. The heart was then excised, wrapped in cellophane and stored at −20° C. for 1.5 hour. The cold heart was cut into 10 cross-sectional slices (2 mm/slice) and each section was numbered and incubated separately in triphenyltetrazolium chloride (1% TTC in PBS) for 10 minutes at 37° C. prior to fixing in 4% formaldehyde. Subsequently, each slice was photographed. For each slice, the "area at risk (AR)" and the "area occupied by necrosis (AN)" were measured by morphometry. The ratio of AN to AR is a measure of the degree of damage resulting from the occlusion (FIG. 17A-FIG. 17B).

Sixty-seven percent of the animals (16/24) survived ligation of the coronary artery and underwent necropsy on day 7 post surgery. Each occlusion was confirmed by ECG analysis during the surgery and ultimately after Evans blue injection on Day 7 at necropsy. All but one rat demonstrated successful occlusion by Evans Blue at necropsy (15/16). A total of 6 PBS-treated, 4 rhmBMP-1-treated and 6 compound (SEQ ID No 45)-treated animals were evaluated at necropsy. Areas of infarct were clearly identified in all heart samples and morphometry was performed on most slices. Treatment-related differences in gross pathology and morphometry were observed. Control rats treated with PBS showed more severe pericarditis at necropsy as compared to minor pericarditis in rats treated with either test compound. The animals treated with 10 mg/kg of the compound showed an 84% reduction in AN/AR ratio as compared to PBS-treated animals whereas animals treated with 160 µg/kg rhmBMP-7 (positive control) had only a 7% reduction in AN/AR ratio as compared to PBS-treated animals. Furthermore, animals treated with the compound showed a 78% reduction in inflammation score as compared to PBS-treated animals (FIG. 17A-FIG. 17B).

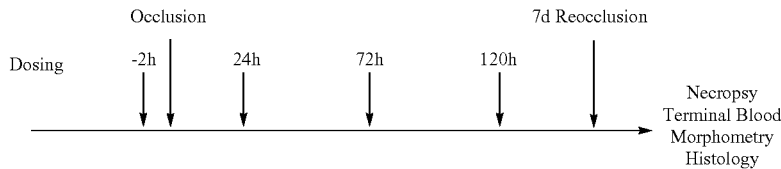

Schematic of Study

II. In Vivo Models of Stroke

A. Severe Hypoxic Ischemia

The effect of TDFRP compound on cell damage due to severe hypoxic ischemic injury is measured by the method of Hughes and coworkers (Hughes et al., Methods of providing neuroprotection and/or neurorestoration via the neural activin type IIB receptor, U.S. patent application Ser. No. 10/177,735, filed Jun. 5, 2003). Unilateral hypoxic-ischemic brain injury is induced in 21-day-old Wistar rats using a modified version of the "Levine" rat preparation as described previously (Sirimanne E. S., Guan J., Williams C. E., and Gluckman P. D. (1994). J. Neurosci. Meth., 55:7-14; Vannucci, R. C. (1993) APMIS 101, 89-95; Levine (1960) Am. J. Path. 36, 1-17). Briefly, rats of both sexes weighing 40-49 g are anesthetized and maintained on a 2% halothane/oxygen mixture. A 10 mm incision is made along the midline of the neck exposing the right common carotid artery, which is double ligated using 4-0 silk surgical thread. Following a 1 h recovery period in an infant incubator kept at a stable thermoneutral environment (34° C., 85.+−.5% humidity), the rats are subsequently exposed to severe inhalation hypoxia of 8% oxygen in nitrogen for 60 minutes, at 34° C. and 80% humidity. They are then removed from the incubator and held at room temperature of 22° C. and 55=5% relative humidity, and fed food and water ad libitum. Two controls are used: control rats, which did not undergo either ligation or hypoxia; and "sham" ligated rats, which underwent anesthesia and incision (but not ligation) and hypoxia. Administration of TDFRP compound and measurement of ischemia-induced brain damage by histological analysis and behavioral testing are performed as described below.

B. Middle Cerebral Artery (MCA) Occlusion Ischemia Model.

The middle cerebral artery (MCA) occlusion model is a well-accepted model of a focal ischemic episode or stroke (Gotti, et al., (1990) Brain Res. 522: 290-307). Focal ischemia is produced by obstructing blood flow through the MCA, resulting in infarction of the brain locus supplied by this artery. The MCA model is reasonably predictive of the ability and efficacy of drugs, such as TDFRP or BMP, to alter functional recovery in humans in whom central nervous system tissue has been damaged or lost due to stroke. For example, the MCA model is deemed reasonably predictive of drug efficacy to restore or detectably improve motor coordination, sensory perception, speech or any other central nervous system function naturally contributed to by tissue within the territory of the MCA.

Chang and coworkers (Chang et al., Stroke. 2003 February; 34(2):558-64) have previously reported that bone morphogenetic protein-7 (BMP-7), given before middle cerebral artery occlusion (MCAO), reduces ischemic injury in brain. Recent studies have indicated that receptors for BMP are upregulated after brain ischemia. This upregulation may facilitate endogenous neurorepair in the ischemic brain.

The effect of the TDFRP compound on cell damage due to hypoxic ischemic injury are measured by the method of Weaver and coworkers (Weaver, et al., (1997) Proc Natl Acad Sci USA. 1997 Sep. 16; 94(19):10450-4), Chang and coworkers (Chang et al., Stroke. 2003 February; 34(2):558-64), or U.S. Pat. No. 6,407,060, issued Jun. 18, 2002. For example, MCA occlusion is performed under halothane anesthesia in male Wistar rats (290-320 g, Charles River Breeding Laboratory) as described (Oliff et al., (1995) Brain Res. 699, 329-331). Briefly, a chronic in-dwelling catheter for the administration of steroid or vehicle is placed in the left jugular vein. Both common carotid arteries (CCA) are isolated, and a loose silk ligature is place around each artery. The left MCA is exposed, and after permanent ligation of the ipsilateral CCA, the MCA is coagulated from its origin to the olfactory tract. The contralateral CCA is occluded for a period of 2 h.

Alternatively, adult Sprague-Dawley rats are anesthetized with chloral hydrate. The middle cerebral artery is transiently occluded by a filament inserted through the right internal carotid artery. The filament is removed after 60-minute ischemia to allow reperfusion.

Further still, male Sprague-Dawley rats weighing 250-300 grams (Charles River) are anesthetized with 2% halothane in 70% $NO_2$/30% $O_2$. The tail artery is cannulated in order to monitor blood gases and blood glucose. Body temperature is monitored using a rectal probe and is maintained at 37.+−.0.5° C. with a heating pad. The proximal right middle cerebral artery (MCA) is occluded permanently using a modification of the method of Tamura, et al. (1981, J. Cereb. Blood Flow Metab. 1: 53-60). Briefly, the proximal MCA is exposed transcranially without removing the zygomatic arch or transacting the facial nerve. The artery is then electrocoagulated using a bipolar microcoagulator from just proximal to the olfactory tract to the inferior cerebral vein, and is then transected (Bederson, et al., (1986) Stroke 17: 472-476). Rats are observed until they regained consciousness and are then returned to their home cages. Cefazolin sodium (40 mg/kg, i.p.), an antibiotic, is administered to all animals on the day before and just after stroke surgery in order to prevent infection. During stroke surgery, there are no differences in the levels of blood gases or glucose among animals that subsequently received TDF, e.g., BMP-7, TDFRP, or vehicle treatment.

Administration of TDFRP compound and measurement of ischemia-induced brain damage by histological analysis and behavioral testing are performed as described below.

C. Prophylactic and Therapeutic Treatment

The effect of TDFRP compound on ischemia-mediated tissue damage is assessed by administration of the TDFRP compound alone or in combination with TDF 0-60 minutes before (prophylaxis) or after (therapeutic) occlusion of the contralateral CCA. For example, rats are administered an i.v. loading dose 0.000001-10,000 mg/kg TDFRP compound or TDF followed by i.v. infusion of TDRF or TDF at 0.000001-10,000 mg/kg per h until sacrifice. Control rats are treated with vehicle (0.1 M phosphate buffer, pH 7.4/5% DMSO/10% cyclodextrin). Alternatively, animals receive a single dose (0.000001-10,0000 mg/kg) of intravenous TDF, e.g., BMP-7, TDFRP compound and/or vehicle at 0-24 h before (prophylaxis) or after (therapeutic) ischemia treatment.

Further still, animals in the treatment group receive TDF, e.g., BMP-7, and/or TDFRP compound intracisternally at a dose of 0.1-100 μg/injection. Control animals receive vehicle solutions lacking TDFRP compound but with all other components at equivalent final concentrations. Intracisternal injections are made starting 24 hours after stroke and may be are repeated up to 30 days thereafter.

To administer the intercisternal injection, the animals are anesthetized with halothane in 70% $NO_2$/30% $O_2$ and placed in a stereotaxic frame. The procedure for intracisternal injection of TDFRP compound or TDF-containing solutions or vehicle-only solutions is identical. Using aseptic technique, TDFRP compound or an equivalent volume of vehicle or TDF-containing solution are introduced by percutaneous injection (~10 μl/injection) into the cisterna magna using a Hamilton syringe fitted with a 26 gauge needle (Yamada, et al., (1991) J. Cereb. Blood Flow Metab. 11: 472-478). Before each injection, ~1-2 μl of cerebrospinal fluid (CSF) is drawn back through the Hamilton syringe to verify needle placement in the subarachnoid space. Using this technique 1% Evans blue dye diffuses freely through the basal cisterns and over the cerebral cortex within one hour of injection.

D. Behavioral Testing

To accustom the animals to handling, necessary for behavioral/functional testing, they are handled for three days before surgery, for 10 minutes each day. Following surgery, the animals are housed in individual cages. Four standard functional/behavioral tests are used to assess sensorimotor and reflex function after infarction. The tests have been fully described in the literature, including Bederson, et al., (1986) Stroke 17: 472-476; DeRyck, et al., (1992) Brain Res. 573: 44-60; Markgraf, et al., (1992) Brain Res. 575: 238-246; and Alexis, et al., (1995) Stroke 26: 2338-2346.

i. The Forelimb Placing Test

Briefly, the forelimb-placing test is comprised of three subtests. Separate scores are obtained for each forelimb. Normal placing of the limb on the table is scored as "0," delayed placing (<2 sec) is scored as "1," and no or very delayed placing (>2 sec) is scored as "2." Separate scores are obtained first as the animal is brought forward and then again as the animal is brought sideways to the table (maximum score per limb=4; in each case higher numbers denote greater deficits). For the tactile placing subtest, the animal is held so that it cannot see or touch the tabletop with its whiskers. The dorsal forepaw is touched lightly to the tabletop as the animal is first brought forward and then brought sideways to the table. Placing each time is scored as above (maximum score per limb=4). For the proprioceptive placing subtest, the animal is brought forward only and greater pressure is applied to the dorsal forepaw; placing is scored as above (maximum score per limb=2). These subscores are added to give the total forelimb placing score per limb (range=010). In some animals, the whisker-placing subtest was done, in which the ability of the animal to place the forelimb in response to whisker stimulation by the tabletop was tested (maximum score per limb=2). Then subscores were added to give the total forelimb placing score per limb (range=0-10, 0-12 with whisker subtest. Normalization of the score in one or more subtest in animals treated with TDFRP compound toward the subtest scores observed in sham-operated animals not receiving TDFRP compound and away from the subtest scores observed in control ischemic animals not receiving TDFRP compound indicates that the TDFRP has a prophylactic or therapeutic effect.

ii. The Hindlimb Placing Test

The hindlimb-placing test is conducted in the same manner as the forelimb-placing test but involves only tactile and proprioceptive subtests of the hindlimbs (maximal scores 4 and 2, respectively; total score range=0-6). Normalization of the hindlimb placement score in animals treated with TDFRP compound toward the score observed in sham-operated animals not receiving TDFRP compound and away from the score of control ischemic animals not receiving TDFRP compound indicates that the TDFRP has a prophylactic or therapeutic effect.

iii. The Modified Balance Beam Test

The modified balance beam test examines vestibular motor reflex activity as the animal balances on a narrow beam (30.times.1.3 cm) for 60 seconds. The animal's ability to balance on the beam is scored as follows: 1—animal balances with all four paws on top of beam; 2—animal puts paws on side of beam or wavers on beam; 3—one or two limbs slip off beam; 4—three limbs slip off beam; 5—animal attempts to balance with paws on beam but falls off; 6—animal drapes over beam, then falls off; 7—animal falls off beam without an attempt to balance. Animals received three training trials before surgery: the score of the last of these is taken as the baseline score. Normalization of the score in the modified balance beam test in animals treated with TDFRP compound toward the score observed in sham-operated animals not receiving TDFRP compound and away from score observed in control ischemic animals not receiving TDFRP compound indicates that the TDFRP has a prophylactic or therapeutic effect.

iiii. The Postural Reflex Test

The postural reflex test measures both reflex and sensorimotor function Animals are first held by the tail suspended above the floor. Animals that reach symmetrically toward the floor with both forelimbs are scored "0." Animals showing abnormal postures (flexing of a limb, rotation of the body) are then placed on a plastic-backed sheet of paper. Those animals able to resist side-to-side movement with gentle lateral pressure are scored "1," while those unable to resist such movement are scored "2." All functional/behavioral tests are administered just before stroke surgery and then every other day from post-stroke day 1 thereon. At each session, animals are allowed to adapt to the testing room for 30 minutes before testing is begun. Normalization of the score in the postural reflex test in animals treated with TDFRP compound toward the score observed in sham-operated animals not receiving TDFRP compound and away from score observed in control ischemic animals not receiving TDFRP compound indicates that the TDFRP has a prophylactic or therapeutic effect.

E. Histological Analysis i. Hematoxylin and Eosin Staining of Brain Tissue

Up to 30 or more days after MCA occlusion, animals are anesthetized deeply with pentobarbital and perfused transcardially with heparinized saline followed by 10% buffered formalin. Brains are removed, cut into three pieces, and stored in 10% buffered formalin before dehydration and embedding in paraffin. Coronal sections (5 .mu.m) are cut on a sliding microtome, mounted onto glass slides, and stained with hematoxylin and eosin. The area of cerebral infarcts on each of seven slices (+4.7, +2.7, +0.7, −1.3, −3.3, −5.3, and −7.3 compared to bregma) is determined using a computer interfaced imaging system (Rioquant, R&M Biometnix, Inc., Nashville, Teen.). Total infarct area per slice is determined by the "indirect method" as [the area of the intact contralateral hemisphere]−[the area of the intact ipsilateral hemisphere] to correct for brain shrinkage during processing (Swanson, et al., (1990) J. Cereb. Blood Flow Metab. 10: 290-293). Infarct volume is then expressed as a percentage of the intact contralateral hemispheric volume. The volumes of infarction in cortex and striatum are also determined separately using these methods.

Analysis is performed with the observer blind to the treatment group. Reduction in the infarct volume in the presence of TDFRP compound indicates that the TDFRP compound has a protective or therapeutic effect.

ii. 2,3,5-Tetrazolium Chloride Staining of Brain

Rats are euthanized with an overdose of pentobarbital up to 30 or more days following surgical treatment. Brains are sliced into 2 mm coronal sections, and stained with 2,3,5-triphenyl tetrazolium chloride by methods well known in the art. Cortical and subcortical infarct volumes are calculated by integration of the area of infarct and the distance between slices using an image analysis system (NIH IMAGE). Analysis is performed with the observer blind to the treatment group. Reduction in the infarct volume in the presence of TDFRP compound indicates that the TDFRP compound has a protective or therapeutic effect.

III. In Vivo Models of Renal Injury or Disease

In vivo assays for biological activity of the full-length BMP-7, in rat models are described in Borovecki et al., The Role of Bone Morphogenetic Proteins in Kidney Development and Repair, pp 263-288 in Bone Morphogenetic Proteins, Sampath, K. ed., (Birkhauser Verlag, Basel Switzerland (2002)), incorporated herein by reference. BMP-7, administered systemically to rats, halts the progression of end stage renal failure in a remnant kidney (5/6 nephrectomy). A second assay cited therein discloses short-term prophylaxis by BMP-7 when administered systemically to rats with unilateral ureteral obstruction (UUO). As described below, rodent models provide for mammalian models of kidney disease, treatable prophylactically and therapeutically by the TDFRP compounds of the present invention (FIG. 4-FIG. 6D).

A. In Vivo Study on the Efficacy of Compound (SEQ ID #45) to Ameliorate the Renal Toxic Effects of Chemotherapeutic Compound Cisplatin in the Rat Overview Compound (SEQ ID #45) was tested in male Sprague-Dawley rats (250 gm to 300 gm) to establish the dose range and the extent to which the compound is able to prophylactically and therapeutically ameliorate the renal toxic effects of cisplatin. The cisplatin dosing level was the chemotherapeutic level used in humans, 40 ug/kg bw. The end points were the level of creatinine in serum and kidney histology. The positive control used was 250 ug/kg bw of the mature form of recombinant human BMP-7 (rhmBMP-7).

Animal: Male Sprague-Dawley Rat

| Groups: | Dose | Number/group |
|---|---|---|
| Group 1: | Vehicle PBS pH 7.2 + 5% Mannitol | (n = 10) |
| Group 2: | 0.28 mg/kg SEQ ID # 45 | (n = 10) |
| Group 3: | 2.8 mg/kg SEQ ID # 45 | (n = 8) |
| Group 4: | 28 mg/kg SEQ ID # 45 | (n = 8) |
| Group 5: | 250 µg/kg rhmBMP-7 | (n = 8) |
| | | 44 rats |

| | | | TimeLine | | | | |
|---|---|---|---|---|---|---|---|
| | −2 hr | 0 | Day 1 | Day 2 | Day 3 | Day 4 | Day 7 |
| Cisplatin Dosing | + | 40 ug/kg | + | + | + | + | |
| Bleeding | | + | + | + | + | + | + |
| Sac | | | | | | | + |

A stock solution (70 mg/ml) of the test article (SEQ ID #45) was made by dissolving it in 20 mM Acetate (ph 4.2). The stock solution was further diluted into phosphate buffered saline (PBS, pH 7.2) plus 5% Mannitol to compound concentrations of 14 mg/ml (28 mg/kg dose), 1.4 mg/ml (2.8 mg/kg dose) and 0.14 mg/ml (0.28 mg/kg dose).

Figure 18:
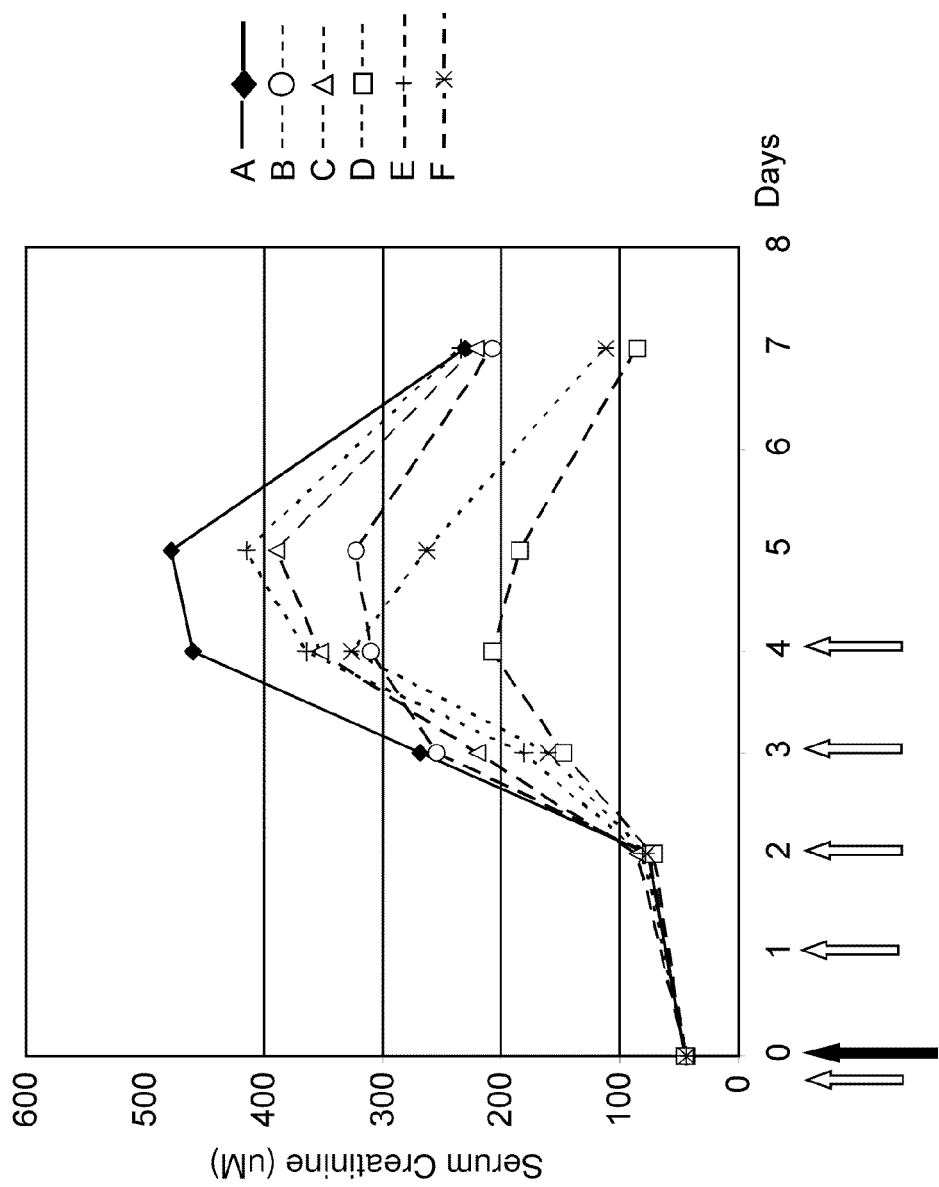

Cisplatin was administered via i.p. injection (40 ug/kg bw) at time zero. Administration of therapeutic dosing of the compound, the rhmBMP-7 positive control and vehicle negative control were by slow bolus i.v. injection through the tail vein at five time points: 2 hours before the administration of cisplatin, then at 24 hours, 48 hours, 72 hours and 96 hours post cisplatin administration. Blood samples were collected through the tail vein at time points of 0, 24, 48, 72 and 96 hours. At seven day sample was collected by exsanguination at sacrifice. Serum was prepared from the blood samples and analyzed for creatinine concentration. The serum concentration of creatinine, a byproduct of muscle activity that is released into the blood stream and cleared through the kidneys, is a marker of kidney function that tends to rise when kidney function becomes severely compromised (FIG. 18).

Upon sacrifice at seven days, the kidneys were harvested, fixed in formalin and imbedded in paraffin. They were then sagitally sectioned and stained in H&E stain. Kidney sections were also stained with anti-bodies against proliferating cell nuclear antigen (PCNA) (to identify sites of cell regeneration), macrophages, ICAM-1, and smooth muscle. Also collected at sacrifice were tissues at and around the injection site (FIG. 19A-FIG. 19B).

The compound at the highest dose was more efficacious than the positive control at reducing the level serum creatinine rise following cisplatin administration (FIG. 18) thereby showing that the compound was more efficacious than the positive control at preserving kidney function subsequent to cisplatin administration. At even the 2.8 mg/kg bw dose level, the compound significantly reduced the level of cisplatin-induced inflammation of the kidney cortex (FIG. 20), and reduced the amount if ICAM-1 release (FIG. 21A-FIG. 21B), macrophage infiltration, smooth muscle loss, and increased the degree of cellular regeneration (FIG. 22A-23).

Peptide Formulation 313.0 mg of SEQ ID #45 was dissolved in 4.5 ml of 20 mM Acetate (pH 4.2). 17.86 ml PBS (pH 7.2)+5% Mannitol was added (total volume=22.36 ml; 14 mg/ml SEQ ID #45, or 7 mg/0.5 ml, the highest dose, 28 mg/kg). 20 ml of this was used for the 40 doses in the "28 mg/kg" arm. 2.36 ml of the remaining was added to 21.24 ml of PBS (total vol.=23.600 ml). 21 ml was used for the 40 doses in the "2.8 mg/kg" arm. 2.6 ml of this was added to 23.4 ml PBS (total vol.=26.00 ml). This was used for the 50 doses in the "0.14 mg/kg" arm.

Cisplatin Dose

Cisplatin was used at a dose of 40 ug/kg (0.25 kg/rat=10 ug/rat in 0.5 ml PBS (pH 7.2) for a total of 10 ug/rat (*44 rats=0.44 mg). The stock solution was 40 ug/kg (0.25 kg/rat/ 0.5 ml/rat=20 ug/ml).

rhmBMP-7 Dose 8 rats were evaluated at 5 doses of BMP-7 (0.25 kg/rat*250 ug/kg=3.13 mg).

B. In Vivo Model of Renal Fibrogenesis (Unilateral Ureteral Ligation)

The effects of TDFRP compound on cell damage due to renal fibrogenesis are measured by the method of Hruska and coworkers (Hruska et al., (2000) Am. J. Physiol. Renal Physiol. 279 F130-F143). Briefly, Sprague-Dawley rats (250 g) undergo either a sham operation (ureter manipulated but not ligated) or unilateral ureteral ligation (UUO). Two ligatures, 5 mm apart, are placed in the upper two-thirds of the ureter over a section of polyethylene tubing placed around the ureter. Ureteral obstruction is confirmed by observation of dilation of the pelvis and proximal ureter and collapse of the distal ureter. The suture tied to obstruct the ureter is removed along with the tubing at day 5, relieving the obstruction. Urine cultures obtained at time of release are assessed for bacteria. The following groups are studied at day 10: sham-operated animals; animals with release of ureteral obstruction at 5 days; and animals with sustained unilateral ureteral obstruction for 10 days. Sham-operated rats and rats with unilateral uretheral obstruction of 5 days duration is studied by inulin and p-aminohippurate (PAH) clearances at day 10. The rats receive one of the following 10 min before the unilateral ureteral obstruction TDFRP compound and TDF, e.g., BMP-7, are administered alone or in combination (0.000001-10, 000 mg/kg up to every three days; enalapril (~25 mg/kg body wt/day ingested) in the drinking water; or vehicle. The same experimental protocol is used in rats with unilateral urethral obstruction of 10 days duration.

The effects of TDFRP compound and TDF are compared with placebo (vehicle-treated) and to a positive control (enalapril treatment) known to ameliorate the fibrogenesis resulting from unilateral urethral obstruction (UUO) (Ishidoya et al., (1996) Kidney Int., 49: 1110-1119). The enalapril dose has previously been demonstrated to be effective in ameliorating the fibrogenesis resulting from unilateral urethral obstruction (Ishidoya et al., (1996) Kidney Int., 49: 1110-1119, Kaneto et al., (1994) Kidney Int., 45: 1637-1647). It is a high dose, much greater than that required for modulation of the systemic renin-angiotensin system. Studies are performed in a blinded fashion. Treatment solutions are made by an investigator who is not part of the study and are assigned a letter. Investigators performing the study are unaware of the content of the various treatments until after clearance studies and histopathological grading are completed. Histopathological slides are graded by individuals also blinded to the treatment groups.

Assessment of Renal Function

Renal function is determined by measuring glomerular filtration rate (GFR) of individual kidneys by inulin clearances and by estimating renal blood flow (RBF) by PAH clearances as previously reported (Miller et al., (1994) Am. J. Physiol. Renal Fluid Electrolyte Physiol., 266: F129-F134; Miller et al., (1994) Kidney Int., 46: 201-207). Rats are anesthetized with intraperitoneal Nembutal, and catheters are placed in the femoral artery and vein and both ureters. The animals are allowed to awaken in a Plexiglas restrainer, and the clearance studies are performed in awake animals. Normalization of GFR and RBF toward control levels in UUO animals treated with TDFRP compound compared with the GFR and RBF observed in UUO animals not treated with TDFRP compound indicates that the TDFRP compound has a prophylactic or therapeutic effect on renal fibrogenesis.

After completing the clearance studies, the animals are euthanized (methoxyflurane anesthesia), and the kidneys are thoroughly perfused with ice-cold Hanks' balanced salt solution (HBSS) to remove blood-borne cells. Kidneys are rapidly removed and sliced on a cold glass plate. For histological studies, 2-mm coronal sections of the HBSS-perfused kidneys are immersed in Histochoice (Amresco, Solon, Ohio) or in buffered Formalin. Kidney sections are embedded in paraffin, and 5-μm sections are analyzed microscopically.

Renal fibrosis is also assessed by determining interstitial collagen deposition and measuring interstitial volume, immunostaining for type IV collagen, immunostaining for α-smooth muscle actin (α-SMA), and by quantitating monocyte/macrophage infiltration as well as cellular apoptosis, i.e., deoxynucleotidyl transferase-mediated dUTP nick-end labeling (TUNEL) assays, as previously reported (Ishidoya et al., (1996) Kidney Int., 49: 1110-1119; Kaneto et al., (1994) Kidney Int., 45: 1637-1647; Modi et al., (1990) Kidney Int., 38: 843-850).

Several kidney diseases lead histological changes in the kidney such as the to the expansion of the tubulointerstitial area. Histological grading of the fibrosis of the tubulointerstitial area is closely correlated with loss of renal function. Stromal elements that contribute to the derangement of renal tubulointerstitium and to eventual development of fibrosis include myofibroblasts, infiltration monocytes and an overproduction of extracellular matrix proteins.

Ureteral obstruction is characterized by a progressive increase of the interstitial volume of the kidney cortex. Even after release of the ligation, profibrotic forces still prevail such that the interstitial volume increases from the 7 to 8% found in the kidneys of sham-operated animals to the 17 to 20% found in the obstructed-released kidneys. If the obstruction is not released, the interstitial volume can increase to approximately 50% by 10 days of continuous obstruction (Hruska et al., (2000) Am. J. Physiol., 280: F130-3; Ishidoya et al., (1996) Kidney Int., 49: 1110-1119).

In the kidney of normal or sham-operated animals and the contralateral kidneys of rats with UUO, collagen IV is found in the basement membrane surrounding tubules, in capillaries, and in the mesangial matrix. In the setting of fibrosis associated with ureteral obstruction, collagen IV becomes an interstitial matrix protein (Hruska et al., (2000) Am. J. Physiol., 280: F130-3; Ishidoya et al., (1996) Kidney Int., 49: 1110-1119, Morrissey et al., (1998) Semin Nephrol., 18: 603-11) in addition to its presence in basement membranes. The collagen IV matrix score is another means of quantifying interstitial fibrosis (Hruska et al., (2000) Am. J. Physiol., 280: F130-315, Morrissey et al., (1998) Semin Nephrol., 18: 603-11).

There is an inexorable loss of tubule epithelial cells through apoptosis during the progression of kidney disease (Truong et al., (1998) Semin Nephrol., 18: 641-51; Savill et al., (1994) J. Am. Soc. Nephrol. 5: 12-21) resulting in tubule atrophy. This loss is measured at intervals of time by the terminal deoxynucleotidyl transferase-mediated dUTP nick-end labeling (TUNEL) assays (Ishidoya et al., (1996) Kidney Int., 49: 1110-1119) as the number of cells undergoing apoptosis at that point in time. Another means by which tubule atrophy may be determined is by measuring tubule diameter, which would be an index of all apoptotic cell loss up to the point in time when kidney biopsy is obtained.

A reduction epithelial cell apoptosis, interstitial collagen deposition, interstitial volume, type IV collagen, α-smooth muscle actin (α-SMA), and/or monocyte/macrophage infiltration in UUO animals treated with TDFRP compound compared with the level observed in UUO animals not treated with TDFRP compound indicates that the TDFRP compound has a prophylactic or therapeutic effect on renal fibrogenesis.

C. In Vivo Model of Acute Renal Failure

The effects of TDFRP compound on tissue damage due to acute renal failure are measured by the bilateral clamp method of Vukicevic and coworkers (Vukicevic et al., JCI-102(1):202). Briefly, Wistar male rats of 200-250 g (Pliva Breeding Laboratory, Zagreb, Croatia) are fasted for 12 h before surgery. After intraperitoneal administration of ketamin (20 mg/kg) anesthetic, both renal arteries are dorsally occluded for 60 min with microaneurysm clamps (Roboz). Vehicle buffer, TDFRP COMPOUND and/or TDF, e.g., BMP-7, containing 20 mM sodium acetate buffer (500 µl) is administered via the tail vein. All animals are subjected to intraperitoneal administration of 1-3 ml of prewarmed (37° C.) saline (0.9% NaCl) to compensate any fluid loss during the surgery. Experiments are blinded and rats are terminated at different time intervals ranging from 30 min to 18 d. Blood samples (0.5 ml) are obtained from the orbital plexus at, for example, 0, 24, 48, and 72 h and, in some cases, at, for example, 30 min; 2, 8, and 96 h; and 18 d after reperfusion. For GFR measurements, urine is collected on metabolic cages for 24 h as previously described (Vukicevic et al., (1989) Bone Miner., 6: 125-139). Serum and urine creatinine is measured by a Jaffe method (Whelton et al., (1994) In Clinical Chemistry. C. A. Burtis and E. R. Ashwood, Eds. W.B. Saunders, Philadelphia, Pa. Pp. 1513-1575. BUN is measured by a glutamate dehydrogenase ultraviolet procedure, phosphorus by a molybdate method, and calcium by an o-cresolphtaleine method. Serum electrolytes are measured by indirect potentiometry. For a prophylactic mode, BMP-7 and/or TDFRP compound (0.000001-10,000 mg/kg) is given 10 min before surgery and then up to 72 h thereafter and for a therapeutic mode, the first BMP-7 and/or TDFRP compound (0.000001-10,0000 mg/kg) injection is given either at 1-16 h, and then at 24 h intervals up to 96 h after reperfusion.

Normalization of GFR, BUN, serum creatinine and or blood creatinine toward control levels in injured animals treated with TDFRP compound compared with the GFR, BUN, serum creatinine and or blood creatinine levels observed in injured animals not treated with TDFRP compound indicates that the TDFRP compound has a prophylactic or therapeutic effect on renal fibrogenesis.

D. In Vivo Models of Diabetic Nephropathy (Streptozoticin)

The effect of TDFRP compounds on cell damage due to diabetic nephropathy is measured by the method of Wang and coworkers (Wang et al., (2003) 63(6): 2037). Diabetes is induced in 200 g rats by a single dose of streptozotocin. After 16 weeks, glomerular hypertrophy and proteinuria are established, and therapy with TDFRP compound and/or TDF, e.g., BMP-7, (0.000001-10,0000 mg/kg intravenously, preferably 1-10000 micrograms/kg, and more preferably about 10-1000 micrograms/kg; up to daily administration, enalapril (20 mg/kg), or vehicle is begun and continued until 32 weeks. Kidney weight, glomerular filtration rate (GFR), urine albumin excretion, blood pressure, pathology, and BMP-7 expression are measured as described by Wang and coworkers (Wang et al., (2002) J. Am. Soc. Nephroi., 13: 45A) and as detailed above. Normalization of proteinuria, reduction in glomerular area and interstitial volume in the presence of TDFRP compound compared with the absence of TDFRP compound indicated that TDFRP compound has a prophylactic or therapeutic effect.

Antagonists of TGF-beta1 induced epithelial to mesenchymal transition (EMT), such as BMP-7 and the TDFRP compounds described herein, can ameliorate progression of TGF-beta1 induced chronic renal fibrosis. In addition, the TDFRP compounds, unlike BMP-7, show the additional ability to reverse disease pathogenesis. EMT is necessary for embryonic development, but is also involved in pathological conditions such as tumor progression and organ fibrosis (deposition of collagen, elastin, tenacin, and other matrix molecules) in for example, the liver, lung, and kidney. Compounds such as EGF and TGF-beta1 have been demonstrated to induce EMT in renal tubular epithelial cells, and mammary ductal epithelial cells, producing among other changes, a loss or decrease of E-cadherin expression, inhibition of zonula occludens (ZO-1) protein expression, the loss of tight junctions, and the loss of epithelial cell morphology. Incubation with 100 ng/ml of recombinant human BMP-7 for 48 hours reverses TGF-beta1 induced EMT, resulting in restoration of E-cadherin and ZO-1 expression, the formation of tight junctions and the re-establishment of epithelial cell morphology. Similar effects are seen with TDFRP compounds, (CYFDDSSNVLCKKYRS, SEQ ID NO:45) at similar dosages, i.e., 0.1 to 100 milligrams/kg of TDFRP compounds. Without being restricted to theory, it is believed that binding to ALK receptors leads to intracellular signalling pathways mediated by Smad proteins, particularly Smad1, Smad5 and Smad8, which transduce both BMP-7 and TDFRP actions in epithelial cells. In vitro experiments using renal distal tubular epithelial cells (NP1) as ligand-independent systems support these conclusions. The cells, transfected to express constitutively active cDNA constructs expressing ALK5, Smad3 (to mimic TGF-beta1 and Smad dependant signalling pathways) or ALK3 and Smad5 (to mimic BMP-7 and Smad dependant signalling pathways), confirm the above (see, Zeisberg et al., Nature Medicine, 9; 7 pp 964-968, (2003)).

E. In Vivo Models of Chronic Renal Failure

Nephrotoxic serum nephritis (NTN) is a model of progressive chronic renal injury. Mice given injections of nephrotoxic serum (NTS) develop glomerulonephritis, leading to tubulointerstitial disease associated with EMT, and ultimately renal fibrosis, over a period of about six weeks. Researchers have reported that treatment of mice with recombinant human BMP-7, about 300 micrograms/kg, starting after one week of NTN, is sufficient to prevent progression to chronic renal disease, and prevented tubular atrophy and accumulation of interstitial fibroblasts. Initiation of treatment from week 3 through week 6 and from week 4 through week 6 almost completely reversed renal pathology, showing significant improvements in renal function as measured by serum creatinine levels and blood urea nitrogen levels. In these studies, BMP-7 was able to restore expression of E-cadherin proteins in previously damaged tubules. In untreated kidneys, phosphorylated Smad2 and Smad3, indicative of TGF-beta1 signalling, were observed in the nuclei of tubules with attenuated E-cadherin expression. Phosphorylated Smad1, indicative of BMP-7 signalling, was observed in the nuclei of treated tubules. For a review of the above see, Zeisberg et al., Nature Medicine, 9; 7 pp 964-968, (2003) and Kalluri et al., J. Clin Investigation 112:1776-1784 (2003). Similar results to BMP-7 in reversing kidney fibrosis are observed with the present TDFRP compounds (CYFDDSSNVLCKKYRS, SEQ ID NO:45) given orally at a dose of, 5 milligrams/kg/24 hours.

F. Inhibition of or Repair of Renal Necrosis and Cardiomyopathy

Numerous therapeutic compounds are well known to cause systemic toxic effects to the immune system, organs and tissues, for example renal toxicity seen with cisplatin and its analogs, as well as other chemotherapy drugs, and cardiac toxicity seen with certain antibiotics. The TDFRP compounds of the present invention can act as prophylactics and therapeutics, when administered as described above. For example, a representative TDFRP compound disclosed herein (CYFDDSSNVLCKKYRS, SEQ ID NO:45) binds preferentially to BMP type I receptors (ALK3), differentially expresses on kidney proximal tubules. Exposure of kidney cells to an inflammatory agent, e.g., TNF-alpha, causes an inflammatory response measurable by detection of an increase in IL-6 in the proximal tubule cells. Administration of CYFDDSSNVLCKKYRS, SEQ ID NO:45 can alleviate this inflammatory response. Likewise, administration of CYFDDSSNVLCKKYRS, SEQ ID NO:45 can reduce or ameliorate the nephrotoxic effects of cisplatin exposure, in part by promoting induction of tissue specific regeneration pathways.

Similar cardioprotective effects are seen with CYFDDSSNVLCKKYRS, SEQ ID NO:45 as the compound demonstrates the ability to ameliorate inflammation and cytotoxic effects toward cardiomyocytes following myocardial infarction (myocardial ischemia and reperfusion injury).

G. Pharmaceutical Formulations of TDFRP Compounds

The TDFRP compounds are prepared as pharmaceutical formulations for administration to a patient as described above. Generally, the TDFRP compounds are small molecules, including peptides and peptidomimetics, and can be prepared into any peptide-based pharmaceutical formulation, as would be known in the pharmaceutical arts. However, the compounds are potent inducers of tissue growth and differentiation, and as such it is desirable to incorporate the TDFRP compounds into sustained or controlled release formulations, for example, in controlled release microspheres. Exemplary microspheres include ProMaxx® microspheres (Epic Therapeutics) as described in U.S. Pat. No. 6,458,387, incorporated herein by reference.

The TDFRP microspheres have a generally uniform size and shape, ranging in size from about 0.5 microns to about 20 microns, depending upon the fabrication conditions. The characteristics of the microspheres may be altered during preparation by manipulating the water-soluble polymer concentration, reaction temperature, pH, protein concentration, cross linking agent, and/or the length of time the TDFRP compound is exposed to the cross linking agent and/or the energy source. The microspheres are prepared by mixing or dissolving TDFRP compounds with a water-soluble polymer or mixture of water-soluble polymers, such as linear or branched polymers, at a pH near the isoelectric point of the TDFRP compound. The TDFRP compound and polymer mixture is exposed to a cross linking agent and/or an energy source, such as heat, under conditions sufficient to stabilize the microspheres. The microspheres are then separated from the unincorporated reagents by separation methods such as filtration or centrifugation. In general, the TDFRP compound is at least 40% and less than 100% by weight of the final weight of each microsphere. Preferably, the polymer concentration in the microsphere is greater than 0% and less than or equal to 30% by weight. The outer surface of each microsphere is permeable to water and dissolved TDFRP compounds and not only allows aqueous fluids to enter the microsphere, but also allows solubilized TDFRP compound and polymer to exit the microsphere. The microspheres can be made to release TDFRP compounds and polymer from the interior of the microsphere when placed in an appropriate aqueous medium, such as body fluids or a physiologically acceptable buffer under physiological conditions over a prolonged period of time, thereby providing sustained release of TDFRP compounds. In addition, the microspheres can be made to release TDFRP compounds without an initial burst or rapid release, thereby minimizing the unwanted effects seen with larger quantities of localized TDFRP compounds. Sustained release is defined herein as release of TDFRP compounds over an extended period of time. The amount of time over which the TDFRP compounds continue to be released from the microsphere depends on the characteristics of the TDFRP compound being released and the parameters used to form the microspheres, but in all cases is longer than that of free aqueous diffusion of the TDFRP compound.

Formation of Microspheres

Microspheres are produced by mixing TDFRP compounds in an aqueous mixture with a water-soluble polymer or mixture of polymers to form the microspheres and optionally, thereafter contacting the microspheres with a crosslinking agent and/or an energy source, preferably heat, under conditions sufficient to stabilize the microspheres. The solution is preferably an aqueous solution. Either the TDFRP compound in solution is added to the polymer or the polymer solution is added to the TDFRP compound in solution to cause removal of water from, or dehydration of, the TDFRP compound. This process is also referred to as volume exclusion. The pH of the TDFRP compound-polymer solution is adjusted, either before, after or during the mixing of the polymer with the TDFRP compound, to a pH near the isoelectric point (pI) of the TDFRP compound, preferably within 3 to 4 pH units of the pI of the TDFRP compound, most preferably within 1.5 to 2 pH units of the pI of the TDFRP compound.

The pH adjustment may be made by adding an acid, base, either in solution or solid form, or a buffer or other pH-adjusting solution or salt, to either the TDFRP compound, the polymer solution, or to the mixture of TDFRP compound and polymer in accordance with methods well known to those skilled in the art. Preferably the polymer is dissolved in a buffer having a pH near the pI of the TDFRP compound, and then the pH-adjusted polymer solution is added to the TDFRP compound, which has been dissolved in an aqueous solution. The pH of the final solution should remain near the pI of the TDFRP compound.

The TDFRP compound and polymer solution is then exposed to a crosslinking agent and/or an energy source, such as heat, radiation, or ionization, alone or in combination with sonication, vortexing, mixing or stirring, for a predetermined length of time to stabilize the microspheres. The resulting microspheres are then separated from any unincorporated components present in the solution by physical separation methods well known to those skilled in the art and may then be washed.

The length of incubation time is dependent upon the respective concentrations of polymer and TDFRP compound and the level of energy of the energy source. Microsphere stabilization can begin to occur immediately upon exposure to the energy source. Preferably, the TDFRP compound and polymer mixture is heated at a temperature greater than room temperature for between approximately 5 minutes and 24 hours. Most preferably, the polymer and TDFRP compound are mixed, by stiffing or rocking, for 30 minutes at a temperature between approximately 37 degrees C. and 70 degrees C. When preparing microspheres containing TDFRP compounds, a protein stabilizer such as glycerol, fatty acids, sugars such as sucrose, ions such as zinc, sodium chloride, or any other protein stabilizers known to those skilled in the art may be added prior to the addition of the polymers during microsphere formation to minimize protein denaturation.

Coated Microspheres

Molecules, distinct from the TDFRP compounds of which the microspheres are composed, may be attached to the outer surface of the microspheres by methods known to those skilled in the art to "coat" or "decorate" the microspheres. The ability to attach molecules to the outer surface of the microsphere is due to the high concentration of TDFRP compound in the microsphere. These molecules are attached for purposes such as to facilitate targeting, enhance receptor mediation, and provide escape from endocytosis or destruction, for example, using parts of the Fc fragment of an antibody (see, U.S. Pat. Nos. 6,485,726 and 6,538,124). For example, biomolecules such as phospholipids may be attached to the surface of the microsphere to prevent endocytosis by endosomes; receptors, antibodies or hormones may be attached to the surface to promote or facilitate targeting of the microsphere to the desired organ, tissue or cells of the body; and polysaccharides, such as glucans, may be attached to the outer surface of the microsphere to enhance or to avoid uptake by macrophages.

In addition, one or more cleavable molecules may be attached to the outer surface of or within the microspheres. The cleavable molecules are designed so that the microspheres are first targeted to a predetermined site under appropriate biological conditions and then, upon exposure to a change in the biological conditions, such as a pH change, the molecules are cleaved causing release of the microsphere from the target site. In this way, microspheres are attached to or taken up by cells due to the presence of the molecules attached to the surface of the microspheres. When the molecule is cleaved, the microspheres remain in the desired location, such as within the cytoplasm or nucleus of a cell, and are free to release the TDFRP compounds of which the microspheres are composed. This is particularly useful for drug delivery, wherein the microspheres contain a drug that is targeted to a specific site requiring treatment, and the drug can be slowly released at that site. The preferred site of cleavage is a diester bond.

The microspheres may also be coated with one or more stabilizing substances, which may be particularly useful for long term depoting with parenteral administration or for oral delivery by allowing passage of the microspheres through the stomach or gut without dissolution. For example, microspheres intended for oral delivery may be stabilized with a coating of a substance such as mucin, a secretion containing mucopolysaccharides produced by the goblet cells of the intestine, the submaxillary glands, and other mucous glandular cells.

Additionally, the particles can be non-covalently coated with compounds such as fatty acids or lipids. The coating may be applied to the microspheres by immersion in the solubilized coating substance, spraying the microspheres with the substance or other methods well known to those skilled in the art.

In general, the microspheres of the invention are formed by mixing the protein together with at least one water soluble polymer under suitable conditions which, preferably, permit the water soluble polymer to remove water from ("dehydrate") the protein within specified or preferred ratios (wt/wt) of protein to water soluble polymer (e.g., ratios range from about 1 protein: 1 polymer to about 1 protein: 1000 polymer). The preferred ratio of protein to water soluble polymer in the microsphere formation reaction is in the range from about 1 protein: 5 polymer to about 1 protein: 30 polymer. As noted above, a "water soluble polymer" of the invention refers to a polymer or mixture of polymers, which preferably, are capable of interacting with the macromolecule (e.g., protein or other molecule) to cause volume exclusion. Thus, the preferred process involves using an entirely aqueous system with no oil or organic solvents involved. Suitable water-soluble polymers include soluble linear or branched polymers, preferably those having a high molecular weight. Polymers can be highly water-soluble, moderately-water soluble, or slightly water soluble (greater than 2% wt/vol water soluble). The preferred water-soluble polymers are water soluble or soluble in a water miscible solvent. The water-soluble polymers may be solubilized by first being dissolved in a water miscible solvent and then combining the polymer solution with an aqueous solvent. In the particularly preferred embodiments, the water-soluble polymer is a carbohydrate-based polymer.

The preferred polymer is polyvinylpyrrolidone, polyethylene glycol, dextran, polyoxyethylene-polyoxypropylene copolymer, polyvinyl alcohol, starch, hetastarch, or mixtures thereof, the characteristics of which are described in more detail below. The polymer or polymer mixture may be prepared in accordance with the methods set forth in U.S. Pat. No. 5,525,519, or PCT Patent Application No. US93-00073 (International Publication No. WO 93/14110), in which the polymer is dissolved in water or an aqueous solution, such as a buffer, in a concentration between approximately 1 and 50 g/100 ml depending on the molecular weight of the polymer. The preferred total polymer concentration in the polymer solution is between 10% and 80%, expressed as weight/volume percent. The preferred concentration of each polymer in the polymer solution is between 5% and 50%. As discussed above, the pH of the polymer solution may be adjusted before being combined with the macromolecule so that the addition of the polymer causes a pH adjustment of the macromolecule solution, most preferably within one pH unit of the pI. The pH may be adjusted during the preparation of the polymer solution by preparing the polymer in a buffer having a predetermined pH. Alternatively, the pH may be adjusted after preparation of the polymer solution with an acid or a base. Polyoxyethylene-polyoxypropylene copolymer, also known as poloxamer, is sold by BASF (Parsippany, N.J.) and is available in a variety of forms with different relative percentages of polyoxyethylene and polyoxypropylene within the copolymer. PVP is a non-ionogenic, hydrophilic polymer having a mean molecular weight ranging from approximately 10,000 to 700,000 and the chemical formula $(C_6H_9NO)$ [n]. PVP is also known as poly[1-(2-oxo-1-pyrrolidinyl)ethylene], Povidone, Polyvidone, RP 143, Kollidon, Peregal ST, Periston, Plasdone, Plasmosan, Protagent, Subtosan, and Vinisil. PVP is non-toxic, highly hygroscopic and readily dissolves in water or organic solvents. Polyethylene glycol (PEG), also known as poly(oxyethylene)glycol, is a condensation polymer of ethylene oxide and water having the general chemical formula $HO(CH_2CH_2O)[n]H$. Dextran is a term applied to polysaccharides produced by bacteria growing on a sucrose substrate. Native dextrans produced by bacteria such as *Leuconostoc mesenteroides* and *Lactobacteria dextranicum* usually have a high molecular weight. Dextrans are routinely available and are used in injectable form as plasma expanders in humans. Polyvinyl alcohol (PVA) is a polymer prepared from polyvinyl acetates by replacement of the acetate groups with hydroxyl groups and has the formula $(CH_2 CHOH)[n]$. Most polyvinyl alcohols are soluble in water. PEG, dextran, PVA and PVP are commercially available from chemical suppliers such as the Sigma Chemical Company (St. Louis, Mo.). Most preferably, the polymer is a polymer mixture containing an aqueous solution of PVP having a molecular weight between 10,000 and 360,000, most preferably 40,000, and PEG having a molecular weight between 200 and 35,000. PVP having a molecular weight of 40,000 and PEG having a molecular weight of 3500 is preferred. Preferably, the PVP is dissolved in an acetate buffer and PEG is added to the aqueous PVP solution. The concentration of each polymer is preferably between 1 and 40 g/100 ml depending of the molecular weight of each polymer. Equal concentrations of PVP and PEG generally provide the most favorable polymer mixture for the formation of microspheres. An alternative preferred polymer is a dextran, having a molecular weight from approximately 3000 to 500,000 daltons. The volume of polymer added to the macromolecule varies depending on the size, quantity and concentration of the macromolecule. Preferably, two volumes of the polymer mixture at a 5-50% total polymer concentration are added to one volume of a solution containing the macromolecule. The polymer is present in a liquid phase during the reaction with macromolecule. In certain of the embodiments and, in particular, the embodiments of the microspheres which do not further contain a complexing agent, the water soluble polymer preferably is not PEG, PVP, dextran, nonylphenolethoxylates, and/or polyvinyl alcohol. According to another aspect of the invention, a microsphere further including a complexing agent is provided. A complexing agent refers to a molecule, which is capable of facilitating loading, retaining and/or otherwise delaying the release of the therapeutic agent from the microsphere. These are well known in the pharmaceutical arts.

The microspheres may be administered alone or in combination with other drug therapies as part of a pharmaceutical composition. Such a pharmaceutical composition may include the microspheres in combination with any standard physiologically and/or pharmaceutically acceptable carriers, which are known in the art, for example cisplatin administered with TDFRP compounds. The compositions should be sterile and contain a therapeutically effective amount of the microsphere in a unit of weight or volume suitable for administration to a patient. The term "pharmaceutically-acceptable carrier" as used herein means one or more compatible solid or liquid filler, diluents or encapsulating substances which are suitable for administration into a human or other animal. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction, which would substantially impair the desired pharmaceutical efficacy. Pharmaceutically acceptable further means a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, desiccants, bulking agents, propellants, acidifying agents, coating agents, solubilizers, and other materials, which are well known in the art. Carrier formulations suitable for oral, subcutaneous, intravenous, intramuscularly, etc. administrations can be found in Remington's Pharmaceutical Sciences, Mack Publishing Co., Easton, Pa.

A variety of administration routes are available. The particular mode selected will depend, of course, upon the TDFRP compound selected, the severity of the condition being treated, and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. The term "parenteral" includes subcutaneous, intravenous, intramuscular, or infusion. Oral administration will be preferred for prophylactic treatment because of the convenience to the patient as well as the dosing schedule. The microspheres are useful for therapy or prophylaxis when it is desirable the TDFRP compound is delivered to a patient and slowly released from the microspheres over time. If the TDFRP compound cannot be formed into a particle, then it is complexed to a carrier, such as albumin, and the carrier-pharmaceutical compound complex is formed into a microsphere. The microsphere can either provide for the slow release of the TDFRP compound throughout the body or the microsphere can include an affinity molecule specific for a target tissue, and be injected into a patient for targeted controlled release of the TDFRP compound.

Example 4

Use of TDFRP Compounds as Coatings for Devices

The TDFRP compounds of the present invention are useful in the prevention or therapeutic treatment of, e.g., inflammation, apoptosis, cellular adhesion, and, in particular, atherosclerosis, and vascular restenosis after angioplasty. The TDFRP compound can be used in combination with medical devices, e.g., stents or catheters, to prevent or treat, for example, vascular restenosis after angioplasty. The proliferation and migration of smooth muscle cells have been acknowledged as playing a key role in the pathophysiology of cardiovascular disease (Martinez-Gonzalez J et al., Circ Res.; 92(1):96-103 (2003)), including post-angioplasty restenosis leading to neointima formation (Segev A, et al., Cardiovasc Res; 53(1):232-41 (2002)).

The present invention also provides stents and catheters, comprising a generally tubular structure (which includes for example, spiral shapes), the surface of which is coated with a TDFRP compound, a polynucleotide encoding a TDFRP compound or a virus carrying a construct encoding a TDFRP compound described above. A stent is a scaffolding, usually cylindrical in shape, that may be inserted into a body passageway (e.g., bile ducts) or a portion of a body passageway, which has been narrowed, irregularly contoured, obstructed, or occluded by a disease process (e.g., ingrowth by a tumor) in order to prevent closure or reclosure of the passageway. Stents act by physically holding open the walls of the body passage into which they are inserted.

In one aspect, the invention provides a coated implantable medical device which, when implanted in to a mammal it prevents or treats a disorder in the mammal. The coating on the implantable medical device can contain an amino acid sequence selected from the group consisting of, SEQ ID NOs:1-314, or polynucleotides encoding SEQ ID NOs:1-314, and variants, analogs, homologs, or fragments thereof. An implantable medical device refers to, and includes, devices contained within the mammalian body such as a stent, or those partially included within the mammalian body such as a trochar, catheter, or port.

In another aspect, the invention provides a method of making a device suitable form implantation into a mammal by obtaining an implantable medical device and coating the medical device. The coating on the implantable device can contain an amino acid sequence selected from the group consisting of, SEQ ID NOs:1-314, or polynucleotides encoding SEQ ID NOs:1-314, and variants, analogs, homologs, or fragments thereof.

In another aspect, the invention provides a method of using a device to prevent or treat a disorder in a mammal. The method includes identifying a mammal with a disorder, then obtaining an implantable medical device further having a coating comprised of an amino acid sequence selected from the group consisting of, SEQ ID NOs:1-314, or polynucleotides encoding SEQ ID NOs:1-314, and variants, analogs, homologs, or fragments thereof; and implanting the device into a mammal. In one embodiment, the device is implanted into a mammal with a disorder of the cardiovascular system.

Commercially available poly(ethylene oxide) [PEO] and poly(acrylic acid) [PAA] gel-coated balloon angioplasty catheters can be used as local drug delivery systems (Gehrke et al., in Intelligent Materials & Novel Concepts for Controlled Release Technologies, S. Dinh and J. DeNuzzio, Eds., ACS Symposium Series, Washington, D.C., 728, 43-53 (1999)). Loading of TDFRP compound, polynucleotides encoding TDFRP compounds, or virus carrying a vector encoding a TDFRP compound, in PEO-gel coatings can be approximately doubled with the addition of soluble dextran to the loading solution. Release of solutes, e.g., TDFRP compound or virus carrying polynucleotides encoding TDFRP compound, from gel coatings is diffusion limited, though resistance may be due to the boundary layer as well as the gel.

A variety of stents and catheters may be utilized within the context of the present invention, including, for example, esophageal stents, vascular stents, biliary stents, pancreatic stents, ureteric and urethral stents, lacrimal stents, Eustachiana tube stents, fallopian tube stents and tracheal/bronchial stents, vascular catheters, and urethral catheters.

Stents and catheters may be readily obtained from commercial sources, or constructed in accordance with well-known techniques. Representative examples of stents amenable to coating with TDFRP compound, polynucleotides encoding TDFRP compounds, or virus carrying a vector encoding a TDFRP compound, include those described in U.S. Pat. No. 4,768,523, entitled "Hydrogel Adhesive," U.S. Pat. No. 4,776,337, entitled "Expandable Intraluminal Graft, and Method and Apparatus for Implanting and Expandable Intraluminal Graft;" U.S. Pat. No. 5,041,126 entitled "Endovascular Stent and Delivery System;" U.S. Pat. No. 5,052,998 entitled "Indwelling Stent and Method of Use," U.S. Pat. No. 5,064,435 entitled "Self-Expanding Prosthesis Having Stable Axial Length;" U.S. Pat. No. 5,089,606, entitled "Water-insoluble Polysaccharide Hydrogel Foam for Medical Applications;" U.S. Pat. No. 5,147,370, entitled "Nitinol Stent for Hollow Body Conduits;" U.S. Pat. No. 5,176,626, entitled "Indwelling Stent;" U.S. Pat. No. 5,213,580, entitled "Biodegradable polymeric Endoluminal Sealing Process," U.S. Pat. No. 5,685,847, entitled "Stent and therapeutic delivery system," U.S. Pat. No. 5,683,448, entitled "Intraluminal stent and graft," U.S. Pat. No. 5,681,274, entitled "Variable length uretheral stent," U.S. Pat. No. 5,665,115, entitled "Intraluminal stent," U.S. Pat. No. 6,699,278, entitled "Stent with optimal strength and radiopacity characteristics," U.S. Pat. No. 8 6,679,911, entitled "Flexible stent," U.S. Pat. No. 9 6,673, 106, entitled "Intravascular stent device."

Stents and catheters may be coated with TDFRP compound, or polynucleotide encoding a TDFRP compound, or virus containing a vector encoding a TDFRP compound, in a variety of manners, including for example: (a) by directly affixing to the device a TDFRP compound, or polynucleotide encoding a TDFRP compound, or virus containing a vector encoding a TDFRP compound (e.g., by either spraying the stent with a polymer/drug film, or by dipping the stent into a polymer/drug solution), (b) by coating the device with a substance such as a hydrogel which will in turn absorb the TDFRP compound, or polynucleotide encoding a TDFRP compound, or virus containing a vector encoding a TDFRP compound, (c) by interweaving TDFRP compound, or polynucleotide encoding a TDFRP compound, or virus containing a vector encoding a TDFRP compound coated thread (or the polymer itself formed into a thread) into the device structure, (d) by inserting the device into a sleeve or mesh which is comprised of or coated with a TDFRP compounds, or polynucleotide encoding a TDFRP compound, or virus containing a vector encoding a TDFRP compound, or (e) constructing the device itself with a TDFRP compound. Within preferred embodiments of the invention, the TDFRP compound, or polynucleotide encoding a TDFRP compound, or virus containing a vector encoding a TDFRP compound should firmly adhere to the device during storage and at the time of insertion. The TDFRP compounds, or polynucleotide encoding a TDFRP compound, or virus containing a vector encoding a TDFRP compound should also preferably not degrade during storage, prior to insertion, or when warmed to body temperature after expansion inside the body. In addition, it should preferably coat the device smoothly and evenly, with a uniform distribution of TDFRP compounds, or polynucleotides encoding a TDFRP compound, or virus containing a vector encoding a TDFRP compound, while not changing the device contour. Within preferred embodiments of the invention, the release of the TDFRP compound, or polynucleotide encoding a TDFRP compound, or virus containing a vector encoding a TDFRP compound should be uniform, predictable, and may be prolonged into the tissue surrounding the device once it has been deployed. For vascular stents and catheters, in addition to the above properties, the TDFRP compound, or polynucleotide encoding a TDFRP compound, or virus containing a vector encoding a TDFRP compound should not render the stent or catheter thrombogenic (causing blood clots to form), or cause significant turbulence in blood flow (more than the stent itself would be expected to cause if it was uncoated).

Patches may also be prepared from materials that contain TDFRP compound or polynucleotide encoding TDFRP compound, with or without a viral carrier. For example, patch materials, e.g., but not limited to, Gelfoam or Polyvinyl alcohol (PVA), or other suitable material, may be used. Such patches may be used prophylactically or therapeutically to deliver TDFRP compound or polynucleotide encoding TDFRP compound when contacted with a cell.

Example 5

In Vivo Measurement of the Effect of TDFRP on Rat Carotid Arterial Neointima Formation TDFRP compound, polynucleotides encoding a TDFRP compound, or a virus, e.g., but not limited to, adenovirus, containing a TDFRP compound-encoding construct (e.g., vector) are tested for their effect in a rat model of vessel balloon injury. For example, adult Sprague-Dawley male rats weighing 450-600 g are anesthetized with intraperitoneal injections of ketamine (150 mg/kg body wt) and xylazine (15 mg/kg body wt). Following a neck incision, a 2F Fogarty balloon catheter (Baxter, Irvine, Calif.) is inserted via an arteriotomy into the left common carotid artery. To ensure adequate and reproducible injury, the balloon catheter is inflated with a calibrated inflation device to a pressure of 2 ATM for 5 min. The balloon is passed back and forth three times and removed. A plastic catheter (27 gaugel/2) is introduced through the external carotid arteriotomy, and the common carotid artery is flushed with PBS before introduction of a suitable vehicle alone, or vehicle containing TDFRP compound (0.000001 mg protein/kg body weight-100,000 mg protein/kg body weight). Alternatively, a vehicle containing polynucleotide encoding a TDFRP compound (0.000001 mg polynucleotide/kg body weight-100,000 mg polynucleotide/kg body weight), or a viral carrier, e.g., adenovirus, containing an appropriate polynucleotide construct encoding TDFRP (1 pfu/ml to $1 \times 10^{14}$ pfu/ml) is administered.

For example, recombinant adenovirus stocks are used within 2 h of thawing. Fifty microliters of 1 pfu/ml to $1 \times 10^{14}$ pfu/ml adenoviral vector (AdLacZ or Ad-TDFRP) or DMEM are instilled into the injured isolated common carotid segment through the plastic catheter. After 15 min, the adenovirus or DMEM is aspirated. The proximal external carotid artery is ligated, and blood flow through the common and internal carotid is reestablished. Two weeks after balloon injury, the contralateral control artery (which received neither injury nor adenovirus treatment), and the balloon-injured artery with no adenovirus treatment (DMEM) or adenovirus treatment (Ad-LacZ or Ad-TDFRP) are harvested and fixed in 4% paraformaldehyde for 48 h at 4° C., embedded in paraffin blocks, sectioned (5 gm), and stained either with hematoxylin and eosin or by Von Giesen method to reveal the internal and external elastic lamina. Images are acquired and analyzed for the cross-sectional areas of neointima and media using the NIH Image program, and the area ratio are calculated.

A reduction in the neointima to media ratio in angioplasty-treated vessels receiving TDFRP compared with the neointima to media ratio observed in angioplasty-treated vessels receiving vehicle alone indicates that the TDFRP has an anti-restenosis effect. Similarly, a reduction in the neointima to media ratio in angioplasty-treated vessels receiving a polynucleotide encoding a TDFRP compared with the neointima to media ratio observed in angioplasty-treated vessels receiving vehicle alone indicates that the polynucleotide encoding the TDFRP has an anti-restenosis effect. Moreover, a reduction in the neointima to media ratio observed in angioplasty-treated vessels receiving a viral carrier containing a polynucleotide construct encoding a TDFRP compared with the neointima to media ratio observed in angioplasty-treated vessels receiving a viral carrier containing a polynucleotide construct that does not encode a TDFRP indicates that the TDFRP has an anti-restenosis effect. A Student t-test is employed to assess differences in the neointima to media ratios observed between treatment groups. "P" values less than or equal to 0.05 are considered significant.

Pig Arterial Injury Model

Adenovirus-mediated gene transfer is performed in the iliac arteries of domestic Hampshire pigs (15 kg), with adenovirus containing an polynucleotide sequence encoding a TDFRP compound (Ad-TDFRP) or with a reporter gene (Ad-LacZ). After sedation with Ketamine (20 mg/kg body wt) and xylazine (2 mg/kg), the pigs are intubated and anesthetized with Isoflurane/NO. Under sterile surgical techniques, a #3 French-balloon catheter is inserted into the iliac artery through the internal iliac artery and inflated to 2 atm for 5 min. The arterial segment is rinsed with 5 mL saline solution. Recombinant adenovirus stocks are used within 2 h of thawing. One ml of $10^{10}$ pfu/ml adenoviral vector (Ad-LacZ or Ad-TDFRP) or DMEM is instilled into the injured isolated iliac artery segment through the plastic catheter. After 30 min, the adenovirus or DMEM is aspirated. After adenovirus treatment, the catheter is removed, and arterial flow is restored. Animals are killed three weeks after adenovirus treatment and the angioplastied segments of the iliac arteries are harvested along with more distal segments used as negative, normal control segments.

The harvested vessel tissue is fixed in 4% paraformaldehyde for 48 h at 4° C., embedded in paraffin blocks, sectioned (5 um), and stained either with hematoxylin and eosin or by Von Giesen method to reveal the internal and external elastic lamina. Images are acquired and analyzed for the cross-sectional areas of neointima and media using the NIH Image program, and the area ratio was calculated. A Student t-test is employed to assess the statistical significance of the intima to media ratios observed the treatment groups. A "P" value less than or equal to 0.05 are considered significant.

Example 6

In Vivo Measurement of the Effect of TDFRP Compound on Rabbit Atherosclerosis

TDFRP compound, polynucleotide encoding a TDFRP compound, or a virus, e.g., but not limited to, adenovirus, containing a TDFRP compound-encoding construct (e.g., vector) are tested for their effect in a rabbit model of atherosclerosis as described by Simari and coworkers (Simari et al., *Clin. Invest.*, 98: 225-35 (1996). Briefly, NZW rabbits are sedated with ketamine (35 mg/kg i.m.) and xylazine (5 mg/kg i.m.) and intubated. Anesthesia is maintained with isoflurane. Before surgery, blood chemistries and serum cholesterol and triglyceride levels are measured (Roche Biomedical Laboratories, Nutley, N.J.). Surgical exposure and arteriotomy of the right femoral artery is performed, and a 3-French Fogarty balloon catheter (Baxter Healthcare Corp., Mundelein, Ill.) is passed into the common iliac artery. The balloon is inflated in the right iliac artery and withdrawn three times. The right femoral artery is ligated distally, and the incision is closed. After surgery, the rabbits are fed a high fat diet consisting of 0.5% cholesterol and 2.3% peanut oil until they are killed. All animals receive aspirin, 10 mg/kg, three times a week. Two rabbits are killed 3 wk after denuding injury and cholesterol feeding, and the iliac arteries are analyzed to determine the extent of atherosclerotic lesions.

Three weeks after the first vascular injury, an angioplasty balloon injury is performed in the right iliac artery. Serum cholesterol and triglyceride levels are measured. A midline abdominal incision is made, and the distal aorta and iliac common arteries are isolated. Side branches in the iliac arteries are isolated and ligated. A 2-2.75-mm balloon angioplasty catheter (SciMed, BSC, Maple Grove, Minn.) is advanced via a distal aortotomy into the right iliac artery. The angioplasty balloon is inflated to six atmospheres of pressure for 1 min and deflated. Balloon inflation and deflation is repeated two times.

Treatment of the vessel with test agent is performed by withdrawing the balloon catheter to a position just proximal to the injury site. The arterial segment is isolated with temporary ligatures and rinsed with 5 ml of phosphate-buffered saline before introduction of a suitable vehicle alone, vehicle containing TDFRP compound (0.000001 mg protein/kg body weight-100,000 mg protein/kg body weight), or vehicle containing polynuceotide encoding TDFRP (0.000001 mg polynucleotide/kg body weight-100,000 mg polynucleotide/kg body weight). Alternatively, a viral carrier, e.g., adenovirus, containing an appropriate polynucleotide vector encoding TDFRP compound (1 pfu/ml to $1\times10^{14}$ pfu/ml) is administered. For example, recombinant adenovirus stocks are used within 2 h of thawing. Fifty microliters of 1 pfu/ml to $1\times10^{14}$ pfu/ml adenoviral vector (AdLacZ or Ad-TDFRP) or DMEM are instilled into the injured isolated common carotid segment through the plastic catheter. After 15 min, the adenovirus or DMEM is aspirated. The proximal external carotid artery is ligated, and blood flow through the common and internal carotid is reestablished.

Three weeks after treatment, the contralateral control artery (which received neither injury nor adenovirus treatment), and the balloon-injured artery with no treatment (control) or test treatment (i.e., TDFRP compound, polynucleotide encoding test compound or virus carrying a vector encoding a TDFRP compound) are harvested and fixed in 4% paraformaldehyde for 48 h at 4° C., embedded in paraffin blocks, sectioned (5 um), and stained either with hematoxylin and eosin or by Von Giesen method to reveal the internal and external elastic lamina. Images are acquired and analyzed for the cross-sectional areas of neointima and media using the NIH Image program, and the area ratio are calculated.

A reduction in the neointima to media ratio in angioplasty-treated vessels receiving TDFRP compound compared with the neointima to media ratio observed in angioplasty-treated vessels receiving vehicle alone indicates that the TDFRP compound has an anti-restenosis effect. Similarly, reduction in the neointima to media ratio in angioplasty-treated vessels receiving polynucleotide encoding TDFRP compound compared with the neointima to media ratio observed in angioplasty-treated vessels receiving vehicle alone indicates that the TDFRP compound has an anti-restenosis effect. Moreover, a reduction in the neointima to media ratio observed in angioplasty-treated vessels receiving a viral carrier containing a polynucleotide construct encoding a TDFRP compound compared with the neointima to media ratio observed in angioplasty-treated vessels receiving a viral carrier containing a polynucleotide construct that does not encode a TDFRP compound or vehicle alone indicates that the TDFRP compound has an anti-restenosis effect. A Student t-test is employed to assess differences in the neointima to media ratios observed between treatment groups. "P" values less than or equal to 0.05 are considered significant.

Example 7

In Vivo Measurement of the Effect of TDFRP Compound Delivered by a Stent on Rabbit Atherosclerosis TDFRP compound, a polynucleotide encoding a TDFRP compound, or a virus, e.g., but not limited to, adenovirus, containing a TDFRP compound-encoding construct are tested for their effect, being delivered by a stent in a rabbit model of vessel balloon injury (Rogers et al., *Circulation* 91:2995-3001 (1995)).

New Zealand White rabbits (Millbrook Farm Breeding Labs) weighing 3 to 4 kg, housed individually in steel mesh cages and fed rabbit chow and water ad libitum, are anesthetized with 35 mg/kg IM ketamine (Aveco Co) and 4 mg/kg IV sodium Nembutal (Abbott Laboratories). Each femoral artery is exposed and ligated, and iliac arterial endothelium is removed by a 3F balloon embolectomy catheter (Baxter Healthcare Corp, Edwards Division) passed via arteriotomy retrograde into the abdominal aorta and withdrawn inflated three times. A 7 mm long, stainless steel stent is mounted coaxially on a 3-mm angioplasty balloon and passed retrograde via arteriotomy into each iliac artery, and expand with A-10-second inflation at 2- to 10-atm pressure. Four stents are coated with 3-μm-thick coating of 25% (w/v) pluronic F-127 gel solution (BASF Wyandotte Co., Wyandotte, Mich., USA) and another four stents are coated with the same gel solution with a vehicle containing TDFRP compound (0.000001 mg protein/ml-100,000 mg protein/kg body weight) dissolved in it and another four stents are coated with the same gel solution with a vehicle alone. Alternatively, four stents are coated with 3-μm-thick coating of 25% (w/v) pluronic F-127 gel solution (BASF Wyandotte Co., Wyandotte, Mich., USA) and another four stents are coated with the same gel solution with a vehicle containing a polynucleotide encoding TDFRP compound (0.000001 mg polynucleotide/ml-100,000 mg polynucleotide/ml) dissolved in it and another four stents are coated with the same gel solution with a vehicle. Alternatively, another four stents are coated with a 3-μm-thick coating of 25% (w/v) pluronic F-127 gel solution (BASF Wyandotte Co., Wyandotte, Mich., USA) and another four stents are coated with the same gel solution with a vehicle containing with a viral carrier, e.g., adenovirus, containing an appropriate polynucleotide construct encoding TDFRP (1 pfu/ml to $1\times10^{14}$ pfu/ml). Four iliac arteries subject only to balloon withdrawal injury without stent placement are also harvested and processed for histological analysis.

Rabbits are given aspirin (Sigma Chemical Co) 0.07 mg/mL in drinking water 1 day before surgery to achieve an approximate dose of 5 mg/kg per day for the duration of the experiment and received a single bolus of standard anticoagulant heparin (100 U/kg, Elkin-Sinn Inc) intravenously at the time of surgery. Two weeks after balloon injury, iliac arteries are harvested. Under deep anesthesia with intravenous sodium Nembutal, inferior vena cava exsanguination is followed by perfusion with lactated Ringer's solution via left ventricular puncture. Both iliac arteries are excised and fixed in 4% paraformaldehyde for 48 h at 4° C., embedded in paraffin blocks, sectioned (5 gm), and stained either with hematoxylin and eosin or by Von Giesen method to reveal the internal and external elastic lamina. Images are acquired and analyzed for the cross-sectional areas of neointima and media using the NIH Image program, and the area ratio are calculated.

A reduction in the neointima to media ratio in angioplasty-treated vessels receiving stent coated with gel including TDFRP compound compared with the neointima to media ratio observed in angioplasty-treated vessels receiving stent plus gel with vehicle alone, or stent alone, indicates that the TDFRP compound has an anti-restenosis effect. Similarly, reduction in the neointima to media ratio in angioplasty-treated vessels receiving stent coated with gel including polynucleotide encoding TDFRP compared with the neointima to media ratio observed in angioplasty-treated vessels receiving stent plus gel with vehicle, or stent plus gel alone, or stent alone, indicates that the polynucleotide encoding the TDFRP compound has an anti-restenosis effect. Moreover, a reduction in the neointima to media ratio observed in angioplasty-treated vessels receiving a stent coated with a gel mixed with a viral carrier containing a polynucleotide construct encoding a TDFRP compound compared with the neointima to media ratio observed in angioplasty-treated vessels receiving stent coated with a gel mixed with a viral carrier alone indicates that the viral carrier containing a polynucleotide encoding a TDFRP compound has an anti-restenosis effect. A Student t-test is employed to assess differences in the neointima to media ratios observed between treatment groups. "P" values less than or equal to 0.05 are considered significant.

Example 8

Preparation of TDFRP-Coated Devices

Reagents and equipment which are utilized within the following experiments include (medical grade stents obtained commercially from a variety of manufacturers; e.g., Cordis and Boston Scientific) and holding apparatus, 20 ml glass scintillation vial with cap (plastic insert type), TLC atomizer, Nitrogen gas tank, glass test tubes (various sizes from 1 ml and up), glass beakers (various sizes). Pasteur pipette, tweezers, Polycaprolactone ("PCL"—mol wt 10,000 to 20,000; Polysciences), TDFRP compound or polynucleotide encoding a TDFRP compound or infected by a virus, e.g., but not limited to, adenovirus, containing such TDFRP constructs, Ethylene vinyl acetate ("EVA"—washed—see previous). Poly (DL) lactic acid ("PLA"—mol wt 15,000 to 25,000; Polysciences), dichloromethane ("DCM"—HPLC grade, Fisher Scientific). It is to be understood that these procedures can be used to coat the surface of many different types of devices such as stents and catheters.

A. Procedure for Sprayed Stents

The following describes a method using a 3 mm crimped diameter interleaving metal wire stent of approximately 3 cm length. For larger diameter stents, larger volumes of polymer/drug solution are used. Briefly, a sufficient quantity of polymer is weighed directly into a 20 ml glass scintillation vial, and sufficient DCM added in order to achieve a 2% w/v solution. The vial is then capped and mixed by hand in order to dissolve the polymer. The stent is then assembled in a vertical orientation, tying the stent to a retort stand with nylon. Position this stent holding apparatus 6 to 12 inches above the fume hood floor on a suitable support (e.g., inverted 2000 ml glass beaker) to enable horizontal spraying. Using an automatic pipette, a suitable volume (minimum 5 ml) of the 2% polymer solution is transferred to a separate 20 ml glass scintillation vial. An appropriate amount of TDFRP compound or polynucleotide encoding a TDFRP compound or a viral carrier, e.g., but not limited to, adenovirus, containing a vector encoding a TDFRP compound is then added to the solution and dissolved by hand shaking. To prepare for spraying, the vial cap is removed and the barrel (only) of an TLC atomizer is dipped into the polymer solution. The reservoir of the atomizer need not be used in this procedure: the 20 ml glass vial acts as a reservoir. A nitrogen tank is connected to the gas inlet of the atomizer. The pressure is gradually increased until atomization and spraying begins. The pressure is noted and this pressure is used throughout the procedure. The stent is sprayed using 5 second oscillating sprays with a 15 second dry time between sprays. After 5 sprays, the stent is rotated 90° and sprayed again. This procedure is repeated until all sides of the stent have been sprayed. During the dry time, the gas line is finger crimped to avoid wastage of the spray. Spraying is continued until a suitable amount of polymer is deposited on the stents. The amount may be based on the specific stent application in vivo. To determine the amount, the stent is weighed after spraying has been completed and the stent has dried. The original weight of the stent is subtracted from the finished weight and this produces the amount of polymer (plus TDFRP compound) applied to the stent. The coated stents are typically stored in a sealed container until use.

B. Procedure for Dipped Stents

The following describes a method using a 3 mm crimped diameter interleaving metal wire stent of approximately 3 cm length. For larger diameter stents, larger volumes of polymer/drug solution are used in larger sized test tubes.

Two grams of EVA is weighed into a 20 ml glass scintillation vial and 20 ml of DCM is added. The vial is capped and left for 2 hours to dissolve (the vial is shaken frequently to assist the dissolving process). A known amount of TDFRP compound, or polynucleotide encoding a TDFRP compound is placed into a 1 ml glass test tube and 0.5 ml of the polymer solution of the polymer solution. Using a glass Pasteur pipette, the TDFRP compound, polynucleotide encoding a TDFRP compound, or a viral carrier, e.g., but not limited to, adenovirus, containing a vector encoding a TDFRP compound is suspended/dissolved by gently pumping the polymer solution. Once the materials are suitably mixed or dissolved, the test tube is held in a near horizontal position (the sticky polymer solution does not flow out). The stent is inserted into the tube all the way to the bottom using a pair of tweezers. The polymer-containing solution is allowed to flow almost to the mouth of the test tube by angling the mouth below horizontal and then restoring the test tube to an angle slightly above the horizontal. The stent is slowly rotated in the tube and then carefully removed (approximately 30 seconds). The coated stent is dried in a vertical position. The coated stents are typically stored in a sealed container until use.

Example 9

TDFRP Compounds Co-administered with Bone Morphogenetic Proteins and Other Mediators of the Hedgehog Signalling Pathway The TDFRP compounds are functional agonists and antagonists of ALK receptors, and mediate biological activities that are propagated through these receptors. Similar biological activities are seen with Bone Morphogenetic Proteins, particularly BMP-7 (OP-1) as discussed throughout this application. These biological effects, common to BMP family proteins and the TDFRP compounds described herein may be described generally as tissue differentiation-like effects, growth factor-like effects, lineage commitment, and tissue renewal and repair. Other effects are described above and in more detail. These biological effects are similar to those observed with mediators of the Hedgehog signalling pathway. For example, members of the Hedgehog family of signaling molecules mediate many important short- and long-range patterning processes during invertebrate and vertebrate development. In the fly, a single Hedgehog gene regulates segmental and imaginal disc patterning. While only one Hedgehog gene has been found in *Drosophila* and other invertebrates, multiple Hedgehog genes are present in vertebrates, where a Hedgehog gene family is involved in the control of, for example, left-right asymmetry, polarity in the CNS, somites and limb, organogenesis, chondrogenesis and spermatogenesis. Likewise, several Hedgehog homologues have been isolated from various vertebrate species.

The vertebrate family of Hedgehog genes includes at least four members, e.g., paralogs of the single *Drosophila* hedgehog gene. Exemplary Hedgehog genes and proteins are described in PCT publications WO 95/18856 and WO 96/17924. Three of these members, herein referred to as Desert Hedgehog (Dhh), Sonic Hedgehog (Shh) and Indian Hedgehog (Ihh), apparently exist in all vertebrates, including fish, birds, and mammals. A fourth member, herein referred to as tiggie-winkle Hedgehog (Thh), appears specific to fish. Desert Hedgehog is expressed principally in the testes, both in mouse embryonic development and in the adult rodent and human; Indian Hedgehog is involved in bone development during embryogenesis and in bone formation in the adult; and Sonic Hedgehog is primarily involved in morphogenic and neuroinductive activities. Given the critical inductive roles of Hedgehog polypeptides in the development and maintenance of vertebrate organs, the identification of Hedgehog interacting or modulating proteins is of paramount significance in both clinical and research contexts.

In vertebrates, several hedgehog genes have been cloned in the past few years. Of these genes, Shh has received most of the experimental attention, as it is expressed in different organizing centers, which are the sources of signals that pattern neighboring tissues. Recent evidence indicates that Shh is involved in these interactions. The expression of Shh starts shortly after the onset of gastrulation in the presumptive midline mesoderm, the node in the mouse (Chang et al. (1994) supra; Echelard, Y. et al. (1993) Cell 75:1417-1430), the rat (Roelink, H. et al. (1994) Cell 76:761-775) and the chick (Riddle, R. D. et al. (1993) Cell 75:1401-1416), and the shield in the zebrafish (Ekker et al. (1995) supra; Krauss, S. et al., (1993) Cell 75:1431-1444). In chick embryos, the Shh expression pattern in the node develops a left-right asymmetry, which appears to be responsible for the left-right situs of the heart (Levin, M. et al. (1995) Cell 82:803-814). In the CNS, Shh from the notochord and the floorplate appears to induce ventral cell fates. When ectopically expressed, Shh leads to a ventralization of large regions of the mid- and hindbrain in mouse (Echelard et al. (1993) supra; Goodrich, L. V. et al. (1996) Genes Dev. 10:301-312), *Xenopus* (Roelink, H. et al. (1994) supra; Ruiz Altaba, A. et al. (1995) Mol. Cell. Neurosci. 6:106-121), and zebrafish (Ekker et al. (1995) supra; Krauss et al. (1993) supra; Hammerschmidt, M., et al. (1996) Genes Dev. 10:647-658). In explants of intermediate neuroectoderm at spinal cord levels, Shh protein induces floorplate and motor neuron development with distinct concentration thresholds, floor plate at high and motor neurons at lower concentrations (Roelink et al. (1995) supra; Mart et al. (1995) supra; Tanabe, Y. et al. (1995) Curr. Biol. 5:651-658). Moreover, antibody blocking suggests that Shh produced by the notochord is required for notochord-mediated induction of motor neuron fates (Mart' et al. (1995) supra). Thus, high concentration of Shh on the surface of Shh-producing midline cells appears to account for the contact-mediated induction of floorplate observed in vitro (Placzek, M. et al. (1993) Development 117:205-218), and the midline positioning of the floorplate immediately above the notochord in vivo. Lower concentrations of Shh released from the notochord and the floorplate presumably induce motor neurons at more distant ventrolateral regions in a process that has been shown to be contact-independent in vitro (Yamada, T. et al. (1993) Cell 73:673-686). In explants taken at midbrain and forebrain levels, Shh also induces the appropriate ventrolateral neuronal cell types, dopaminergic (Heynes, M. et al. (1995) Neuron 15:35-44; Wang, M. Z. et al. (1995) Nature Med. 1:1184-1188) and cholinergic (Ericson, J. et al. (1995) Cell 81:747-756) precursors, respectively, indicating that Shh is a common inducer of ventral specification over the entire length of the CNS. Shh from the midline also patterns the paraxial regions of the vertebrate embryo, the somites in the trunk (Fan et al. (1995) supra) and the head mesenchyme rostral of the somites (Hammerschmidt et al. (1996) supra). In chick and mouse paraxial mesoderm explants, Shh promotes the expression of sclerotome specific markers like Paxl and Twist, at the expense of the dermamyotomal marker Pax3. Moreover, filter barrier experiments suggest that Shh mediates the induction of the sclerotome directly rather than by activation of a secondary signaling mechanism (Fan, C.-M. and Tessier-Lavigne, M. (1994) Cell 79, 1175-1186). Shh also induces myotomal gene expression (Hammerschmidt et al. (1996) supra; Johnson, R. L. et al. (1994) Cell 79:1165-1173; Munsterberg, A. E. et al. (1995) Genes Dev. 9:2911-2922; Weinberg, E. S. et al. (1996) Development 122:271-280), although recent experiments indicate that members of the WNT family, vertebrate homologues of *Drosophila*, Wingless, are required in concert (Munsterberg et al. (1995) supra). Puzzlingly, myotomal induction in chicks requires higher Shh concentrations than the induction of sclerotomal markers (Munsterberg et al. (1995) supra), although the sclerotome originates from somitic cells positioned much closer to the notochord. Similar results were obtained in the zebrafish, where high concentrations of Hedgehog induce myotomal and repress sclerotomal marker gene expression (Hammerschmidt et al. (1996) supra). In contrast to amniotes, however, these observations are consistent with the architecture of the fish embryo, as here, the myotome is the predominant and more axial component of the somites. Thus, modulation of Shh signaling and the acquisition of new signaling factors may have modified the somite structure during vertebrate evolution.

In the vertebrate limb buds, a subset of posterior mesenchymal cells, the "Zone of polarizing activity" (ZPA), regulates anteroposterior digit identity (reviewed in Honig, L. S. (1981) Nature 291:72-73). Ectopic expression of Shh or application of beads soaked in Shh peptide mimics the effect of anterior ZPA grafts, generating a mirror image duplication of digits (Chang et al. (1994) supra; Lopez-Martinez et al. (1995) supra; Riddle et al. (1993) supra). Thus, digit identity appears to depend primarily on Shh concentration, although it is possible that other signals may relay this information over the substantial distances that appear to be required for AP patterning (100-150 micrometers). Similar to the interaction of HH and DPP in the *Drosophila* imaginal discs, Shh in the vertebrate limb bud activates the expression of Bmp2 (Francis, P. H. et al. (1994) Development 120:209-218), a dpp homologue. However, unlike DPP in *Drosophila*, Bmp2 fails to mimic the polarizing effect of Shh upon ectopic application in the chick limb bud (Francis et al. (1994) supra). In addition to anteroposterior patterning, Shh also appears to be involved in the regulation of the proximodistal outgrowth of the limbs by inducing the synthesis of the fibroblast growth factor FGF4 in the posterior apical ectodermal ridge (Laufer, E. et al. (1994) Cell 79:993-1003; Niswander, L. et al. (1994) Nature 371:609-612).

The close relationship between Hedgehog proteins and BMPs is likely to have been conserved at many, but probably not all sites of vertebrate Hedgehog expression. For example, in the chick hindgut, Shh has been shown to induce the expression of Bmp4, another vertebrate dpp homologue (Roberts, D. J. et al. (1995) Development 121:3163-3174). Furthermore, Shh and Bmp2, 4, or 6 show a striking correlation in their expression in epithelial and mesenchymal cells of the stomach, the urogenital system, the lung, the tooth buds and the hair follicles (Bitgood, M. J. and McMahon, A. P. (1995) Dev. Biol. 172:126-138).

Recent evidence suggests a model in which Indian hedgehog (Ihh) plays a crucial role in the regulation of chondrogenic development. Ihh, one of the two other mouse Hedgehog genes, is expressed adjacent to BMP expressing cells in the gut and developing cartilage (Bitgood and McMahon (1995) supra). During cartilage formation, chondrocytes proceed from a proliferating state via an intermediate, prehypertrophic state to differentiated hypertrophic chondrocytes. Ihh is expressed in the prehypertrophic chondrocytes and initiates a signaling cascade that leads to the blockage of chondrocyte differentiation. Its direct target is the perichondrium around the Ihh expression domain, which responds by the expression of Gli and Patched (Ptc), conserved transcriptional targets of Hedgehog signals. Most likely, this leads to secondary signaling resulting in the synthesis of parathyroid hormone-related protein (PTHrP) in the periarticular perichondrium. PTHrP itself signals back to the prehypertrophic chondrocytes, blocking their further differentiation. At the same time, PTHrP represses expression of Ihh, thereby forming a negative feedback loop that modulates the rate of chondrocyte differentiation.

The TDFRP compounds described herein are suitable for administration to a mammal in conjunction with BMPs and other mediators of the Hedgehog pathway. This includes co-administration of TDFRPs with BMPs and Hedgehog mediators, for example as part of a single pharmaceutical formulation. Co-administration also includes providing the TDFRP compounds and the Hedgehog mediators and/or BMPs to the mammal in separate pharmaceutical formulations. Co-administration includes providing the TDFRP compounds, the Hedgehog mediators and/or BMPs concurrently or intermittently, for example multiple doses per day, one dose per day, one dose every other day, administration weekly or monthly, etc.

Example 9

TDFRP Compounds and p38 MAPK Signalling Pathways

Smad proteins are the substrates and the mediators of BMP bound serine/threonine receptor kinases. Ligand-induced activation of BMP receptors with intrinsic serine/threonine kinase activity trigger phosphorylation of receptor-regulated Smads (R-Smads) Smad 1, Smad 3 and Smad 8. The multifunctional and context dependency of BMP responses are reflected in the function of Smads as signal integrators. Certain Smads are somatically mutated at high frequency in particular types of human cancers. The differential phosphorylation of R-Smads may be influenced by MAPK signaling. MAPK consensus sites are found in all Smads, including Smad 1, Smad 5 and Smad 8 that relay actions of BMPs. Moreover, it has been shown that engagement of receptor tyrosine kinases leads to phosphorylation of MAPK consensus sites on R-Smads in the linker region between their conserved Mad Homology 1 (MH1) and MH2 domains (Massague J (2003) Genes & Dev. 17, 2993-2997). At the cellular level, the linker mutation affects cell contacts, actin cytoskeleton, and nuclear beta-catenin accumulation, which correlate with the retention of Smad 1 at the membrane. Also, Smad and MAPK pathways act synergistically in the BMP pathway to control limb development (Zuzarte-Luis et al. (2004) Dev Biol. 272, 39-52). Recently, BMP-7 has been shown to act through Smad and p38 MAPK pathways in a dose-dependent activity gradient to control rates of cell proliferation, tubule growth, and branching during kidney development (Hu et al. (2004) J Biol. Chem. 279, 12051-12059). Thus, the p38 MAPK pathway appears to control responses to low doses of BMP-7 leading to increased cell proliferation and branching, whereas Smads control responses to higher doses of BMP-7 to suppress cell proliferation and branching. In another study, BMP-activated Smads and ATF2 (a down stream target for p38 MAPK) were shown to act cooperatively to control beta-myosin heavy chain gene expression and cardiomyocyte differentiation (Monzen et al. (2001) J. Cell Biol. 153, 687-698). The TDFRP compounds may activate both Smad and p38 MAPK signaling pathways.

Therapeutic Indications

Therapeutic or prophylactic administration of TDFRP compounds, with either or both of the Hedgehog pathway mediators and/or BMPs are suitable for treating numerous cellular disorders. Hedgehog proteins suitable for use herein include Shh, Ihh or Dhh, and a Hedgehog mediator suitable for use herein includes compounds that upregulate or downregulate the expression of Shh, Ihh or Dhh. The BMPs suitable for co-administration with TDFRP compounds include BMP-1, BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16 further including any dimeric proteins such as homodimers, heterodimers, or combinations thereof, alone or together with other molecules capable of inducing an upstream or downstream effect of a BMP such as Hedgehog proteins, TDFRPs or the DNA's encoding them and any combinations thereof. These Hedgehog, BMP and TDFRP compounds are collectively referred to as "compounds" hereafter, and formulations comprising Hedgehog, BMP and TDFRP compounds in various combinations, are suitable for the following indications using the dosages described herein and in the cited references.

The term "hedgehog signaling pathway", "hedgehog pathway" and "hedgehog signal transduction pathway" are all used to refer to the chain of events normally mediated by hedgehog, smoothened, ptc, and gli, among others, and resulting in a changes in gene expression and other phenotypic changes typical of hedgehog activity. Activating a downstream component can activate the hedgehog pathway even in the absence of a hedgehog protein. For example, overexpression of smoothened will activate the pathway in the absence of hedgehog. gli and ptc gene expression are indicators of an active hedgehog-signaling pathway. The term "hedgehog antagonist" refers to an agent that potentiates or recapitulates the bioactivity of patched, such as to repress transcription of target genes. Preferred hedgehog antagonists can be used to overcome a ptc loss-of-function and/or a smoothened gain-of-function, the latter also being referred to as smoothened antagonists. Other preferred hedgehog antagonists can be used to overcome an inappropriate increase in hedgehog signal transduction, whether said increase in signal transduction is the result in a mutation/lesion in a component of the hedgehog signaling pathway (e.g., ptc, gli1, gli3, smoothened, etc) or whether said increase in signal transduction occurs in the context of a cell which does not comprise a mutation/lesion in a component of the hedgehog signaling pathway (e.g., a wildtype cell with respect to components of the hedgehog signaling pathway). The term 'hedgehog antagonist' as used herein refers not only to any agent that may act by directly inhibiting the normal function of the hedgehog protein, but also to any agent that inhibits the hedgehog signalling pathway, and thus recapitulates the function of ptc. A hedgehog antagonist may be a small molecule, an antibody (including but not restricted to: a diabody, single chain antibody, monoclonal antibody, IgG, IgM, IgA, IgD, IgE, or an antibody fragment comprising at least one pair of variable regions), an antisense nucleic acid, PNA or ribozyme, RNAi construct, or a mutant hedgehog protein that can disrupt or inhibit hedgehog signaling. An antibody may be directed to a protein encoded by any of the genes in the hedgehog pathway, including sonic, indian or desert hedgehog, smoothened, ptc-1, ptc-2, gli-1, gli-2, gli-3, etc. In most cases, the antibody would inhibit the activity of the target protein, but in the case of patched, such an antibody would be an activator of patched. An antisense nucleic acid would likewise decrease production of a protein encoded by any of the genes in the hedgehog pathway, with the exception of patched or other genes encoding negative regulators of the hedgehog-signaling pathway. The term "hedgehog gain-of-function" refers to an aberrant modification or mutation of a ptc gene, hedgehog gene, or smoothened gene, or a decrease (or loss) in the level of expression of such a gene, which results in a phenotype which resembles contacting a cell with a hedgehog protein, e.g., aberrant activation of a hedgehog pathway. The gain-of-function may include a loss of the ability of the ptc gene product to regulate the level of expression of Ci genes, e.g., Gli1, Gli2, and Gli3. The term "hedgehog gain-of-function" is also used herein to refer to any similar cellular phenotype (e.g., exhibiting excess proliferation) that occurs due to an alteration anywhere in the hedgehog signal transduction pathway, including, but not limited to, a modification or mutation of hedgehog itself. For example, a tumor cell with an abnormally high proliferation rate due to activation of the hedgehog signalling pathway would have a "hedgehog gain-of-function" phenotype, even if hedgehog is not mutated in that cell.

One aspect of the present application relates to a method for modulating the growth state of an lung tissue, or a cell thereof, e.g., by ectopically contacting the tissue, in vitro or in vivo, with a Hedgehog mediator or a BMP, with a TDFRP compound in an amount effective to alter the rate (promote or inhibit) of proliferation of cells in the lung tissue, e.g., relative to the absence of administration of the Hedgehog mediator or BMP, with the TDFRP, or without any TDFRP. The subject method can be used, for example, to modulate the growth state of epithelial and/or mesenchymal cells of a lung tissue, such as may be useful as part of a regimen for prevention of a disease state, or in the treatment of an existing disease state or other damage to the lung tissue. In certain embodiments, the Hedgehog polypeptide is modified with one or more sterol moieties, e.g., cholesterol or a derivative thereof. In certain embodiments, the Hedgehog polypeptide is modified with one or more fatty acid moieties, such as a fatty acid moiety selected from the group consisting of myristoyl, palmitoyl, stearoyl, and arachidoyl. In certain preferred embodiments, the Hedgehog mediator is a peptide that has an amino acid sequence at least 60, 75, 85, or 95 percent identical with a Hedgehog protein, preferably a polypeptide including a Hedgehog portion comprising at least a bioactive extracellular portion of a Hedgehog protein, e.g., the Hedgehog portion includes at least 50, 100 or 150 (contiguous) amino acid residues of an N-terminal half of a Hedgehog protein. In preferred embodiments, the Hedgehog portion includes at least a portion of the Hedgehog protein corresponding to a 19 kDa fragment of the extracellular domain of a Hedgehog protein. In certain embodiments, the Hedgehog mediator is an antisense construct which inhibits the expression of a Hedgehog protein, which is involved in the signal transduction pathway of patched and the expression of which antagonizes Hedgehog-mediated signals. The antisense construct is preferably an oligonucleotide of about 20-30 nucleotides in length and having a GC content of at least 50 percent. In still another embodiment, the Hedgehog mediator is short interfering RNA (siRNA) of about 8-30 nucleotides, preferably 15-20 nucleotides, which causes the intracellular sequestration and catalysis of Hedgehog RNA, thereby reducing levels of Hedgehog in the cells. For a further discussion of the regulation of lung tissue by Hedgehog-like polypeptides and formulations and uses related thereto, see United States Patent Application 20040171546 to Pepicelli, et al.

For a discussion of the regulation of adipocytes by Hedgehog-like polypeptides and formulations and uses related thereto, see United States Patent Application 20040171533, to Zehentner, et al.

The TGF-beta family of growth factors, particularly the bone morphogenetic protein (BMP)-2/4 homolog decapentaplegic (dpp), are specifically required to maintain germline stem cells and promote their division. Overexpression of dpp blocks germline stem cell differentiation. Mutations in dpp or its receptor saxophone accelerate stem cell loss and retard stem cell division. dpp signaling is directly received by germline stem cells, and thus dpp signaling helps define a niche that controls germline stem cell proliferation. United States Patent Application 20040157324 to Spradling, et al. discusses method for maintenance and propagation of germline stem cells using members of the TGF-beta family of growth factors (BMPs). For discussion regarding the differentiation of stem cells by Hedgehog-like polypeptides and formulations and uses related thereto, see United States Patent Application 20040171153 to Andrews, et al.

The present invention relates to the discovery that signal transduction pathways regulated by hedgehog, patched (ptc), gli and/or smoothened can be inhibited, at least in part, by hedgehog antagonists. While not wishing to be bound by any theory, in the case of small molecule antagonists, the modulation of a receptor may be the mechanism by which these agents act. For example, the ability of these agents to inhibit proliferation of patched loss-of-function (ptc.sup.1of) cells may be due to the ability of such molecules to interact with hedgehog, patched, or smoothened, or at least to interfere with the ability of those proteins to activate a hedgehog, ptc, and/or smoothened-mediated signal transduction pathway. It is, therefore, specifically contemplated that these small molecules which interfere with aspects of hedgehog, ptc, or smoothened signal transduction activity will likewise be capable of changing the role of a cell in tissue development from what would otherwise occur. In preferred embodiments, the cell has a substantially wild-type hedgehog-signaling pathway. It is also contemplated that hedgehog antagonists are particularly effective in treating disorders resulting from hyperactivation of the hedgehog pathway, either as a result of mutations in components of the hedgehog signaling pathway or as a result of inappropriate activation of the hedgehog signaling pathway in cell which do not comprise a mutation/lesion in a component of the hedgehog signaling pathway. Therefore, it is desirable to have a method for identifying those cells in which the hedgehog pathway is hyperactive such that antagonist treatment may be efficiently targeted. One of skill in the art will readily recognize, that antagonists for use in the present invention can antagonize hedgehog signaling at any point in the hedgehog-signaling pathway. That is, an exemplary antagonist can reduce hedgehog signaling by binding to and antagonizing hedgehog, as for example using a hedgehog antibody. Similarly, an exemplary antagonist can interfere with the interaction between hedgehog and the hedgehog receptor patched. Additionally, one of skill in the art will recognize that exemplary antagonists can interfere with hedgehog signaling by acting intracellularly, as for example using a small molecule antagonist that acts on an intracellular component of the hedgehog-signaling pathway. It is contemplated that the hedgehog antagonists of the present invention can be used to antagonize hedgehog signaling in a wild-type cell or in a cell comprising a mutation in a component of the hedgehog-signaling pathway. In certain embodiments, the subject antagonists are organic molecules having a molecular weight less than 2500 amu, more preferably less than 1500 amu, and even more preferably less than 750 amu, and are capable of inhibiting at least some of the biological activities of hedgehog proteins, preferably specifically in target cells. Thus, the methods of the present invention include the use of small molecules that agonize ptc inhibition of hedgehog signaling in the regulation of repair and/or functional performance of a wide range of cells, tissues and organs having the phenotype of hedgehog gain-of-function and in tissues with wild-type hedgehog activity. For instance, the subject method has therapeutic and cosmetic applications ranging from regulation of neural tissues, bone and cartilage formation and repair, regulation of spermatogenesis, regulation of smooth muscle, regulation of lung, liver and tissue of other organs arising from the primitive gut, regulation of hematopoietic function, regulation of skin and hair growth, etc. Moreover, the subject methods can be performed on cells that are provided in culture (in vitro), or on cells in a whole animal (in vivo). See, for example, PCT publications WO 95/18856 and WO 96/17924 (the specifications of which are expressly incorporated by reference herein). In another aspect, the present invention provides pharmaceutical preparations comprising, as an active ingredient, a hedgehog antagonist or ptc agonist such as described herein, formulated in an amount sufficient to inhibit, in vivo, proliferation or other biological consequences of hedgehog gain-of-function. The subject treatments using hedgehog antagonists can be effective for both human and animal subjects Animal subjects to which the invention is applicable extend to both domestic animals and livestock, raised either as pets or for commercial purposes. Examples are dogs, cats, cattle, horses, sheep, hogs, and goats.

Another aspect of the present invention relates to methods of modulating a differentiated state, survival, and/or proliferation of a cell.

For example, it is contemplated that the subject method could be used to inhibit angiogenesis. Hedgehog is known to stimulate angiogenesis. Matrigel plugs impregnated with hedgehog protein and inserted into mice evince substantial neovascularization, whereas Matrigel plugs not carrying hedgehog show comparatively little vascularization. Hedgehog protein is also capable of increasing vascularization of the normally avascular mouse cornea. The ptc-1 gene is expressed in normal vascular tissues, including the endothelial cells of the aorta, vascular smooth muscle cells, adventitial fibroblasts of the aorta, the coronary vasculature and cardiomyocytes of the atria and ventricles. These tissues are also sensitive to hedgehog protein. Treatment with exogenous hedgehog causes upregulation of ptc-1 expression. In addition, hedgehog proteins stimulate proliferation of vascular smooth muscle cells in vivo. Hedgehog proteins also cause fibroblasts to increase expression of angiogenic growth factors such as VEGF, bFGF, Ang-1 and Ang-2. Lastly, hedgehog proteins are known to stimulate recovery from ischemic injury and stimulate formation of collateral vessels.

Given that hedgehog promotes angiogenesis, hedgehog antagonists are expected to act as angiogenesis inhibitors, particularly in situations where some level of hedgehog signaling is necessary for angiogenesis.

Angiogenesis is fundamental to many disorders. Persistent, unregulated angiogenesis occurs in a range of disease states, tumor metastases and abnormal growths by endothelial cells. The vasculature created as a result of angiogenic processes supports the pathological damage seen in these conditions. The diverse pathological states created due to unregulated angiogenesis have been grouped together as angiogenic dependent or angiogenic associated diseases. Therapies directed at control of the angiogenic processes could lead to the abrogation or mitigation of these diseases.

Diseases caused by, supported by or associated with angiogenesis include ocular neovascular disease, age-related macular degeneration, diabetic retinopathy, retinopathy of prematurity, corneal graft rejection, neovascular glaucoma, retrolental fibroplasia, epidemnic keratoconjunctivitis, Vitamin A deficiency, contact lens overwear, atopic keratitis, superior limbic keratitis, pterygium keratitis sicca, sjogrens, acne rosacea, phylectenulosis, syphilis, *Mycobacteria* infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginal keratolysis, rheumatoid arthritis, systemic lupus, polyarteritis, trauma, Wegeners sarcoidosis, Scleritis, Steven's Johnson disease, periphigoid radial keratotomy, corneal graft rejection, rheumatoid arthritis, osteoarthritis chronic inflammation (e.g., ulcerative colitis or Crohn's disease), hemangioma, Osler-Weber-Rendu disease, and hereditary hemorrhagic telangiectasia.

In addition, angiogenesis plays a critical role in cancer. A tumor cannot expand without a blood supply to provide nutrients and remove cellular wastes. Tumors in which angiogenesis is important include solid tumors such as rhabdomyosarcomas, retinoblastoma, Ewing sarcoma, neuroblastoma, and osteosarcoma, and benign tumors such as acoustic neuroma, neurofibroma, trachoma and pyogenic granulomas. Angiogenic factors have been found associated with several solid tumors. Prevention of angiogenesis could halt the growth of these tumors and the resultant damage to the animal due to the presence of the tumor. Angiogenesis is also associated with blood-born tumors such as leukemias, any of various acute or chronic neoplastic diseases of the bone marrow in which unrestrained proliferation of white blood cells occurs, usually accompanied by anemia, impaired blood clotting, and enlargement of the lymph nodes, liver, and spleen. It is believed that angiogenesis plays a role in the abnormalities in the bone marrow that give rise to leukemia-like tumors.

In addition to tumor growth, angiogenesis is important in metastasis. Initially, angiogenesis is important is in the vascularization of the tumor which allows cancerous cells to enter the blood stream and to circulate throughout the body. After the tumor cells have left the primary site, and have settled into the secondary, metastasis site, angiogenesis must occur before the new tumor can grow and expand. Therefore, prevention of angiogenesis could lead to the prevention of metastasis of tumors and possibly contain the neoplastic growth at the primary site.

Angiogenesis is also involved in normal physiological processes such as reproduction and wound healing. Angiogenesis is an important step in ovulation and also in implantation of the blastula after fertilization. Prevention of angiogenesis could be used to induce amenorrhea, to block ovulation or to prevent implantation by the blastula.

It is anticipated that the invention will be useful for the treatment and/or prevention of respiratory distress syndrome or other disorders resulting from inappropriate lung surface tension. Respiratory distress syndrome results from insufficient surfactant in the alveolae of the lungs. The lungs of vertebrates contain surfactant, a complex mixture of lipids and protein that causes surface tension to rise during lung inflation and decrease during lung deflation. During lung deflation, surfactant decreases such that there are no surface forces that would otherwise promote alveolar collapse. Aerated alveoli that have not collapsed during expiration permit continuous oxygen and carbon dioxide transport between blood and alveolar gas and require much less force to inflate during the subsequent inspiration. During inflation, lung surfactant increases surface tension as the alveolar surface area increases. A rising surface tension in expanding alveoli opposes over-inflation in those airspaces and tends to divert inspired air to less well-aerated alveoli, thereby facilitating even lung aeration.

Respiratory distress syndrome is particularly prevalent among premature infants. Lung surfactant is normally synthesized at a very low rate until the last six weeks of fetal life. Human infants born more than six weeks before the normal term of a pregnancy have a high risk of being born with inadequate amounts of lung surfactant and inadequate rates of surfactant synthesis. The more prematurely an infant is born, the more severe the surfactant deficiency is likely to be. Severe surfactant deficiency can lead to respiratory failure within a few minutes or hours of birth. The surfactant deficiency produces progressive collapse of alveoli (atelectasis) because of the decreasing ability of the lung to expand despite maximum inspiratory effort. As a result, inadequate amounts of oxygen reach the infant's blood. RDS can occur in adults as well, typically as a consequence of failure in surfactant biosynthesis.

Lung tissue of premature infants shows high activity of the hedgehog-signaling pathway Inhibition of this pathway using hedgehog antagonists increases the formation of lamellated bodies and increases the expression of genes involved in surfactant biosynthesis. Lamellar bodies are subcellular structures associated with surfactant biosynthesis. For these reasons, treatment of premature infants with a hedgehog antagonist should stimulate surfactant biosynthesis and ameliorate RDS. In cases where adult RDS is associated with hedgehog pathway activation, treatment with hedgehog antagonists should also be effective.

It is further contemplated that the use of hedgehog antagonists may be specifically targeted to disorders where the affected tissue and/or cells evince high hedgehog pathway activation. Expression of gli genes is activated by the hedgehog-signaling pathway, including gli-1, gli-2 and gli-3. gli-1 expression is most consistently correlated with hedgehog signaling activity across a wide range of tissues and disorders, while gli-3 is somewhat less so. The gli genes encode transcription factors that activate expression of many genes needed to elicit the full effects of hedgehog signaling. However, the Gli-3 transcription factor can also act as a repressor of hedgehog effector genes, and therefore, expression of gli-3 can cause a decreased effect of the hedgehog-signaling pathway. Whether Gli-3 acts as a transcriptional activator or repressor depends on post-translational events, and therefore it is expected that methods for detecting the activating form (versus the repressing form) of Gli-3 protein would also be a reliable measure of hedgehog pathway activation. gli-2 gene expression is expected to provide a reliable marker for hedgehog pathway activation. The gli-1 gene is strongly expressed in a wide array of cancers, hyperplasias and immature lungs, and serves as a marker for the relative activation of the hedgehog pathway. In addition, tissues, such as immature lung, that have high gli gene expression are strongly affected by hedgehog inhibitors. Accordingly, it is contemplated that the detection of gli gene expression may be used as a powerful predictive tool to identify tissues and disorders that will particularly benefit from treatment with a hedgehog antagonist.

In preferred embodiments, gli-1 expression levels are detected, either by direct detection of the transcript or by detection of protein levels or activity. Transcripts may be detected using any of a wide range of techniques that depend primarily on hybridization of probes to the gli-1 transcripts or to cDNAs synthesized therefrom. Well known techniques include Northern blotting, reverse-transcriptase PCR (RT-PCR) and microarray analysis of transcript levels. Methods for detecting Gli protein levels include Western blotting, immunoprecipitation, two-dimensional polyacrylamide gel electrophoresis (2D SDS-PAGE) (preferably compared against a standard wherein the position of the Gli proteins has been determined), and mass spectroscopy. Mass spectroscopy may be coupled with a series of purification steps to allow high-throughput identification of many different protein levels in a particular sample. Mass spectroscopy and 2D SDS-PAGE can also be used to identify post-transcriptional modifications to proteins including proteolytic events, ubiquitination, phosphorylation, lipid modification etc. Gli activity may also be assessed by analyzing binding to substrate DNA or in vitro transcriptional activation of target promoters. Gel shift assays, DNA footprinting assays and DNA-protein crosslinking assays are all methods that may be used to assess the presence of a protein capable of binding to Gli binding sites on DNA. (J Mol Med 1999 June; 77(6):459-68; Cell 2000 Feb. 18; 100(4):423-34; Development 2000; 127(19): 4293-4301)

In preferred embodiments, gli transcript levels are measured and diseased or disordered tissues showing abnormally high gli levels are treated with a hedgehog antagonist. Premature lung tissue, lung cancers (e.g., adenocarcinomas, broncho-alveolar adenocarcinomas, small cell carcinomas), breast cancers (e.g., inferior ductal carcinomas, inferior lobular carcinomas, tubular carcinomas), prostate cancers (e.g., adenocarcinomas), and benign prostatic hyperplasias all show strongly elevated gli-1 expression levels in certain cases. Accordingly, gli-1 expression levels are a powerful diagnostic device to determine which of these tissues should be treated with a hedgehog antagonist. In addition, there is substantial correlative evidence that cancers of urothelial cells (e.g., bladder cancer, other urogenital cancers) will also have elevated gli-1 levels in certain cases. For example, it is known that loss of heterozygosity on chromosome 9q22 is common in bladder cancers. The ptc-1 gene is located at this position and ptc-1 loss of function is probably a partial cause of hyperproliferation, as in many other cancer types. Accordingly, such cancers would also show high gli expression and would be particularly amenable to treatment with a hedgehog antagonist.

Expression of ptc-1 and ptc-2 is also activated by the hedgehog-signaling pathway, but these genes are inferior to the gli genes as markers of hedgehog pathway activation. In certain tissues only one of ptc-1 or ptc-2 is expressed although the hedgehog pathway is highly active. For example, in testicular development, Indian hedgehog plays an important role and the hedgehog pathway is activated, but only ptc-2 is expressed. Accordingly, these genes are individually unreliable as markers for hedgehog pathway activation, although simultaneous measurement of both genes is contemplated as a useful indicator for tissues to be treated with a hedgehog antagonist.

It is anticipated that any degree of gli overexpression may be useful in determining that a hedgehog antagonist will be an effective therapeutic. In preferred embodiments, gli should be expressed at a level at least twice as high as normal. In particularly preferred embodiments, expression is four, six, eight or ten times as high as normal.

For instance, it is contemplated by the invention that, in light of the findings of an apparently broad involvement of hedgehog, ptc, and smoothened in the formation of ordered spatial arrangements of differentiated tissues in vertebrates, the subject method could be used as part of a process for generating and/or maintaining an array of different vertebrate tissue both in vitro and in vivo. The hedgehog antagonist, whether inductive or anti-inductive with respect to proliferation or differentiation of a given tissue, can be, as appropriate, any of the preparations described above.

For example, the present method is applicable to cell culture techniques wherein it is desirable to reduce the level of hedgehog signaling. In vitro neuronal culture systems have proved to be fundamental and indispensable tools for the study of neural development, as well as the identification of neurotrophic factors such as nerve growth factor (NGF), ciliary trophic factors (CNTF), and brain derived neurotrophic factor (BDNF). One use of the present method may be in cultures of neuronal stem cells, such as in the use of such cultures for the generation of new neurons and glia. In such embodiments of the subject method, the cultured cells can be contacted with a hedgehog antagonist of the present invention in order to alter the rate of proliferation of neuronal stem cells in the culture and/or alter the rate of differentiation, or to maintain the integrity of a culture of certain terminally differentiated neuronal cells. In an exemplary embodiment, the subject method can be used to culture, for example, sensory neurons or, alternatively, motor neurons. Such neuronal cultures can be used as convenient assay systems as well as sources of implantable cells for therapeutic treatments.

To further illustrate other uses of the subject hedgehog antagonists, it is noted that intracerebral grafting has emerged as an additional approach to central nervous system therapies. For example, one approach to repairing damaged brain tissues involves the transplantation of cells from fetal or neonatal animals into the adult brain (Dunnett et al. (1987) J Exp Biol 123:265-289; and Freund et al. (1985) J Neurosci 5:603-616). Fetal neurons from a variety of brain regions can be successfully incorporated into the adult brain, and such grafts can alleviate behavioral defects. For example, movement disorder induced by lesions of dopaminergic projections to the basal ganglia can be prevented by grafts of embryonic dopaminergic neurons. Complex cognitive functions that are impaired after lesions of the neocortex can also be partially restored by grafts of embryonic cortical cells. The subject method can be used to regulate the growth state in the culture, or where fetal tissue is used, especially neuronal stem cells, can be used to regulate the rate of differentiation of the stem cells.

Stem cells useful in the present invention are generally known. For example, several neural crest cells have been identified, some of which are multipotent and likely represent uncommitted neural crest cells, and others of which can generate only one type of cell, such as sensory neurons, and likely represent committed progenitor cells. The role of hedgehog antagonists employed in the present method to culture such stem cells can be to regulate differentiation of the uncommitted progenitor, or to regulate further restriction of the developmental fate of a committed progenitor cell towards becoming a terminally differentiated neuronal cell. For example, the present method can be used in vitro to regulate the differentiation of neural crest cells into glial cells, Schwann cells, chromaffin cells, cholinergic sympathetic or parasympathetic neurons, as well as peptidenergic and serotonergic neurons. The hedgehog antagonists can be used alone, or can be used in combination with other neurotrophic factors that act to more particularly enhance a particular differentiation fate of the neuronal progenitor cell.

In addition to the implantation of cells cultured in the presence of the subject hedgehog antagonists, yet another aspect of the present invention concerns the therapeutic application of a hedgehog antagonist to regulate the growth state of neurons and other neuronal cells in both the central nervous system and the peripheral nervous system. The ability of ptc, hedgehog, and smoothened to regulate neuronal differentiation during development of the nervous system and also presumably in the adult state indicates that, in certain instances, the subject hedgehog antagonists can be expected to facilitate control of adult neurons with regard to maintenance, functional performance, and aging of normal cells; repair and regeneration processes in chemically or mechanically lesioned cells; and treatment of degeneration in certain pathological conditions. In light of this understanding, the present invention specifically contemplates applications of the subject method to the treatment protocol of (prevention and/or reduction of the severity of) neurological conditions deriving from: (i) acute, subacute, or chronic injury to the nervous system, including traumatic injury, chemical injury, vascular injury and deficits (such as the ischemia resulting from stroke), together with infectious/inflammatory and tumor-induced injury; (ii) aging of the nervous system including Alzheimer's disease; (iii) chronic neurodegenerative diseases of the nervous system, including Parkinson's disease, Huntington's chorea, amyotrophic lateral sclerosis and the like, as well as spinocerebellar degenerations; and (iv) chronic immunological diseases of the nervous system or affecting the nervous system, including multiple sclerosis.

As appropriate, the subject method can also be used in generating nerve prostheses for the repair of central and peripheral nerve damage. In particular, where a crushed or severed axon is intubated by use of a prosthetic device, hedgehog antagonists can be added to the prosthetic device to regulate the rate of growth and regeneration of the dendritic processes. Exemplary nerve guidance channels are described in U.S. Pat. Nos. 5,092,871 and 4,955,892.

In another embodiment, the subject method can be used in the treatment of neoplastic or hyperplastic transformations such as may occur in the central nervous system. For instance, the hedgehog antagonists can be utilized to cause such transformed cells to become either post-mitotic or apoptotic. The present method may, therefore, be used as part of a treatment for, e.g., malignant gliomas, meningiomas, medulloblastomas, neuroectodermal tumors, and ependymomas.

In a preferred embodiment, the subject method can be used as part of a treatment regimen for malignant medulloblastoma and other primary CNS malignant neuroectodermal tumors.

In certain embodiments, the subject method is used as part of treatment program for medulloblastoma. Medulloblastoma, a primary brain tumor, is the most common brain tumor in children. A medulloblastoma is a primitive neuroectodermal tumor arising in the posterior fossa. They account for approximately 25% of all pediatric brain tumors (Miller). Histologically, they are small round cell tumors commonly arranged in true rosettes, but may display some differentiation to astrocytes, ependymal cells or neurons (Rorke; Kleihues). PNET's may arise in other areas of the brain including the pineal gland (pineoblastoma) and cerebrum. Those arising in the supratentorial region generally fare worse than their PF counterparts.

Medulloblastoma/PNET's are known to recur anywhere in the CNS after resection, and can even metastasize to bone. Pretreatment evaluation should therefore include an examination of the spinal cord to exclude the possibility of "dropped metastases". Gadolinium-enhanced MRI has largely replaced myelography for this purpose, and CSF cytology is obtained postoperatively as a routine procedure.

In other embodiments, the subject method is used as part of treatment program for ependymomas. Ependymomas account for approximately 10% of the pediatric brain tumors in children. Grossly, they are tumors that arise from the ependymal lining of the ventricles and microscopically form rosettes, canals, and perivascular rosettes. In the CHOP series of 51 children reported with ependymomas, b {fraction (¾)} were histologically benign, approximately ⅔ arose from the region of the 4th ventricle, and one third presented in the supratentorial region. The median age is about 5 years and the age at presentation peaks between birth and 4 years, as demonstrated by SEER data, as well as data from CHOP information. Because so many children with this disease are babies, they often require multimodal therapy.

Yet another aspect of the present invention concerns the observation in the art that ptc, hedgehog, and/or smoothened are involved in morphogenic signals involved in other vertebrate organogenic pathways in addition to neuronal differentiation as described above, having apparent roles in other endodermal patterning, as well as both mesodermal and endodermal differentiation processes. Thus, it is contemplated by the invention that compositions comprising hedgehog antagonists can also be utilized for both cell culture and therapeutic methods involving generation and maintenance of non-neuronal tissue.

In one embodiment, the present invention makes use of the discovery that ptc, hedgehog, and smoothened are apparently involved in controlling the development of stem cells responsible for formation of the digestive tract, liver, lungs, and other organs which derive from the primitive gut. Shh serves as an inductive signal from the endoderm to the mesoderm, which is critical to gut morphogenesis. Therefore, for example, hedgehog antagonists of the instant method can be employed for regulating the development and maintenance of an artificial liver that can have multiple metabolic functions of a normal liver. In an exemplary embodiment, the subject method can be used to regulate the proliferation and differentiation of digestive tube stem cells to form hepatocyte cultures which can be used to populate extracellular matrices, or which can be encapsulated in biocompatible polymers, to form both implantable and extracorporeal artificial livers.

In another embodiment, therapeutic compositions of hedgehog antagonists can be utilized in conjunction with transplantation of such artificial livers, as well as embryonic liver structures, to regulate uptake of intraperitoneal implantation, vascularization, and in vivo differentiation and maintenance of the engrafted liver tissue.

In yet another embodiment, the subject method can be employed therapeutically to regulate such organs after physical, chemical or pathological insult. For instance, therapeutic compositions comprising hedgehog antagonists can be utilized in liver repair subsequent to a partial hepatectomy.

The generation of the pancreas and small intestine from the embryonic gut depends on intercellular signalling between the endodermal and mesodermal cells of the gut. In particular, the differentiation of intestinal mesoderm into smooth muscle has been suggested to depend on signals from adjacent endodermal cells. One candidate mediator of endodermally derived signals in the embryonic hindgut is Sonic hedgehog. See, for example, Apelqvist et al. (1997) Curr Biol 7:801-4. The Shh gene is expressed throughout the embryonic gut endoderm with the exception of the pancreatic bud endoderm, which instead expresses high levels of the homeodomain protein Ipf1/Pdx1 (insulin promoter factor 1/pancreatic and duodenal homeobox 1), an essential regulator of early pancreatic development. Apelqvist et al., supra, have examined whether the differential expression of Shh in the embryonic gut tube controls the differentiation of the surrounding mesoderm into specialised mesoderm derivatives of the small intestine and pancreas. To test this, they used the promoter of the Ipf1/Pdx1 gene to selectively express Shh in the developing pancreatic epithelium. In Ipf1/Pdx1-Shh transgenic mice, the pancreatic mesoderm developed into smooth muscle and interstitial cells of Cajal, characteristic of the intestine, rather than into pancreatic mesenchyme and spleen. Also, pancreatic explants exposed to Shh underwent a similar program of intestinal differentiation. These results provide evidence that the differential expression of endodermally derived Shh controls the fate of adjacent mesoderm at different regions of the gut tube.

In the context of the present invention, it is contemplated therefore that the subject hedgehog antagonists can be used to control or regulate the proliferation and/or differentiation of pancreatic tissue both in vivo and in vitro.

In another embodiment, hedgehog antagonists are used to generate endodermal tissue from non-endodermal stem cells including mesenchymal stem cells and stem cells derived from mesodermal tissues. Exemplary mesodermal tissues from which stem cells may be isolated include skeletal muscle, cardiac muscle, kidney, bone, cartilage, and fat.

There are a wide variety of pathological cell proliferative and differentiative conditions for which the inhibitors of the present invention may provide therapeutic benefits, with the general strategy being, for example, the correction of aberrant insulin expression, or modulation of differentiation. More generally, however, the present invention relates to a method of inducing and/or maintaining a differentiated state, enhancing survival and/or affecting proliferation of pancreatic cells, by contacting the cells with the subject inhibitors. For instance, it is contemplated by the invention that, in light of the apparent involvement of ptc, hedgehog, and smoothened in the formation of ordered spatial arrangements of pancreatic tissues, the subject method could be used as part of a technique to generate and/or maintain such tissue both in vitro and in vivo. For instance, modulation of the function of hedgehog can be employed in both cell culture and therapeutic methods involving generation and maintenance of .beta.-cells and possibly also for non-pancreatic tissue, such as in controlling the development and maintenance of tissue from the digestive tract, spleen, lungs, urogenital organs (e.g., bladder), and other organs which derive from the primitive gut.

In an exemplary embodiment, the present method can be used in the treatment of hyperplastic and neoplastic disorders effecting pancreatic tissue, particularly those characterized by aberrant proliferation of pancreatic cells. For instance, pancreatic cancers are marked by abnormal proliferation of pancreatic cells, which can result in alterations of insulin secretory capacity of the pancreas. For instance, certain pancreatic hyperplasias, such as pancreatic carcinomas, can result in hypoinsulinemia due to dysfunction of beta-cells or decreased islet cell mass.

Moreover, manipulation of hedgehog signaling properties at different points may be useful as part of a strategy for reshaping/repairing pancreatic tissue both in vivo and in vitro. In one embodiment, the present invention makes use of the apparent involvement of ptc, hedgehog, and smoothened in regulating the development of pancreatic tissue. In general, the subject method can be employed therapeutically to regulate the pancreas after physical, chemical or pathological insult. In yet another embodiment, the subject method can be applied to cell culture techniques, and in particular, may be employed to enhance the initial generation of prosthetic pancreatic tissue devices. Manipulation of proliferation and differentiation of pancreatic tissue, for example, by altering hedgehog activity, can provide a means for more carefully controlling the characteristics of a cultured tissue. In an exemplary embodiment, the subject method can be used to augment production of prosthetic devices, which require beta-islet cells, such as may be used in the encapsulation devices described in, for example, the Aebischer et al. U.S. Pat. No. 4,892,538, the Aebischer et al. U.S. Pat. No. 5,106,627, the Lim U.S. Pat. No. 4,391,909, and the Sefton U.S. Pat. No. 4,353,888. Early progenitor cells to the pancreatic islets are multipotent, and apparently coactivate all the islet-specific genes from the time they first appear. As development proceeds, expression of islet-specific hormones, such as insulin, becomes restricted to the pattern of expression characteristic of mature islet cells. The phenotype of mature islet cells, however, is not stable in culture, as reappearance of embryonal traits in mature beta-cells can be observed. By utilizing the subject hedgehog antagonists, the differentiation path or proliferative index of the cells can be regulated.

Furthermore, manipulation of the differentiative state of pancreatic tissue can be utilized in conjunction with transplantation of artificial pancreas. For instance, manipulation of hedgehog function to affect tissue differentiation can be utilized as a means of maintaining graft viability.

Bellusci et al. (1997) Development 124:53 report that Sonic hedgehog regulates lung mesenchymal cell proliferation in vivo. Accordingly, the present method can be used to regulate regeneration of lung tissue, e.g., in the treatment of emphysema.

Fujita et al. (1997) Biochem Biophys Res Commun 238: 658 reported that Sonic hedgehog is expressed in human lung squamous carcinoma and adenocarcinoma cells. The expression of Sonic hedgehog was also detected in the human lung squamous carcinoma tissues, but not in the normal lung tissue of the same patient. They also observed that Sonic hedgehog stimulates the incorporation of BrdU into the carcinoma cells and stimulates their cell growth, while anti-Shh-N inhibited their cell growth. These results suggest that a ptc, hedgehog, and/or smoothened is involved in the cell growth of such transformed lung tissue and therefore indicates that the subject method can be used as part of a treatment of lung carcinoma and adenocarcinomas, and other proliferative disorders involving the lung epithelia.

Many other tumors may, based on evidence such as involvement of the hedgehog pathway in these tumors, or detected expression of hedgehog or its receptor in these tissues during development, be affected by treatment with the subject compounds. Such tumors include, but are by no means limited to, tumors related to Gorlin's syndrome (e.g., medulloblastoma, meningioma, etc.), tumors evidenced in ptc knock-out mice (e.g., hemangioma, rhabdomyosarcoma, etc.), tumors resulting from gli-1 amplification (e.g., glioblastoma, sarcoma, etc.), tumors connected with TRC8, a ptc homolog (e.g., renal carcinoma, thyroid carcinoma, etc.), Ext-1-related tumors (e.g., bone cancer, etc.), Shh-induced tumors (e.g., lung cancer, chondrosarcomas, etc.), and other tumors (e.g., breast cancer, urogenital cancer (e.g., kidney, bladder, ureter, prostate, etc.), adrenal cancer, gastrointestinal cancer (e.g., stomach, intestine, etc.), etc.).

Exemplary forms of cancer which may be treated by the subject methods include, but are not limited to, prostate cancer, bladder cancer, lung cancer (including either small cell or non-small cell cancer), colon cancer, kidney cancer, liver cancer, breast cancer, cervical cancer, endometrial or other uterine cancer, ovarian cancer, testicular cancer, cancer of the penis, cancer of the vagina, cancer of the urethra, gall bladder cancer, esophageal cancer, or pancreatic cancer. Additional exemplary forms of cancer which may be treated by the subject methods include, but are not limited to, cancer of skeletal or smooth muscle, stomach cancer, cancer of the small intestine, cancer of the salivary gland, anal cancer, rectal cancer, thyroid cancer, parathyroid cancer, pituitary cancer, and nasopharyngeal cancer. Further exemplary forms of cancer, which can be treated with the hedgehog antagonists of the present invention include, cancers comprising hedgehog-expressing cells. Still further exemplary forms of cancer, which can be treated with the hedgehog antagonists of the present invention include, cancers comprising gli-expressing cells. In one embodiment, the cancer is not characterized by a mutation in patched-1.

In still another embodiment of the present invention, compositions comprising hedgehog antagonists can be used in the in vitro generation of skeletal tissue, such as from skeletogenic stem cells, as well as the in vivo treatment of skeletal tissue deficiencies. The present invention particularly contemplates the use of hedgehog antagonists to regulate the rate of chondrogenesis and/or osteogenesis. By "skeletal tissue deficiency", it is meant a deficiency in bone or other skeletal connective tissue at any site where it is desired to restore the bone or connective tissue, no matter how the deficiency originated, e.g., whether as a result of surgical intervention, removal of tumor, ulceration, implant, fracture, or other traumatic or degenerative conditions.

For instance, the method of the present invention can be used as part of a regimen for restoring cartilage function to a connective tissue. Such methods are useful in, for example, the repair of defects or lesions in cartilage tissue which is the result of degenerative wear such as that which results in arthritis, as well as other mechanical derangements which may be caused by trauma to the tissue, such as a displacement of torn meniscus tissue, meniscectomy, a laxation of a joint by a torn ligament, malignment of joints, bone fracture, or by hereditary disease. The present reparative method is also useful for remodeling cartilage matrix, such as in plastic or reconstructive surgery, as well as periodontal surgery. The present method may also be applied to improving a previous reparative procedure, for example, following surgical repair of a meniscus, ligament, or cartilage. Furthermore, it may prevent the onset or exacerbation of degenerative disease if applied early enough after trauma.

In one embodiment of the present invention, the subject method comprises treating the afflicted connective tissue with a therapeutically sufficient amount of a hedgehog antagonist, particularly an antagonist selective for Indian hedgehog signal transduction, to regulate a cartilage repair response in the connective tissue by managing the rate of differentiation and/or proliferation of chondrocytes embedded in the tissue. Such connective tissues as articular cartilage, interarticular cartilage (menisci), costal cartilage (connecting the true ribs and the sternum), ligaments, and tendons are particularly amenable to treatment in reconstructive and/or regenerative therapies using the subject method. As used herein, regenerative therapies include treatment of degenerative states which have progressed to the point of which impairment of the tissue is obviously manifest, as well as preventive treatments of tissue where degeneration is in its earliest stages or imminent.

In an illustrative embodiment, the subject method can be used as part of a therapeutic intervention in the treatment of cartilage of a diarthroidal joint, such as a knee, an ankle, an elbow, a hip, a wrist, a knuckle of either a finger or toe, or a tempomandibular joint. The treatment can be directed to the meniscus of the joint, to the articular cartilage of the joint, or both. To further illustrate, the subject method can be used to treat a degenerative disorder of a knee, such as which might be the result of traumatic injury (e.g., a sports injury or excessive wear) or osteoarthritis. The subject antagonists may be administered as an injection into the joint with, for instance, an arthroscopic needle. In some instances, the injected agent can be in the form of a hydrogel or other slow release vehicle described above in order to permit a more extended and regular contact of the agent with the treated tissue.

The present invention further contemplates the use of the subject method in the field of cartilage transplantation and prosthetic device therapies. However, problems arise, for instance, because the characteristics of cartilage and fibrocartilage varies between different tissue: such as between articular, meniscal cartilage, ligaments, and tendons, between the two ends of the same ligament or tendon, and between the superficial and deep parts of the tissue. The zonal arrangement of these tissues may reflect a gradual change in mechanical properties, and failure occurs when implanted tissue, which has not differentiated under those conditions, lacks the ability to appropriately respond. For instance, when meniscal cartilage is used to repair anterior cruciate ligaments, the tissue undergoes a metaplasia to pure fibrous tissue. By regulating the rate of chondrogenesis, the subject method can be used to particularly address this problem, by helping to adaptively control the implanted cells in the new environment and effectively resemble hypertrophic chondrocytes of an earlier developmental stage of the tissue.

In similar fashion, the subject method can be applied to enhancing both the generation of prosthetic cartilage devices and to their implantation. The need for improved treatment has motivated research aimed at creating new cartilage that is based on collagen-glycosaminoglycan templates (Stone et al. (1990) Clin Orthop Relat Red 252:129), isolated chondrocytes (Grande et al. (1989) J Orthop Res 7:208; and Takigawa et al. (1987) Bone Miner 2:449), and chondrocytes attached to natural or synthetic polymers (Walitani et al. (1989) J Bone Jt Surg 71B:74; Vacanti et al. (1991) Plast Reconstr Surg 88:753; von Schroeder et al. (1991) J Biomed Mater Res 25:329; Freed et al. (1993) J Biomed Mater Res 27:11; and the Vacanti et al. U.S. Pat. No. 5,041,138). For example, chondrocytes can be grown in culture on biodegradable, biocompatible highly porous scaffolds formed from polymers such as polyglycolic acid, polylactic acid, agarose gel, or other polymers that degrade over time as function of hydrolysis of the polymer backbone into innocuous monomers. The matrices are designed to allow adequate nutrient and gas exchange to the cells until engraftment occurs. The cells can be cultured in vitro until adequate cell volume and density has developed for the cells to be implanted. One advantage of the matrices is that they can be cast or molded into a desired shape on an individual basis, so that the final product closely resembles the patient's own ear or nose (by way of example), or flexible matrices can be used which allow for manipulation at the time of implantation, as in a joint.

In one embodiment of the subject method, the implants are contacted with a hedgehog antagonist during certain stages of the culturing process in order to manage the rate of differentiation of chondrocytes and the formation of hypertrophic chrondocytes in the culture.

In another embodiment, the implanted device is treated with a hedgehog antagonist in order to actively remodel the implanted matrix and to make it more suitable for its intended function. As set out above with respect to tissue transplants, the artificial transplants suffer from the same deficiency of not being derived in a setting which is comparable to the actual mechanical environment in which the matrix is implanted. The ability to regulate the chondrocytes in the matrix by the subject method can allow the implant to acquire characteristics similar to the tissue for which it is intended to replace.

In yet another embodiment, the subject method is used to enhance attachment of prosthetic devices. To illustrate, the subject method can be used in the implantation of a periodontal prosthesis, wherein the treatment of the surrounding connective tissue stimulates formation of periodontal ligament about the prosthesis.

In still further embodiments, the subject method can be employed as part of a regimen for the generation of bone (osteogenesis) at a site in the animal where such skeletal tissue is deficient. India hedgehog is particularly associated with the hypertrophic chondrocytes that are ultimately replaced by osteoblasts. For instance, administration of a hedgehog antagonists of the present invention can be employed as part of a method for regulating the rate of bone loss in a subject. For example, preparations comprising hedgehog antagonists can be employed, for example, to control endochondral ossification in the formation of a "model" for ossification.

In yet another embodiment of the present invention, a hedgehog antagonist can be used to regulate spermatogenesis. The hedgehog proteins, particularly Dhh, have been shown to be involved in the differentiation and/or proliferation and maintenance of testicular germ cells. Dhh expression is initiated in Sertoli cell precursors shortly after the activation of Sry (testicular determining gene) and persists in the testis into the adult. Males are viable but infertile, owing to a complete absence of mature sperm. Examination of the developing testis in different genetic backgrounds suggests that Dhh regulates both early and late stages of spermatogenesis. Bitgood et al. (1996) Curr Biol 6:298. In a preferred embodiment, the hedgehog antagonist can be used as a contraceptive. In similar fashion, hedgehog antagonists of the subject method are potentially useful for modulating normal ovarian function.

The subject method also has wide applicability to the treatment or prophylaxis of disorders afflicting epithelial tissue, as well as in cosmetic uses. In general, the method can be characterized as including a step of administering to an animal an amount of a hedgehog antagonist effective to alter the growth state of a treated epithelial tissue. The mode of administration and dosage regimens will vary depending on the epithelial tissue(s) that is to be treated. For example, topical formulations will be preferred where the treated tissue is epidermal tissue, such as dermal or mucosal tissues.

A method that "promotes the healing of a wound" results in the wound healing more quickly as a result of the treatment than a similar wound heals in the absence of the treatment. "Promotion of wound healing" can also mean that the method regulates the proliferation and/or growth of, inter alia, keratinocytes, or that the wound heals with less scarring, less wound contraction, less collagen deposition and more superficial surface area. In certain instances, "promotion of wound healing" can also mean that certain methods of wound healing have improved success rates, (e.g., the take rates of skin grafts) when used together with the method of the present invention.

Despite significant progress in reconstructive surgical techniques, scarring can be an important obstacle in regaining normal function and appearance of healed skin. This is particularly true when pathologic scarring such as keloids or hypertrophic scars of the hands or face causes functional disability or physical deformity. In the severest circumstances, such scarring may precipitate psychosocial distress and a life of economic deprivation. Wound repair includes the stages of hemostasis, inflammation, proliferation, and remodeling. The proliferative stage involves multiplication of fibroblasts and endothelial and epithelial cells. Through the use of the subject method, the rate of proliferation of epithelial cells in and proximal to the wound can be controlled in order to accelerate closure of the wound and/or minimize the formation of scar tissue.

The present treatment can also be effective as part of a therapeutic regimen for treating oral and paraoral ulcers, e.g., resulting from radiation and/or chemotherapy. Such ulcers commonly develop within days after chemotherapy or radiation therapy. These ulcers usually begin as small, painful irregularly shaped lesions usually covered by a delicate gray necrotic membrane and surrounded by inflammatory tissue. In many instances, lack of treatment results in proliferation of tissue around the periphery of the lesion on an inflammatory basis. For instance, the epithelium bordering the ulcer usually demonstrates proliferative activity, resulting in loss of continuity of surface epithelium. These lesions, because of their size and loss of epithelial integrity, dispose the body to potential secondary infection. Routine ingestion of food and water becomes a very painful event and, if the ulcers proliferate throughout the alimentary canal, diarrhea usually is evident with all its complicating factors. According to the present invention, a treatment for such ulcers that includes application of a hedgehog antagonist can reduce the abnormal proliferation and differentiation of the affected epithelium, helping to reduce the severity of subsequent inflammatory events.

The subject method and compositions can also be used to treat wounds resulting from dermatological diseases, such as lesions resulting from autoimmune disorders such as psoriasis. Atopic dermatitis refers to skin trauma resulting from allergies associated with an immune response caused by allergens such as pollens, foods, dander, insect venoms and plant toxins.

In other embodiments, antiproliferative preparations of hedgehog antagonists can be used to inhibit lens epithelial cell proliferation to prevent post-operative complications of extracapsular cataract extraction. Cataract is an intractable eye disease and various studies on a treatment of cataract have been made. But at present, the treatment of cataract is attained by surgical operations. Cataract surgery has been applied for a long time and various operative methods have been examined. Extracapsular lens extraction has become the method of choice for removing cataracts. The major medical advantages of this technique over intracapsular extraction are lower incidence of aphakic cystoid macular edema and retinal detachment. Extracapsular extraction is also required for implantation of posterior chamber-type intraocular lenses, which are now considered to be the lenses of choice in most cases.

However, a disadvantage of extracapsular cataract extraction is the high incidence of posterior lens capsule opacification, often called after-cataract, which can occur in up to 50% of cases within three years after surgery. After-cataract is caused by proliferation of equatorial and anterior capsule lens epithelial cells that remain after extracapsular lens extraction. These cells proliferate to cause Sommerling rings, and along with fibroblasts, which also deposit and occur on the posterior capsule, cause opacification of the posterior capsule, which interferes with vision. Prevention of after-cataract would be preferable to treatment. To inhibit secondary cataract formation, the subject method provides a means for inhibiting proliferation of the remaining lens epithelial cells. For example, such cells can be induced to remain quiescent by instilling a solution containing a hedgehog antagonist preparation into the anterior chamber of the eye after lens removal. Furthermore, the solution can be osmotically balanced to provide minimal effective dosage when instilled into the anterior chamber of the eye, thereby inhibiting subcapsular epithelial growth with some specificity.

The subject method can also be used in the treatment of comeopathies marked by corneal epithelial cell proliferation, as for example in ocular epithelial disorders such as epithelial downgrowth or squamous cell carcinomas of the ocular surface, or for preventing corneal epithelialization such as following a LASIK procedure.

Levine et al. (1997) J Neurosci 17:6277 show that hedgehog proteins can regulate mitogenesis and photoreceptor differentiation in the vertebrate retina, and Ihh is a candidate factor from the pigmented epithelium to promote retinal progenitor proliferation and photoreceptor differentiation. Likewise, Jensen et al. (1997) Development 124:363 demonstrated that treatment of cultures of perinatal mouse retinal cells with the amino-terminal fragment of Sonic hedgehog protein results in an increase in the proportion of cells that incorporate bromodeoxyuridine, in total cell numbers, and in rod photoreceptors, amacrine cells and Muller glial cells, suggesting that Sonic hedgehog promotes the proliferation of retinal precursor cells. Thus, the subject method can be used in the treatment of proliferative diseases of retinal cells and regulate photoreceptor differentiation.

Yet another aspect of the present invention relates to the use of the subject method to control hair growth. Hair is basically composed of keratin, a tough and insoluble protein; its chief strength lies in its disulfide bond of cystine. Each individual hair comprises a cylindrical shaft and a root, and is contained in a follicle, a flask-like depression in the skin. The bottom of the follicle contains a finger-like projection termed the papilla, which consists of connective tissue from which hair grows, and through which blood vessels supply the cells with nourishment. The shaft is the part that extends outwards from the skin surface, whilst the root has been described as the buried part of the hair. The base of the root expands into the hair bulb, which rests upon the papilla. Cells from which the hair is produced grow in the bulb of the follicle; they are extruded in the form of fibers as the cells proliferate in the follicle. Hair "growth" refers to the formation and elongation of the hair fiber by the dividing cells.

As is well known in the art, the common hair cycle is divided into three stages: anagen, catagen and telogen. During the active phase (anagen), the epidermal stem cells of the dermal papilla divide rapidly. Daughter cells move upward and differentiate to form the concentric layers of the hair itself. The transitional stage, catagen, is marked by the cessation of mitosis of the stem cells in the follicle. The resting stage is known as telogen, where the hair is retained within the scalp for several weeks before an emerging new hair developing below it dislodges the telogen-phase shaft from its follicle. From this model it has become clear that the larger the pool of dividing stem cells that differentiate into hair cells, the more hair growth occurs. Accordingly, methods for increasing or reducing hair growth can be carried out by potentiating or inhibiting, respectively, the proliferation of these stem cells. In certain embodiments, the subject method can be employed as a way of reducing the growth of human hair as opposed to its conventional removal by cutting, shaving, or depilation. For instance, the present method can be used in the treatment of trichosis characterized by abnormally rapid or dense growth of hair, e.g., hypertrichosis. In an exemplary embodiment, hedgehog antagonists can be used to manage hirsutism, a disorder marked by abnormal hairiness. The subject method can also provide a process for extending the duration of depilation.

Moreover, because a hedgehog antagonist will often be cytostatic to epithelial cells, rather than cytotoxic, such agents can be used to protect hair follicle cells from cytotoxic agents that require progression into S-phase of the cell cycle for efficacy, e.g., radiation-induced death. Treatment by the subject method can provide protection by causing the hair follicle cells to become quiescent, e.g., by inhibiting the cells from entering S phase, and thereby preventing the follicle cells from undergoing mitotic catastrophe or programmed cell death. For instance, hedgehog antagonists can be used for patients undergoing chemo- or radiation-therapies that ordinarily result in hair loss. By inhibiting cell-cycle progression during such therapies, the subject treatment can protect hair follicle cells from death, which might otherwise result from activation of cell death programs. After the therapy has concluded, the instant method can also be removed with concomitant relief of the inhibition of follicle cell proliferation.

The subject method can also be used in the treatment of folliculitis, such as folliculitis decalvans, folliculitis ulerythematosa reticulata or keloid folliculitis. For example, a cosmetic preparation of a hedgehog antagonist can be applied topically in the treatment of pseudofolliculitis, a chronic disorder occurring most often in the submandibular region of the neck and associated with shaving, the characteristic lesions of which are erythematous papules and pustules containing buried hairs.

In another aspect of the invention, the subject method can be used to induce differentiation and/or inhibit proliferation of epithelial derived tissue. Such forms of these molecules can provide a basis for differentiation therapy for the treatment of hyperplastic and/or neoplastic conditions involving epithelial tissue. For example, such preparations can be used for the treatment of cutaneous diseases in which there is abnormal proliferation or growth of cells of the skin.

For instance, the pharmaceutical preparations of the invention are intended for the treatment of hyperplastic epidermal conditions, such as keratosis, as well as for the treatment of neoplastic epidermal conditions such as those characterized by a high proliferation rate for various skin cancers, as for example squamous cell carcinoma. The subject method can also be used in the treatment of autoimmune diseases affecting the skin, in particular, of dermatological diseases involving morbid proliferation and/or keratinization of the epidermis, as for example, caused by psoriasis or atopic dermatosis.

Many common diseases of the skin, such as psoriasis, squamous cell carcinoma, keratoacanthoma and actinic keratosis are characterized by localized abnormal proliferation and growth. For example, in psoriasis, which is characterized by scaly, red, elevated plaques on the skin, the keratinocytes are known to proliferate much more rapidly than normal and to differentiate less completely.

In one embodiment, the preparations of the present invention are suitable for the treatment of dermatological ailments linked to keratinization disorders causing abnormal proliferation of skin cells, which disorders may be marked by either inflammatory or non-inflammatory components. To illustrate, therapeutic preparations of a hedgehog antagonist, e.g., which promotes quiescence or differentiation can be used to treat varying forms of psoriasis, be they cutaneous, mucosal or ungual. Psoriasis, as described above, is typically characterized by epidermal keratinocytes that display marked proliferative activation and differentiation along a "regenerative" pathway. Treatment with an antiproliferative embodiment of the subject method can be used to reverse the pathological epidermal activation and can provide a basis for sustained remission of the disease.

A variety of other keratotic lesions are also candidates for treatment with the subject method. Actinic keratoses, for example, are superficial inflammatory premalignant tumors arising on sun-exposed and irradiated skin. The lesions are erythematous to brown with variable scaling. Current therapies include excisional and cryosurgery. These treatments are painful, however, and often produce cosmetically unacceptable scarring. Accordingly, treatment of keratosis, such as actinic keratosis, can include application, preferably topical, of a hedgehog antagonist composition in amounts sufficient to inhibit hyperproliferation of epidermal/epidermoid cells of the lesion.

Acne represents yet another dermatologic ailment which may be treated by the subject method. Acne vulgaris, for instance, is a multifactor disease most commonly occurring in teenagers and young adults, and is characterized by the appearance of inflammatory and noninflammatory lesions on the face and upper trunk. The basic defect which gives rise to acne vulgaris is hypercomification of the duct of a hyperactive sebaceous gland. Hypercomification blocks the normal mobility of skin and follicle microorganisms, and in so doing, stimulates the release of lipases by *Propinobacterium acnes* and *Staphylococcus epidennidis* bacteria and *Pitrosporum ovale*, a yeast. Treatment with an antiproliferative hedgehog antagonist, particularly topical preparations, may be useful for preventing the transitional features of the ducts, e.g., hypercomification, which lead to lesion formation. The subject treatment may further include, for example, antibiotics, retinoids and antiandrogens.

The present invention also provides a method for treating various forms of dermatitis. Dermatitis is a descriptive term referring to poorly demarcated lesions that are either pruritic, erythematous, scaly, blistered, weeping, fissured or crusted. These lesions arise from any of a wide variety of causes. The most common types of dermatitis are atopic, contact and diaper dermatitis. For instance, seborrheic dermatitis is a chronic, usually pruritic, dermatitis with erythema, dry, moist, or greasy scaling, and yellow-crusted patches on various areas, especially the scalp, with exfoliation of an excessive amount of dry scales. The subject method can also be used in the treatment of stasis dermatitis, an often chronic, usually eczematous dermatitis. Actinic dermatitis is dermatitis that due to exposure to actinic radiation such as that from the sun, ultraviolet waves, or x- or gamma-radiation. According to the present invention, the subject method can be used in the treatment and/or prevention of certain symptoms of dermatitis caused by unwanted proliferation of epithelial cells. Such therapies for these various forms of dermatitis can also include topical and systemic corticosteroids, antipruritics, and antibiotics. Ailments that may be treated by the subject method are disorders specific to non-humans, such as mange.

In still another embodiment, the subject method can be used in the treatment of human cancers, such as tumors of epithelial tissues such as the skin. For example, hedgehog antagonists can be employed in the subject method as part of a treatment for human carcinomas, adenocarcinomas, sarcomas and the like. Exemplary forms of cancer which may be treated by the subject methods include, but are not limited to, prostate cancer, bladder cancer, lung cancer (including either small cell or non-small cell cancer), colon cancer, kidney cancer, liver cancer, breast cancer, cervical cancer, endometrial or other uterine cancer, ovarian cancer, testicular cancer, cancer of the penis, cancer of the vagina, cancer of the urethra, gall bladder cancer, esophageal cancer, or pancreatic cancer. Additional exemplary forms of cancer which may be treated by the subject methods include, but are not limited to, cancer of skeletal or smooth muscle, stomach cancer, cancer of the small intestine, cancer of the salivary gland, anal cancer, rectal cancer, thyroid cancer, parathyroid cancer, pituitary cancer, and nasopharyngeal cancer. Further exemplary forms of cancer, which can be treated with the hedgehog antagonists of the present invention include, cancers comprising hedgehog-expressing cells. Still further exemplary forms of cancer, which can be treated with the hedgehog antagonists of the present invention include, cancers comprising gli-expressing cells. In one embodiment, the cancer is not characterized by a mutation in patched-1.

In another aspect, the present invention provides pharmaceutical preparations comprising hedgehog antagonists. The hedgehog antagonists for use in the subject method may be conveniently formulated for administration with a biologically acceptable medium, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the hedgehog antagonist, its use in the pharmaceutical preparation of the invention is contemplated. Suitable vehicles and their formulation inclusive of other proteins are described, for example, in the book Remington's Pharmaceutical Sciences (Remington's Pharmaceutical Sciences. Mack Publishing Company, Easton, Pa., USA 1985). These vehicles include injectable "deposit formulations". Pharmaceutical formulations of the present invention can also include veterinary compositions, e.g., pharmaceutical preparations of the hedgehog antagonists suitable for veterinary uses, e.g., for the treatment of livestock or domestic animals, e.g., dogs. Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a hedgehog antagonist at a particular target site. The preparations of the present invention may be given orally, parenterally, topically, or rectally. They are, of course, given by forms suitable for each administration route. For example, they are administered in tablets or capsule form, by injection, inhalation, eye lotion, ointment, suppository, controlled release patch, etc. administration by injection, infusion or inhalation; topical by lotion or ointment; and rectal by suppositories. Oral and topical administrations are preferred. The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These Hedgehog, BMP and TDFRP compounds (collectively referred to as "compounds") may be administered to humans and other animals for therapy by any suitable route of administration, including orally, nasally, as by, for example, a spray, rectally, intravaginally, parenterally, intracistemally and topically, as by powders, ointments or drops, including buccally and sublingually. Regardless of the route of administration selected, the compounds of the present invention, which may be used in a suitable hydrated form, and/or the pharmaceutical compositions of the present invention, are formulated into pharmaceutically acceptable dosage forms such as described below or by other conventional methods known to those of skill in the art. Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient. The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular hedgehog antagonist employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required to achieve the desired therapeutic effect and gradually increase the dosage until the desired effect is achieved. In general, a suitable daily dose of a compound of the invention will be that amount of the compound that is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day. If desired, the effective daily dose of the active compound may be administered as two, three, four, five, six or more sub-doses administered separately at appropriate intervals throughout the day, optionally, in unit dosage forms. The term "treatment" is intended to encompass also prophylaxis, therapy and cure. The patient receiving this treatment is any animal in need, including primates, in particular humans, and other mammals such as equines, cattle, swine and sheep; and poultry and pets in general. The compound of the invention can be administered as such or in admixtures with pharmaceutically acceptable and/or sterile carriers and can also be administered in conjunction with other antimicrobial agents such as penicillins, cephalosporins, aminoglycosides and glycopeptides. Conjunctive therapy thus includes sequential, simultaneous and separate administration of the active compound in a way that the therapeutic effects of the first administered one is not entirely disappeared when the subsequent is administered.

Example 10

Treatment of Rheumatoid Arthritis and Osteoarthritis

Osteoarthritis is a degenerative joint disease, which commonly affects both axial and peripheral diarthrodial joints in humans. The TDFRP compounds disclosed herein are useful in the prevention and treatment of osteoarthritis. A preferred TDFRP is CYFDDSSNVLCKKYRS, SEQ ID NO:45.

Joints are the intersections of two bones. The ends of the bones are covered with cartilage. Cartilage also acts as a cushioning device to absorb force applied to the joints. Synovial fluid carries nutrients to the cartilage, preventing it from becoming dry and brittle and keeping its surface lubricated so the joints can work smoothly. A structure called the joint capsule keeps the synovial fluid within the joint. The capsule encloses the joint and protects it. Osteoarthritis is the deterioration of cartilage in the joints, resulting in pain and soreness. It produces little inflammation and the pain and soreness is caused by deterioration of cartilage in the joints. Osteoarthritis is the most common type of arthritis, a disease of cartilage, resulting from non-inflammatory deterioration of the joint. It occurs with the normal process of aging. Another cause is trauma, such as an injury to a joint. A patient who fractures an anklebone is more likely to develop osteoarthritis in the ankle later. Overuse may also cause cartilage to break down.

Osteoarthritis is difficult to treat. There is no present cure save that described herein, and treatment focuses on relieving pain and preventing the affected joint from becoming deformed. Nonsteroidal anti-inflammatory drugs (NSAIDs) are used to relieve pain. As indicated by U.S. Pat. No. 4,997,850 and U.S. Pat. No. 4,944,949 many such nonsteroidal anti-inflammatory drugs are known and are frequently effective in reducing the symptoms of osteoarthritis. If these measures are unsuccessful, physicians may prescribe steroid injections to reduce swelling. Physical therapy, orthotic shoe inserts such as described in U.S. Pat. No. 5,727,335 and custom-fitted braces also may also be recommended. If the patient develops hallux rigidus, a condition in which the big toe (hallux) becomes painfully stiff or rigid, the podiatrist may recommend a larger, stiffer shoe with an inflexible sole. This limits the toe's movement and reduces weight bearing, particularly in walking, and prevents the surfaces of the toe joint from grinding painfully against each other. In severe cases, joint replacement may be necessary. This is especially true in the hips and knees. Joints in the lower leg are smaller, more complex, and difficult to replace. If a joint is extremely painful and cannot be replaced, it may be fused. This procedure stops the pain, but results in the permanent loss of joint function, making walking and bending difficult. A method for the treatment of osteoarthritis, which comprises administering a therapeutically effective amount of cetyl myristoleate, is known from U.S. Pat. No. 5,569,676.

Rheumatoid arthritis (RA) is a common autoimmune disease characterized by joint swelling, deformation and, ultimately, destruction, culminating in severe physical disability. De Graaf et al., in The Epidemiolog of Chronic Rheumatism, Dellgren and Ball, eds. (Blackwell, Oxford, 1963), pp. 446-56; Meenam et al., Arthritis Rheum., 24:544-50 (1981); Gabriel et al., J. Rheumatol, 26:1269-74 (1999); James, Clin Exp. Rheumatol, 17:392-93 (1999). RA is a progressive condition with well-recognized symptoms including symmetrical peripheral joint swelling and synovial inflammation while sparing the axial skeleton; the presence of rheumatoid factor (RF) auto antibodies; increased concentrations of interleukin-6 (IL-6), interleukin-1beta (IL-1beta), and granulocyte/macrophage colony-stimulating factor (GM-CSF) in serum and synovial fluid; low concentrations of interleukin-ra (IL-ra); and pregnancy-induced disease remission followed by severe postpartum flares, that is, while women with RA commonly undergo remission during pregnancy, the disease returns and may be even more severe and show a new onset or more accelerated course after delivery. See, Turgen, in Immunology and Serology in Laboratory Medicine. 2nd edition, Shanahan ed. (Mosby Year Book, St. Louis, 1996), pp. 387-98; Hirano et al., Eur. J. Immunol, 18:1797-1801 (1988); Wilder et al., Ann N.Y. Acad. Sci., 876:14-31 (1999); Iijima et al., J. Rheumatol, 26:755-56 (1999); Ostensen, Ann N.Y. Acad. Sci., 876:13143 (1999). In medical research directed to understanding, diagnosing and treating RA, several animal models of the disease have been described, but no spontaneous animal model that closely mimics all the features of the human disease has been discovered (See, for example, Hang et al., 1982. J. Exp. Med., 155:1690-1701; and Kouskoff et al., 1996. Cell, 87:811-822). Kouskoff et al. report a RA mouse model that exhibits aggressive arthritis, produced by mating a T cell receptor (TCR) transgenic mouse strain with a NOD strain. This RA mouse model is strictly dependent on the presence of the KRN transgene and is characterized by several inherent symptomological features of RA that distinguish it from human RA (hRA), however, including: 100% penetrance, early (i.e., 25-35 days) onset of disease, attack of the distal interphalangeal joints, inflammation of the spine, large excess of myeloid cells over T lymphocytes and plasma cells in the synovial membrane, a total absence of rheumatoid factor (RF) auto antibodies, and a coating of IgG deposits on internal organs. These features result in a more aggressive RA than the RA typically found in humans. Human RA has preferential disease expression in middle-aged females, peripheral disease sparing of the DIP joints, rheumatoid factor auto antibodies, similar peripheral and joint cytokine derangements, etc. The mechanism of development of arthritis-like disease in NOD/TCR mice differs dramatically from that of natural RA expression in humans, limiting the utility of this RA mouse as a model for hRA. It has now been surprisingly discovered that a particular breed of mouse commonly used in diabetes research, i.e., the nonobese diabetic or "NOD" mouse, can be used to produce offspring that exhibit a physical symptomology closely matching the symptomology of hRA, including: incomplete penetrance with increased incidence in females comparable to that of hRA, disease onset later in life (5-8 months) with exacerbation or early onset due to pregnancy comparable to that of hRA, no inflammation of the spine comparable to that of hRA, and histological and serological profiles comparable to that of hRA. A mouse model for rheumatoid arthritis is described in United States Patent Application 20040031066.

To treat osteoarthritis or rheumatoid arthritis, a patient, preferably a human subject is given the TDFRP compounds as described above. Assays for determining the integrity of connective tissue in the joint are well known in the art, and the physician monitors the patient for a change in the competency of the joint tissue in response to the dosing regimens discussed. A halt in the progression of degeneration of the joint, or an increase in the amount and integrity of the joint tissues indicate a therapeutic effect is being obtained. Secondary considerations including diminishment of pain, and an increase in flexibility of the joints.

Example 11

The following TDFRP compounds represent non-naturally occurring modifications or analogs of the native BMP-7 active fragment, for example, having non-peptide bonds and non-natural amino acids. These TDFRP compounds have similar biological activity as compared to the native BMP-7 active fragment as measured by the assays described herein. These TDFRP compounds are useful in treating the disorders described, particularly those treatable by regeneration of kidney, connective, and cardiac tissues, when administered at the doses and through the administration methods described.

```
                     115                                                          130
Native Sequence: NH2-Leu-Tyr-Phe-Asp-Asp-Ser-Ser-Asn-Val-Ile-Leu-Lys-Lys-Tyr-Arg-Asn-OH
```

General Structure:

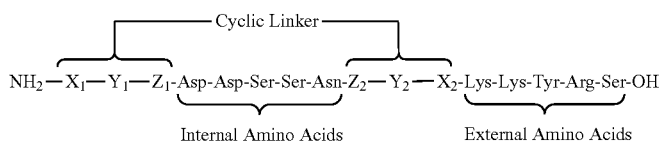

```
Cyclic Linker X, Y, Z:
Cys, Pen, Asp, Glu, Dap, Dab, Orn, Lys, Ser, Thr,

Tyr

Non Linker X, Y, Z:
Gly, Ala, Abu, Leu, Ile, Val, Pro, Phe, Tyr,

His or None

Internal Amino Acids:
Asp, Glu, Asn, Gln, Ser, Thr, Tyr, His

External Amino Acids:
Lys, Arg, Tyr, Phe, His, Asn, Gln, Ser, Thr
```

The above structures disclose SEQ ID NOS 563-565, respectively, in order of appearance.

```
                     115                                                          130
Native Sequence: NH2-Leu-Tyr-Phe-Asp-Asp-Ser-Ser-Asn-Val-Ile-Leu-Lys-Lys-Tyr-Arg-Asn-OH
```

1. Disulfide Analogs:

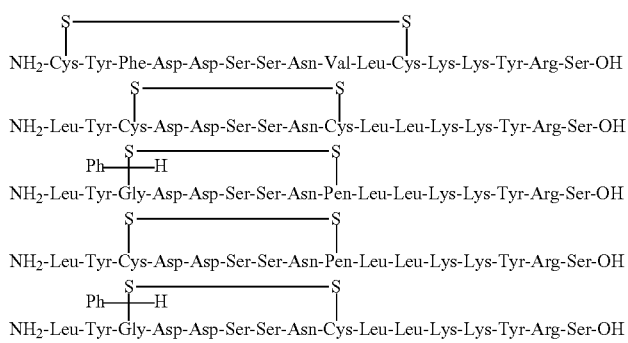

The above structures disclose SEQ ID NOS 563, 45 and 566-569, respectively, in order of appearance.

1. Disulfide Analogs (Cont.):

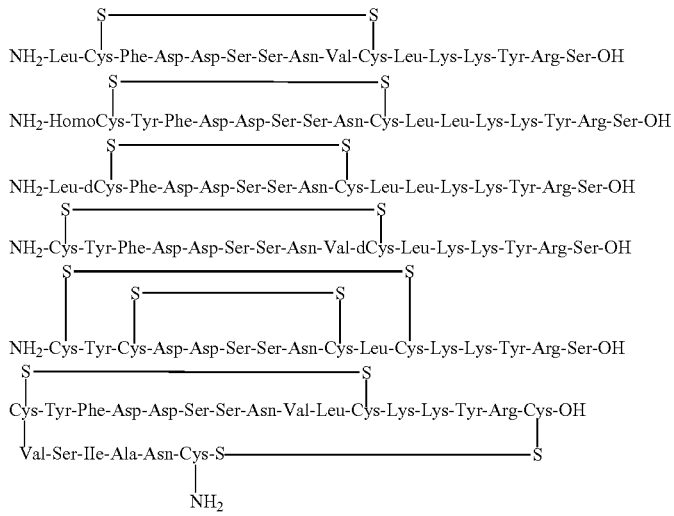

The above structures disclose SEQ ID NOS 570-573, respectively, in order of appearance.

1. Disulfide Analogs (Cont.):

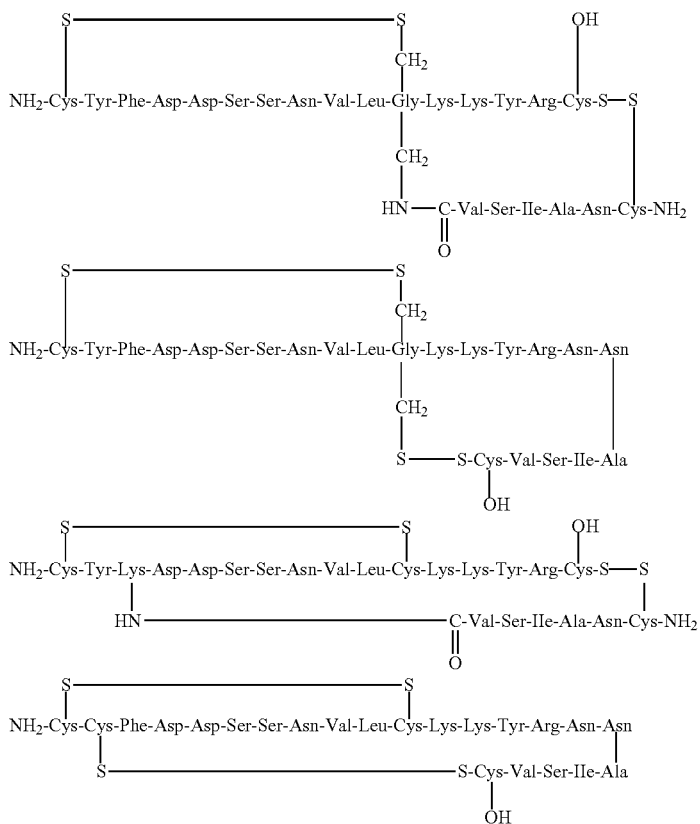

The above structures disclose SEQ ID NOS 574-575, respectively, in order of appearance.

```
                   115                                           130
Native Sequence: NH2-Leu-Tyr-Phe-Asp-Asp-Ser-Ser-Asn-Val-Ile-Leu-Lys-Lys-Tyr-Arg-Asn-OH
```

2. Lactam Analogs:
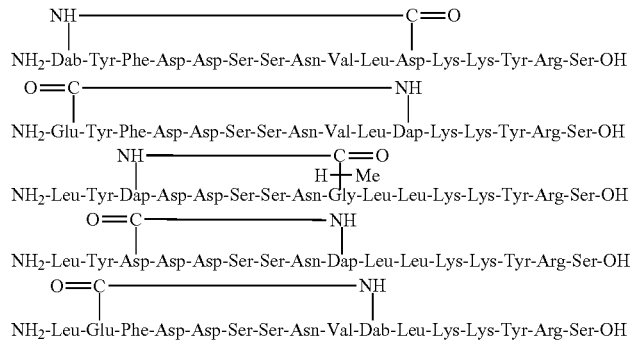
The above structures disclose SEQ ID NOS 563 and 576-580, respectively, in order of appearance.
2. Lactam Analogs (Cont.):
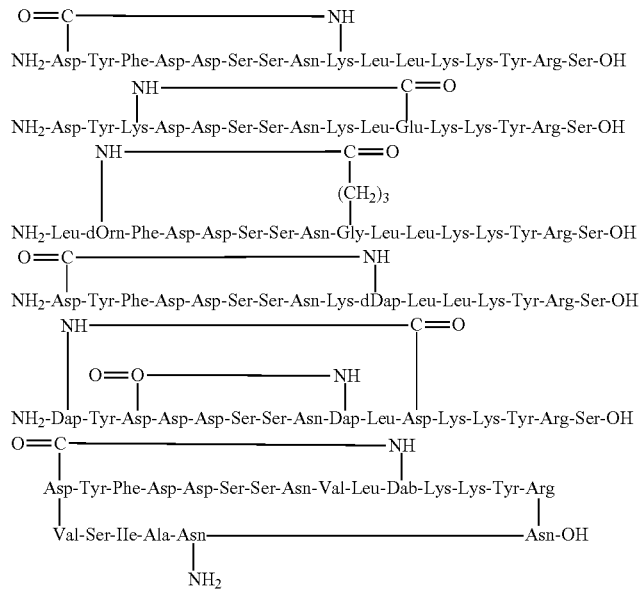
The above structures disclose SEQ ID NOS 581-584, respectively, in order of appearance.
2. Lactam Analogs (Cont.):
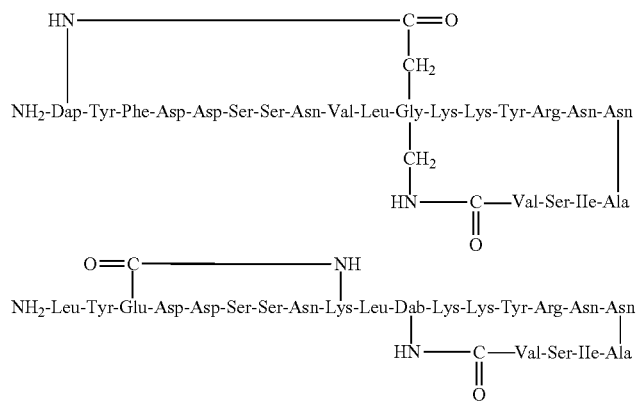

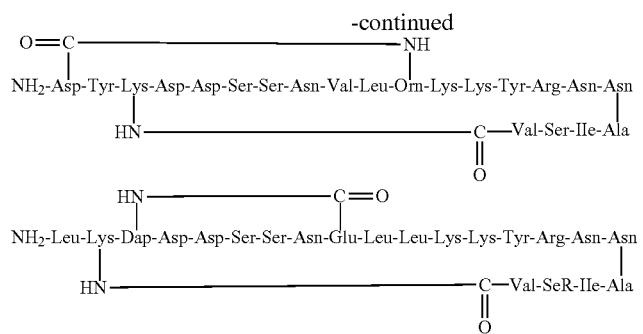
The above structures disclose SEQ ID NOS 585-588, respectively, in order of appearance.
```
                      115                                              130
Native Sequence: NH₂-Leu-Tyr-Phe-Asp-Asp-Ser-Ser-Asn-Val-Ile-Leu-Lys-Lys-Tyr-Arg-Asn-OH
```
3. Cyclic Carboxylate Analogs:
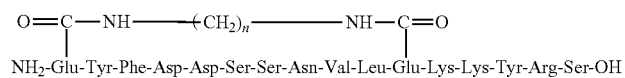
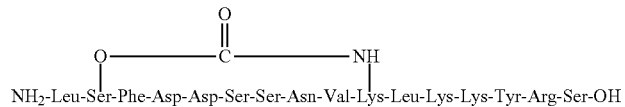
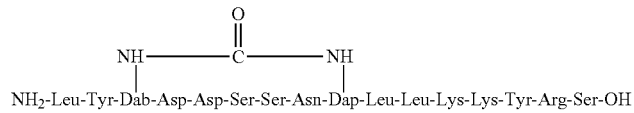
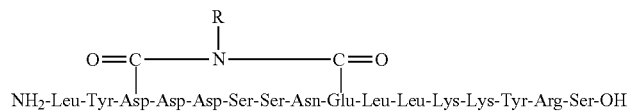
The above structures disclose SEQ ID NOS 563 and 589-593, respectively, in order of appearance.
3. Cyclic Carboxylate Analogs (Cont.):
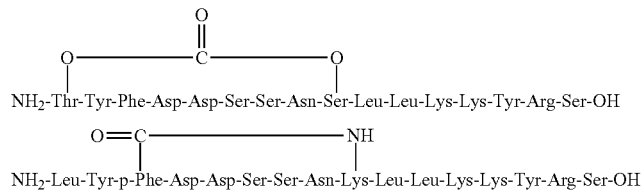

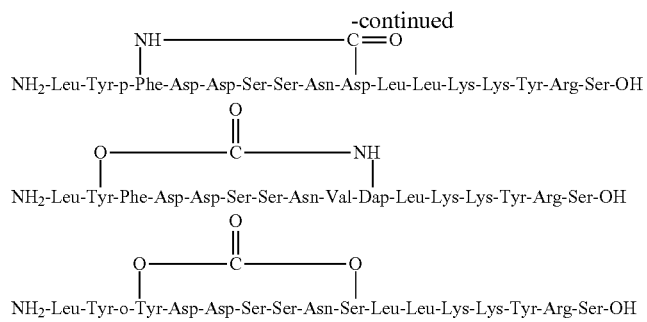
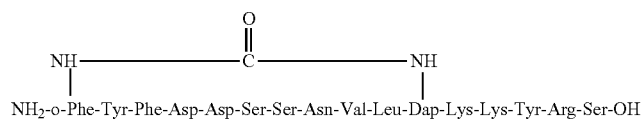
The above structures disclose SEQ ID NOS 594-599, respectively, in order of appearance.
```
                         115                                          130
Native Sequence: NH2-Leu-Tyr-Phe-Asp-Asp-Ser-Ser-Asn-Val-Ile-Leu-Lys-Lys-Tyr-Arg-Asn-OH
```
4. Cyclic Heteroatom Analogs:
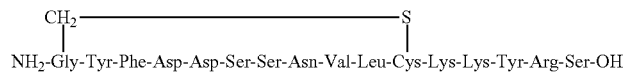
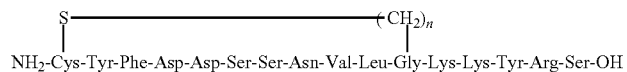
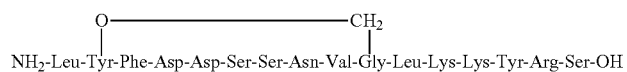
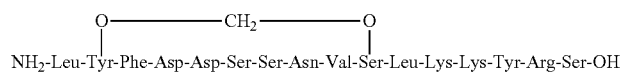
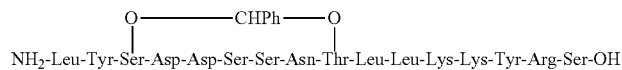
The above structures disclose SEQ ID NOS 563 and 600-604, respectively, in order of appearance.
4. Cyclic Heteroatom Analogs (Cont.):
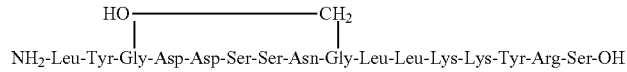
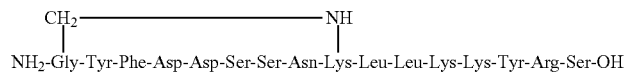

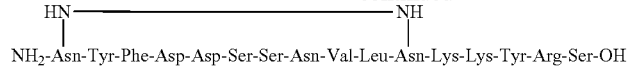
NH₂-Asn-Tyr-Phe-Asp-Asp-Ser-Ser-Asn-Val-Leu-Asn-Lys-Lys-Tyr-Arg-Ser-OH

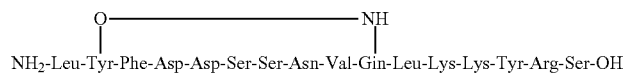
NH₂-Leu-Tyr-Phe-Asp-Asp-Ser-Ser-Asn-Val-Gln-Leu-Lys-Lys-Tyr-Arg-Ser-OH

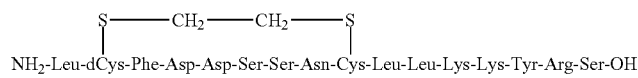
NH₂-Leu-dCys-Phe-Asp-Asp-Ser-Ser-Asn-Cys-Leu-Leu-Lys-Lys-Tyr-Arg-Ser-OH

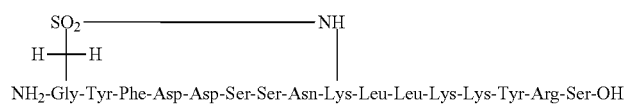
NH₂-Gly-Tyr-Phe-Asp-Asp-Ser-Ser-Asn-Lys-Leu-Leu-Lys-Lys-Tyr-Arg-Ser-OH The above structures disclose SEQ ID NOS 605-609, respectively, in order of appearance.

```
                      115                                                    130
Native Sequence: NH₂-Leu-Tyr-Phe-Asp-Asp-Ser-Ser-Asn-Val-Ile-Leu-Lys-Lys-Tyr-Arg-Asn-OH
```

5. Side-Chain Backbone Analogs:

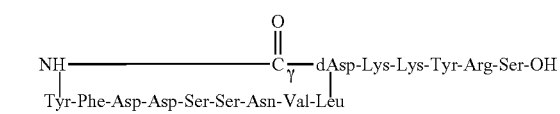

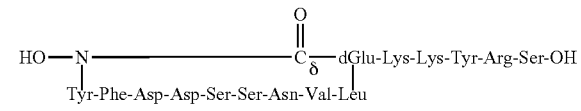

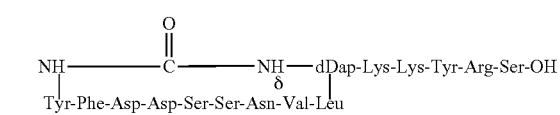

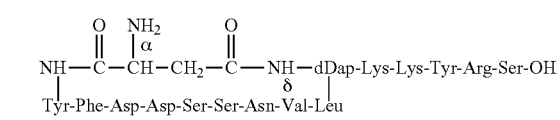

The above structures disclose SEQ ID NO: 563.
5. Side-Chain Backbone Analogs (Cont.):

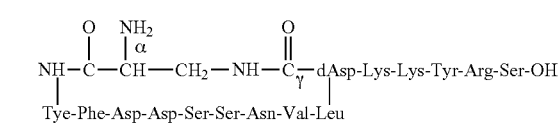

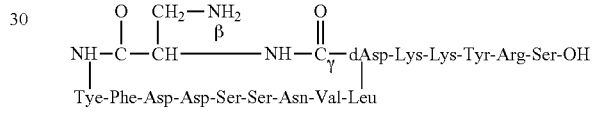

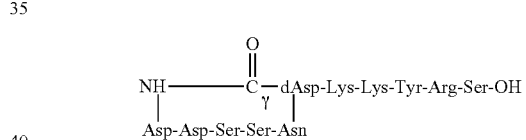

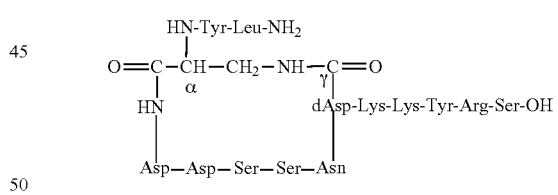

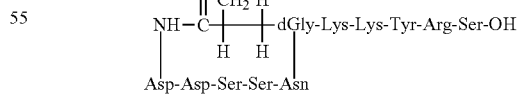

```
                      115                                                    130
Native Sequence: NH₂-Leu-Tyr-Phe-Asp-Asp-Ser-Ser-Asn-Val-Ile-Leu-Lys-Lys-Tyr-Arg-Asn-OH
```

6. Dipeptide Analogs:
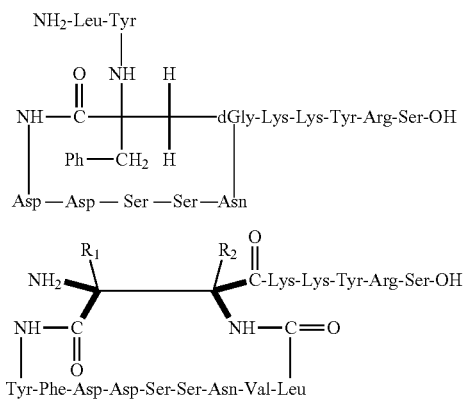
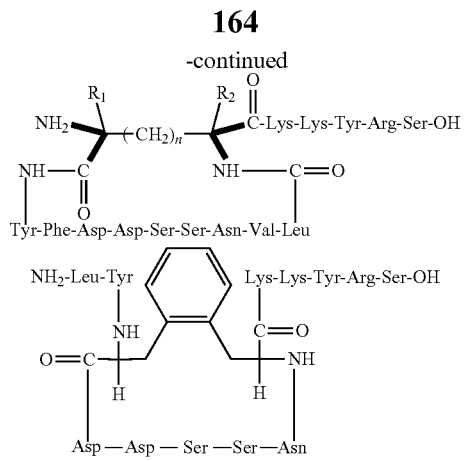
The above structures disclose SEQ ID NOS 563, 225, 610, 225, 611, 225 and 322, respectively, in order of appearance.
6. Dipeptide Analogs (Cont.):
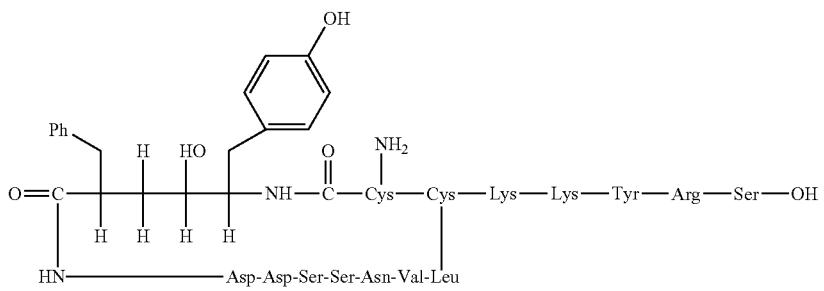
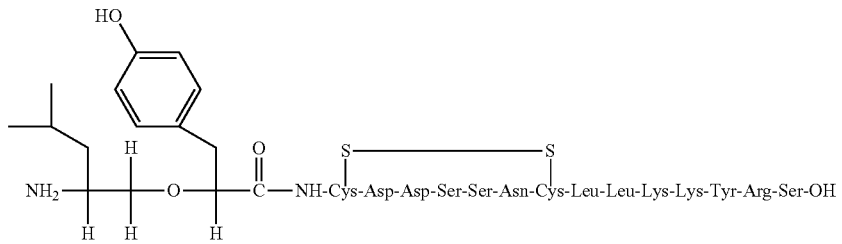
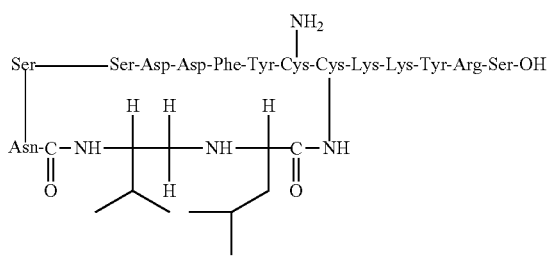
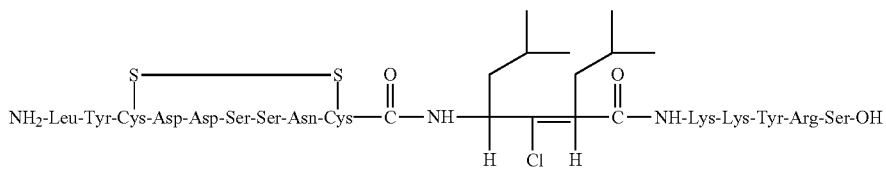

The above structures disclose SEQ ID NOS 612-614 and 225, respectively, in order of appearance.

The compounds of the present invention can be synthesized using standard synthetic methods known to those skilled in the art. Preferred methods include but are not limited to those methods described below.

Generally, peptides are elongated by deprotecting the alpha-amine of the C-terminal residue and coupling the next suitably protected amino acid through a peptide linkage using the methods described. This deprotection and coupling procedure is repeated until the desired sequence is obtained. This coupling can be performed with the constituent amino acids in a stepwise fashion, or condensation of fragments (two to several amino acids), or combination of both processes, or by solid phase peptide synthesis according to the method originally described by Merrifield, J. Am. Chem. Soc., 85, 2149-2154 (1963), the disclosure of which is hereby incorporated by reference.

The compounds of the invention may also be synthesized using automated peptide synthesizing equipment. In addition to the foregoing, procedures for peptide synthesis are described in Stewart and Young, "Solid Phase Peptide Synthesis", 2nd ed, Pierce Chemical Co., Rockford, Ill. (1984); Gross, Meienhofer, Udenfriend, Eds., "The Peptides: Analysis, Synthesis, Biology, Vol. 1, 2, 3, 5, and 9, Academic Press, New York, (1980-1987); Chan and White, "Fmoc Solid Phase Peptide Synthesis", Oxford University Press, Oxford (2000); Bodanszky, "Peptide Chemistry: A Practical Textbook", Springer-Verlag, New York (1988); and Bodanszky et al. "The Practice of Peptide Synthesis" Springer-Verlag, New York (1984), the disclosures of which are hereby incorporated by reference.

The coupling between two amino acid derivatives, an amino acid and a peptide, two peptide fragments, or the cyclization of a peptide can be carried out using standard coupling procedures such as the azide method, mixed carbonic acid anhydride (isobutyl chloroformate) method, carbodiimide(dicyclohexylcarbodiimide, diisopropylcarbodiimide, or water-soluble carbodiimides) method, active ester (p-nitrophenyl ester, N-hydroxysuccinic imido ester) method, Woodward reagent K method, carbonyldiimidazole method, phosphorus reagents such as BOP-Cl, or oxidation-reduction method. Some of these methods (especially the carbodiimide) can be enhanced by the addition of 1-hydroxybenzotriazole. These coupling reactions may be performed in either solution (liquid phase) or solid phase.

The functional groups of the constituent amino acids must be protected during the coupling reactions to avoid undesired bonds being formed. The protecting groups that can be used are listed in Greene, "Protective Groups in Organic Synthesis" John Wiley & Sons, New York (1981) and "The Peptides: Analysis, Synthesis, Biology, Vol. 3, Academic Press, New York (1981), the disclosure of which is hereby incorporated by reference.

The alpha-carboxyl group of the C-terminal residue is usually protected by an ester that can be cleaved to give the carboxylic acid. These protecting groups include: 1) alkyl esters such as methyl and t-butyl, 2) aryl esters such as benzyl and substituted benzyl, or 3) esters which can be cleaved by mild base treatment or mild reductive means such as trichloroethyl and phenacyl esters. In the solid phase case, the C-terminal amino acid is attached to an insoluble carrier (usually polystyrene). These insoluble carriers contain a group, which will react with the carboxyl group to form a bond, which is stable to the elongation conditions but readily cleaved later. Examples of which are: oxime resin (DeGrado and Kaiser (1980) J. Org. Chem. 45, 1295-1300) chloro or bromomethyl resin, hydroxymethyl resin, and aminomethyl resin. Many of these resins are commercially available with the desired C-terminal amino acid already incorporated.

The alpha-amino group of each amino acid must be protected. Any protecting group known in the art can be used. Examples of these are: 1) acyl types such as formyl, trifluoroacetyl, phthalyl, and p-toluenesulfonyl; 2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl. The preferred alpha-amino protecting group is either Boc or Fmoc. Many amino acid derivatives suitably protected for peptide synthesis are commercially available.

The alpha-amino protecting group is cleaved prior to the coupling of the next amino acid. When the Boc group is used, the methods of choice are trifluoroacetic acid, neat or in dichloromethane, or HCl in dioxane. The resulting ammonium salt is then neutralized either prior to the coupling or in situ with basic solutions such as aqueous buffers, or tertiary amines in dichloromethane or dimethylformamide. When the Fmoc group is used, the reagents of choice are piperidine or substituted piperidines in dimethylformamide, but any secondary amine or aqueous basic solutions can be used. The deprotection is carried out at a temperature between 0 degrees C. and room temperature.

Any of the amino acids bearing side chain functionalities must be protected during the preparation of the peptide using any of the above-identified groups. Those skilled in the art will appreciate that the selection and use of appropriate protecting groups for these side chain functionalities will depend upon the amino acid and presence of other protecting groups in the peptide. The selection of such a protecting group is important in that it must not be removed during the deprotection and coupling of the alpha-amino group. For example, when Boc is chosen for the alpha-amine protection the following protecting groups are acceptable: p-toluenesulfonyl (tosyl) moieties and nitro for arginine; benzyloxycarbonyl, substituted benzyloxycarbonyls, or tosyl for lysine; benzyl or alkyl esters such as cyclopentyl for glutamic and aspartic acids; benzyl ethers for serine and threonine; benzyl ethers, substituted benzyl ethers or 2-bromobenzyloxycarbonyl for tyrosine; p-methylbenzyl, p-methoxybenzyl, acetamidomethyl, benzyl, or t-butylsulfonyl for cysteine; and the indole of tryptophan can either be left unprotected or protected with a formyl group. When Fmoc is chosen for the alpha-amine protection usually tert-butyl based protecting groups is acceptable. For instance, Boc can be used for lysine, tert-butyl ether for serine, threonine and tyrosine, and tert-butyl ester for glutamic and aspartic acids.

Once the elongation and cyclization of the peptide is completed all of the protecting groups are removed. For the liquid phase synthesis the protecting groups are removed in whatever manner as dictated by the choice of protecting groups. These procedures are well known to those skilled in the art. When a solid phase synthesis is used, the peptide should be removed from the resin without simultaneously removing protecting groups from functional groups that might interfere with the cyclization process. Thus, if the peptide is to be cyclized in solution, the cleavage conditions need to be chosen such that a free alpha-carboxylate and a free alpha-amino group are generated without simultaneously removing other protecting groups. Alternatively, the peptide may be removed from the resin by hydrazinolysis, and then coupled by the azide method. Another very convenient method involves the synthesis of peptides on an oxime resin, followed by intramolecular nucleophilic displacement from the resin, which generates a cyclic peptide (Osapay, Profit, and Taylor (1990) Tetrahedron Letters 43, 6121-6124). When the oxime resin is employed, the Boc protection scheme is generally chosen. Then, the preferred method for removing side chain protecting groups generally involves treatment with anhydrous HF containing additives such as dimethyl sulfide, anisole, thioanisole, or p-cresol at 0 degrees C. The cleavage of the peptide can also be accomplished by other acid reagents such as trifluoromethanesulfonic acid/trifluoroacetic acid mixtures.

Unusual amino acids used in this invention can be synthesized by standard methods familiar to those skilled in the art ("The Peptides: Analysis, Synthesis, Biology, Vol. 5, pp. 342-449, Academic Press, New York (1981)). N-Alkyl amino acids can be prepared using procedures described in previously (Cheung et al., (1977) Can. J. Chem. 55, 906; Freidinger et al., (1982) J. Org. Chem. 48, 77 (1982)), which are incorporated here by reference.

Additional unusual amino acids can be prepared using procedures described previously (Sandberg et al., (1998) J. Med. Chem. 41: 2481; Kawahata et al., (1999) J. Org. Chem. 64: 4362; Weerapana and Imperiali, (2003) Org. Biomol. Chem. 1: 93; Kim and Ahn, (1997) Bull. Korean Chem. Soc. 18: 461; Ghosh et al., (1999) Chem. Commun. 1025; Scott et al., (2002) J. Org. Chem. 67: 2960; Han et al., (2002) J. Org. Chem. 67: 5085; Hedenstrom et al., (2002) J. Med. Chem. 45: 2501; Yuan et al., (2002) J. Med. Chem. 45: 2512; Mustapa et al., (2003) J. Org. Chem. 68: 8193; Kawabata et al., (2003) J. Am. Chem. Soc. 125: 13012; Ghosh et al., (2001) J. Med. Chem. 44: 2865; Scarborough and Gretler, (2000) J. Med. Chem. 43: 1). Commercial sources of unusual amino acids (catalog listings) are available from the following representative large companies: BACHEM Bioscience Inc., King of Prussia, Pa.; Multiple Peptide Systems, San Diego, Calif.; NovaBiochem, San Diego, Calif., Sigma-Aldrich, St. Louis, Mo. plus a number of specialized manufacturers.

REFERENCE LIST

Each reference listed below and those indicated throughout this disclosure are hereby incorporated herein by reference in their entireties.

1. Agrotis et al., Biochem. Biophys. Res. Commun 1996 Feb. 15; 219(2):613-8.
2. Aoki et al., J Cell Sci 2001 April; 114(Pt. 8):1483-9.
3. Chien et al., J Periodontal Res. 1999 August; 34(6):301-9.
4. De Winter et al., Exp Cell Res. 1996 May 1; 224(2):323-34.
5. Dewulf et al., Endocrinology. 1995 June; 136(6):2652-63.
7. Goggins et al., Cancer Res. 1998 Dec. 1; 58(23):5529-32.
8. Haaijman et al., Growth Factors. 2000; 17(3):177-92.
9. Kawai et al., Biochem Biophys Res Commun. 2000 May 19; 271(3):682-7.
10. ten Dijke et al., Science. 1994 Apr. 1; 264(5155):101-4.
11. ten Dijke et al., J Biol Chem 1994 Jun. 24; 269(25):16985-8.
12. ten Dijke et al., Oncogene 1993 October; 8(10):2879-87.
13. Valcourt et al., J Biol Chem 2002 Sep. 13; 277(37):33545-58.
14. Abdalla et al., Eur J Hum Genet. 2003 April; 11(4):279-87.
15. Agrotis et al., FEBS Lett 2000 Feb. 4; 467(1):128-32.
16. Akiyama et al., Cell Struct. Funct. 2000 June; 25(3):195-204.
17. Ali et al., Pharmacology. 1998 July; 57(1):20-7.
18. Armes et al., Development. 1997 October; 124(19):3797-804.
19. Aspenberg et al., Acta Orthop Scand. 2000 December; 71(6):558-62.
20. Bobik et al., Circulation 1999 Jun. 8; 99(22):2883-91.
21. Choi et al., Am J Physiol 1997 September; 273(3 pt 2):F386-95.
22. Chow et al., Mol Hum Reprod 2001 November; 7(11):1047-56.
23. Goumans et al., Int J Dev Biol 2000 April; 44(3):253-65.
24. Goumans et al., Differentiation 1998 July; 63(3):101-13.
25. Inman et al., Mol Pharmacol 2002 July; 62(1):65-74.
26. Gold et al., Am J Pathol 1997 January; 150(1):209-22.
27. Kang et al., Biochem Mol Biol Int. 1996 November; 40(5):993-1001.
28. Kim et al., Exp Cell Res 1998 May 25; 241(1):151-60.
29. Laping et al., Mol Pharmacol 2002 July; 62(1):58-64.
30. Larsson et al., EMBO J. 2001 Apr. 2; 20(7):1663-73.
31. Lui et al., Kidney Int. 1998 March; 53(3):716-25.
32. Lui et al., Dev Dyn. 2000 April; 217(4):343-60.
33. Liu et al., Zhonghua Xue Ye Xue Za Zhi 2002 October; 23(10):524-7.
34. Lui et al., FEBS Lett. 2002 May 22; 519(1-3):93-8.
35. Lux et al., J Biol. Chem. 1999 Apr. 9; 274(15):9984-92.
36. Machida et al., Eur J Endocrinol 2000 November; 143(5):705-10.
37. Miettinen et al., J Cell Biol 1994 December; 127(6 pt 2):2021-36.
38. Mishina et al., Genes Dev. 1995 Dec. 15; 9(24):3027-37.
39. Mo et al., J Biol Chem 2002 Dec. 27; 277(52):50788-94. Epub 2002 Oct. 18.
40. Morita et al., Brain Res Mol Brain Res 1996 December; 42(2):263-71.
41. Panchenko et al., Am J Physiol 1996 April; 270(4 pt 1):L547-58.
42. Piek et al., J Cell Sci 1999 December; 12(pt 24):4557-68.
43. Ramp et al., Lab Invest. 1997 May; 76(5):739-49.
44. Ryden et al., J Biol Chem 1996 Nov. 29; 271(48):30603-9.
45. Takumi et al., Exp Cell Res 1995 January; 216(1):208-14.
46. Ward et al., Arterioscler Thromb Vasc Biol 1997 November; 17(11):2461-70.
47. Ward et al., Arterioscler Thromb Vasc. Biol 2002 Jun. 1; 22(6):940-8.
48. Ward et al., FEBS Lett 1998 Jan. 30; 422(2):197-200.
49. Ward et al., Atherosclerosis. 1998 April; 137(2):267-75.
50. Wilson et al., Biol Reprod 2001 April; 64(4):1225-35.
51. Wu et al., J Cell Physiol 1996 August; 168(2):453-61.
52. Abe et al., J Bone Min. Res. 2000 April; 15(4):663-73.
53. Adelman et al., Development. 2002 January; 129(2):539-49.
54. Akiyama et al., Exp Cell Res 1997 Sep. 15; 235(2):362-9.
55. Ashique et al., Int J Dev Biol 2002 March; 46(2):243-53.
56. Baur et al., Development 2000 February; 127(3):605-19.
57. Beck et al., BMC Neurosci. 2001; 2(1):12 Epub 2001 Sep. 11.
58. Belecky-Adams et al., J Comp Neruol. 2001 Feb. 19; 430(4):562-72.
59. Botchkarev et al., FASEB J. 2001 October; 15(12):2205-14.
60. Buurma et al., Eur J Oral Sci. 1999 August; 107(4):282-9.
61. Chang et al., Dev Biol. 2002 Nov. 15; 251(2):380-94.
62. Cheifetz, Crit. Rev Oral Biol Med. 1999; 10(2):182-98.
63. Cheifetz, Eur J Oral Sci 1998 January; 106 Suppl 1:174-8.

64. Coskun, et al., J Neurosci Res. 2002 Sep. 15; 69(6):795-802.
65. De Caestecker et al., Respir Res. 2001; 2(4):193-7.
66. Deng et al., Zhonghua Wai Ke Za Zhi. 2002 August; 40(8):592-5.
67. Ebisawa et al., J Cell Sci 1999 October; 112 (Pt 20):3519-27.
68. Enomoto-Iwamoto et al., J Cell Biol 1998 Jan. 26; 140(2):409-18.
69. Erickson et al., Reprod Biol Endocrinol. 2003 Feb. 5; 1(1):9 Epub 2003.
70. Erlacher et al., J Bone Miner Res 1998 March; 13(3):383-92.
71. Franzen et al., Endocrinology. 1999 September; 140(9):4300-10.
72. Fujii et al., Mol Biol Cell. 1999 November; 10(11):3801-13.
73. Gouedard et al., J Biol. Chem. 2000 Sep. 8; 275(36):27973-8.
74. Gould et al., Kidney Int. 2002 January; 61(1):51-60.
75. Gu et al., Arch Oral Biol 1996 October; 41(10):919-23.
76. Guo et al., Clin Orthop. 1999 August; (365):175-83.
77. Haaijman et al., Growth Factors. 2000; 17(3):177-92.
78. Hanada et al., J Cell Biochem. 2001 Mar. 26; 81(2):284-94.
79. Hillmann et al., Biomaterials 2002 March; 23(6):1461-9.
80. Hoshi et al., Bone. 1997 August; 21(2):155-62.
81. Howe et al., Nat Genet. 2001 June; 28(2):184-7.
82. Ide et al., Cancer Res. 1997 Nov. 15; 57(22):5022-7.
83. Ide et al., Oncogene 1997 Mar. 20; 14(11):1377-82.
84. Ikeda et al., Dev Dyn 1996 July; 206(3):318-29.
85. Ishidou et al., J Bone Miner Res 1995 November; 10(11):1651-9.
86. Jazwinska et al., Cell. 1999 Feb. 19; 96(4):563-73.
87. Jikko et al., J Bone Miner Res 1999 July; 14(7):1075-83.
88. Jin et al., Oral Oncol 2001 April; 37(3):225-33.
89. Kaneko et al., Bone. 2000 October; 27(4):479-86.
90. Kawakami et al., Development 1996 November; 122(11):3557-66.
91. Kim et al., Cancer Res 2000 Jun. 1; 60(11):2840-4.
92. Kirsch et al., EMBO J. 2000 Jul. 3; 19(13):3314-24.
93. Kitten et al., J Cell Physiol 1999 December; 181(3):410-5.
94. Kleeff et al, Gastroenterology. 1999 May; 116(5):1202-16.
95. Kloen et al., J Bone Joint Surg. Am. 2002 November; 84-A(11):1909-18.
96. Koenig et al., Mol Cell Biol 1994 September; 14(9):5961-74.
97. Lecerf et al., Nucleic Acids Res 2001 Sep. 1; 29(17):E87-7.
98. Li et al., J Bone Miner Res 2001 June; 16(6):1068-76.
99. Liu et al., Mol Cell Biol 1995 July; 15(7):3479-86.
100. Liu et al., Dev Biol 2003 Apr. 1; 256(1):34-48.
101. Macias-Silva et al., J Biol Chem 1998 Oct. 2; 273(40):25628-36.
102. Marinova-Mutafchieva et al., Arthritis Rheum. 2002 February; 46(2):507-13.
103. Martinez et al., Int J Dev Biol 2002; 46(4):525-33.
104. Martinez et al., Exp Nephrol. 2001; 9(6):372-9.
105. McNatty et al., Reprod Fertil Dev. 2001; 13(7-8):549-55
106. McPherson et al., Dev Biol 2000 May 1-221(1):220-32.
107. Ming et al., Neuroscience 2002; 114(4):849-57.
108. Miyazoro et al., J Clin Invest 2000 April; 105(7):863-73.
109. Monsoro-Burq et al., Mech Dev. 2000 October; 97(1-2):105-8.
110. Mori et al., Bone 1998 February; 22(2):99-105.
111. Nakase et al., J Orthop Res 2001 November; 19(6):1085-8.
112. Namiki et al., J Biol. Chem. 1997 Aug. 29; 272(35):22046-52.
113. Natsume et al., J Biol Chem 1997 Apr. 25; 272(17):11353-40.
114. Nikaido et al., Mech Dev. 1999 April; 82(1-2):219-22.
115. Nikaido et al., Development. 1999 January; 126(1):181-90.
116. Nishihara et al., Biochem Biophys Res Commun 2003 Feb. 7; 301(2):617-22.
117. Nishimura et al., J Biol Chem 1998 Jan. 23; 274(4):1872-9.
118. Nishitoh et al., J Biol. Chem. 1996 Aug. 30; 271(35):21345-52.
119. Obata et al., Acta Ophthalmol Scand. 1999 April; 77(2):151-6.
120. Onishi et al., Bone 1998 June; 22(6):605-12.
121. Panchision et al., Genes Dev 2001 Aug. 15; 15(16):2094-110.
122. Roelen et al., Int J Dev Biol 1997 August; 41(4):541-9.
123. Sakou et al., J Bone Miner Res. 1999 July; 14(7):1145-52.
124. Sanyal et al., J Orthop Res 2002 January; 20(1):58-65.
125. Shimizu et al., Bone 1998 August; 23(2):127-33.
126. Shukunami et al., FEBS Lett 2000 Mar. 3; 469(1):83-7.
127. Skillington et al., J Cell Biol 2002 Oct. 14; 159(1):135-46.
128. Soderstrom et al., Cell Tissue Res 1996 November; 286(2):269-79.
129. Takae et al., Spine 1999 Jul. 15; 24(14):13897-401.
130. Takeda, Kokubyo Gakkai Zasshi, 1994 December; 61(4):512-26.
131. Takeda et al., Biochem Biophys Res Commun 1994 Oct. 14; 204(1):203-9.
132. Tmaki et al., J Cell Physiol. 1998 November; 177(2):355-63.
133. Toyono et al., J Dent Res. 1997 September; 76(9):1555-60.
134. Toyono et al., Arch Oral Biol 1997 July; 42(7):481-8.
135. van der Horst et al., Bone 2002 December; 31(6):661-9.
136. Varley et al., Dev Biol 1998 Apr. 1; 196(1):107-18.
137. Volk et al., J Bone Miner Res 2000 August; 15(8):1630-9.
138. Wada et al., Bone 1998 May; 22(5):479-85.
139. Wollina et al., Acta Derm Venereol. 1999 May; 79(3):183-6140.
140. Wu et al., J Cell Physiol 1996 August; 168(2):453-61.
141. Yamada et al., Jpn J Opthalmol 1999 July-August; 43(4):290-4.
142. Yamada et al., Br J Cancer 1996 March; 73(5):624-9.
143. Yaoita et al., J Bone Miner Metab 2000; 18(2):63-70.
144. Yazaki et al., Anticancer Res 1998 July-August; 18(4A):2239-44.
145. Yeh et al., J Cell Physiol 2002 March; 190(3):322-31.
146. Yeh et al., J Cell Physiol 2000 October; 185(1):87-97.
147. Yeh et al., J Bone Miner Res 1998 December; 13(12):1870-9.
148. Yi et al., Proc Natl Acad Sci USA 2001 Jul. 3; 98(14):7994-9 Epub 2001 Jun. 19.
149. Yi et al., Development 2000 February; 127(3):621-30.
150. Yonemori et al., Am J Pathol 1997 April; 150(4):1335-47.
151. You et al., Invest Ophthalmol V is Sci 1999 February; 40(2):296-311.
152. Zehentner et al., J Bone Miner Res 1999 October; 14(10):17.4-41.

153. Zhang et al., J Neurosci 1998 May 1; 18(9):3314-26.
154. Zhao et al., J Bone Miner Res 2002 August; 17(8):1441-51.
155. Zou et al., Genes Dev. 1997 Sep. 1; 11(17):2191-203.
156. Miyazono, Kohei; et al., Antibodies which bind specifically to activin receptor like kinases, Publ. No. 20020123139, U.S. patent application Ser. No. 10/903,068, filed Sep. 5, 2002.
157. Caniggia, Isabella et al., Methods to diagnose a required regulation of trophoblast invasion, Publ. No. 20020110833, U.S. patent application Ser. No. 10/028,158. filed Aug. 15, 2002.
158. Plowman, Gregory et al., Diagnosis and treatment of ALK-7 related disorders, Publ. No. 20030073143, U.S. patent application Ser. No. 10/069,228, filed Apr. 17, 2003.
159. Rosenbaum, Jan Susan, Use of a BMP protein receptor complex for screening bone metabolism actives and cells cotransfected with a type II BMP receptor and a type I BMP receptor, 20030096296, U.S. patent application Ser. No. 10/742,153, filed May 22, 2003.
160. Hughes, Paul E, et al., Methods of providing neuroprotection and/or neurorestoration via the neural activin type IIB receptor, Publ. No. 20030103959, U.S. patent application Ser. No. 10/177,735, filed Jun. 5, 2003.
161. Ibañez et al., Antibodies that specifically bind to ALK-7, a novel serine theronine kinase receptor, U.S. Pat. No. 5,811,245, issued Sep. 22, 1998.
162. ten Dijke et al., Methods of antagonizing OP-1 binding to a cell surface receptor utilizing ALK polypeptides, U.S. Pat. No. 5,863,738, issued Jan. 26, 1999.
163. Ibañez et al, Serine threonine kinase receptor, ALK-7, U.S. Pat. No. 5,891,638, issued Apr. 6, 1999.
164. Ichijo et al., Method for identifying an OP-1 analog which binds an ALK-1 receptor, U.S. Pat. No. 5,968,752, Oct. 19, 1999.
165. Miyazono et al., Activin receptor-like kinases, ALK-3 and ALK-6, and nucleic acids encoding them, U.S. Pat. No. 6,207,814, issued Mar. 27, 2001.
166. Rosenbaum, Use of a BMP protein receptor complex for screening bone metabolism actives and cells cotransfected with a type II BMP receptor and type I BMP receptor, U.S. Pat. No. 6,210,899, issued Apr. 3, 2001.
167. Rosenbaum et al., cDNA encoding a BMP type II receptor, U.S. Pat. No. 6,306,622, issued Oct. 23, 2001
168. Miyazono et al., Activin receptor-like kinases, proteins having serine threonine kinase domains and polynucleotides encoding same, U.S. Pat. No. 6,316,217, Nov. 13, 2001
169. Miyazono et al., Isolated nucleic acid molecules which encode activin-receptor like kinases, expression vectors and cells containing these, U.S. Pat. No. 6,331,621, issued Dec. 18, 2001
170. Caniggia et al., Methods to diagnose a required regulation of trophoblast invasion, U.S. Pat. No. 6,376,199, issued Apr. 23, 2002

EQUIVALENTS

From the foregoing detailed description of the specific embodiments of the invention, it should be apparent that unique bioactive peptides have been described. Although particular embodiments have been disclosed herein in detail, this has been done by way of example for purposes of illustration only, and is not intended to be limiting with respect to the scope of the appended claims which follow. In particular, it is contemplated by the inventor that various substitutions, alterations, and modifications may be made to the invention without departing from the spirit and scope of the invention as defined by the claims.

We claim:

1. A purified polypeptide comprising the amino acid sequence set forth as SEQ ID NO:217.

2. A pharmaceutical composition comprising the polypeptide of claim 1, and a pharmaceutically acceptable carrier.

3. A kit comprising in one or more containers, the pharmaceutical composition of claim 2 and instructions for using the contents therein.

4. A purified polypeptide for use in treating a tissue differentiation factor-associated disorder or disease, wherein the compound comprises the amino acid sequence set forth as SEQ ID NO:217.

5. A device comprising an implantable medical device having a coating wherein the coating consists of the amino acid sequence set forth as SEQ ID NO:217, and wherein the device, when implanted into a mammal, treats or prevents a disorder in the mammal.

6. The purified polypeptide of claim 1, consisting of the amino acid sequence set forth as SEQ ID NO:217.

7. The purified polypeptide of claim 4, consisting of the amino acid sequence set forth as SEQ ID NO:217.

8. The device of claim 5, wherein the coating consists of the amino acid sequence set forth as SEQ ID NO:217.

9. The purified polypeptide of claim 1 or 4, wherein the amino acid sequence set forth as SEQ ID NO:217 is linear or cyclized.

10. The device of claim 5, wherein the amino acid sequence set forth for as SEQ ID NO:217 is linear or cyclized.

* * * * *

SEQUENCE LISTING

```
<160> NUMBER OF SEQ ID NOS: 614

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(20)
<223> OTHER INFORMATION: Any amino acid; sequence may encompass 3 to 20
      residues
<220> FEATURE:
<223> OTHER INFORMATION: See specification as filed for detailed
      description of substitutions and preferred embodiments

<400> SEQUENCE: 1

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (2)..(2)
<223> OTHER INFORMATION: Tyr, Ile, any aromatic amino acid, any
      aliphatic amino acid or any polar amino acid
<220> FEATURE:
<221> NAME/KEY: MOD_RES
<222> LOCATION: (3)..(3)
<223> OTHER INFORMATION: Phe, Val, any aromatic amino acid or any
      aliphatic amino acid
<220> FEATURE:
<221> NAME/KEY: MOD_RES
<222> LOCATION: (4)..(4)
<223> OTHER INFORMATION: Asp or any acidic amino acid
<220> FEATURE:
<221> NAME/KEY: MOD_RES
<222> LOCATION: (5)..(5)
<223> OTHER INFORMATION: Asp, Glu or an acidic amino acid
<220> FEATURE:
<221> NAME/KEY: MOD_RES
<222> LOCATION: (6)..(6)
<223> OTHER INFORMATION: Ser, Asn or any polar amino acid
<220> FEATURE:
<221> NAME/KEY: MOD_RES
<222> LOCATION: (7)..(7)
<223> OTHER INFORMATION: Ser or any polar amino acid
<220> FEATURE:
<221> NAME/KEY: MOD_RES
<222> LOCATION: (8)..(8)
<223> OTHER INFORMATION: Asn, Gln or any polar amino acid
<220> FEATURE:
<221> NAME/KEY: MOD_RES
<222> LOCATION: (9)..(9)
<223> OTHER INFORMATION: Val or any aliphatic amino acid
<220> FEATURE:
<221> NAME/KEY: MOD_RES
<222> LOCATION: (10)..(10)
<223> OTHER INFORMATION: Ile, Val, Leu or any aliphatic amino acid
<220> FEATURE:
<221> NAME/KEY: MOD_RES
<222> LOCATION: (12)..(13)
<223> OTHER INFORMATION: Lys or any basic amino acid
<220> FEATURE:
<221> NAME/KEY: MOD_RES
<222> LOCATION: (14)..(14)
<223> OTHER INFORMATION: Tyr or any polar amino acid
<220> FEATURE:
<221> NAME/KEY: MOD_RES
<222> LOCATION: (15)..(15)
<223> OTHER INFORMATION: Arg or any basic amino acid
<220> FEATURE:
<221> NAME/KEY: MOD_RES
<222> LOCATION: (16)..(16)
<223> OTHER INFORMATION: Ser or any polar amino acid

<400> SEQUENCE: 2

Cys Xaa Xaa Xaa Xaa Xaa Xaa Xaa Xaa Cys Xaa Xaa Xaa Xaa Xaa
1               5                   10                  15

<210> SEQ ID NO 3
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys Lys Lys His Glu Leu Tyr Val Ser Phe Arg Asp Leu Gly Trp Gln
1               5                   10                  15

Asp Trp Ile Ile Ala Pro Glu Gly Tyr Ala Ala Tyr Tyr Cys Glu Gln
            20                  25                  30

<210> SEQ ID NO 4
```

```
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Glu Leu Tyr Val Ser Phe Arg Asp Leu Gly Trp Gln Asp Trp Ile
1               5                   10                  15

Ile Ala Pro Glu Gly Tyr Ala Ala Tyr Cys
            20                  25

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys Phe Arg Asp Leu Gly Trp Gln Asp Trp Ile Ile Ala Pro Cys
1               5                   10                  15

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Glu Cys Arg Asp Leu Gly Trp Gln Asp Trp Cys
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Arg Asp Leu Gly Trp Gln Asp Trp Ile Ile Ala Pro Cys
1               5                   10

<210> SEQ ID NO 8
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Cys Leu Asn Ala Ile Ser Val Leu Tyr Phe Asp Asp Ser Ser Asn Val
1               5                   10                  15

Ile Leu Lys Lys Tyr Arg Asn Met Val Val Arg Cys
            20                  25

<210> SEQ ID NO 9
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 9

Cys Phe Asp Asp Ser Ser Asn Val Cys Leu Lys Lys Tyr Arg Ser
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Cys Phe Asp Asp Ser Ser Asn Val Ile Cys Lys Lys Tyr Arg Ser
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Cys Tyr Phe Asp Asp Ser Ser Asn Val Cys Leu Lys Lys Tyr Arg Ser
1               5                   10                  15

<210> SEQ ID NO 12
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Cys Ala Phe Pro Leu Asn Ser Tyr Met Asn Ala Thr Asn His Ala Ile
1               5                   10                  15

Val Gln Thr Leu Val His Phe Ile Asn Pro Glu Thr Val Pro Lys Cys
            20                  25                  30

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Cys Leu Asn Ser Tyr Met Asn Ala Thr Asn His Ala Cys
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14
```

```
Cys Phe Ile Asn Pro Glu Thr Val Pro Lys Cys
1               5                  10
```

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

```
Cys Leu Phe Asp Asp Ser Ser Asn Val Ile Cys Lys Lys Tyr Arg Ser
1               5                  10                  15
```

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

```
Cys Ile Val Asn Ser Ser Asp Asp Phe Leu Cys Lys Lys Tyr Arg Ser
1               5                  10                  15
```

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated

<400> SEQUENCE: 17

```
Cys Tyr Phe Asp Asp Ser Ser Asn Val Ile Cys
1               5                  10
```

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 18

```
Cys Tyr Phe Asp Asp Ser Ser Asn Val Ile Cys
1               5                  10
```

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<223> OTHER INFORMATION: C-term amidated

<400> SEQUENCE: 19

Cys Tyr Phe Asp Asp Ser Ser Asn Val Ile Cys

```
<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Cys Tyr Phe Asp Asp Ser Ser Asn Val Ile Cys Lys Lys
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Cys Tyr Phe Asp Asp Ser Ser Asn Val Ile Cys Lys
1               5                   10

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Cys Phe Ile Asn Pro Glu Thr Val Cys
1               5

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Cys Tyr Phe Asp Asp Ser Ser Asn Val Ile Cys Lys Lys Tyr Lys Ser
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Cys Tyr Phe Asp Asp Ser Ser Asn Val Ile Cys Lys Arg Tyr Arg Ser
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 25

Cys Tyr Phe Asp Asp Ser Ser Asn Val Ile Cys Arg Lys Tyr Arg Ser
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Cys Tyr Leu Asp Glu Asn Glu Lys Val Val Cys Lys Asn Tyr Gln Ser
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Cys Tyr Leu Asp Glu Tyr Asp Lys Val Val Cys Lys Asn Tyr Gln Ser
1               5                   10                  15

<210> SEQ ID NO 28
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ile Ser Val Cys Tyr Phe Asp Asp Ser Ser Asn Val Ile Cys Lys Lys
1               5                   10                  15

Tyr Arg Ser

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Cys Tyr Phe Asp Asp Ser Ser Asn Val Ile Cys
1               5                   10

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Cys Tyr Leu Asp Asp Ser Ser Asn Val Ile Cys Lys Lys Tyr Arg Ser
1               5                   10                  15

```
<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Cys Tyr Leu Asp Asp Ser Ser Asn Val Leu Cys Lys Lys Tyr Arg Ser
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Cys Tyr Phe Glu Asp Ser Ser Asn Val Ile Cys Lys Lys Tyr Arg Ser
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 33

Cys Tyr Phe Asp Asp Ser Ser Asn Val Leu Cys Lys Lys Tyr Arg Ser
1               5                   10                  15

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 34

Cys Tyr Leu Asp Glu Asp Ser Ser Lys Val Leu Cys Lys Asn Tyr Arg
1               5                   10                  15

Ser

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 35

Cys Tyr Phe Asp Glu Ser Ser Lys Val Leu Cys Lys Lys Tyr Arg Ser
1               5                   10                  15
```

```
<210> SEQ ID NO 36
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 36

Cys Tyr Phe Asp Asp Ser Ser Asn Val Leu Cys Lys Lys Tyr Arg Ser
1               5                   10                  15

Gly Ser Gly Gly Gly Cys
            20

<210> SEQ ID NO 37
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 37

Cys Gly Gly Gly Ser Gly Ser Cys Tyr Phe Asp Asp Ser Ser Asn Val
1               5                   10                  15

Leu Cys Lys Lys Tyr Arg Ser
            20

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Cys Tyr Phe Asp Asp Ser Ser Asn Val Ile Cys Lys Lys Tyr Arg Ser
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Cys Ile Phe Asp Asp Ser Ser Asn Val Ile Cys Lys Lys Tyr Arg Ser
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Cys Tyr Val Asp Asp Ser Ser Asn Val Ile Cys Lys Lys Tyr Arg Ser
1               5                   10                  15
```

<210> SEQ ID NO 41
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Cys Tyr Phe Asp Glu Ser Ser Asn Val Ile Cys Lys Lys Tyr Arg Ser
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Cys Tyr Phe Asp Asp Asn Ser Asn Val Ile Cys Lys Lys Tyr Arg Ser
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Cys Tyr Phe Asp Asp Ser Ser Gln Val Ile Cys Lys Lys Tyr Arg Ser
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Cys Tyr Phe Asp Asp Ser Ser Asn Val Val Cys Lys Lys Tyr Arg Ser
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(11)
<223> OTHER INFORMATION: Disulfide bridge

<400> SEQUENCE: 45

Cys Tyr Phe Asp Asp Ser Ser Asn Val Leu Cys Lys Lys Tyr Arg Ser
1               5                   10                  15

<210> SEQ ID NO 46
<211> LENGTH: 16
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 46

Cys Ile Val Asp Asp Ser Ser Asn Val Ile Cys Lys Lys Tyr Arg Ser
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Cys Ile Phe Asp Glu Ser Ser Asn Val Ile Cys Lys Lys Tyr Arg Ser
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Cys Ile Phe Asp Asp Asn Ser Asn Val Ile Cys Lys Lys Tyr Arg Ser
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Cys Ile Phe Asp Asp Ser Ser Gln Val Ile Cys Lys Lys Tyr Arg Ser
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Cys Ile Phe Asp Asp Ser Ser Asn Val Val Cys Lys Lys Tyr Arg Ser
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Cys Ile Phe Asp Asp Ser Ser Asn Val Leu Cys Lys Lys Tyr Arg Ser
1               5                   10                  15
```

<210> SEQ ID NO 52
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Cys Tyr Val Asp Glu Ser Ser Asn Val Ile Cys Lys Lys Tyr Arg Ser
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Cys Tyr Val Asp Asp Asn Ser Asn Val Ile Cys Lys Lys Tyr Arg Ser
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Cys Tyr Val Asp Asp Ser Ser Gln Val Ile Cys Lys Lys Tyr Arg Ser
1               5                   10                  15

<210> SEQ ID NO 55
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Cys Tyr Val Asp Asp Ser Ser Asn Val Val Cys Lys Lys Tyr Arg Ser
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Cys Tyr Val Asp Asp Ser Ser Asn Val Leu Cys Lys Lys Tyr Arg Ser
1               5                   10                  15

<210> SEQ ID NO 57
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 57

Cys Tyr Phe Asp Glu Asn Ser Asn Val Ile Cys Lys Lys Tyr Arg Ser
1               5                   10                  15

<210> SEQ ID NO 58
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Cys Tyr Phe Asp Glu Ser Ser Gln Val Ile Cys Lys Lys Tyr Arg Ser
1               5                   10                  15

<210> SEQ ID NO 59
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Cys Tyr Phe Asp Glu Ser Ser Asn Val Val Cys Lys Lys Tyr Arg Ser
1               5                   10                  15

<210> SEQ ID NO 60
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Cys Tyr Phe Asp Glu Ser Ser Asn Val Leu Cys Lys Lys Tyr Arg Ser
1               5                   10                  15

<210> SEQ ID NO 61
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Cys Tyr Phe Asp Asp Asn Ser Gln Val Ile Cys Lys Lys Tyr Arg Ser
1               5                   10                  15

<210> SEQ ID NO 62
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Cys Tyr Phe Asp Asp Asn Ser Asn Val Val Cys Lys Lys Tyr Arg Ser
1               5                   10                  15

<210> SEQ ID NO 63
<211> LENGTH: 16
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 63

Cys Tyr Phe Asp Asp Asn Ser Asn Val Leu Cys Lys Lys Tyr Arg Ser
1               5                   10                  15

<210> SEQ ID NO 64
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Cys Tyr Phe Asp Asp Ser Ser Gln Val Val Cys Lys Lys Tyr Arg Ser
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Cys Tyr Phe Asp Asp Ser Ser Gln Val Leu Cys Lys Lys Tyr Arg Ser
1               5                   10                  15

<210> SEQ ID NO 66
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Cys Ile Val Asp Glu Ser Ser Asn Val Ile Cys Lys Lys Tyr Arg Ser
1               5                   10                  15

<210> SEQ ID NO 67
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Cys Ile Val Asp Asp Asn Ser Asn Val Ile Cys Lys Lys Tyr Arg Ser
1               5                   10                  15

<210> SEQ ID NO 68
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Cys Ile Val Asp Asp Ser Ser Gln Val Ile Cys Lys Lys Tyr Arg Ser
1               5                   10                  15
```

<210> SEQ ID NO 69
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 69

Cys Ile Val Asp Asp Ser Ser Asn Val Val Cys Lys Lys Tyr Arg Ser
1               5                   10                  15

<210> SEQ ID NO 70
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 70

Cys Ile Val Asp Asp Ser Ser Asn Val Leu Cys Lys Lys Tyr Arg Ser
1               5                   10                  15

<210> SEQ ID NO 71
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 71

Cys Ile Phe Asp Glu Asn Ser Asn Val Ile Cys Lys Lys Tyr Arg Ser
1               5                   10                  15

<210> SEQ ID NO 72
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 72

Cys Ile Phe Asp Glu Ser Ser Gln Val Ile Cys Lys Lys Tyr Arg Ser
1               5                   10                  15

<210> SEQ ID NO 73
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 73

Cys Ile Phe Asp Glu Ser Ser Asn Val Val Cys Lys Lys Tyr Arg Ser
1               5                   10                  15

<210> SEQ ID NO 74
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 74

Cys Ile Phe Asp Glu Ser Ser Asn Val Leu Cys Lys Lys Tyr Arg Ser
1               5                   10                  15

<210> SEQ ID NO 75
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Cys Ile Phe Asp Asp Asn Ser Gln Val Ile Cys Lys Lys Tyr Arg Ser
1               5                   10                  15

<210> SEQ ID NO 76
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Cys Ile Phe Asp Asp Asn Ser Asn Val Val Cys Lys Lys Tyr Arg Ser
1               5                   10                  15

<210> SEQ ID NO 77
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Cys Ile Phe Asp Asp Asn Ser Asn Val Leu Cys Lys Lys Tyr Arg Ser
1               5                   10                  15

<210> SEQ ID NO 78
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Cys Ile Phe Asp Asp Ser Ser Gln Val Val Cys Lys Lys Tyr Arg Ser
1               5                   10                  15

<210> SEQ ID NO 79
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Cys Ile Phe Asp Asp Ser Ser Gln Val Leu Cys Lys Lys Tyr Arg Ser
1               5                   10                  15

<210> SEQ ID NO 80
<211> LENGTH: 16

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Cys Tyr Val Asp Glu Asn Ser Asn Val Ile Cys Lys Lys Tyr Arg Ser
1               5                   10                  15

<210> SEQ ID NO 81
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Cys Tyr Val Asp Glu Ser Ser Gln Val Ile Cys Lys Lys Tyr Arg Ser
1               5                   10                  15

<210> SEQ ID NO 82
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Cys Tyr Val Asp Glu Ser Ser Asn Val Val Cys Lys Lys Tyr Arg Ser
1               5                   10                  15

<210> SEQ ID NO 83
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Cys Tyr Val Asp Glu Ser Ser Asn Val Leu Cys Lys Lys Tyr Arg Ser
1               5                   10                  15

<210> SEQ ID NO 84
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Cys Tyr Val Asp Asp Asn Ser Gln Val Ile Cys Lys Lys Tyr Arg Ser
1               5                   10                  15

<210> SEQ ID NO 85
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Cys Tyr Val Asp Asp Asn Ser Asn Val Val Cys Lys Lys Tyr Arg Ser
```

```
<210> SEQ ID NO 86
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Cys Tyr Val Asp Asp Asn Ser Asn Val Leu Cys Lys Lys Tyr Arg Ser
1               5                   10                  15

<210> SEQ ID NO 87
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Cys Tyr Val Asp Asp Ser Ser Gln Val Val Cys Lys Lys Tyr Arg Ser
1               5                   10                  15

<210> SEQ ID NO 88
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Cys Tyr Val Asp Asp Ser Ser Gln Val Leu Cys Lys Lys Tyr Arg Ser
1               5                   10                  15

<210> SEQ ID NO 89
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Cys Tyr Phe Asp Glu Asn Ser Gln Val Ile Cys Lys Lys Tyr Arg Ser
1               5                   10                  15

<210> SEQ ID NO 90
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Cys Tyr Phe Asp Glu Asn Ser Asn Val Val Cys Lys Lys Tyr Arg Ser
1               5                   10                  15

<210> SEQ ID NO 91
<211> LENGTH: 16
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 91

Cys Tyr Phe Asp Glu Asn Ser Asn Val Leu Cys Lys Lys Tyr Arg Ser
1               5                   10                  15

<210> SEQ ID NO 92
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Cys Tyr Phe Asp Glu Ser Ser Gln Val Val Cys Lys Lys Tyr Arg Ser
1               5                   10                  15

<210> SEQ ID NO 93
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Cys Tyr Phe Asp Glu Ser Ser Gln Val Leu Cys Lys Lys Tyr Arg Ser
1               5                   10                  15

<210> SEQ ID NO 94
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Cys Tyr Phe Asp Asp Asn Ser Gln Val Val Cys Lys Lys Tyr Arg Ser
1               5                   10                  15

<210> SEQ ID NO 95
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Cys Tyr Phe Asp Asp Asn Ser Gln Val Leu Cys Lys Lys Tyr Arg Ser
1               5                   10                  15

<210> SEQ ID NO 96
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Cys Ile Val Asp Glu Asn Ser Asn Val Ile Cys Lys Lys Tyr Arg Ser
1               5                   10                  15

<210> SEQ ID NO 97

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Cys Ile Val Asp Glu Ser Ser Gln Val Ile Cys Lys Lys Tyr Arg Ser
1               5                   10                  15

<210> SEQ ID NO 98
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Cys Ile Val Asp Glu Ser Ser Asn Val Val Cys Lys Lys Tyr Arg Ser
1               5                   10                  15

<210> SEQ ID NO 99
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Cys Ile Val Asp Glu Ser Ser Asn Val Leu Cys Lys Lys Tyr Arg Ser
1               5                   10                  15

<210> SEQ ID NO 100
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Cys Ile Val Asp Asp Asn Ser Gln Val Ile Cys Lys Lys Tyr Arg Ser
1               5                   10                  15

<210> SEQ ID NO 101
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Cys Ile Val Asp Asp Asn Ser Asn Val Val Cys Lys Lys Tyr Arg Ser
1               5                   10                  15

<210> SEQ ID NO 102
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102
```

```
Cys Ile Val Asp Asp Asn Ser Asn Val Leu Cys Lys Lys Tyr Arg Ser
1               5                   10                  15
```

<210> SEQ ID NO 103
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

```
Cys Ile Val Asp Asp Ser Ser Gln Val Val Cys Lys Lys Tyr Arg Ser
1               5                   10                  15
```

<210> SEQ ID NO 104
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

```
Cys Ile Val Asp Asp Ser Ser Gln Val Leu Cys Lys Lys Tyr Arg Ser
1               5                   10                  15
```

<210> SEQ ID NO 105
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

```
Cys Ile Phe Asp Glu Asn Ser Gln Val Ile Cys Lys Lys Tyr Arg Ser
1               5                   10                  15
```

<210> SEQ ID NO 106
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

```
Cys Ile Phe Asp Glu Asn Ser Asn Val Val Cys Lys Lys Tyr Arg Ser
1               5                   10                  15
```

<210> SEQ ID NO 107
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

```
Cys Ile Phe Asp Glu Asn Ser Asn Val Leu Cys Lys Lys Tyr Arg Ser
1               5                   10                  15
```

<210> SEQ ID NO 108
<211> LENGTH: 16
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 108

Cys Ile Phe Asp Glu Ser Ser Gln Val Val Cys Lys Lys Tyr Arg Ser
1               5                   10                  15

<210> SEQ ID NO 109
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Cys Ile Phe Asp Glu Ser Ser Gln Val Leu Cys Lys Lys Tyr Arg Ser
1               5                   10                  15

<210> SEQ ID NO 110
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Cys Ile Phe Asp Asp Asn Ser Gln Val Val Cys Lys Lys Tyr Arg Ser
1               5                   10                  15

<210> SEQ ID NO 111
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Cys Ile Phe Asp Asp Asn Ser Gln Val Leu Cys Lys Lys Tyr Arg Ser
1               5                   10                  15

<210> SEQ ID NO 112
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Cys Tyr Val Asp Glu Asn Ser Gln Val Ile Cys Lys Lys Tyr Arg Ser
1               5                   10                  15

<210> SEQ ID NO 113
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Cys Tyr Val Asp Glu Asn Ser Asn Val Val Cys Lys Lys Tyr Arg Ser
1               5                   10                  15
```

```
<210> SEQ ID NO 114
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Cys Tyr Val Asp Glu Asn Ser Asn Val Leu Cys Lys Lys Tyr Arg Ser
1               5                   10                  15

<210> SEQ ID NO 115
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Cys Tyr Val Asp Glu Ser Ser Gln Val Val Cys Lys Lys Tyr Arg Ser
1               5                   10                  15

<210> SEQ ID NO 116
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Cys Tyr Val Asp Glu Ser Ser Gln Val Leu Cys Lys Lys Tyr Arg Ser
1               5                   10                  15

<210> SEQ ID NO 117
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Cys Tyr Val Asp Asp Asn Ser Gln Val Val Cys Lys Lys Tyr Arg Ser
1               5                   10                  15

<210> SEQ ID NO 118
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Cys Tyr Val Asp Asp Asn Ser Gln Val Leu Cys Lys Lys Tyr Arg Ser
1               5                   10                  15

<210> SEQ ID NO 119
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119
```

Cys Tyr Phe Asp Glu Asn Ser Gln Val Val Cys Lys Lys Tyr Arg Ser
1               5                   10                  15

<210> SEQ ID NO 120
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Cys Tyr Phe Asp Glu Asn Ser Gln Val Leu Cys Lys Lys Tyr Arg Ser
1               5                   10                  15

<210> SEQ ID NO 121
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Cys Ile Val Asp Glu Asn Ser Gln Val Ile Cys Lys Lys Tyr Arg Ser
1               5                   10                  15

<210> SEQ ID NO 122
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Cys Ile Val Asp Glu Asn Ser Asn Val Val Cys Lys Lys Tyr Arg Ser
1               5                   10                  15

<210> SEQ ID NO 123
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Cys Ile Val Asp Glu Asn Ser Asn Val Leu Cys Lys Lys Tyr Arg Ser
1               5                   10                  15

<210> SEQ ID NO 124
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Cys Ile Phe Asp Glu Asn Ser Gln Val Val Cys Lys Lys Tyr Arg Ser
1               5                   10                  15

<210> SEQ ID NO 125
<211> LENGTH: 16
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 125

Cys Ile Phe Asp Glu Asn Ser Gln Val Leu Cys Lys Lys Tyr Arg Ser
1               5                   10                  15

<210> SEQ ID NO 126
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Cys Tyr Val Asp Glu Asn Ser Gln Val Val Cys Lys Lys Tyr Arg Ser
1               5                   10                  15

<210> SEQ ID NO 127
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Cys Tyr Val Asp Glu Asn Ser Gln Val Leu Cys Cys Lys Tyr Arg Ser
1               5                   10                  15

<210> SEQ ID NO 128
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Cys Ile Val Asp Glu Asn Ser Gln Val Val Cys Lys Lys Tyr Arg Ser
1               5                   10                  15

<210> SEQ ID NO 129
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Cys Ile Val Asp Glu Asn Ser Gln Val Leu Cys Lys Lys Tyr Arg Ser
1               5                   10                  15

<210> SEQ ID NO 130
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Cys Tyr Phe Asp Asp Ser Ser Lys Val Ile Cys Lys Lys Tyr Arg Ser
1               5                   10                  15
```

```
<210> SEQ ID NO 131
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Cys Tyr Leu Asp Asp Ser Ser Asn Val Ile Cys Lys Lys Tyr Arg Asn
1               5                   10                  15

<210> SEQ ID NO 132
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Cys Tyr Phe Asp Asp Ser Ser Lys Val Val Cys Lys Lys Tyr Arg Ser
1               5                   10                  15

<210> SEQ ID NO 133
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Cys Tyr Leu Asp Asp Ser Ser Asn Val Val Cys Lys Lys Tyr Arg Ser
1               5                   10                  15

<210> SEQ ID NO 134
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Cys Tyr Phe Asp Asp Ser Ser Lys Val Leu Cys Lys Lys Tyr Arg Ser
1               5                   10                  15

<210> SEQ ID NO 135
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Cys Tyr Leu Asp Asp Ser Ser Asn Val Leu Cys Lys Lys Tyr Arg Asn
1               5                   10                  15

<210> SEQ ID NO 136
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 136

Cys Tyr Phe Asp Asp Asn Ser Lys Val Ile Cys Lys Lys Tyr Arg Ser
1               5                   10                  15

<210> SEQ ID NO 137
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Cys Tyr Phe Asp Glu Ser Ser Lys Val Ile Cys Lys Lys Tyr Arg Ser
1               5                   10                  15

<210> SEQ ID NO 138
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Cys Tyr Leu Asp Asp Ser Ser Lys Val Ile Cys Lys Lys Tyr Arg Ser
1               5                   10                  15

<210> SEQ ID NO 139
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Cys Tyr Leu Asp Asp Asn Ser Asn Val Ile Cys Lys Lys Tyr Arg Ser
1               5                   10                  15

<210> SEQ ID NO 140
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Cys Tyr Leu Asp Glu Ser Ser Asn Val Ile Cys Lys Lys Tyr Arg Ser
1               5                   10                  15

<210> SEQ ID NO 141
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Cys Tyr Leu Asp Asp Ser Ser Gln Val Ile Cys Lys Lys Tyr Arg Ser
1               5                   10                  15

<210> SEQ ID NO 142
<211> LENGTH: 16
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 142

Cys Tyr Phe Asp Asp Asn Ser Lys Val Val Cys Lys Lys Tyr Arg Ser
1               5                   10                  15

<210> SEQ ID NO 143
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Cys Tyr Phe Asp Glu Ser Ser Lys Val Val Cys Lys Lys Tyr Arg Ser
1               5                   10                  15

<210> SEQ ID NO 144
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Cys Tyr Leu Asp Asp Ser Ser Lys Val Val Cys Lys Lys Tyr Arg Ser
1               5                   10                  15

<210> SEQ ID NO 145
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Cys Tyr Phe Asp Asp Asn Ser Lys Val Leu Cys Lys Lys Tyr Arg Ser
1               5                   10                  15

<210> SEQ ID NO 146
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Cys Tyr Phe Asp Glu Ser Ser Lys Val Leu Cys Lys Lys Tyr Arg Ser
1               5                   10                  15

<210> SEQ ID NO 147
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Cys Tyr Leu Asp Asp Ser Ser Lys Val Leu Cys Lys Lys Tyr Arg Ser
1               5                   10                  15
```

```
<210> SEQ ID NO 148
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Cys Tyr Leu Asp Glu Ser Ser Lys Val Ile Cys Lys Lys Tyr Arg Ser
1               5                   10                  15

<210> SEQ ID NO 149
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Cys Tyr Phe Asp Glu Asn Ser Lys Val Ile Cys Lys Lys Tyr Arg Ser
1               5                   10                  15

<210> SEQ ID NO 150
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Cys Tyr Leu Asp Asp Asn Ser Lys Val Ile Cys Lys Lys Tyr Arg Ser
1               5                   10                  15

<210> SEQ ID NO 151
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Cys Tyr Leu Asp Glu Ser Ser Gln Val Ile Cys Lys Lys Tyr Arg Ser
1               5                   10                  15

<210> SEQ ID NO 152
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Cys Tyr Phe Asp Asp Ser Ser Asn Val Val Cys
1               5                   10

<210> SEQ ID NO 153
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 153

Cys Tyr Phe Asp Asp Ser Ser Asn Val Leu Cys
1               5                   10

<210> SEQ ID NO 154
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Cys Tyr Phe Asp Asp Ser Ser Lys Val Ile Cys
1               5                   10

<210> SEQ ID NO 155
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Cys Tyr Phe Asp Asp Asn Ser Asn Val Ile Cys
1               5                   10

<210> SEQ ID NO 156
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Cys Tyr Phe Asp Glu Ser Ser Asn Val Ile Cys
1               5                   10

<210> SEQ ID NO 157
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Cys Tyr Phe Asp Asp Ser Ser Gln Val Ile Cys
1               5                   10

<210> SEQ ID NO 158
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Cys Tyr Leu Asp Asp Ser Ser Asn Val Ile Cys
1               5                   10

<210> SEQ ID NO 159
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Cys Tyr Leu Asp Asp Asn Ser Lys Val Val Cys Lys Lys Tyr Arg
1               5                   10                  15

<210> SEQ ID NO 160
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Cys Tyr Leu Asp Asp Asn Ser Asn Val Ile Cys Lys Lys Tyr Arg
1               5                   10                  15

<210> SEQ ID NO 161
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Cys Tyr Leu Glu Asp Asn Ser Asn Val Thr Cys Lys Lys Tyr Arg
1               5                   10                  15

<210> SEQ ID NO 162
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Cys Tyr Leu Glu Glu Asn Ser Asn Val Val Cys Lys Lys Tyr Arg
1               5                   10                  15

<210> SEQ ID NO 163
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Cys Tyr Leu Asp Asp Asn Ser Lys Val Thr Cys Lys Lys Tyr Arg
1               5                   10                  15

<210> SEQ ID NO 164
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Cys Tyr Leu Glu Glu Asn Ser Gln Val Ile Cys Lys Lys Tyr Arg
```

```
<210> SEQ ID NO 165
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Cys Tyr Leu Glu Asp Asn Ser Gln Val Val Cys Lys Lys Tyr Arg
1               5                   10                  15

<210> SEQ ID NO 166
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Cys Tyr Leu Asp Asp Asn Ser Asn Phe Ile Cys Lys Lys Tyr Arg
1               5                   10                  15

<210> SEQ ID NO 167
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Cys Tyr Leu Asp Glu Asn Ser Lys Val Val Cys Lys Lys Tyr Arg
1               5                   10                  15

<210> SEQ ID NO 168
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Cys Trp Leu Asp Glu Asn Ser Asn Val Val Cys Lys Lys Tyr Arg
1               5                   10                  15

<210> SEQ ID NO 169
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Cys Tyr Leu Glu Glu Asn Ser Asn Val Ile Cys Lys Lys Tyr Arg
1               5                   10                  15

<210> SEQ ID NO 170
<211> LENGTH: 15
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 170

Cys Tyr Leu Glu Asp Asn Ser Asn Val Val Cys Lys Lys Tyr Arg
1               5                   10                  15

<210> SEQ ID NO 171
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Cys Tyr Leu Asp Glu Asn Ser Lys Val Ile Cys Lys Lys Tyr Arg
1               5                   10                  15

<210> SEQ ID NO 172
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Cys Tyr Leu Asp Glu Asn Ser Gln Val Thr Cys Lys Lys Tyr Arg
1               5                   10                  15

<210> SEQ ID NO 173
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Cys Tyr Leu Glu Asp Asn Ser Asn Val Ile Cys Lys Lys Tyr Arg
1               5                   10                  15

<210> SEQ ID NO 174
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Cys Tyr Leu Asp Asp Asn Ser Lys Val Ile Cys Lys Lys Tyr Arg
1               5                   10                  15

<210> SEQ ID NO 175
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Cys Tyr Leu Asp Glu Asn Ser Asn Val Thr Cys Lys Lys Tyr Arg
1               5                   10                  15

<210> SEQ ID NO 176

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Cys Tyr Leu Asp Asp Asn Ser Gln Val Thr Cys Lys Lys Tyr Arg
1               5                   10                  15

<210> SEQ ID NO 177
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Cys Tyr Leu Asp Glu Asn Ser Gln Val Val Cys Lys Lys Tyr Arg
1               5                   10                  15

<210> SEQ ID NO 178
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Cys Tyr Leu Asp Asp Asn Ser Asn Val Thr Cys Lys Lys Tyr Arg
1               5                   10                  15

<210> SEQ ID NO 179
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Cys Tyr Leu Asp Glu Asn Ser Asn Val Val Cys Lys Lys Tyr Arg
1               5                   10                  15

<210> SEQ ID NO 180
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Cys Tyr Leu Asp Glu Asn Ser Gln Val Ile Cys Lys Lys Tyr Arg
1               5                   10                  15

<210> SEQ ID NO 181
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181
```

Cys Tyr Leu Asp Glu Asn Ser Asn Val Ile Cys Lys Lys Tyr Arg
1               5                   10                  15

<210> SEQ ID NO 182
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Cys Tyr Leu Asp Asp Asn Ser Asn Val Val Cys Lys Lys Tyr Arg
1               5                   10                  15

<210> SEQ ID NO 183
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Cys Tyr Leu Glu Asp Asn Ser Gln Val Ile Cys Lys Lys Tyr Arg
1               5                   10                  15

<210> SEQ ID NO 184
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Cys Tyr Leu Asp Glu Asn Ser Asn Val Thr Cys Lys Lys Trp Arg
1               5                   10                  15

<210> SEQ ID NO 185
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Cys Tyr Leu Asp Asp Asn Ser Asn Val Thr Cys Lys Lys Trp Arg
1               5                   10                  15

<210> SEQ ID NO 186
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Cys Tyr Leu Asp Glu Asn Ser Asn Val Val Cys Lys Lys Trp Arg
1               5                   10                  15

<210> SEQ ID NO 187
<211> LENGTH: 15
<212> TYPE: PRT
<213> ORGANISM: Artificial Sequence
<220> FEATURE:

-continued

```
<223> OTHER INFORMATION: Description of Artificial Sequence: Synthetic
      peptide

<400> SEQUENCE: 187

Cys Tyr Leu Asp Asp Asn Ser Asn Val Val Cys Lys Lys Trp Arg
1               5                   10                  15

<210> SEQ ID NO 188
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Cys Tyr Leu Asp Asp Asn Ser Gln Val Thr Cys Lys Lys Trp Arg
1               5                   10                  15

<210> SEQ ID NO 189
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Cys Tyr Leu Asp Glu Asn Ser Gln Val Val Cys Lys Lys Trp Arg
1               5                   10                  15

<210> SEQ ID NO 190
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Cys Tyr Leu Asp Glu Asn Ser Asn Val Val Cys Lys Gln Tyr Arg
1               5                   10                  15

<210> SEQ ID NO 191
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Cys Tyr Leu Asp Asp Asn Ser Asn Val Thr Cys Lys Gln Tyr Arg
1               5                   10                  15

<210> SEQ ID NO 192
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Cys Tyr Leu Asp Asp Asn Ser Gln Val Val Cys Lys Lys Trp Arg
1               5                   10                  15
```

<210> SEQ ID NO 193
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Cys Tyr Leu Asp Asp Asn Ser Asn Val Val Cys Lys Asn Tyr Arg
1               5                   10                  15

<210> SEQ ID NO 194
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Cys Tyr Leu Asp Asp Asn Ser Asn Val Val Cys Lys Gln Tyr Arg
1               5                   10                  15

<210> SEQ ID NO 195
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Cys Tyr Leu Asp Glu Asn Ser Gln Val Ile Cys Lys Gln Tyr Arg
1               5                   10                  15

<210> SEQ ID NO 196
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Cys Tyr Ala Asp Glu Asn Ser Asn Val Val Cys Lys Lys Trp Arg
1               5                   10                  15

<210> SEQ ID NO 197
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Cys Tyr Ala Asp Asp Asn Ser Asn Val Thr Cys Lys Lys Trp Arg
1               5                   10                  15

<210> SEQ ID NO 198
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

```
Cys Tyr Leu Asp Asp Asn Ser Gln Val Ile Cys Lys Asn Tyr Arg
1               5                   10                  15

<210> SEQ ID NO 199
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Cys Tyr Leu Asp Asp Asn Ser Gln Val Val Cys Lys Gln Tyr Arg
1               5                   10                  15

<210> SEQ ID NO 200
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Cys Tyr Leu Asp Asp Asn Ser Gln Val Ile Cys Lys Gln Tyr Arg
1               5                   10                  15

<210> SEQ ID NO 201
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Cys Tyr Ala Asp Asp Asn Ser Asn Val Val Cys Lys Lys Trp Arg
1               5                   10                  15

<210> SEQ ID NO 202
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Cys Tyr Leu Asp Glu Asn Asp Asn Val Val Cys Lys Lys Trp Arg
1               5                   10                  15

<210> SEQ ID NO 203
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Cys Tyr Leu Asp Asp Asn Asp Asn Val Thr Cys Lys Lys Trp Arg
1               5                   10                  15

<210> SEQ ID NO 204
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 204

Cys Tyr Ala Asp Asp Asn Ser Gln Val Val Cys Lys Lys Trp Arg
1               5                   10                  15

<210> SEQ ID NO 205
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Cys Tyr Ala Asp Asp Asn Ser Asn Val Val Cys Lys Gln Tyr Arg
1               5                   10                  15

<210> SEQ ID NO 206
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Cys Tyr Leu Asp Asp Asn Asp Asn Val Val Cys Lys Lys Trp Arg
1               5                   10                  15

<210> SEQ ID NO 207
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Cys Tyr Leu Asp Asp Asn Ser Asn Ile Ile Cys Lys Lys Trp Arg
1               5                   10                  15

<210> SEQ ID NO 208
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Cys Tyr Phe Asp Asp Ser Asn Asn Val Leu Cys Lys Lys Tyr Arg Ser
1               5                   10                  15

<210> SEQ ID NO 209
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Cys Tyr Phe Asp Asp Ser Ser Ser Val Leu Cys Lys Lys Tyr Arg Ser
1               5                   10                  15
```

<210> SEQ ID NO 210
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Cys Tyr Phe Asn Asp Ser Ser Asn Val Leu Cys Lys Lys Tyr Arg Ser
1               5                   10                  15

<210> SEQ ID NO 211
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Cys His Phe Asp Asp Ser Ser Asn Val Leu Cys Lys Lys Tyr Arg Ser
1               5                   10                  15

<210> SEQ ID NO 212
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Cys Tyr Phe Asp Asp Ser Ser Asn Val Leu Cys Lys Lys Tyr His Ser
1               5                   10                  15

<210> SEQ ID NO 213
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Cys Tyr Phe Asp Asp Ser Ser Asn Val Leu Cys Lys Lys Tyr Arg Asn
1               5                   10                  15

<210> SEQ ID NO 214
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Cys Tyr Phe Asp Asp Ser Ser Asn Val Leu Cys Lys Lys His Arg Ser
1               5                   10                  15

<210> SEQ ID NO 215
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 215

Cys Tyr Phe Asn Asp Ser Ser Gln Val Leu Cys Lys Lys His Arg Ser
1               5                   10                  15

<210> SEQ ID NO 216
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Cys Tyr Trp Asp Asp Ser Ser Asn Val Leu Cys Lys Lys Tyr Arg Ser
1               5                   10                  15

<210> SEQ ID NO 217
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Cys Tyr Tyr Asp Asp Ser Ser Asn Val Leu Cys Lys Lys Tyr Arg Ser
1               5                   10                  15

<210> SEQ ID NO 218
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Cys Tyr Phe Asp Asp Ser Ser Gln Val Leu Cys Lys Arg Tyr Arg Ser
1               5                   10                  15

<210> SEQ ID NO 219
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Cys Tyr Tyr Asp Asp Ser Ser Gln Val Leu Cys Lys Arg Tyr Arg Ser
1               5                   10                  15

<210> SEQ ID NO 220
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Cys Tyr Phe Asn Asp Ser Ser Asp Val Leu Cys Lys Lys Tyr Arg Ser
1               5                   10                  15

<210> SEQ ID NO 221
<211> LENGTH: 16
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 221

Cys Tyr Phe Asn Asp Ser Ser Gln Val Leu Cys Lys Arg Tyr Arg Ser
1               5                   10                  15

<210> SEQ ID NO 222
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 222

Cys Tyr Tyr Asp Asp Ser Ser Asn Val Leu Cys Lys Arg Tyr Arg Ser
1               5                   10                  15

<210> SEQ ID NO 223
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Cys Tyr Phe Asp Asp Ser Ser Asn Val Leu Cys Lys Lys Tyr Arg
1               5                   10                  15

<210> SEQ ID NO 224
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Cys Tyr Phe Asp Asp Ser Ser Asn Val Leu Cys Lys Lys Tyr
1               5                   10

<210> SEQ ID NO 225
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Lys Lys Tyr Arg Ser
1               5

<210> SEQ ID NO 226
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226
```

```
Lys Arg Tyr Arg Ser
1               5
```

<210> SEQ ID NO 227
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

```
Cys Tyr Phe Asp Asp Ser Ser Asn Cys Leu Ile Lys Lys Tyr Arg Ser
1               5                   10                  15
```

<210> SEQ ID NO 228
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

```
Cys Tyr Phe Asp Asp Ser Ser Asn Cys Leu Leu Lys Lys Tyr Arg Ser
1               5                   10                  15
```

<210> SEQ ID NO 229
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

```
Cys Tyr Phe Asn Asp Ser Ser Asn Cys Leu Leu Lys Lys Tyr Arg Ser
1               5                   10                  15
```

<210> SEQ ID NO 230
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

```
Cys Tyr Phe Asp Asn Ser Ser Asn Cys Leu Leu Lys Lys Tyr Arg Ser
1               5                   10                  15
```

<210> SEQ ID NO 231
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

```
Cys Tyr Phe Asn Asn Ser Ser Asn Cys Leu Leu Lys Lys Tyr Arg Ser
1               5                   10                  15
```

<210> SEQ ID NO 232
<211> LENGTH: 16
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 232

Cys Tyr Phe Asp Asp Ser Ser Gln Cys Leu Leu Lys Lys Tyr Arg Ser
1               5                   10                  15

<210> SEQ ID NO 233
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Cys Tyr Tyr Asp Asp Ser Ser Asn Cys Leu Leu Lys Lys Tyr Arg Ser
1               5                   10                  15

<210> SEQ ID NO 234
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Cys Tyr Phe Asp Asp Ser Thr Asn Cys Leu Leu Lys Lys Tyr Arg Ser
1               5                   10                  15

<210> SEQ ID NO 235
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Cys Tyr Phe Asp Asp Ser Ser Ser Cys Leu Leu Lys Lys Tyr Arg Ser
1               5                   10                  15

<210> SEQ ID NO 236
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Cys Tyr Phe Asp Asp Ser Ser Asn Cys Ala Leu Lys Lys Tyr Arg Ser
1               5                   10                  15

<210> SEQ ID NO 237
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Cys Tyr Phe Asp Asp Ser Ser Asn Cys Leu Leu Lys Arg Tyr Arg Ser
1               5                   10                  15
```

<210> SEQ ID NO 238
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Cys Tyr Phe Asp Asp Ser Ser Asn Cys Leu Leu Lys Lys Tyr Arg Asn
1               5                   10                  15

<210> SEQ ID NO 239
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Cys Tyr Phe Asp Asp Ser Ser Asn Cys Leu Leu Lys Lys Tyr Arg
1               5                   10                  15

<210> SEQ ID NO 240
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Cys Tyr Phe Asp Asp Ser Ser Asn Cys Leu Ala Lys Lys Tyr Arg Ser
1               5                   10                  15

<210> SEQ ID NO 241
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Cys Tyr Phe Asp Asp Ser Ser Asn Cys Leu Leu Lys Lys Tyr
1               5                   10

<210> SEQ ID NO 242
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 242

Cys Tyr Phe Asp Asp Ser Ser Asn Cys Leu Leu Lys Lys Tyr Arg Ser
1               5                   10                  15

<210> SEQ ID NO 243
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (10)..(10)
<223> OTHER INFORMATION: Nlu

<400> SEQUENCE: 243

Cys Tyr Phe Asp Asp Ser Ser Asn Val Xaa Cys Lys Lys Tyr Arg Ser
1               5                   10                  15

<210> SEQ ID NO 244
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Abu

<400> SEQUENCE: 244

Cys Tyr Phe Asp Asp Ser Ser Asn Val Xaa Cys Lys Lys Tyr Arg Ser
1               5                   10                  15

<210> SEQ ID NO 245
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Cys Tyr Phe Asp Asp Ser Ser Asn Val Leu Cys Ser Arg Tyr Lys Lys
1               5                   10                  15

<210> SEQ ID NO 246
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Cys Leu Val Asn Ser Ser Asp Asp Phe Tyr Cys Lys Lys Tyr Arg Ser
1               5                   10                  15

<210> SEQ ID NO 247
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Lys Lys Tyr Arg Ser Cys Leu Val Asn Ser Ser Asp Asp Phe Tyr Cys
1               5                   10                  15

<210> SEQ ID NO 248
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 248

Ser Arg Tyr Lys Lys Cys Tyr Phe Asp Asp Ser Ser Asn Val Leu Cys
1               5                   10                  15

<210> SEQ ID NO 249
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Ser Arg Tyr Lys Lys Cys Leu Val Asn Ser Ser Asp Asp Phe Tyr Cys
1               5                   10                  15

<210> SEQ ID NO 250
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(11)
<223> OTHER INFORMATION: Cyclic
<220> FEATURE:
<221> NAME/KEY: MOD_RES
<222> LOCATION: (1)..(1)
<223> OTHER INFORMATION: Des-Asp
<220> FEATURE:
<221> NAME/KEY: MOD_RES
<222> LOCATION: (11)..(11)
<223> OTHER INFORMATION: Dap

<400> SEQUENCE: 250

Asp Tyr Phe Asp Asp Ser Ser Asn Val Leu Xaa Lys Lys Tyr Arg Ser
1               5                   10                  15

<210> SEQ ID NO 251
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(11)
<223> OTHER INFORMATION: Cyclic
<220> FEATURE:
<221> NAME/KEY: MOD_RES
<222> LOCATION: (1)..(1)
<223> OTHER INFORMATION: Dap

<400> SEQUENCE: 251

Xaa Tyr Phe Asp Asp Ser Ser Asn Val Leu Asp Lys Lys Tyr Arg Ser
1               5                   10                  15

<210> SEQ ID NO 252
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(11)
<223> OTHER INFORMATION: Cyclic
```

```
<220> FEATURE:
<221> NAME/KEY: MOD_RES
<222> LOCATION: (1)..(1)
<223> OTHER INFORMATION: Des-amino-Asp
<220> FEATURE:
<221> NAME/KEY: MOD_RES
<222> LOCATION: (11)..(11)
<223> OTHER INFORMATION: Dap

<400> SEQUENCE: 252

Asp Tyr Phe Asp Asp Ser Ser Asn Val Leu Xaa Lys Lys Tyr Arg Ser
1               5                   10                  15

<210> SEQ ID NO 253
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(11)
<223> OTHER INFORMATION: Cyclic
<220> FEATURE:
<221> NAME/KEY: MOD_RES
<222> LOCATION: (1)..(1)
<223> OTHER INFORMATION: Dap

<400> SEQUENCE: 253

Xaa Tyr Phe Asp Asp Ser Ser Asn Val Leu Asp Lys Lys Tyr Arg Ser
1               5                   10                  15

<210> SEQ ID NO 254
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(11)
<223> OTHER INFORMATION: Cyclic
<220> FEATURE:
<221> NAME/KEY: MOD_RES
<222> LOCATION: (1)..(1)
<223> OTHER INFORMATION: Dpr

<400> SEQUENCE: 254

Xaa Tyr Phe Asp Asp Ser Ser Asn Val Leu Asp Lys Lys Tyr Arg Ser
1               5                   10                  15

<210> SEQ ID NO 255
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Tyr, Phe, Met, Ser, any alicyclic amino acid
      or any aromatic amino acid
<220> FEATURE:
<221> NAME/KEY: MOD_RES
<222> LOCATION: (4)..(5)
<223> OTHER INFORMATION: Asp, Asn, Glu, Gln, Ser or any beta-carbonyl
      amino acid
<220> FEATURE:
<221> NAME/KEY: MOD_RES
<222> LOCATION: (6)..(7)
```

```
<223> OTHER INFORMATION: Ser, Thr, Cys, Met, His or any beta-heteroatom
      amino acid
<220> FEATURE:
<221> NAME/KEY: MOD_RES
<222> LOCATION: (8)..(8)
<223> OTHER INFORMATION: Asp, Asn, Glu, Gln, Ser, Thr, Met, His or any
      polar amino acid
<220> FEATURE:
<221> NAME/KEY: MOD_RES
<222> LOCATION: (9)..(9)
<223> OTHER INFORMATION: Val, Ile, Thr, Leu, Ala, Gly, Met, Phe or any
      nonpolar amino acid
<220> FEATURE:
<221> NAME/KEY: MOD_RES
<222> LOCATION: (10)..(10)
<223> OTHER INFORMATION: Ile, Leu, Ala, Gly, Val, Met, Ser, Phe or any
      nonpolar amino acid
<220> FEATURE:
<221> NAME/KEY: MOD_RES
<222> LOCATION: (12)..(13)
<223> OTHER INFORMATION: Lys, Arg, His, Trp or any basic amino acid
<220> FEATURE:
<221> NAME/KEY: MOD_RES
<222> LOCATION: (14)..(14)
<223> OTHER INFORMATION: Tyr, Phe, His, Trp or any aromatic amino acid
<220> FEATURE:
<221> NAME/KEY: MOD_RES
<222> LOCATION: (15)..(15)
<223> OTHER INFORMATION: Arg, Lys, His, Trp or any basic amino acid
<220> FEATURE:
<221> NAME/KEY: MOD_RES
<222> LOCATION: (16)..(16)
<223> OTHER INFORMATION: Ser, Thr, Asp, Asn, Glu, Gln, any polar amino
      acid or absent

<400> SEQUENCE: 255

Cys Xaa Xaa Xaa Xaa Xaa Xaa Xaa Xaa Cys Xaa Xaa Xaa Xaa Xaa
1               5                   10                  15

<210> SEQ ID NO 256
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Tyr, Phe, Met, Ser, any alicyclic amino acid
      or any aromatic amino acid
<220> FEATURE:
<221> NAME/KEY: MOD_RES
<222> LOCATION: (7)..(7)
<223> OTHER INFORMATION: Ser, Thr, Cys, Met, His or any beta-heteroatom
      amino acid
<220> FEATURE:
<221> NAME/KEY: MOD_RES
<222> LOCATION: (8)..(8)
<223> OTHER INFORMATION: Asp, Asn, Glu, Gln, Ser, Thr, Met, His or any
      polar amino acid
<220> FEATURE:
<221> NAME/KEY: MOD_RES
<222> LOCATION: (9)..(9)
<223> OTHER INFORMATION: Val, Ile, Thr, Leu, Ala, Gly, Met, Phe or any
      nonpolar amino acid
<220> FEATURE:
<221> NAME/KEY: MOD_RES
<222> LOCATION: (10)..(10)
<223> OTHER INFORMATION: Ile, Leu, Ala, Gly, Val, Met, Ser, Phe or any
      nonpolar amino acid
<220> FEATURE:
<221> NAME/KEY: MOD_RES
<222> LOCATION: (13)..(13)
<223> OTHER INFORMATION: Lys, Arg, His, Trp or any basic amino acid
<220> FEATURE:
<221> NAME/KEY: MOD_RES
```

```
<222> LOCATION: (14)..(14)
<223> OTHER INFORMATION: Tyr, Phe, His, Trp or any aromatic amino acid
<220> FEATURE:
<221> NAME/KEY: MOD_RES
<222> LOCATION: (16)..(16)
<223> OTHER INFORMATION: Ser, Thr, Asp, Asn, Glu, Gln, any polar amino
      acid or absent

<400> SEQUENCE: 256

Cys Xaa Xaa Asp Asp Ser Xaa Xaa Xaa Xaa Cys Lys Xaa Xaa Arg Xaa
1               5                   10                  15

<210> SEQ ID NO 257
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Tyr, Phe, Met, Ser, any alicyclic amino acid
      or any aromatic amino acid
<220> FEATURE:
<221> NAME/KEY: MOD_RES
<222> LOCATION: (7)..(7)
<223> OTHER INFORMATION: Ser, Thr, Cys, Met, His or any beta-heteroatom
      amino acid
<220> FEATURE:
<221> NAME/KEY: MOD_RES
<222> LOCATION: (8)..(8)
<223> OTHER INFORMATION: Asp, Asn, Glu, Gln, Ser, Thr, Met, His or any
      polar amino acid
<220> FEATURE:
<221> NAME/KEY: MOD_RES
<222> LOCATION: (9)..(9)
<223> OTHER INFORMATION: Val, Ile, Thr, Leu, Ala, Gly, Met, Phe or any
      nonpolar amino acid
<220> FEATURE:
<221> NAME/KEY: MOD_RES
<222> LOCATION: (10)..(10)
<223> OTHER INFORMATION: Ile, Leu, Ala, Gly, Val, Met, Ser, Phe or any
      nonpolar amino acid
<220> FEATURE:
<221> NAME/KEY: MOD_RES
<222> LOCATION: (13)..(13)
<223> OTHER INFORMATION: Lys, Arg, His, Trp or any basic amino acid
<220> FEATURE:
<221> NAME/KEY: MOD_RES
<222> LOCATION: (14)..(14)
<223> OTHER INFORMATION: Tyr, Phe, His, Trp or any aromatic amino acid
<220> FEATURE:
<221> NAME/KEY: MOD_RES
<222> LOCATION: (16)..(16)
<223> OTHER INFORMATION: Ser, Thr, Asp, Asn, Glu, Gln, any polar amino
      acid or absent

<400> SEQUENCE: 257

Cys Xaa Xaa Asn Asp Ser Xaa Xaa Xaa Xaa Cys Lys Xaa Xaa Arg Xaa
1               5                   10                  15

<210> SEQ ID NO 258
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Tyr, Phe, Met, Ser, any alicyclic amino acid
      or any aromatic amino acid
<220> FEATURE:
```

<220> FEATURE:
<221> NAME/KEY: MOD_RES
<222> LOCATION: (7)..(7)
<223> OTHER INFORMATION: Ser, Thr, Cys, Met, His or any beta-heteroatom amino acid
<220> FEATURE:
<221> NAME/KEY: MOD_RES
<222> LOCATION: (8)..(8)
<223> OTHER INFORMATION: Asp, Asn, Glu, Gln, Ser, Thr, Met, His or any polar amino acid
<220> FEATURE:
<221> NAME/KEY: MOD_RES
<222> LOCATION: (9)..(9)
<223> OTHER INFORMATION: Val, Ile, Thr, Leu, Ala, Gly, Met, Phe or any nonpolar amino acid
<220> FEATURE:
<221> NAME/KEY: MOD_RES
<222> LOCATION: (10)..(10)
<223> OTHER INFORMATION: Ile, Leu, Ala, Gly, Val, Met, Ser, Phe or any nonpolar amino acid
<220> FEATURE:
<221> NAME/KEY: MOD_RES
<222> LOCATION: (13)..(13)
<223> OTHER INFORMATION: Lys, Arg, His, Trp or any basic amino acid
<220> FEATURE:
<221> NAME/KEY: MOD_RES
<222> LOCATION: (14)..(14)
<223> OTHER INFORMATION: Tyr, Phe, His, Trp or any aromatic amino acid
<220> FEATURE:
<221> NAME/KEY: MOD_RES
<222> LOCATION: (16)..(16)
<223> OTHER INFORMATION: Ser, Thr, Asp, Asn, Glu, Gln, any polar amino acid or absent

<400> SEQUENCE: 258

Cys Xaa Xaa Asp Asn Ser Xaa Xaa Xaa Xaa Cys Lys Xaa Xaa Arg Xaa
1               5                   10                  15

<210> SEQ ID NO 259
<211> LENGTH: 16
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(3)
<223> OTHER INFORMATION: Tyr, Phe, Met, Ser, any alicyclic amino acid or any aromatic amino acid
<220> FEATURE:
<221> NAME/KEY: MOD_RES
<222> LOCATION: (7)..(7)
<223> OTHER INFORMATION: Ser, Thr, Cys, Met, His or any beta-heteroatom amino acid
<220> FEATURE:
<221> NAME/KEY: MOD_RES
<222> LOCATION: (8)..(8)
<223> OTHER INFORMATION: Asp, Asn, Glu, Gln, Ser, Thr, Met, His or any polar amino acid
<220> FEATURE:
<221> NAME/KEY: MOD_RES
<222> LOCATION: (9)..(9)
<223> OTHER INFORMATION: Val, Ile, Thr, Leu, Ala, Gly, Met, Phe or any nonpolar amino acid
<220> FEATURE:
<221> NAME/KEY: MOD_RES
<222> LOCATION: (10)..(10)
<223> OTHER INFORMATION: Ile, Leu, Ala, Gly, Val, Met, Ser, Phe or any nonpolar amino acid
<220> FEATURE:
<221> NAME/KEY: MOD_RES
<222> LOCATION: (13)..(13)
<223> OTHER INFORMATION: Lys, Arg, His, Trp or any basic amino acid
<220> FEATURE:
<221> NAME/KEY: MOD_RES
<222> LOCATION: (14)..(14)
<223> OTHER INFORMATION: Tyr, Phe, His, Trp or any aromatic amino acid

```
<220> FEATURE:
<221> NAME/KEY: MOD_RES
<222> LOCATION: (16)..(16)
<223> OTHER INFORMATION: Ser, Thr, Asp, Asn, Glu, Gln, any polar amino
      acid or absent

<400> SEQUENCE: 259

Cys Xaa Xaa Asn Asn Ser Xaa Xaa Xaa Xaa Cys Lys Xaa Xaa Arg Xaa
1               5                   10                  15

<210> SEQ ID NO 260
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr, Phe, Met, Ser, any alicyclic amino acid
      or any aromatic amino acid
<220> FEATURE:
<221> NAME/KEY: MOD_RES
<222> LOCATION: (7)..(7)
<223> OTHER INFORMATION: Ser, Thr, Cys, Met, His or any beta-heteroatom
      amino acid
<220> FEATURE:
<221> NAME/KEY: MOD_RES
<222> LOCATION: (8)..(8)
<223> OTHER INFORMATION: Asp, Asn, Glu, Gln, Ser, Thr, Met, His or any
      polar amino acid
<220> FEATURE:
<221> NAME/KEY: MOD_RES
<222> LOCATION: (9)..(9)
<223> OTHER INFORMATION: Val, Ile, Thr, Leu, Ala, Gly, Met, Phe or any
      nonpolar amino acid
<220> FEATURE:
<221> NAME/KEY: MOD_RES
<222> LOCATION: (10)..(10)
<223> OTHER INFORMATION: Ile, Leu, Ala, Gly, Val, Met, Ser, Phe or any
      nonpolar amino acid
<220> FEATURE:
<221> NAME/KEY: MOD_RES
<222> LOCATION: (13)..(13)
<223> OTHER INFORMATION: Lys, Arg, His, Trp or any basic amino acid
<220> FEATURE:
<221> NAME/KEY: MOD_RES
<222> LOCATION: (16)..(16)
<223> OTHER INFORMATION: Ser, Thr, Asp, Asn, Glu, Gln, any polar amino
      acid or absent

<400> SEQUENCE: 260

Cys Tyr Xaa Asp Asp Ser Xaa Xaa Xaa Xaa Cys Lys Xaa Tyr Arg Xaa
1               5                   10                  15

<210> SEQ ID NO 261
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr, Phe, Met, Ser, any alicyclic amino acid
      or any aromatic amino acid
<220> FEATURE:
<221> NAME/KEY: MOD_RES
<222> LOCATION: (7)..(7)
<223> OTHER INFORMATION: Ser, Thr, Cys, Met, His or any beta-heteroatom
      amino acid
<220> FEATURE:
<221> NAME/KEY: MOD_RES
```

```
<222> LOCATION: (8)..(8)
<223> OTHER INFORMATION: Asp, Asn, Glu, Gln, Ser, Thr, Met, His or any
      polar amino acid
<220> FEATURE:
<221> NAME/KEY: MOD_RES
<222> LOCATION: (9)..(9)
<223> OTHER INFORMATION: Val, Ile, Thr, Leu, Ala, Gly, Met, Phe or any
      nonpolar amino acid
<220> FEATURE:
<221> NAME/KEY: MOD_RES
<222> LOCATION: (10)..(10)
<223> OTHER INFORMATION: Ile, Leu, Ala, Gly, Val, Met, Ser, Phe or any
      nonpolar amino acid
<220> FEATURE:
<221> NAME/KEY: MOD_RES
<222> LOCATION: (13)..(13)
<223> OTHER INFORMATION: Lys, Arg, His, Trp or any basic amino acid
<220> FEATURE:
<221> NAME/KEY: MOD_RES
<222> LOCATION: (16)..(16)
<223> OTHER INFORMATION: Ser, Thr, Asp, Asn, Glu, Gln, any polar amino
      acid or absent

<400> SEQUENCE: 261

Cys Tyr Xaa Asn Asp Ser Xaa Xaa Xaa Xaa Cys Lys Xaa Tyr Arg Xaa
1               5                   10                  15

<210> SEQ ID NO 262
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr, Phe, Met, Ser, any alicyclic amino acid
      or any aromatic amino acid
<220> FEATURE:
<221> NAME/KEY: MOD_RES
<222> LOCATION: (7)..(7)
<223> OTHER INFORMATION: Ser, Thr, Cys, Met, His or any beta-heteroatom
      amino acid
<220> FEATURE:
<221> NAME/KEY: MOD_RES
<222> LOCATION: (8)..(8)
<223> OTHER INFORMATION: Asp, Asn, Glu, Gln, Ser, Thr, Met, His or any
      polar amino acid
<220> FEATURE:
<221> NAME/KEY: MOD_RES
<222> LOCATION: (9)..(9)
<223> OTHER INFORMATION: Val, Ile, Thr, Leu, Ala, Gly, Met, Phe or any
      nonpolar amino acid
<220> FEATURE:
<221> NAME/KEY: MOD_RES
<222> LOCATION: (10)..(10)
<223> OTHER INFORMATION: Ile, Leu, Ala, Gly, Val, Met, Ser, Phe or any
      nonpolar amino acid
<220> FEATURE:
<221> NAME/KEY: MOD_RES
<222> LOCATION: (13)..(13)
<223> OTHER INFORMATION: Lys, Arg, His, Trp or any basic amino acid
<220> FEATURE:
<221> NAME/KEY: MOD_RES
<222> LOCATION: (16)..(16)
<223> OTHER INFORMATION: Ser, Thr, Asp, Asn, Glu, Gln, any polar amino
      acid or absent

<400> SEQUENCE: 262

Cys Tyr Xaa Asp Asn Ser Xaa Xaa Xaa Xaa Cys Lys Xaa Tyr Arg Xaa
1               5                   10                  15

<210> SEQ ID NO 263
<211> LENGTH: 16
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr, Phe, Met, Ser, any alicyclic amino acid
      or any aromatic amino acid
<220> FEATURE:
<221> NAME/KEY: MOD_RES
<222> LOCATION: (7)..(7)
<223> OTHER INFORMATION: Ser, Thr, Cys, Met, His or any beta-heteroatom
      amino acid
<220> FEATURE:
<221> NAME/KEY: MOD_RES
<222> LOCATION: (8)..(8)
<223> OTHER INFORMATION: Asp, Asn, Glu, Gln, Ser, Thr, Met, His or any
      polar amino acid
<220> FEATURE:
<221> NAME/KEY: MOD_RES
<222> LOCATION: (9)..(9)
<223> OTHER INFORMATION: Val, Ile, Thr, Leu, Ala, Gly, Met, Phe or any
      nonpolar amino acid
<220> FEATURE:
<221> NAME/KEY: MOD_RES
<222> LOCATION: (10)..(10)
<223> OTHER INFORMATION: Ile, Leu, Ala, Gly, Val, Met, Ser, Phe or any
      nonpolar amino acid
<220> FEATURE:
<221> NAME/KEY: MOD_RES
<222> LOCATION: (13)..(13)
<223> OTHER INFORMATION: Lys, Arg, His, Trp or any basic amino acid
<220> FEATURE:
<221> NAME/KEY: MOD_RES
<222> LOCATION: (16)..(16)
<223> OTHER INFORMATION: Ser, Thr, Asp, Asn, Glu, Gln, any polar amino
      acid or absent

<400> SEQUENCE: 263

Cys Tyr Xaa Asn Asn Ser Xaa Xaa Xaa Xaa Cys Lys Xaa Tyr Arg Xaa
 1               5                  10                  15

<210> SEQ ID NO 264
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Tyr, Phe, Met, Ser, any alicyclic amino acid
      or any aromatic amino acid
<220> FEATURE:
<221> NAME/KEY: MOD_RES
<222> LOCATION: (8)..(8)
<223> OTHER INFORMATION: Asp, Asn, Glu, Gln, Ser, Thr, Met, His or any
      polar amino acid
<220> FEATURE:
<221> NAME/KEY: MOD_RES
<222> LOCATION: (9)..(9)
<223> OTHER INFORMATION: Val, Ile, Thr, Leu, Ala, Gly, Met, Phe or any
      nonpolar amino acid
<220> FEATURE:
<221> NAME/KEY: MOD_RES
<222> LOCATION: (10)..(10)
<223> OTHER INFORMATION: Ile, Leu, Ala, Gly, Val, Met, Ser, Phe or any
      nonpolar amino acid
<220> FEATURE:
<221> NAME/KEY: MOD_RES
<222> LOCATION: (13)..(13)
<223> OTHER INFORMATION: Lys, Arg, His, Trp or any basic amino acid
<220> FEATURE:
<221> NAME/KEY: MOD_RES
```

```
<222> LOCATION: (14)..(14)
<223> OTHER INFORMATION: Tyr, Phe, His, Trp or any aromatic amino acid
<220> FEATURE:
<221> NAME/KEY: MOD_RES
<222> LOCATION: (16)..(16)
<223> OTHER INFORMATION: Ser, Thr, Asp, Asn, Glu, Gln, any polar amino
      acid or absent

<400> SEQUENCE: 264

Cys Xaa Xaa Asp Asp Ser Ser Xaa Xaa Xaa Cys Lys Xaa Xaa Arg Xaa
1               5                   10                  15

<210> SEQ ID NO 265
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Tyr, Phe, Met, Ser, any alicyclic amino acid
      or any aromatic amino acid
<220> FEATURE:
<221> NAME/KEY: MOD_RES
<222> LOCATION: (8)..(8)
<223> OTHER INFORMATION: Asp, Asn, Glu, Gln, Ser, Thr, Met, His or any
      polar amino acid
<220> FEATURE:
<221> NAME/KEY: MOD_RES
<222> LOCATION: (9)..(9)
<223> OTHER INFORMATION: Val, Ile, Thr, Leu, Ala, Gly, Met, Phe or any
      nonpolar amino acid
<220> FEATURE:
<221> NAME/KEY: MOD_RES
<222> LOCATION: (10)..(10)
<223> OTHER INFORMATION: Ile, Leu, Ala, Gly, Val, Met, Ser, Phe or any
      nonpolar amino acid
<220> FEATURE:
<221> NAME/KEY: MOD_RES
<222> LOCATION: (13)..(13)
<223> OTHER INFORMATION: Lys, Arg, His, Trp or any basic amino acid
<220> FEATURE:
<221> NAME/KEY: MOD_RES
<222> LOCATION: (14)..(14)
<223> OTHER INFORMATION: Tyr, Phe, His, Trp or any aromatic amino acid
<220> FEATURE:
<221> NAME/KEY: MOD_RES
<222> LOCATION: (16)..(16)
<223> OTHER INFORMATION: Ser, Thr, Asp, Asn, Glu, Gln, any polar amino
      acid or absent

<400> SEQUENCE: 265

Cys Xaa Xaa Asn Asp Ser Ser Xaa Xaa Xaa Cys Lys Xaa Xaa Arg Xaa
1               5                   10                  15

<210> SEQ ID NO 266
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Tyr, Phe, Met, Ser, any alicyclic amino acid
      or any aromatic amino acid
<220> FEATURE:
<221> NAME/KEY: MOD_RES
<222> LOCATION: (8)..(8)
<223> OTHER INFORMATION: Asp, Asn, Glu, Gln, Ser, Thr, Met, His or any
      polar amino acid
<220> FEATURE:
```

```
<221> NAME/KEY: MOD_RES
<222> LOCATION: (9)..(9)
<223> OTHER INFORMATION: Val, Ile, Thr, Leu, Ala, Gly, Met, Phe or any
      nonpolar amino acid
<220> FEATURE:
<221> NAME/KEY: MOD_RES
<222> LOCATION: (10)..(10)
<223> OTHER INFORMATION: Ile, Leu, Ala, Gly, Val, Met, Ser, Phe or any
      nonpolar amino acid
<220> FEATURE:
<221> NAME/KEY: MOD_RES
<222> LOCATION: (13)..(13)
<223> OTHER INFORMATION: Lys, Arg, His, Trp or any basic amino acid
<220> FEATURE:
<221> NAME/KEY: MOD_RES
<222> LOCATION: (14)..(14)
<223> OTHER INFORMATION: Tyr, Phe, His, Trp or any aromatic amino acid
<220> FEATURE:
<221> NAME/KEY: MOD_RES
<222> LOCATION: (16)..(16)
<223> OTHER INFORMATION: Ser, Thr, Asp, Asn, Glu, Gln, any polar amino
      acid or absent

<400> SEQUENCE: 266

Cys Xaa Xaa Asp Asn Ser Ser Xaa Xaa Xaa Cys Lys Xaa Xaa Arg Xaa
1               5                   10                  15

<210> SEQ ID NO 267
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Tyr, Phe, Met, Ser, any alicyclic amino acid
      or any aromatic amino acid
<220> FEATURE:
<221> NAME/KEY: MOD_RES
<222> LOCATION: (8)..(8)
<223> OTHER INFORMATION: Asp, Asn, Glu, Gln, Ser, Thr, Met, His or any
      polar amino acid
<220> FEATURE:
<221> NAME/KEY: MOD_RES
<222> LOCATION: (9)..(9)
<223> OTHER INFORMATION: Val, Ile, Thr, Leu, Ala, Gly, Met, Phe or any
      nonpolar amino acid
<220> FEATURE:
<221> NAME/KEY: MOD_RES
<222> LOCATION: (10)..(10)
<223> OTHER INFORMATION: Ile, Leu, Ala, Gly, Val, Met, Ser, Phe or any
      nonpolar amino acid
<220> FEATURE:
<221> NAME/KEY: MOD_RES
<222> LOCATION: (13)..(13)
<223> OTHER INFORMATION: Lys, Arg, His, Trp or any basic amino acid
<220> FEATURE:
<221> NAME/KEY: MOD_RES
<222> LOCATION: (14)..(14)
<223> OTHER INFORMATION: Tyr, Phe, His, Trp or any aromatic amino acid
<220> FEATURE:
<221> NAME/KEY: MOD_RES
<222> LOCATION: (16)..(16)
<223> OTHER INFORMATION: Ser, Thr, Asp, Asn, Glu, Gln, any polar amino
      acid or absent

<400> SEQUENCE: 267

Cys Xaa Xaa Asn Asn Ser Ser Xaa Xaa Xaa Cys Lys Xaa Xaa Arg Xaa
1               5                   10                  15

<210> SEQ ID NO 268
<211> LENGTH: 16
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr, Phe, Met, Ser, any alicyclic amino acid
      or any aromatic amino acid
<220> FEATURE:
<221> NAME/KEY: MOD_RES
<222> LOCATION: (8)..(8)
<223> OTHER INFORMATION: Asp, Asn, Glu, Gln, Ser, Thr, Met, His or any
      polar amino acid
<220> FEATURE:
<221> NAME/KEY: MOD_RES
<222> LOCATION: (9)..(9)
<223> OTHER INFORMATION: Val, Ile, Thr, Leu, Ala, Gly, Met, Phe or any
      nonpolar amino acid
<220> FEATURE:
<221> NAME/KEY: MOD_RES
<222> LOCATION: (10)..(10)
<223> OTHER INFORMATION: Ile, Leu, Ala, Gly, Val, Met, Ser, Phe or any
      nonpolar amino acid
<220> FEATURE:
<221> NAME/KEY: MOD_RES
<222> LOCATION: (13)..(13)
<223> OTHER INFORMATION: Lys, Arg, His, Trp or any basic amino acid
<220> FEATURE:
<221> NAME/KEY: MOD_RES
<222> LOCATION: (16)..(16)
<223> OTHER INFORMATION: Ser, Thr, Asp, Asn, Glu, Gln, any polar amino
      acid or absent

<400> SEQUENCE: 268

Cys Tyr Xaa Asp Asp Ser Ser Xaa Xaa Xaa Cys Lys Xaa Tyr Arg Xaa
1               5                   10                  15

<210> SEQ ID NO 269
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr, Phe, Met, Ser, any alicyclic amino acid
      or any aromatic amino acid
<220> FEATURE:
<221> NAME/KEY: MOD_RES
<222> LOCATION: (8)..(8)
<223> OTHER INFORMATION: Asp, Asn, Glu, Gln, Ser, Thr, Met, His or any
      polar amino acid
<220> FEATURE:
<221> NAME/KEY: MOD_RES
<222> LOCATION: (9)..(9)
<223> OTHER INFORMATION: Val, Ile, Thr, Leu, Ala, Gly, Met, Phe or any
      nonpolar amino acid
<220> FEATURE:
<221> NAME/KEY: MOD_RES
<222> LOCATION: (10)..(10)
<223> OTHER INFORMATION: Ile, Leu, Ala, Gly, Val, Met, Ser, Phe or any
      nonpolar amino acid
<220> FEATURE:
<221> NAME/KEY: MOD_RES
<222> LOCATION: (13)..(13)
<223> OTHER INFORMATION: Lys, Arg, His, Trp or any basic amino acid
<220> FEATURE:
<221> NAME/KEY: MOD_RES
<222> LOCATION: (16)..(16)
<223> OTHER INFORMATION: Ser, Thr, Asp, Asn, Glu, Gln, any polar amino
      acid or absent

<400> SEQUENCE: 269
```

```
Cys Tyr Xaa Asn Asp Ser Ser Xaa Xaa Xaa Cys Lys Xaa Tyr Arg Xaa
1               5                   10                  15
```

<210> SEQ ID NO 270
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr, Phe, Met, Ser, any alicyclic amino acid
      or any aromatic amino acid
<220> FEATURE:
<221> NAME/KEY: MOD_RES
<222> LOCATION: (8)..(8)
<223> OTHER INFORMATION: Asp, Asn, Glu, Gln, Ser, Thr, Met, His or any
      polar amino acid
<220> FEATURE:
<221> NAME/KEY: MOD_RES
<222> LOCATION: (9)..(9)
<223> OTHER INFORMATION: Val, Ile, Thr, Leu, Ala, Gly, Met, Phe or any
      nonpolar amino acid
<220> FEATURE:
<221> NAME/KEY: MOD_RES
<222> LOCATION: (10)..(10)
<223> OTHER INFORMATION: Ile, Leu, Ala, Gly, Val, Met, Ser, Phe or any
      nonpolar amino acid
<220> FEATURE:
<221> NAME/KEY: MOD_RES
<222> LOCATION: (13)..(13)
<223> OTHER INFORMATION: Lys, Arg, His, Trp or any basic amino acid
<220> FEATURE:
<221> NAME/KEY: MOD_RES
<222> LOCATION: (16)..(16)
<223> OTHER INFORMATION: Ser, Thr, Asp, Asn, Glu, Gln, any polar amino
      acid or absent

<400> SEQUENCE: 270

```
Cys Tyr Xaa Asp Asn Ser Ser Xaa Xaa Xaa Cys Lys Xaa Tyr Arg Xaa
1               5                   10                  15
```

<210> SEQ ID NO 271
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr, Phe, Met, Ser, any alicyclic amino acid
      or any aromatic amino acid
<220> FEATURE:
<221> NAME/KEY: MOD_RES
<222> LOCATION: (8)..(8)
<223> OTHER INFORMATION: Asp, Asn, Glu, Gln, Ser, Thr, Met, His or any
      polar amino acid
<220> FEATURE:
<221> NAME/KEY: MOD_RES
<222> LOCATION: (9)..(9)
<223> OTHER INFORMATION: Val, Ile, Thr, Leu, Ala, Gly, Met, Phe or any
      nonpolar amino acid
<220> FEATURE:
<221> NAME/KEY: MOD_RES
<222> LOCATION: (10)..(10)
<223> OTHER INFORMATION: Ile, Leu, Ala, Gly, Val, Met, Ser, Phe or any
      nonpolar amino acid
<220> FEATURE:
<221> NAME/KEY: MOD_RES
<222> LOCATION: (13)..(13)
<223> OTHER INFORMATION: Lys, Arg, His, Trp or any basic amino acid
<220> FEATURE:

```
<221> NAME/KEY: MOD_RES
<222> LOCATION: (16)..(16)
<223> OTHER INFORMATION: Ser, Thr, Asp, Asn, Glu, Gln, any polar amino
      acid or absent

<400> SEQUENCE: 271

Cys Tyr Xaa Asn Asn Ser Ser Xaa Xaa Xaa Cys Lys Xaa Tyr Arg Xaa
1               5                   10                  15

<210> SEQ ID NO 272
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Tyr, Phe or any aromatic amino acid
<220> FEATURE:
<221> NAME/KEY: MOD_RES
<222> LOCATION: (4)..(5)
<223> OTHER INFORMATION: Asp, Asn or any beta-carbonyl amino acid
<220> FEATURE:
<221> NAME/KEY: MOD_RES
<222> LOCATION: (6)..(7)
<223> OTHER INFORMATION: Ser, Thr or any beta-heteroatom amino acid
<220> FEATURE:
<221> NAME/KEY: MOD_RES
<222> LOCATION: (8)..(8)
<223> OTHER INFORMATION: Asn, Gln, Ser, Thr, or any polar amino acid
<220> FEATURE:
<221> NAME/KEY: MOD_RES
<222> LOCATION: (9)..(9)
<223> OTHER INFORMATION: Val, Ile, Leu, Ala or any nonpolar amino acid
<220> FEATURE:
<221> NAME/KEY: MOD_RES
<222> LOCATION: (10)..(10)
<223> OTHER INFORMATION: Ile, Leu, Ala, Gly or any nonpolar amino acid
<220> FEATURE:
<221> NAME/KEY: MOD_RES
<222> LOCATION: (12)..(13)
<223> OTHER INFORMATION: Lys, Arg or any basic amino acid
<220> FEATURE:
<221> NAME/KEY: MOD_RES
<222> LOCATION: (14)..(14)
<223> OTHER INFORMATION: Tyr, Phe or any aromatic amino acid
<220> FEATURE:
<221> NAME/KEY: MOD_RES
<222> LOCATION: (15)..(15)
<223> OTHER INFORMATION: Arg, Lys or any basic amino acid
<220> FEATURE:
<221> NAME/KEY: MOD_RES
<222> LOCATION: (16)..(16)
<223> OTHER INFORMATION: Ser, Thr, Asn, Gln, any polar amino acid or
      absent

<400> SEQUENCE: 272

Cys Xaa Xaa Xaa Xaa Xaa Xaa Xaa Xaa Xaa Cys Xaa Xaa Xaa Xaa Xaa
1               5                   10                  15

<210> SEQ ID NO 273
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Tyr, Phe or any aromatic amino acid
<220> FEATURE:
<221> NAME/KEY: MOD_RES
```

```
<222> LOCATION: (7)..(7)
<223> OTHER INFORMATION: Ser, Thr or any beta-heteroatom amino acid
<220> FEATURE:
<221> NAME/KEY: MOD_RES
<222> LOCATION: (8)..(8)
<223> OTHER INFORMATION: Asn, Gln, Ser, Thr, or any polar amino acid
<220> FEATURE:
<221> NAME/KEY: MOD_RES
<222> LOCATION: (9)..(9)
<223> OTHER INFORMATION: Val, Ile, Leu, Ala or any nonpolar amino acid
<220> FEATURE:
<221> NAME/KEY: MOD_RES
<222> LOCATION: (10)..(10)
<223> OTHER INFORMATION: Ile, Leu, Ala, Gly or any nonpolar amino acid
<220> FEATURE:
<221> NAME/KEY: MOD_RES
<222> LOCATION: (13)..(13)
<223> OTHER INFORMATION: Lys, Arg or any basic amino acid
<220> FEATURE:
<221> NAME/KEY: MOD_RES
<222> LOCATION: (14)..(14)
<223> OTHER INFORMATION: Tyr, Phe or any aromatic amino acid
<220> FEATURE:
<221> NAME/KEY: MOD_RES
<222> LOCATION: (16)..(16)
<223> OTHER INFORMATION: Ser, Thr, Asn, Gln, any polar amino acid or
      absent

<400> SEQUENCE: 273

Cys Xaa Xaa Asp Asp Ser Xaa Xaa Xaa Xaa Cys Lys Xaa Xaa Arg Xaa
1               5                   10                  15

<210> SEQ ID NO 274
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Tyr, Phe or any aromatic amino acid
<220> FEATURE:
<221> NAME/KEY: MOD_RES
<222> LOCATION: (7)..(7)
<223> OTHER INFORMATION: Ser, Thr or any beta-heteroatom amino acid
<220> FEATURE:
<221> NAME/KEY: MOD_RES
<222> LOCATION: (8)..(8)
<223> OTHER INFORMATION: Asn, Gln, Ser, Thr, or any polar amino acid
<220> FEATURE:
<221> NAME/KEY: MOD_RES
<222> LOCATION: (9)..(9)
<223> OTHER INFORMATION: Val, Ile, Leu, Ala or any nonpolar amino acid
<220> FEATURE:
<221> NAME/KEY: MOD_RES
<222> LOCATION: (10)..(10)
<223> OTHER INFORMATION: Ile, Leu, Ala, Gly or any nonpolar amino acid
<220> FEATURE:
<221> NAME/KEY: MOD_RES
<222> LOCATION: (13)..(13)
<223> OTHER INFORMATION: Lys, Arg or any basic amino acid
<220> FEATURE:
<221> NAME/KEY: MOD_RES
<222> LOCATION: (14)..(14)
<223> OTHER INFORMATION: Tyr, Phe or any aromatic amino acid
<220> FEATURE:
<221> NAME/KEY: MOD_RES
<222> LOCATION: (16)..(16)
<223> OTHER INFORMATION: Ser, Thr, Asn, Gln, any polar amino acid or
      absent

<400> SEQUENCE: 274

Cys Xaa Xaa Asn Asp Ser Xaa Xaa Xaa Xaa Cys Lys Xaa Xaa Arg Xaa
1               5                   10                  15
```

```
<210> SEQ ID NO 275
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Tyr, Phe or any aromatic amino acid
<220> FEATURE:
<221> NAME/KEY: MOD_RES
<222> LOCATION: (7)..(7)
<223> OTHER INFORMATION: Ser, Thr or any beta-heteroatom amino acid
<220> FEATURE:
<221> NAME/KEY: MOD_RES
<222> LOCATION: (8)..(8)
<223> OTHER INFORMATION: Asn, Gln, Ser, Thr, or any polar amino acid
<220> FEATURE:
<221> NAME/KEY: MOD_RES
<222> LOCATION: (9)..(9)
<223> OTHER INFORMATION: Val, Ile, Leu, Ala or any nonpolar amino acid
<220> FEATURE:
<221> NAME/KEY: MOD_RES
<222> LOCATION: (10)..(10)
<223> OTHER INFORMATION: Ile, Leu, Ala, Gly or any nonpolar amino acid
<220> FEATURE:
<221> NAME/KEY: MOD_RES
<222> LOCATION: (13)..(13)
<223> OTHER INFORMATION: Lys, Arg or any basic amino acid
<220> FEATURE:
<221> NAME/KEY: MOD_RES
<222> LOCATION: (14)..(14)
<223> OTHER INFORMATION: Tyr, Phe or any aromatic amino acid
<220> FEATURE:
<221> NAME/KEY: MOD_RES
<222> LOCATION: (16)..(16)
<223> OTHER INFORMATION: Ser, Thr, Asn, Gln, any polar amino acid or
      absent

<400> SEQUENCE: 275

Cys Xaa Xaa Asp Asn Ser Xaa Xaa Xaa Xaa Cys Lys Xaa Xaa Arg Xaa
1               5                   10                  15

<210> SEQ ID NO 276
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Tyr, Phe or any aromatic amino acid
<220> FEATURE:
<221> NAME/KEY: MOD_RES
<222> LOCATION: (7)..(7)
<223> OTHER INFORMATION: Ser, Thr or any beta-heteroatom amino acid
<220> FEATURE:
<221> NAME/KEY: MOD_RES
<222> LOCATION: (8)..(8)
<223> OTHER INFORMATION: Asn, Gln, Ser, Thr, or any polar amino acid
<220> FEATURE:
<221> NAME/KEY: MOD_RES
<222> LOCATION: (9)..(9)
<223> OTHER INFORMATION: Val, Ile, Leu, Ala or any nonpolar amino acid
<220> FEATURE:
<221> NAME/KEY: MOD_RES
<222> LOCATION: (10)..(10)
<223> OTHER INFORMATION: Ile, Leu, Ala, Gly or any nonpolar amino acid
<220> FEATURE:
<221> NAME/KEY: MOD_RES
<222> LOCATION: (13)..(13)
```

```
<223> OTHER INFORMATION: Lys, Arg or any basic amino acid
<220> FEATURE:
<221> NAME/KEY: MOD_RES
<222> LOCATION: (14)..(14)
<223> OTHER INFORMATION: Tyr, Phe or any aromatic amino acid
<220> FEATURE:
<221> NAME/KEY: MOD_RES
<222> LOCATION: (16)..(16)
<223> OTHER INFORMATION: Ser, Thr, Asn, Gln, any polar amino acid or
      absent

<400> SEQUENCE: 276

Cys Xaa Xaa Asn Asn Ser Xaa Xaa Xaa Xaa Cys Lys Xaa Xaa Arg Xaa
1               5                   10                  15

<210> SEQ ID NO 277
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr, Phe or any aromatic amino acid
<220> FEATURE:
<221> NAME/KEY: MOD_RES
<222> LOCATION: (7)..(7)
<223> OTHER INFORMATION: Ser, Thr or any beta-heteroatom amino acid
<220> FEATURE:
<221> NAME/KEY: MOD_RES
<222> LOCATION: (8)..(8)
<223> OTHER INFORMATION: Asn, Gln, Ser, Thr, or any polar amino acid
<220> FEATURE:
<221> NAME/KEY: MOD_RES
<222> LOCATION: (9)..(9)
<223> OTHER INFORMATION: Val, Ile, Leu, Ala or any nonpolar amino acid
<220> FEATURE:
<221> NAME/KEY: MOD_RES
<222> LOCATION: (10)..(10)
<223> OTHER INFORMATION: Ile, Leu, Ala, Gly or any nonpolar amino acid
<220> FEATURE:
<221> NAME/KEY: MOD_RES
<222> LOCATION: (13)..(13)
<223> OTHER INFORMATION: Lys, Arg or any basic amino acid
<220> FEATURE:
<221> NAME/KEY: MOD_RES
<222> LOCATION: (16)..(16)
<223> OTHER INFORMATION: Ser, Thr, Asn, Gln, any polar amino acid or
      absent

<400> SEQUENCE: 277

Cys Tyr Xaa Asp Asp Ser Xaa Xaa Xaa Xaa Cys Lys Xaa Tyr Arg Xaa
1               5                   10                  15

<210> SEQ ID NO 278
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr, Phe or any aromatic amino acid
<220> FEATURE:
<221> NAME/KEY: MOD_RES
<222> LOCATION: (7)..(7)
<223> OTHER INFORMATION: Ser, Thr or any beta-heteroatom amino acid
<220> FEATURE:
<221> NAME/KEY: MOD_RES
<222> LOCATION: (8)..(8)
<223> OTHER INFORMATION: Asn, Gln, Ser, Thr, or any polar amino acid
```

```
<220> FEATURE:
<221> NAME/KEY: MOD_RES
<222> LOCATION: (9)..(9)
<223> OTHER INFORMATION: Val, Ile, Leu, Ala or any nonpolar amino acid
<220> FEATURE:
<221> NAME/KEY: MOD_RES
<222> LOCATION: (10)..(10)
<223> OTHER INFORMATION: Ile, Leu, Ala, Gly or any nonpolar amino acid
<220> FEATURE:
<221> NAME/KEY: MOD_RES
<222> LOCATION: (13)..(13)
<223> OTHER INFORMATION: Lys, Arg or any basic amino acid
<220> FEATURE:
<221> NAME/KEY: MOD_RES
<222> LOCATION: (16)..(16)
<223> OTHER INFORMATION: Ser, Thr, Asn, Gln, any polar amino acid or
      absent

<400> SEQUENCE: 278

Cys Tyr Xaa Asn Asp Ser Xaa Xaa Xaa Xaa Cys Lys Xaa Tyr Arg Xaa
1               5                   10                  15

<210> SEQ ID NO 279
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr, Phe or any aromatic amino acid
<220> FEATURE:
<221> NAME/KEY: MOD_RES
<222> LOCATION: (7)..(7)
<223> OTHER INFORMATION: Ser, Thr or any beta-heteroatom amino acid
<220> FEATURE:
<221> NAME/KEY: MOD_RES
<222> LOCATION: (8)..(8)
<223> OTHER INFORMATION: Asn, Gln, Ser, Thr, or any polar amino acid
<220> FEATURE:
<221> NAME/KEY: MOD_RES
<222> LOCATION: (9)..(9)
<223> OTHER INFORMATION: Val, Ile, Leu, Ala or any nonpolar amino acid
<220> FEATURE:
<221> NAME/KEY: MOD_RES
<222> LOCATION: (10)..(10)
<223> OTHER INFORMATION: Ile, Leu, Ala, Gly or any nonpolar amino acid
<220> FEATURE:
<221> NAME/KEY: MOD_RES
<222> LOCATION: (13)..(13)
<223> OTHER INFORMATION: Lys, Arg or any basic amino acid
<220> FEATURE:
<221> NAME/KEY: MOD_RES
<222> LOCATION: (16)..(16)
<223> OTHER INFORMATION: Ser, Thr, Asn, Gln, any polar amino acid or
      absent

<400> SEQUENCE: 279

Cys Tyr Xaa Asp Asn Ser Xaa Xaa Xaa Xaa Cys Lys Xaa Tyr Arg Xaa
1               5                   10                  15

<210> SEQ ID NO 280
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr, Phe or any aromatic amino acid
<220> FEATURE:
```

```
<221> NAME/KEY: MOD_RES
<222> LOCATION: (7)..(7)
<223> OTHER INFORMATION: Ser, Thr or any beta-heteroatom amino acid
<220> FEATURE:
<221> NAME/KEY: MOD_RES
<222> LOCATION: (8)..(8)
<223> OTHER INFORMATION: Asn, Gln, Ser, Thr, or any polar amino acid
<220> FEATURE:
<221> NAME/KEY: MOD_RES
<222> LOCATION: (9)..(9)
<223> OTHER INFORMATION: Val, Ile, Leu, Ala or any nonpolar amino acid
<220> FEATURE:
<221> NAME/KEY: MOD_RES
<222> LOCATION: (10)..(10)
<223> OTHER INFORMATION: Ile, Leu, Ala, Gly or any nonpolar amino acid
<220> FEATURE:
<221> NAME/KEY: MOD_RES
<222> LOCATION: (13)..(13)
<223> OTHER INFORMATION: Lys, Arg or any basic amino acid
<220> FEATURE:
<221> NAME/KEY: MOD_RES
<222> LOCATION: (16)..(16)
<223> OTHER INFORMATION: Ser, Thr, Asn, Gln, any polar amino acid or
      absent

<400> SEQUENCE: 280

Cys Tyr Xaa Asn Asn Ser Xaa Xaa Xaa Xaa Cys Lys Xaa Tyr Arg Xaa
1               5                  10                  15

<210> SEQ ID NO 281
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Tyr, Phe or any aromatic amino acid
<220> FEATURE:
<221> NAME/KEY: MOD_RES
<222> LOCATION: (8)..(8)
<223> OTHER INFORMATION: Asn, Gln, Ser, Thr, or any polar amino acid
<220> FEATURE:
<221> NAME/KEY: MOD_RES
<222> LOCATION: (9)..(9)
<223> OTHER INFORMATION: Val, Ile, Leu, Ala or any nonpolar amino acid
<220> FEATURE:
<221> NAME/KEY: MOD_RES
<222> LOCATION: (10)..(10)
<223> OTHER INFORMATION: Ile, Leu, Ala, Gly or any nonpolar amino acid
<220> FEATURE:
<221> NAME/KEY: MOD_RES
<222> LOCATION: (13)..(13)
<223> OTHER INFORMATION: Lys, Arg or any basic amino acid
<220> FEATURE:
<221> NAME/KEY: MOD_RES
<222> LOCATION: (14)..(14)
<223> OTHER INFORMATION: Tyr, Phe or any aromatic amino acid
<220> FEATURE:
<221> NAME/KEY: MOD_RES
<222> LOCATION: (16)..(16)
<223> OTHER INFORMATION: Ser, Thr, Asn, Gln, any polar amino acid or
      absent

<400> SEQUENCE: 281

Cys Xaa Xaa Asp Asp Ser Ser Xaa Xaa Xaa Cys Lys Xaa Xaa Arg Xaa
1               5                  10                  15

<210> SEQ ID NO 282
<211> LENGTH: 16
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Tyr, Phe or any aromatic amino acid
<220> FEATURE:
<221> NAME/KEY: MOD_RES
<222> LOCATION: (8)..(8)
<223> OTHER INFORMATION: Asn, Gln, Ser, Thr, or any polar amino acid
<220> FEATURE:
<221> NAME/KEY: MOD_RES
<222> LOCATION: (9)..(9)
<223> OTHER INFORMATION: Val, Ile, Leu, Ala or any nonpolar amino acid
<220> FEATURE:
<221> NAME/KEY: MOD_RES
<222> LOCATION: (10)..(10)
<223> OTHER INFORMATION: Ile, Leu, Ala, Gly or any nonpolar amino acid
<220> FEATURE:
<221> NAME/KEY: MOD_RES
<222> LOCATION: (13)..(13)
<223> OTHER INFORMATION: Lys, Arg or any basic amino acid
<220> FEATURE:
<221> NAME/KEY: MOD_RES
<222> LOCATION: (14)..(14)
<223> OTHER INFORMATION: Tyr, Phe or any aromatic amino acid
<220> FEATURE:
<221> NAME/KEY: MOD_RES
<222> LOCATION: (16)..(16)
<223> OTHER INFORMATION: Ser, Thr, Asn, Gln, any polar amino acid or
      absent

<400> SEQUENCE: 282

Cys Xaa Xaa Asn Asp Ser Ser Xaa Xaa Xaa Cys Lys Xaa Xaa Arg Xaa
1               5                   10                  15

<210> SEQ ID NO 283
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Tyr, Phe or any aromatic amino acid
<220> FEATURE:
<221> NAME/KEY: MOD_RES
<222> LOCATION: (8)..(8)
<223> OTHER INFORMATION: Asn, Gln, Ser, Thr, or any polar amino acid
<220> FEATURE:
<221> NAME/KEY: MOD_RES
<222> LOCATION: (9)..(9)
<223> OTHER INFORMATION: Val, Ile, Leu, Ala or any nonpolar amino acid
<220> FEATURE:
<221> NAME/KEY: MOD_RES
<222> LOCATION: (10)..(10)
<223> OTHER INFORMATION: Ile, Leu, Ala, Gly or any nonpolar amino acid
<220> FEATURE:
<221> NAME/KEY: MOD_RES
<222> LOCATION: (13)..(13)
<223> OTHER INFORMATION: Lys, Arg or any basic amino acid
<220> FEATURE:
<221> NAME/KEY: MOD_RES
<222> LOCATION: (14)..(14)
<223> OTHER INFORMATION: Tyr, Phe or any aromatic amino acid
<220> FEATURE:
<221> NAME/KEY: MOD_RES
<222> LOCATION: (16)..(16)
<223> OTHER INFORMATION: Ser, Thr, Asn, Gln, any polar amino acid or
      absent

<400> SEQUENCE: 283

Cys Xaa Xaa Asp Asn Ser Ser Xaa Xaa Xaa Cys Lys Xaa Xaa Arg Xaa
1               5                   10                  15
```

```
<210> SEQ ID NO 284
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Tyr, Phe or any aromatic amino acid
<220> FEATURE:
<221> NAME/KEY: MOD_RES
<222> LOCATION: (8)..(8)
<223> OTHER INFORMATION: Asn, Gln, Ser, Thr, or any polar amino acid
<220> FEATURE:
<221> NAME/KEY: MOD_RES
<222> LOCATION: (9)..(9)
<223> OTHER INFORMATION: Val, Ile, Leu, Ala or any nonpolar amino acid
<220> FEATURE:
<221> NAME/KEY: MOD_RES
<222> LOCATION: (10)..(10)
<223> OTHER INFORMATION: Ile, Leu, Ala, Gly or any nonpolar amino acid
<220> FEATURE:
<221> NAME/KEY: MOD_RES
<222> LOCATION: (13)..(13)
<223> OTHER INFORMATION: Lys, Arg or any basic amino acid
<220> FEATURE:
<221> NAME/KEY: MOD_RES
<222> LOCATION: (14)..(14)
<223> OTHER INFORMATION: Tyr, Phe or any aromatic amino acid
<220> FEATURE:
<221> NAME/KEY: MOD_RES
<222> LOCATION: (16)..(16)
<223> OTHER INFORMATION: Ser, Thr, Asn, Gln, any polar amino acid or
      absent

<400> SEQUENCE: 284

Cys Xaa Xaa Asn Asn Ser Ser Xaa Xaa Xaa Cys Lys Xaa Xaa Arg Xaa
1               5                   10                  15

<210> SEQ ID NO 285
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr, Phe or any aromatic amino acid
<220> FEATURE:
<221> NAME/KEY: MOD_RES
<222> LOCATION: (8)..(8)
<223> OTHER INFORMATION: Asn, Gln, Ser, Thr, or any polar amino acid
<220> FEATURE:
<221> NAME/KEY: MOD_RES
<222> LOCATION: (9)..(9)
<223> OTHER INFORMATION: Val, Ile, Leu, Ala or any nonpolar amino acid
<220> FEATURE:
<221> NAME/KEY: MOD_RES
<222> LOCATION: (10)..(10)
<223> OTHER INFORMATION: Ile, Leu, Ala, Gly or any nonpolar amino acid
<220> FEATURE:
<221> NAME/KEY: MOD_RES
<222> LOCATION: (13)..(13)
<223> OTHER INFORMATION: Lys, Arg or any basic amino acid
<220> FEATURE:
<221> NAME/KEY: MOD_RES
<222> LOCATION: (16)..(16)
<223> OTHER INFORMATION: Ser, Thr, Asn, Gln, any polar amino acid or
      absent

<400> SEQUENCE: 285
```

Cys Tyr Xaa Asp Asp Ser Ser Xaa Xaa Xaa Cys Lys Xaa Tyr Arg Xaa
1               5                   10                  15

<210> SEQ ID NO 286
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr, Phe or any aromatic amino acid
<220> FEATURE:
<221> NAME/KEY: MOD_RES
<222> LOCATION: (8)..(8)
<223> OTHER INFORMATION: Asn, Gln, Ser, Thr, or any polar amino acid
<220> FEATURE:
<221> NAME/KEY: MOD_RES
<222> LOCATION: (9)..(9)
<223> OTHER INFORMATION: Val, Ile, Leu, Ala or any nonpolar amino acid
<220> FEATURE:
<221> NAME/KEY: MOD_RES
<222> LOCATION: (10)..(10)
<223> OTHER INFORMATION: Ile, Leu, Ala, Gly or any nonpolar amino acid
<220> FEATURE:
<221> NAME/KEY: MOD_RES
<222> LOCATION: (13)..(13)
<223> OTHER INFORMATION: Lys, Arg or any basic amino acid
<220> FEATURE:
<221> NAME/KEY: MOD_RES
<222> LOCATION: (16)..(16)
<223> OTHER INFORMATION: Ser, Thr, Asn, Gln, any polar amino acid or
      absent

<400> SEQUENCE: 286

Cys Tyr Xaa Asn Asp Ser Ser Xaa Xaa Xaa Cys Lys Xaa Tyr Arg Xaa
1               5                   10                  15

<210> SEQ ID NO 287
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr, Phe or any aromatic amino acid
<220> FEATURE:
<221> NAME/KEY: MOD_RES
<222> LOCATION: (8)..(8)
<223> OTHER INFORMATION: Asn, Gln, Ser, Thr, or any polar amino acid
<220> FEATURE:
<221> NAME/KEY: MOD_RES
<222> LOCATION: (9)..(9)
<223> OTHER INFORMATION: Val, Ile, Leu, Ala or any nonpolar amino acid
<220> FEATURE:
<221> NAME/KEY: MOD_RES
<222> LOCATION: (10)..(10)
<223> OTHER INFORMATION: Ile, Leu, Ala, Gly or any nonpolar amino acid
<220> FEATURE:
<221> NAME/KEY: MOD_RES
<222> LOCATION: (13)..(13)
<223> OTHER INFORMATION: Lys, Arg or any basic amino acid
<220> FEATURE:
<221> NAME/KEY: MOD_RES
<222> LOCATION: (16)..(16)
<223> OTHER INFORMATION: Ser, Thr, Asn, Gln, any polar amino acid or
      absent

<400> SEQUENCE: 287

```
Cys Tyr Xaa Asp Asn Ser Ser Xaa Xaa Xaa Cys Lys Xaa Tyr Arg Xaa
1               5                   10                  15
```

<210> SEQ ID NO 288
<211> LENGTH: 16
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(3)
<223> OTHER INFORMATION: Tyr, Phe or any aromatic amino acid
<220> FEATURE:
<221> NAME/KEY: MOD_RES
<222> LOCATION: (8)..(8)
<223> OTHER INFORMATION: Asn, Gln, Ser, Thr, or any polar amino acid
<220> FEATURE:
<221> NAME/KEY: MOD_RES
<222> LOCATION: (9)..(9)
<223> OTHER INFORMATION: Val, Ile, Leu, Ala or any nonpolar amino acid
<220> FEATURE:
<221> NAME/KEY: MOD_RES
<222> LOCATION: (10)..(10)
<223> OTHER INFORMATION: Ile, Leu, Ala, Gly or any nonpolar amino acid
<220> FEATURE:
<221> NAME/KEY: MOD_RES
<222> LOCATION: (13)..(13)
<223> OTHER INFORMATION: Lys, Arg or any basic amino acid
<220> FEATURE:
<221> NAME/KEY: MOD_RES
<222> LOCATION: (16)..(16)
<223> OTHER INFORMATION: Ser, Thr, Asn, Gln, any polar amino acid or absent

<400> SEQUENCE: 288

```
Cys Tyr Xaa Asn Asn Ser Ser Xaa Xaa Xaa Cys Lys Xaa Tyr Arg Xaa
1               5                   10                  15
```

<210> SEQ ID NO 289
<211> LENGTH: 16
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(3)
<223> OTHER INFORMATION: Tyr or Phe
<220> FEATURE:
<221> NAME/KEY: MOD_RES
<222> LOCATION: (4)..(5)
<223> OTHER INFORMATION: Asp or Asn
<220> FEATURE:
<221> NAME/KEY: MOD_RES
<222> LOCATION: (6)..(7)
<223> OTHER INFORMATION: Ser or Thr
<220> FEATURE:
<221> NAME/KEY: MOD_RES
<222> LOCATION: (8)..(8)
<223> OTHER INFORMATION: Asn, Gln, Ser or Thr
<220> FEATURE:
<221> NAME/KEY: MOD_RES
<222> LOCATION: (9)..(9)
<223> OTHER INFORMATION: Val, Ile, Leu or Ala
<220> FEATURE:
<221> NAME/KEY: MOD_RES
<222> LOCATION: (10)..(10)
<223> OTHER INFORMATION: Ile, Leu, Ala or Gly
<220> FEATURE:
<221> NAME/KEY: MOD_RES
<222> LOCATION: (12)..(13)
<223> OTHER INFORMATION: Lys or Arg
<220> FEATURE:

```
<221> NAME/KEY: MOD_RES
<222> LOCATION: (14)..(14)
<223> OTHER INFORMATION: Tyr or Phe
<220> FEATURE:
<221> NAME/KEY: MOD_RES
<222> LOCATION: (15)..(15)
<223> OTHER INFORMATION: Arg or Lys
<220> FEATURE:
<221> NAME/KEY: MOD_RES
<222> LOCATION: (16)..(16)
<223> OTHER INFORMATION: Ser, Thr, Asn, Gln or absent

<400> SEQUENCE: 289

Cys Xaa Xaa Xaa Xaa Xaa Xaa Xaa Xaa Cys Xaa Xaa Xaa Xaa Xaa
1               5                   10                  15

<210> SEQ ID NO 290
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Tyr or Phe
<220> FEATURE:
<221> NAME/KEY: MOD_RES
<222> LOCATION: (7)..(7)
<223> OTHER INFORMATION: Ser or Thr
<220> FEATURE:
<221> NAME/KEY: MOD_RES
<222> LOCATION: (8)..(8)
<223> OTHER INFORMATION: Asn, Gln, Ser or Thr
<220> FEATURE:
<221> NAME/KEY: MOD_RES
<222> LOCATION: (9)..(9)
<223> OTHER INFORMATION: Val, Ile, Leu or Ala
<220> FEATURE:
<221> NAME/KEY: MOD_RES
<222> LOCATION: (10)..(10)
<223> OTHER INFORMATION: Ile, Leu, Ala or Gly
<220> FEATURE:
<221> NAME/KEY: MOD_RES
<222> LOCATION: (13)..(13)
<223> OTHER INFORMATION: Lys or Arg
<220> FEATURE:
<221> NAME/KEY: MOD_RES
<222> LOCATION: (14)..(14)
<223> OTHER INFORMATION: Tyr or Phe
<220> FEATURE:
<221> NAME/KEY: MOD_RES
<222> LOCATION: (16)..(16)
<223> OTHER INFORMATION: Ser, Thr, Asn, Gln or absent

<400> SEQUENCE: 290

Cys Xaa Xaa Asp Asp Ser Xaa Xaa Xaa Xaa Cys Lys Xaa Xaa Arg Xaa
1               5                   10                  15

<210> SEQ ID NO 291
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Tyr or Phe
<220> FEATURE:
<221> NAME/KEY: MOD_RES
<222> LOCATION: (7)..(7)
<223> OTHER INFORMATION: Ser or Thr
```

```
<220> FEATURE:
<221> NAME/KEY: MOD_RES
<222> LOCATION: (8)..(8)
<223> OTHER INFORMATION: Asn, Gln, Ser or Thr
<220> FEATURE:
<221> NAME/KEY: MOD_RES
<222> LOCATION: (9)..(9)
<223> OTHER INFORMATION: Val, Ile, Leu or Ala
<220> FEATURE:
<221> NAME/KEY: MOD_RES
<222> LOCATION: (10)..(10)
<223> OTHER INFORMATION: Ile, Leu, Ala or Gly
<220> FEATURE:
<221> NAME/KEY: MOD_RES
<222> LOCATION: (13)..(13)
<223> OTHER INFORMATION: Lys or Arg
<220> FEATURE:
<221> NAME/KEY: MOD_RES
<222> LOCATION: (14)..(14)
<223> OTHER INFORMATION: Tyr or Phe
<220> FEATURE:
<221> NAME/KEY: MOD_RES
<222> LOCATION: (16)..(16)
<223> OTHER INFORMATION: Ser, Thr, Asn, Gln or absent

<400> SEQUENCE: 291

Cys Xaa Xaa Asn Asp Ser Xaa Xaa Xaa Xaa Cys Lys Xaa Xaa Arg Xaa
1               5                   10                  15

<210> SEQ ID NO 292
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Tyr or Phe
<220> FEATURE:
<221> NAME/KEY: MOD_RES
<222> LOCATION: (7)..(7)
<223> OTHER INFORMATION: Ser or Thr
<220> FEATURE:
<221> NAME/KEY: MOD_RES
<222> LOCATION: (8)..(8)
<223> OTHER INFORMATION: Asn, Gln, Ser or Thr
<220> FEATURE:
<221> NAME/KEY: MOD_RES
<222> LOCATION: (9)..(9)
<223> OTHER INFORMATION: Val, Ile, Leu or Ala
<220> FEATURE:
<221> NAME/KEY: MOD_RES
<222> LOCATION: (10)..(10)
<223> OTHER INFORMATION: Ile, Leu, Ala or Gly
<220> FEATURE:
<221> NAME/KEY: MOD_RES
<222> LOCATION: (13)..(13)
<223> OTHER INFORMATION: Lys or Arg
<220> FEATURE:
<221> NAME/KEY: MOD_RES
<222> LOCATION: (14)..(14)
<223> OTHER INFORMATION: Tyr or Phe
<220> FEATURE:
<221> NAME/KEY: MOD_RES
<222> LOCATION: (16)..(16)
<223> OTHER INFORMATION: Ser, Thr, Asn, Gln or absent

<400> SEQUENCE: 292

Cys Xaa Xaa Asp Asn Ser Xaa Xaa Xaa Xaa Cys Lys Xaa Xaa Arg Xaa
1               5                   10                  15

<210> SEQ ID NO 293
<211> LENGTH: 16
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Tyr or Phe
<220> FEATURE:
<221> NAME/KEY: MOD_RES
<222> LOCATION: (7)..(7)
<223> OTHER INFORMATION: Ser or Thr
<220> FEATURE:
<221> NAME/KEY: MOD_RES
<222> LOCATION: (8)..(8)
<223> OTHER INFORMATION: Asn, Gln, Ser or Thr
<220> FEATURE:
<221> NAME/KEY: MOD_RES
<222> LOCATION: (9)..(9)
<223> OTHER INFORMATION: Val, Ile, Leu or Ala
<220> FEATURE:
<221> NAME/KEY: MOD_RES
<222> LOCATION: (10)..(10)
<223> OTHER INFORMATION: Ile, Leu, Ala or Gly
<220> FEATURE:
<221> NAME/KEY: MOD_RES
<222> LOCATION: (13)..(13)
<223> OTHER INFORMATION: Lys or Arg
<220> FEATURE:
<221> NAME/KEY: MOD_RES
<222> LOCATION: (14)..(14)
<223> OTHER INFORMATION: Tyr or Phe
<220> FEATURE:
<221> NAME/KEY: MOD_RES
<222> LOCATION: (16)..(16)
<223> OTHER INFORMATION: Ser, Thr, Asn, Gln or absent

<400> SEQUENCE: 293

Cys Xaa Xaa Asn Asn Ser Xaa Xaa Xaa Xaa Cys Lys Xaa Xaa Arg Xaa
1               5                   10                  15

<210> SEQ ID NO 294
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr or Phe
<220> FEATURE:
<221> NAME/KEY: MOD_RES
<222> LOCATION: (7)..(7)
<223> OTHER INFORMATION: Ser or Thr
<220> FEATURE:
<221> NAME/KEY: MOD_RES
<222> LOCATION: (8)..(8)
<223> OTHER INFORMATION: Asn, Gln, Ser or Thr
<220> FEATURE:
<221> NAME/KEY: MOD_RES
<222> LOCATION: (9)..(9)
<223> OTHER INFORMATION: Val, Ile, Leu or Ala
<220> FEATURE:
<221> NAME/KEY: MOD_RES
<222> LOCATION: (10)..(10)
<223> OTHER INFORMATION: Ile, Leu, Ala or Gly
<220> FEATURE:
<221> NAME/KEY: MOD_RES
<222> LOCATION: (13)..(13)
<223> OTHER INFORMATION: Lys or Arg
<220> FEATURE:
<221> NAME/KEY: MOD_RES
<222> LOCATION: (16)..(16)
<223> OTHER INFORMATION: Ser, Thr, Asn, Gln or absent
```

<400> SEQUENCE: 294

Cys Tyr Xaa Asp Asp Ser Xaa Xaa Xaa Xaa Cys Lys Xaa Tyr Arg Xaa
1               5                   10                  15

<210> SEQ ID NO 295
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr or Phe
<220> FEATURE:
<221> NAME/KEY: MOD_RES
<222> LOCATION: (7)..(7)
<223> OTHER INFORMATION: Ser or Thr
<220> FEATURE:
<221> NAME/KEY: MOD_RES
<222> LOCATION: (8)..(8)
<223> OTHER INFORMATION: Asn, Gln, Ser or Thr
<220> FEATURE:
<221> NAME/KEY: MOD_RES
<222> LOCATION: (9)..(9)
<223> OTHER INFORMATION: Val, Ile, Leu or Ala
<220> FEATURE:
<221> NAME/KEY: MOD_RES
<222> LOCATION: (10)..(10)
<223> OTHER INFORMATION: Ile, Leu, Ala or Gly
<220> FEATURE:
<221> NAME/KEY: MOD_RES
<222> LOCATION: (13)..(13)
<223> OTHER INFORMATION: Lys or Arg
<220> FEATURE:
<221> NAME/KEY: MOD_RES
<222> LOCATION: (16)..(16)
<223> OTHER INFORMATION: Ser, Thr, Asn, Gln or absent

<400> SEQUENCE: 295

Cys Tyr Xaa Asn Asp Ser Xaa Xaa Xaa Xaa Cys Lys Xaa Tyr Arg Xaa
1               5                   10                  15

<210> SEQ ID NO 296
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr or Phe
<220> FEATURE:
<221> NAME/KEY: MOD_RES
<222> LOCATION: (7)..(7)
<223> OTHER INFORMATION: Ser or Thr
<220> FEATURE:
<221> NAME/KEY: MOD_RES
<222> LOCATION: (8)..(8)
<223> OTHER INFORMATION: Asn, Gln, Ser or Thr
<220> FEATURE:
<221> NAME/KEY: MOD_RES
<222> LOCATION: (9)..(9)
<223> OTHER INFORMATION: Val, Ile, Leu or Ala
<220> FEATURE:
<221> NAME/KEY: MOD_RES
<222> LOCATION: (10)..(10)
<223> OTHER INFORMATION: Ile, Leu, Ala or Gly
<220> FEATURE:
<221> NAME/KEY: MOD_RES
<222> LOCATION: (13)..(13)

```
<223> OTHER INFORMATION: Lys or Arg
<220> FEATURE:
<221> NAME/KEY: MOD_RES
<222> LOCATION: (16)..(16)
<223> OTHER INFORMATION: Ser, Thr, Asn, Gln or absent

<400> SEQUENCE: 296

Cys Tyr Xaa Asp Asn Ser Xaa Xaa Xaa Xaa Cys Lys Xaa Tyr Arg Xaa
1               5                   10                  15

<210> SEQ ID NO 297
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr or Phe
<220> FEATURE:
<221> NAME/KEY: MOD_RES
<222> LOCATION: (7)..(7)
<223> OTHER INFORMATION: Ser or Thr
<220> FEATURE:
<221> NAME/KEY: MOD_RES
<222> LOCATION: (8)..(8)
<223> OTHER INFORMATION: Asn, Gln, Ser or Thr
<220> FEATURE:
<221> NAME/KEY: MOD_RES
<222> LOCATION: (9)..(9)
<223> OTHER INFORMATION: Val, Ile, Leu or Ala
<220> FEATURE:
<221> NAME/KEY: MOD_RES
<222> LOCATION: (10)..(10)
<223> OTHER INFORMATION: Ile, Leu, Ala or Gly
<220> FEATURE:
<221> NAME/KEY: MOD_RES
<222> LOCATION: (13)..(13)
<223> OTHER INFORMATION: Lys or Arg
<220> FEATURE:
<221> NAME/KEY: MOD_RES
<222> LOCATION: (16)..(16)
<223> OTHER INFORMATION: Ser, Thr, Asn, Gln or absent

<400> SEQUENCE: 297

Cys Tyr Xaa Asn Asn Ser Xaa Xaa Xaa Xaa Cys Lys Xaa Tyr Arg Xaa
1               5                   10                  15

<210> SEQ ID NO 298
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Tyr or Phe
<220> FEATURE:
<221> NAME/KEY: MOD_RES
<222> LOCATION: (8)..(8)
<223> OTHER INFORMATION: Asn, Gln, Ser or Thr
<220> FEATURE:
<221> NAME/KEY: MOD_RES
<222> LOCATION: (9)..(9)
<223> OTHER INFORMATION: Val, Ile, Leu or Ala
<220> FEATURE:
<221> NAME/KEY: MOD_RES
<222> LOCATION: (10)..(10)
<223> OTHER INFORMATION: Ile, Leu, Ala or Gly
<220> FEATURE:
<221> NAME/KEY: MOD_RES
```

```
<222> LOCATION: (13)..(13)
<223> OTHER INFORMATION: Lys or Arg
<220> FEATURE:
<221> NAME/KEY: MOD_RES
<222> LOCATION: (14)..(14)
<223> OTHER INFORMATION: Tyr or Phe
<220> FEATURE:
<221> NAME/KEY: MOD_RES
<222> LOCATION: (16)..(16)
<223> OTHER INFORMATION: Ser, Thr, Asn, Gln or absent

<400> SEQUENCE: 298

Cys Xaa Xaa Asp Asp Ser Ser Xaa Xaa Xaa Cys Lys Xaa Xaa Arg Xaa
1               5                   10                  15

<210> SEQ ID NO 299
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Tyr or Phe
<220> FEATURE:
<221> NAME/KEY: MOD_RES
<222> LOCATION: (8)..(8)
<223> OTHER INFORMATION: Asn, Gln, Ser or Thr
<220> FEATURE:
<221> NAME/KEY: MOD_RES
<222> LOCATION: (9)..(9)
<223> OTHER INFORMATION: Val, Ile, Leu or Ala
<220> FEATURE:
<221> NAME/KEY: MOD_RES
<222> LOCATION: (10)..(10)
<223> OTHER INFORMATION: Ile, Leu, Ala or Gly
<220> FEATURE:
<221> NAME/KEY: MOD_RES
<222> LOCATION: (13)..(13)
<223> OTHER INFORMATION: Lys or Arg
<220> FEATURE:
<221> NAME/KEY: MOD_RES
<222> LOCATION: (14)..(14)
<223> OTHER INFORMATION: Tyr or Phe
<220> FEATURE:
<221> NAME/KEY: MOD_RES
<222> LOCATION: (16)..(16)
<223> OTHER INFORMATION: Ser, Thr, Asn, Gln or absent

<400> SEQUENCE: 299

Cys Xaa Xaa Asn Asp Ser Ser Xaa Xaa Xaa Cys Lys Xaa Xaa Arg Xaa
1               5                   10                  15

<210> SEQ ID NO 300
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Tyr or Phe
<220> FEATURE:
<221> NAME/KEY: MOD_RES
<222> LOCATION: (8)..(8)
<223> OTHER INFORMATION: Asn, Gln, Ser or Thr
<220> FEATURE:
<221> NAME/KEY: MOD_RES
<222> LOCATION: (9)..(9)
<223> OTHER INFORMATION: Val, Ile, Leu or Ala
<220> FEATURE:
```

```
<221> NAME/KEY: MOD_RES
<222> LOCATION: (10)..(10)
<223> OTHER INFORMATION: Ile, Leu, Ala or Gly
<220> FEATURE:
<221> NAME/KEY: MOD_RES
<222> LOCATION: (13)..(13)
<223> OTHER INFORMATION: Lys or Arg
<220> FEATURE:
<221> NAME/KEY: MOD_RES
<222> LOCATION: (14)..(14)
<223> OTHER INFORMATION: Tyr or Phe
<220> FEATURE:
<221> NAME/KEY: MOD_RES
<222> LOCATION: (16)..(16)
<223> OTHER INFORMATION: Ser, Thr, Asn, Gln or absent

<400> SEQUENCE: 300

Cys Xaa Xaa Asp Asn Ser Ser Xaa Xaa Xaa Cys Lys Xaa Xaa Arg Xaa
1               5                   10                  15

<210> SEQ ID NO 301
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Tyr or Phe
<220> FEATURE:
<221> NAME/KEY: MOD_RES
<222> LOCATION: (8)..(8)
<223> OTHER INFORMATION: Asn, Gln, Ser or Thr
<220> FEATURE:
<221> NAME/KEY: MOD_RES
<222> LOCATION: (9)..(9)
<223> OTHER INFORMATION: Val, Ile, Leu or Ala
<220> FEATURE:
<221> NAME/KEY: MOD_RES
<222> LOCATION: (10)..(10)
<223> OTHER INFORMATION: Ile, Leu, Ala or Gly
<220> FEATURE:
<221> NAME/KEY: MOD_RES
<222> LOCATION: (13)..(13)
<223> OTHER INFORMATION: Lys or Arg
<220> FEATURE:
<221> NAME/KEY: MOD_RES
<222> LOCATION: (14)..(14)
<223> OTHER INFORMATION: Tyr or Phe
<220> FEATURE:
<221> NAME/KEY: MOD_RES
<222> LOCATION: (16)..(16)
<223> OTHER INFORMATION: Ser, Thr, Asn, Gln or absent

<400> SEQUENCE: 301

Cys Xaa Xaa Asn Asn Ser Ser Xaa Xaa Xaa Cys Lys Xaa Xaa Arg Xaa
1               5                   10                  15

<210> SEQ ID NO 302
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr or Phe
<220> FEATURE:
<221> NAME/KEY: MOD_RES
<222> LOCATION: (8)..(8)
<223> OTHER INFORMATION: Asn, Gln, Ser or Thr
```

```
<220> FEATURE:
<221> NAME/KEY: MOD_RES
<222> LOCATION: (9)..(9)
<223> OTHER INFORMATION: Val, Ile, Leu or Ala
<220> FEATURE:
<221> NAME/KEY: MOD_RES
<222> LOCATION: (10)..(10)
<223> OTHER INFORMATION: Ile, Leu, Ala or Gly
<220> FEATURE:
<221> NAME/KEY: MOD_RES
<222> LOCATION: (13)..(13)
<223> OTHER INFORMATION: Lys or Arg
<220> FEATURE:
<221> NAME/KEY: MOD_RES
<222> LOCATION: (16)..(16)
<223> OTHER INFORMATION: Ser, Thr, Asn, Gln or absent

<400> SEQUENCE: 302

Cys Tyr Xaa Asp Asp Ser Ser Xaa Xaa Xaa Cys Lys Xaa Tyr Arg Xaa
1               5                   10                  15

<210> SEQ ID NO 303
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr or Phe
<220> FEATURE:
<221> NAME/KEY: MOD_RES
<222> LOCATION: (8)..(8)
<223> OTHER INFORMATION: Asn, Gln, Ser or Thr
<220> FEATURE:
<221> NAME/KEY: MOD_RES
<222> LOCATION: (9)..(9)
<223> OTHER INFORMATION: Val, Ile, Leu or Ala
<220> FEATURE:
<221> NAME/KEY: MOD_RES
<222> LOCATION: (10)..(10)
<223> OTHER INFORMATION: Ile, Leu, Ala or Gly
<220> FEATURE:
<221> NAME/KEY: MOD_RES
<222> LOCATION: (13)..(13)
<223> OTHER INFORMATION: Lys or Arg
<220> FEATURE:
<221> NAME/KEY: MOD_RES
<222> LOCATION: (16)..(16)
<223> OTHER INFORMATION: Ser, Thr, Asn, Gln or absent

<400> SEQUENCE: 303

Cys Tyr Xaa Asn Asp Ser Ser Xaa Xaa Xaa Cys Lys Xaa Tyr Arg Xaa
1               5                   10                  15

<210> SEQ ID NO 304
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr or Phe
<220> FEATURE:
<221> NAME/KEY: MOD_RES
<222> LOCATION: (8)..(8)
<223> OTHER INFORMATION: Asn, Gln, Ser or Thr
<220> FEATURE:
<221> NAME/KEY: MOD_RES
<222> LOCATION: (9)..(9)
```

```
<223> OTHER INFORMATION: Val, Ile, Leu or Ala
<220> FEATURE:
<221> NAME/KEY: MOD_RES
<222> LOCATION: (10)..(10)
<223> OTHER INFORMATION: Ile, Leu, Ala or Gly
<220> FEATURE:
<221> NAME/KEY: MOD_RES
<222> LOCATION: (13)..(13)
<223> OTHER INFORMATION: Lys or Arg
<220> FEATURE:
<221> NAME/KEY: MOD_RES
<222> LOCATION: (16)..(16)
<223> OTHER INFORMATION: Ser, Thr, Asn, Gln or absent

<400> SEQUENCE: 304

Cys Tyr Xaa Asp Asn Ser Ser Xaa Xaa Xaa Cys Lys Xaa Tyr Arg Xaa
1               5                   10                  15

<210> SEQ ID NO 305
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr or Phe
<220> FEATURE:
<221> NAME/KEY: MOD_RES
<222> LOCATION: (8)..(8)
<223> OTHER INFORMATION: Asn, Gln, Ser or Thr
<220> FEATURE:
<221> NAME/KEY: MOD_RES
<222> LOCATION: (9)..(9)
<223> OTHER INFORMATION: Val, Ile, Leu or Ala
<220> FEATURE:
<221> NAME/KEY: MOD_RES
<222> LOCATION: (10)..(10)
<223> OTHER INFORMATION: Ile, Leu, Ala or Gly
<220> FEATURE:
<221> NAME/KEY: MOD_RES
<222> LOCATION: (13)..(13)
<223> OTHER INFORMATION: Lys or Arg
<220> FEATURE:
<221> NAME/KEY: MOD_RES
<222> LOCATION: (16)..(16)
<223> OTHER INFORMATION: Ser, Thr, Asn, Gln or absent

<400> SEQUENCE: 305

Cys Tyr Xaa Asn Asn Ser Ser Xaa Xaa Xaa Cys Lys Xaa Tyr Arg Xaa
1               5                   10                  15

<210> SEQ ID NO 306
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Glu Cys Arg Asp Leu Gly Trp Gln Asp Gln Cys
1               5                   10

<210> SEQ ID NO 307
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 307

Ala Cys Phe Asp Asp Ser Ser Asn Val Ile Cys Lys Lys Tyr Arg Ser
1               5                   10                  15

<210> SEQ ID NO 308
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Ser Arg Tyr Lys Lys Cys Tyr Phe Asp Asp Ser Ser Asn Val Ile Cys
1               5                   10                  15

<210> SEQ ID NO 309
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Glu Cys Arg Asp Leu Gly Trp Gln Asp Gln Cys
1               5                   10

<210> SEQ ID NO 310
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Glu Cys Arg Asp Leu Gly Trp Gln Asp Gln Cys
1               5                   10

<210> SEQ ID NO 311
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Cys Tyr Phe Asp Asp Ser Ser Asn Val Ile Cys
1               5                   10

<210> SEQ ID NO 312
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Ser Arg Tyr Lys Lys Cys Tyr Phe Asp Asp Ser Ser Asn Val Ile Cys
1               5                   10                  15

<210> SEQ ID NO 313
<211> LENGTH: 15

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Cys Phe Arg Asp Leu Gly Trp Gln Asp Trp Ile Ile Ala Pro Cys
1               5                   10                  15

<210> SEQ ID NO 314
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Glu Cys Arg Asp Leu Gly Trp Gln Asp Trp Cys
1               5                   10

<210> SEQ ID NO 315
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
tgtaaaaagc atgagttata tgtaagtttt agagatttag gatggcagga ctggattata       60
gctccagaag gttacgcggc atactattgc gaacaa                                 96

<210> SEQ ID NO 316
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
tgtgagttat acgtaagttt tagagattta ggttggcaag actggattat agctccagaa       60
ggatatgcgg catattgc                                                     78

<210> SEQ ID NO 317
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
tgttttagag atttaggatg gcaagactgg attatagcac catgc                       45

<210> SEQ ID NO 318
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318
```
gaatgtagag atttaggatg gcaagactgg tgc                       33

<210> SEQ ID NO 319
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
tgtagagact taggatggca agattggata attgcaccat gc             42

<210> SEQ ID NO 320
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
tgcttaaatg caataagtgt attatatttt gatgacagct caaatgtaat tttaaagaaa    60
tacagaaata tggtagtaag atgt                                 84

<210> SEQ ID NO 321
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321
tgttttgacg atagctcaaa tgtatgctta aaaaagtata gaagt           45

<210> SEQ ID NO 322
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
tgctttgatg acagtagcaa tgtaatatgt aaaaagtata gatca           45

<210> SEQ ID NO 323
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
tgctattttg acgattcaag caatgtatgt ttaagaaat acagaagt         48

<210> SEQ ID NO 324
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324 tgcgctttc ctttaaatag ttatatgaat gcaacgaatc acgcgattgt acaaacttta       60
gtacatttta taaatccaga aacagtaccg aaatgt                                96

<210> SEQ ID NO 325
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
tgcttaaata gttatatgaa tgcaacaaat catgcttgt                             39

<210> SEQ ID NO 326
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
tgctttataa atcctgaaac agtaccaaaa tgt                                   33

<210> SEQ ID NO 327
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
tgcttatttg acgatagttc aaatgtaata tgtaaaaagt atagaagc                   48

<210> SEQ ID NO 328
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
tgcatagtaa atagctcaga tgactttta tgtaagaaat atagaagt                    48

<210> SEQ ID NO 329
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
tgctattttg acgatagcag taatgtaata tgtaagaaa                             39

<210> SEQ ID NO 330
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 330
tgctattttg acgatagcag taatgtaata tgtaaa                              36

<210> SEQ ID NO 331
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
tgttttataa atccagaaac agtatgc                                        27

<210> SEQ ID NO 332
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 332
tgctattttg atgacagcag taatgtaata tgtaagaaat acaaatca                 48

<210> SEQ ID NO 333
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
tgttactttg acgatagtag caatgtaata tgcaaaagat atagatca                 48

<210> SEQ ID NO 334
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334
tgctattttg atgactcaag caatgtaata tgtagaaaat acagaagt                 48

<210> SEQ ID NO 335
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335
tgctatttag atgaaaatga gaaagtagta tgtaagaatt accaaagt                 48

<210> SEQ ID NO 336
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 336
```
tgttacttag atgaatatga caaagtagta tgcaagaatt atcaaagt                48

<210> SEQ ID NO 337
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 337
ataagtgtat gctattttga tgactcaagt aatgtaattt gtaaaaagta cagaagc      57

<210> SEQ ID NO 338
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 338
tgctattttg atgacagtag caatgtaata tgt                                33

<210> SEQ ID NO 339
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339
tgctacttag acgatagttc aaatgtaata tgtaaaaagt atagaagc                48

<210> SEQ ID NO 340
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
tgctatttag atgacagctc aaatgtatta tgtaagaaat acagaagt                48

<210> SEQ ID NO 341
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
tgctactttg aagatagcag taatgtaata tgtaaaaagt atagatca                48

<210> SEQ ID NO 342
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
tgctatttag acgaagatag ttcaaaagta ttatgtaaga attacagaag c        51

<210> SEQ ID NO 343
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343
tgttactttg atgacagtag caatgtatta tgtaaaaagt atagaagtgg gtcaggaggt    60
ggctgc                                                              66

<210> SEQ ID NO 344
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
tgtggcggtg ggtcaggaag ctgttacttt gacgatagta gcaatgtatt atgcaaaaag    60
tatagaagt                                                           69

<210> SEQ ID NO 345
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345
tgctattttg acgatagttc aaatgtaata tgtaagaaat acagaagc                 48

<210> SEQ ID NO 346
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346 tgcattttg acgatagcag taatgtaata tgtaaaaagt atagatca                  48

<210> SEQ ID NO 347
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
tgctatgtag acgattcaag caatgtaata tgtaaaaagt acagaagt                 48

<210> SEQ ID NO 348
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 348
tgctattttg atgaaagcag taatgtaata tgtaagaaat acagatca    48

<210> SEQ ID NO 349
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
tgctactttg acgataatag taatgtaata tgtaaaaagt atagaagc    48

<210> SEQ ID NO 350
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
tgctattttg atgactcaag ccaagtaata tgtaagaaat acagaagt    48

<210> SEQ ID NO 351
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351
tgctattttg acgatagctc aaatgtagta tgtaaaaagt acagaagt    48

<210> SEQ ID NO 352
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
tgctattttg atgacagtag caatgtatta tgtaaaaagt acagatca    48

<210> SEQ ID NO 353
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
tgcatagtag acgatagcag taatgtaatt tgtaaaaagt atagatca    48

<210> SEQ ID NO 354
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 354
tgcatttttg atgaaagttc aaatgtaata tgtaaaaagt atagaagc                48

<210> SEQ ID NO 355
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
tgcatttttg atgacaatag caatgtaata tgtaaaaagt atagaagt                48

<210> SEQ ID NO 356
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
tgcatatttg acgatagctc acaagtaatt tgtaaaaagt atagaagt                48

<210> SEQ ID NO 357
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 357
tgcatatttg acgattcaag taatgtagta tgtaaaaagt atagaagc                48

<210> SEQ ID NO 358
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 358
tgcatatttg atgacagctc aaatgtatta tgtaaaaagt atagaagt                48

<210> SEQ ID NO 359
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 359
tgttatgtag atgaaagtag caatgtaata tgcaaaaagt acagatca                48

<210> SEQ ID NO 360
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 360
```
tgctacgtag acgataatag taatgtaata tgtaaaaagt atagaagc 48

<210> SEQ ID NO 361
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 361
tgttatgtag acgatagttc acaagtaata tgcaaaaagt acagaagc 48

<210> SEQ ID NO 362
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 362
tgttacgtag atgacagttc aaatgtagta tgcaaaaagt atagaagc 48

<210> SEQ ID NO 363
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 363
tgctacgtag atgacagtag caatgtatta tgtaaaaagt atagatca 48

<210> SEQ ID NO 364
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 364
tgttactttg atgaaaatag caatgtaata tgcaaaaagt atagaagt 48

<210> SEQ ID NO 365
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 365
tgctattttg atgaatcaag tcaagtaata tgtaaaaagt acagaagc 48

<210> SEQ ID NO 366
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 366
tgctattttg atgaatcaag taatgtagta tgtaagaaat acagaagc					48

<210> SEQ ID NO 367
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 367
tgctattttg atgaaagttc aaatgtatta tgtaaaaagt acagaagc					48

<210> SEQ ID NO 368
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368
tgttactttg acgataatag ccaagtaata tgcaaaaagt atagaagt					48

<210> SEQ ID NO 369
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369
tgctattttg atgacaatag taatgtagta tgtaaaaagt acagaagc					48

<210> SEQ ID NO 370
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370
tgctattttg acgataatag caatgtatta tgtaaaaagt acagaagt					48

<210> SEQ ID NO 371
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 371
tgctattttg acgatagcag tcaagtagta tgtaagaaat acagatca					48

<210> SEQ ID NO 372
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 372
tgctactttg acgatagctc acaagtatta tgtaaaaagt atagaagt					48

<210> SEQ ID NO 373
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 373
tgcatagtag atgaatcaag taatgtaatt tgtaaaaagt atagaagc            48

<210> SEQ ID NO 374
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 374
tgcatagtag atgacaatag taatgtaatt tgtaaaaagt atagaagc            48

<210> SEQ ID NO 375
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 375
tgcatagtag acgatagtag ccaagtaatt tgtaaaaagt atagatca            48

<210> SEQ ID NO 376
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 376
tgcatagtag acgattcaag caatgtagta tgtaaaaagt atagaagt            48

<210> SEQ ID NO 377
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 377
tgcatagtag acgatagtag caatgtatta tgtaaaaagt atagatca            48

<210> SEQ ID NO 378
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 378
tgcatttttg atgaaaatag taatgtaata tgtaaaaagt atagaagc            48

<210> SEQ ID NO 379
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 379
tgcatttttg atgaatcaag ccaagtaata tgtaaaaagt atagaagt                48

<210> SEQ ID NO 380
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380
tgcatatttg atgaatcaag taatgtagta tgtaaaaagt atagaagc                48

<210> SEQ ID NO 381
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 381
tgcatatttg atgaaagctc aaatgtatta tgtaaaaagt atagaagt                48

<210> SEQ ID NO 382
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 382
tgcatatttg atgacaatag ccaagtaatt tgtaaaaagt atagaagt                48

<210> SEQ ID NO 383
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 383
tgcatatttg acgataatag caatgtagta tgtaaaaagt atagaagt                48

<210> SEQ ID NO 384
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 384
tgcatatttg atgacaatag caatgtatta tgtaaaaagt atagaagt                48

```
<210> SEQ ID NO 385
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 385
tgcatatttg acgattcaag ccaagtagta tgtaaaaagt atagaagt                 48

<210> SEQ ID NO 386
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 386
tgcatatttg acgatagctc acaagtatta tgtaaaaagt atagaagt                 48

<210> SEQ ID NO 387
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 387
tgctacgtag atgaaaatag taatgtaata tgtaaaaagt atagaagc                 48

<210> SEQ ID NO 388
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 388
tgttacgtag atgaatcaag tcaagtaata tgcaaaaagt atagaagc                 48

<210> SEQ ID NO 389
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 389
tgttatgtag atgaatcaag caatgtagta tgcaaaaagt acagaagt                 48

<210> SEQ ID NO 390
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 390
tgttatgtag atgaaagttc aaatgtatta tgcaagaaat acagaagc                 48

<210> SEQ ID NO 391
```

<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 391
tgttatgtag atgacaatag tcaagtaata tgcaaaaagt acagaagc                48

<210> SEQ ID NO 392
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 392
tgttacgtag atgacaatag caatgtagta tgcaaaaagt atagaagt                48

<210> SEQ ID NO 393
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 393
tgttacgtag atgacaatag taatgtatta tgcaaaaagt atagaagc                48

<210> SEQ ID NO 394
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 394
tgttacgtag acgatagctc acaagtagta tgcaaaaagt atagaagt                48

<210> SEQ ID NO 395
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 395
tgttacgtag acgatagtag ccaagtatta tgcaaaaagt atagatca                48

<210> SEQ ID NO 396
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 396
tgctattttg atgaaaatag ccaagtaata tgtaagaaat acagaagt                48

<210> SEQ ID NO 397
<211> LENGTH: 48

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 397
tgctattttg atgaaaatag caatgtagta tgtaaaaagt acagaagt            48

<210> SEQ ID NO 398
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 398
tgctattttg atgaaaatag taatgtatta tgtaaaaagt acagaagc            48

<210> SEQ ID NO 399
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 399
tgctattttg atgaaagtag ccaagtagta tgtaagaaat acagatca            48

<210> SEQ ID NO 400
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 400
tgttactttg atgaaagtag ccaagtatta tgcaaaaagt atagatca            48

<210> SEQ ID NO 401
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 401
tgctactttg atgacaatag tcaagtagta tgtaaaaagt atagaagc            48

<210> SEQ ID NO 402
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 402
tgttactttg acgataatag ccaagtatta tgcaaaaagt atagaagt            48

<210> SEQ ID NO 403
<211> LENGTH: 48
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 403
tgcatagtag atgaaaatag taatgtaatt tgtaaaaagt atagaagc                    48

<210> SEQ ID NO 404
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 404
tgcatagtag atgaatcaag tcaagtaatt tgtaaaaagt atagaagc                    48

<210> SEQ ID NO 405
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 405
tgtatagtag atgaatcaag taatgtagta tgcaaaaagt atagaagc                    48

<210> SEQ ID NO 406
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 406
tgtatagtag atgaaagcag taatgtatta tgcaaaaagt atagatca                    48

<210> SEQ ID NO 407
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 407
tgcattgtag atgacaatag tcaagtaata tgtaaaaagt atagaagc                    48

<210> SEQ ID NO 408
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 408
tgtatagtag acgataatag taatgtagta tgcaaaaagt atagaagc                    48

<210> SEQ ID NO 409
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 409
tgcatagtag atgacaatag caatgtatta tgtaaaaagt atagaagt                48

<210> SEQ ID NO 410
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 410
tgcatagtag atgactcaag ccaagtagta tgtaaaaagt atagaagt                48

<210> SEQ ID NO 411
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 411
tgtatagtag atgacagcag tcaagtatta tgcaaaaagt atagatca                48

<210> SEQ ID NO 412
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 412 tgcattttg atgaaaatag ccaagtaata tgtaaaaagt atagaagt                 48

<210> SEQ ID NO 413
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 413
tgcatatttg atgaaaatag taatgtagta tgtaaaaagt atagaagc                48

<210> SEQ ID NO 414
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 414
tgcatatttg atgaaaatag caatgtatta tgtaaaaagt atagaagt                48

<210> SEQ ID NO 415
<211> LENGTH: 48
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 415
tgcatatttg atgaaagcag tcaagtagta tgtaaaaagt atagatca              48

<210> SEQ ID NO 416
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 416
tgcatatttg atgaaagcag tcaagtatta tgtaaaaagt atagatca              48

<210> SEQ ID NO 417
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 417
tgcatatttg atgacaatag tcaagtagta tgtaaaaagt atagaagc              48

<210> SEQ ID NO 418
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 418
tgcatatttg acgataatag tcaagtatta tgtaaaaagt atagaagc              48

<210> SEQ ID NO 419
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 419
tgctatgtag atgaaaatag tcaagtaata tgtaaaaagt acagaagc              48

<210> SEQ ID NO 420
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 420
tgttatgtag atgaaaatag taatgtagta tgcaaaaagt acagaagc              48

<210> SEQ ID NO 421
<211> LENGTH: 48
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 421
tgttacgtag atgaaaatag taatgtatta tgcaaaaagt atagaagc        48

<210> SEQ ID NO 422
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 422
tgttatgtag atgaaagttc acaagtagta tgcaaaaagt acagaagc        48

<210> SEQ ID NO 423
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 423
tgctacgtag atgaatcaag tcaagtatta tgtaaaaagt atagaagc        48

<210> SEQ ID NO 424
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 424
tgctacgtag atgacaatag tcaagtagta tgtaaaaagt atagaagc        48

<210> SEQ ID NO 425
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 425
tgttatgtag atgacaatag tcaagtatta tgcaagaaat acagaagc        48

<210> SEQ ID NO 426
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 426
tgctattttg atgaaaatag tcaagtagta tgtaagaaat acagaagc        48

<210> SEQ ID NO 427
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 427
tgctattttg atgaaaatag ccaagtatta tgtaagaaat acagaagt    48

<210> SEQ ID NO 428
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 428
tgtattgtag atgaaaatag tcaagtaata tgcaaaaagt atagaagc    48

<210> SEQ ID NO 429
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 429
tgtatagtag atgaaaatag taatgtagta tgcaaaaagt atagaagc    48

<210> SEQ ID NO 430
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 430
tgtatagtag atgaaaatag taatgtatta tgcaaaaagt atagaagc    48

<210> SEQ ID NO 431
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 431
tgcatatttg atgaaaatag tcaagtagta tgtaaaaagt atagaagc    48

<210> SEQ ID NO 432
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 432
tgcatatttg atgaaaatag ccaagtatta tgtaaaaagt atagaagt    48

<210> SEQ ID NO 433
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 433
tgctatgtag atgaaaatag ccaagtagta tgtaagaaat acagaagt                48

<210> SEQ ID NO 434
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 434
tgctatgtag atgaaaatag ccaagtatta tgttgtaaat acagaagt                48

<210> SEQ ID NO 435
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 435
tgtatagtag atgaaaatag ccaagtagta tgcaaaaagt atagaagt                48

<210> SEQ ID NO 436
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 436
tgcatagtag atgaaaatag tcaagtatta tgtaaaaagt atagaagc                48

<210> SEQ ID NO 437
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 437
tgctactttg atgactcaag caaagtaata tgtaaaaagt atagaagt                48

<210> SEQ ID NO 438
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 438
tgctatttag atgacagtag caatgtaata tgtaaaaagt acagatca                48

<210> SEQ ID NO 439
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 439
tgttactttg acgatagctc aaaagtagta tgcaaaaagt atagaagt         48

<210> SEQ ID NO 440
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 440
tgctacttag acgatagctc aaatgtagta tgtaaaaagt atagaagt         48

<210> SEQ ID NO 441
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 441
tgctactttg atgactcaag taaagtatta tgtaaaaagt atagaagc         48

<210> SEQ ID NO 442
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 442
tgctatttag atgacagtag caatgtatta tgtaaaaagt acagaaat         48

<210> SEQ ID NO 443
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 443
tgctattttg atgacaatag taaagtaata tgtaagaaat acagaagc         48

<210> SEQ ID NO 444
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 444
tgttactttg atgaaagtag caaagtaata tgcaaaaagt atagatca         48

<210> SEQ ID NO 445
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 445
tgctatttag atgacagttc aaaagtaata tgtaagaaat acagaagc        48

<210> SEQ ID NO 446
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 446
tgttacttag atgacaatag caatgtaata tgcaaaaagt atagaagt          48

<210> SEQ ID NO 447
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 447
tgctacttag atgaaagtag caatgtaata tgtaaaaagt atagatca          48

<210> SEQ ID NO 448
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 448
tgctatttag acgatagtag ccaagtaata tgtaaaaagt acagatca          48

<210> SEQ ID NO 449
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 449
tgctattttg atgacaatag caaagtagta tgtaagaaat acagaagt          48

<210> SEQ ID NO 450
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 450
tgttactttg atgaaagctc aaaagtagta tgcaaaaagt atagaagt          48

<210> SEQ ID NO 451
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 451
tgctatttag acgatagctc aaaagtagta tgtaagaaat acagaagt          48

<210> SEQ ID NO 452
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 452
tgctattttg atgacaatag taaagtatta tgtaagaaat acagaagc                48

<210> SEQ ID NO 453
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 453
tgttactttg atgaaagttc aaaagtatta tgcaaaaagt atagaagc                48

<210> SEQ ID NO 454
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 454
tgttacttag atgacagctc aaaagtatta tgcaaaaagt atagaagt                48

<210> SEQ ID NO 455
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 455
tgctatttag atgaaagcag taaagtaata tgtaaaaagt acagatca                48

<210> SEQ ID NO 456
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 456
tgttactttg atgaaaatag caaagtaata tgcaaaaagt atagaagt                48

<210> SEQ ID NO 457
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 457
tgctatttag acgataatag taagtaata tgtaaaaagt acagaagc                48

<210> SEQ ID NO 458
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 458
tgctacttag atgaaagctc acaagtaata tgtaaaaagt atagaagt                48

<210> SEQ ID NO 459
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 459
tgctattttg atgacagtag caatgtagta tgt                                33

<210> SEQ ID NO 460
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 460
tgctattttg atgacagtag caatgtatta tgt                                33

<210> SEQ ID NO 461
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 461
tgctattttg atgacagtag caaagtaata tgt                                33

<210> SEQ ID NO 462
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 462
tgctattttg atgacaatag taatgtaata tgt                                33

<210> SEQ ID NO 463
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 463
tgctattttg atgaaagcag taatgtaata tgt                                33

<210> SEQ ID NO 464
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 464
tgctattttg acgatagtag ccaagtaata tgt                33

<210> SEQ ID NO 465
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 465
tgctatttag atgacagtag caatgtaata tgt                33

<210> SEQ ID NO 466
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 466
tgctatttag atgacaatag taaagtagta tgtaaaaagt acaga                45

<210> SEQ ID NO 467
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 467
tgctacttag acgataatag taatgtaata tgtaaaaagt ataga                45

<210> SEQ ID NO 468
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 468
tgttacttag aagataatag taatgtaaca tgcaaaaagt ataga                45

<210> SEQ ID NO 469
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 469
tgctatttag aagagaatag taatgtagta tgtaaaaagt acaga                45

<210> SEQ ID NO 470

-continued

```
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 470
tgttacttag atgacaatag taaagtaaca tgcaaaaagt ataga              45

<210> SEQ ID NO 471
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 471
tgctatttag aggaaaatag tcaagtaata tgtaaaaagt acaga              45

<210> SEQ ID NO 472
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 472
tgttacttag aagataatag tcaagtagta tgcaaaaagt ataga              45

<210> SEQ ID NO 473
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 473
tgctacttag acgataatag taattttata tgtaaaaagt ataga              45

<210> SEQ ID NO 474
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 474
tgctacttag atgaaaatag taaagtagta tgtaaaaagt ataga              45

<210> SEQ ID NO 475
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 475
tgctggttag atgaaaatag taatgtagta tgtaaaaagt ataga              45

<210> SEQ ID NO 476
<211> LENGTH: 45
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 476
tgttacttag aggaaaatag taatgtaata tgcaaaaagt ataga              45

<210> SEQ ID NO 477
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 477
tgttacttag aagataatag taatgtagta tgcaaaaagt ataga              45

<210> SEQ ID NO 478
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 478
tgttacttag atgaaaatag taaagtaata tgcaaaaagt ataga              45

<210> SEQ ID NO 479
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 479
tgctatttag atgaaaatag tcaagtaaca tgtaagaaat acaga              45

<210> SEQ ID NO 480
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 480
tgctacttag aagataatag taatgtaata tgtaaaaagt ataga              45

<210> SEQ ID NO 481
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 481
tgctatttag acgataatag taaagtaata tgtaagaaat acaga              45

<210> SEQ ID NO 482
<211> LENGTH: 45
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 482
tgctatttag atgaaaatag taatgtaaca tgtaaaaagt acaga                    45

<210> SEQ ID NO 483
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 483
tgttacttag acgataatag tcaagtaaca tgcaaaaagt ataga                    45

<210> SEQ ID NO 484
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 484
tgttacttag atgaaaatag tcaagtagta tgcaaaaagt ataga                    45

<210> SEQ ID NO 485
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 485
tgctatttag atgacaatag taatgtaaca tgtaaaaagt acaga                    45

<210> SEQ ID NO 486
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 486
tgctatttag atgaaaatag taatgtagta tgtaagaaat acaga                    45

<210> SEQ ID NO 487
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 487
tgctacttag atgaaaatag tcaagtaata tgtaaaaagt ataga                    45

<210> SEQ ID NO 488
<211> LENGTH: 45
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 488
tgctacttag atgaaaatag taatgtaata tgtaaaaagt ataga          45

<210> SEQ ID NO 489
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 489
tgctatttag atgacaatag taatgtagta tgtaagaaat acaga          45

<210> SEQ ID NO 490
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 490
tgctatttag aagataatag tcaagtaata tgtaagaaat acaga          45

<210> SEQ ID NO 491
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 491
tgctatttag atgaaaatag taatgtaaca tgtaagaaat ggaga          45

<210> SEQ ID NO 492
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 492
tgctatttag acgataatag taatgtaaca tgtaagaaat ggaga          45

<210> SEQ ID NO 493
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 493
tgctatttag atgaaaatag taatgtagta tgtaaaaagt ggaga          45

<210> SEQ ID NO 494
<211> LENGTH: 45
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 494
tgctatttag atgacaatag taatgtagta tgtaagaaat ggaga          45

<210> SEQ ID NO 495
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 495
tgctatttag acgataatag tcaagtaaca tgtaagaaat ggaga          45

<210> SEQ ID NO 496
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 496
tgctatttag atgaaaatag tcaagtagta tgtaagaaat ggaga          45

<210> SEQ ID NO 497
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 497
tgctacttag atgaaaatag taatgtagta tgtaaacaat ataga          45

<210> SEQ ID NO 498
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 498
tgctacttag acgataatag taatgtaaca tgtaaacaat ataga          45

<210> SEQ ID NO 499
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 499
tgctatttag acgataatag tcaagtagta tgtaaaagt ggaga          45

<210> SEQ ID NO 500
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 500
tgttacttag acgataatag taatgtagta tgcaaaaatt ataga            45

<210> SEQ ID NO 501
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 501
tgctatttag acgataatag taatgtagta tgtaaacaat acaga            45

<210> SEQ ID NO 502
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 502
tgttacttag atgaaaatag tcaagtaata tgcaaacagt ataga            45

<210> SEQ ID NO 503
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 503
tgctatgcag atgaaaatag taatgtagta tgtaagaaat ggaga            45

<210> SEQ ID NO 504
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 504
tgttatgcag atgacaatag taatgtaaca tgcaagaaat ggaga            45

<210> SEQ ID NO 505
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 505
tgctacttag acgataatag tcaagtaata tgtaaaaatt ataga            45

<210> SEQ ID NO 506
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 506
tgctacttag atgacaatag tcaagtagta tgtaaacagt ataga			45

<210> SEQ ID NO 507
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 507
tgttacttag atgacaatag tcaggtaata tgcaaacaat ataga			45

<210> SEQ ID NO 508
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 508
tgttatgcag acgataatag taatgtagta tgcaaaaagt ggaga			45

<210> SEQ ID NO 509
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 509
tgctatttag atgaaaatga caatgtagta tgtaaaaagt ggaga			45

<210> SEQ ID NO 510
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 510
tgctatttag atgacaatga taatgtaaca tgtaaaaagt ggaga			45

<210> SEQ ID NO 511
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 511
tgttatgcag atgacaatag tcaagtagta tgcaaaaagt ggaga			45

<210> SEQ ID NO 512
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 512
tgctatgcag acgataatag taatgtagta tgtaaacaat acaga            45

<210> SEQ ID NO 513
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 513
tgctatttag atgacaatga taatgtagta tgtaagaaat ggaga            45

<210> SEQ ID NO 514
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 514
tgttatttag acgataatag taatataatt tgcaagaaat ggaga            45

<210> SEQ ID NO 515
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 515
tgctattttg atgacagcaa taatgtatta tgtaaaaagt acagaagt         48

<210> SEQ ID NO 516
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 516
tgctattttg acgatagttc aagcgtatta tgtaaaaagt acagaagt         48

<210> SEQ ID NO 517
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 517
tgctacttta atgatagttc aaatgtatta tgtaaaaagt atagaagc         48

<210> SEQ ID NO 518
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 518
tgccattttg atgacagcag taatgtatta tgtaaaaagt atagatca       48

<210> SEQ ID NO 519
<211> LENGTH: 48
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 519
tgctattttg acgatagcag taatgtatta tgtaagaaat accattca       48

<210> SEQ ID NO 520
<211> LENGTH: 48
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 520
tgctactttg acgatagtag caatgtatta tgtaaaaagt atagaaat       48

<210> SEQ ID NO 521
<211> LENGTH: 48
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 521
tgctattttg acgattcaag caatgtatta tgtaaaaagc atagaagt       48

<210> SEQ ID NO 522
<211> LENGTH: 48
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 522
tgttatttta atgatagttc acaagtatta tgcaaaaagc atagaagc       48

<210> SEQ ID NO 523
<211> LENGTH: 48
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 523
tgttattggg atgacagctc aaatgtatta tgcaagaaat acagaagt       48

<210> SEQ ID NO 524
<211> LENGTH: 48
<212> TYPE: DNA
<213> ORGANISM: Artificial Sequence
<220> FEATURE:
<223> OTHER INFORMATION: Description of Artificial Sequence: Synthetic
    oligonucleotide <400> SEQUENCE: 524
tgctattacg atgactcaag caatgtatta tgtaaaaagt atagaagt       48

<210> SEQ ID NO 525
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 525
tgctactttg atgactcaag tcaagtatta tgtaaaagat atagaagc                48

<210> SEQ ID NO 526
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 526
tgctactatg acgatagttc acaagtatta tgtaaaagat atagaagc                48

<210> SEQ ID NO 527
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 527
tgctactttA atgatagttc agacgtatta tgtaaaaagt atagaagc                48

<210> SEQ ID NO 528
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 528
tgttactttA atgattcaag ccaagtatta tgcaaaagat atagaagt                48

<210> SEQ ID NO 529
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 529
tgttactatg atgactcaag taatgtatta tgcaaaagat atagaagc                48

<210> SEQ ID NO 530
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 530
tgctattttg atgacagtag caatgtatta tgtaaaaagt acaga                   45

<210> SEQ ID NO 531
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 531
tgttactttg acgatagtag caatgtatta tgcaaaaagt at                          42

<210> SEQ ID NO 532
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 532
aaaaagtata gaagt                                                        15

<210> SEQ ID NO 533
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 533
aaaagatata gaagt                                                        15

<210> SEQ ID NO 534
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 534
tgctattttg atgacagttc aaattgttta ataagaaat acagaagc                     48

<210> SEQ ID NO 535
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 535
tgctactttg acgattcaag caattgttta ttaagaaat atagaagt                     48

<210> SEQ ID NO 536
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 536
tgttatttta atgatagttc aaattgctta ttaaaaagt acagaagc                     48

```
<210> SEQ ID NO 537
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 537
tgttactttg ataatagtag caattgctta ttaaaaagt atagatca                    48

<210> SEQ ID NO 538
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 538
tgctacttta ataattcaag taattgttta ttaaaaaagt atagaagc                    48

<210> SEQ ID NO 539
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 539
tgttactttg acgatagcag tcaatgctta ttaaaaaagt atagatca                    48

<210> SEQ ID NO 540
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 540
tgctattacg acgatagcag taattgttta ttaaaaaagt atagatca                    48

<210> SEQ ID NO 541
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 541
tgctattttg acgatagtac aaattgttta ttaaagaaat acagaagc                    48

<210> SEQ ID NO 542
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 542
tgttattttg atgactcaag tagctgctta ttaaagaaat acagaagt                    48

<210> SEQ ID NO 543
```

```
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 543
tgctattttg acgattcaag taattgtgca ttaaagaaat acagaagc              48

<210> SEQ ID NO 544
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 544
tgctactttg acgatagtag caattgttta ttaaaaagat atagatca              48

<210> SEQ ID NO 545
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 545
tgctactttg acgatagtag caattgttta ttaaaaaagt atagaaat              48

<210> SEQ ID NO 546
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 546
tgttactttg acgatagcag taattgctta ttaaaaagt ataga                  45

<210> SEQ ID NO 547
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 547
tgctattttg acgatagcag taattgttta gcaaaaagt acagatca               48

<210> SEQ ID NO 548
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 548
tgctactttg atgacagcag taattgttta ttaaagaaat at                    42

<210> SEQ ID NO 549
<211> LENGTH: 48
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 549
tgttactttg acgattcaag caatgtatta tgcagtagat ataagaaa          48

<210> SEQ ID NO 550
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 550
tgtttagtaa attcaagcga tgactttac tgcaaaaagt atagaagt            48

<210> SEQ ID NO 551
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 551
aaaaagtata gaagttgttt agtaaatagc tcagatgact tttactgc           48

<210> SEQ ID NO 552
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 552
agtagatata agaaatgcta ctttgatgac agctcaaatg tattatgt           48

<210> SEQ ID NO 553
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 553
agcagatata agaaatgttt agtaaattca agtgatgact tttactgc           48

<210> SEQ ID NO 554
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 554
gaatgcagag acttaggatg gcaagatcag tgt                           33

<210> SEQ ID NO 555
<211> LENGTH: 48
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 555
gcatgttttg acgatagcag taatgtaata tgcaaaaagt atagatca                  48

<210> SEQ ID NO 556
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 556
agcagatata agaaatgtta ctttgatgac tcaagtaatg taatatgc                  48

<210> SEQ ID NO 557
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 557

Cys Phe Asp Asp Ser Ser Asn Val Ile Cys Lys Lys Tyr Arg Ser
1               5                   10                  15

<210> SEQ ID NO 558
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 558

Ala Cys Phe Asp Asp Ser Ser Asn Val Ile Cys Lys Lys Tyr Arg Ser
1               5                   10                  15

<210> SEQ ID NO 559
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 559

Cys Tyr Phe Asp Asp Ser Ser Asn Val Ile Cys Lys Lys Tyr Arg Ser
1               5                   10                  15

<210> SEQ ID NO 560
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 560

Cys Tyr Phe Asp Asp Ser Ser Asn Val Ile Cys
1               5                   10
```

```
<210> SEQ ID NO 561
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 561

Cys Phe Arg Asp Leu Gly Trp Gln Asp Trp Ile Ile Ala Pro Cys
1               5                   10                  15

<210> SEQ ID NO 562
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 562

Cys Phe Arg Asp Leu Gly Trp Gln Asp Trp Ile Ile Ala Pro Cys
1               5                   10                  15

<210> SEQ ID NO 563
<211> LENGTH: 16
<212> TYPE: PRT
<213> ORGANISM: Unknown Organism
<220> FEATURE:
<223> OTHER INFORMATION: Description of Unknown Organism: Native BMP-7
      sequence

<400> SEQUENCE: 563

Leu Tyr Phe Asp Asp Ser Ser Asn Val Ile Leu Lys Lys Tyr Arg Asn
1               5                   10                  15

<210> SEQ ID NO 564
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 564

Asp Asp Ser Ser Asn
1               5

<210> SEQ ID NO 565
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 565

Lys Lys Tyr Arg Ser
1               5

<210> SEQ ID NO 566
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
```

```
<222> LOCATION: (3)..(9)
<223> OTHER INFORMATION: Disulfide bridge

<400> SEQUENCE: 566

Leu Tyr Cys Asp Asp Ser Ser Asn Cys Leu Leu Lys Lys Tyr Arg Ser
1               5                   10                  15

<210> SEQ ID NO 567
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (3)..(9)
<223> OTHER INFORMATION: Disulfide bridge
<220> FEATURE:
<221> NAME/KEY: MOD_RES
<222> LOCATION: (9)..(9)
<223> OTHER INFORMATION: Pen

<400> SEQUENCE: 567

Leu Tyr Gly Asp Asp Ser Ser Asn Xaa Leu Leu Lys Lys Tyr Arg Ser
1               5                   10                  15

<210> SEQ ID NO 568
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (3)..(9)
<223> OTHER INFORMATION: Disulfide bridge
<220> FEATURE:
<221> NAME/KEY: MOD_RES
<222> LOCATION: (9)..(9)
<223> OTHER INFORMATION: Pen

<400> SEQUENCE: 568

Leu Tyr Cys Asp Asp Ser Ser Asn Xaa Leu Leu Lys Lys Tyr Arg Ser
1               5                   10                  15

<210> SEQ ID NO 569
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (3)..(9)
<223> OTHER INFORMATION: Disulfide bridge

<400> SEQUENCE: 569

Leu Tyr Gly Asp Asp Ser Ser Asn Cys Leu Leu Lys Lys Tyr Arg Ser
1               5                   10                  15

<210> SEQ ID NO 570
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: misc_feature
<222> LOCATION: (2)..(10)
<223> OTHER INFORMATION: Disulfide bridge

<400> SEQUENCE: 570

Leu Cys Phe Asp Asp Ser Ser Asn Val Cys Leu Lys Lys Tyr Arg Ser
1               5                   10                  15

<210> SEQ ID NO 571
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(9)
<223> OTHER INFORMATION: Disulfide bridge
<220> FEATURE:
<221> NAME/KEY: MOD_RES
<222> LOCATION: (1)..(1)
<223> OTHER INFORMATION: HomoCys

<400> SEQUENCE: 571

Cys Tyr Phe Asp Asp Ser Ser Asn Cys Leu Leu Lys Lys Tyr Arg Ser
1               5                   10                  15

<210> SEQ ID NO 572
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(11)
<223> OTHER INFORMATION: Disulfide bridge
<220> FEATURE:
<221> NAME/KEY: misc_feature
<222> LOCATION: (3)..(9)
<223> OTHER INFORMATION: Disulfide bridge

<400> SEQUENCE: 572

Cys Tyr Cys Asp Asp Ser Ser Asn Cys Leu Cys Lys Lys Tyr Arg Ser
1               5                   10                  15

<210> SEQ ID NO 573
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(22)
<223> OTHER INFORMATION: Disulfide bridge
<220> FEATURE:
<221> NAME/KEY: misc_feature
<222> LOCATION: (7)..(17)
<223> OTHER INFORMATION: Disulfide bridge

<400> SEQUENCE: 573

Cys Asn Ala Ile Ser Val Cys Tyr Phe Asp Asp Ser Ser Asn Val Leu
1               5                   10                  15

Cys Lys Lys Tyr Arg Cys
            20
```

```
<210> SEQ ID NO 574
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(11)
<223> OTHER INFORMATION: Disulfide bridge
<220> FEATURE:
<221> NAME/KEY: misc_feature
<222> LOCATION: (11)..(22)
<223> OTHER INFORMATION: Disulfide bridge

<400> SEQUENCE: 574

Cys Tyr Phe Asp Asp Ser Ser Asn Val Leu Gly Lys Lys Tyr Arg Asn
1               5                   10                  15

Asn Ala Ile Ser Val Cys
            20

<210> SEQ ID NO 575
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(11)
<223> OTHER INFORMATION: Disulfide bridge
<220> FEATURE:
<221> NAME/KEY: misc_feature
<222> LOCATION: (2)..(22)
<223> OTHER INFORMATION: Disulfide bridge

<400> SEQUENCE: 575

Cys Cys Phe Asp Asp Ser Ser Asn Val Leu Cys Lys Lys Tyr Arg Asn
1               5                   10                  15

Asn Ala Ile Ser Val Cys
            20

<210> SEQ ID NO 576
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(11)
<223> OTHER INFORMATION: Cyclic
<220> FEATURE:
<221> NAME/KEY: MOD_RES
<222> LOCATION: (1)..(1)
<223> OTHER INFORMATION: Dab

<400> SEQUENCE: 576

Xaa Tyr Phe Asp Asp Ser Ser Asn Val Leu Asp Lys Lys Tyr Arg Ser
1               5                   10                  15

<210> SEQ ID NO 577
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: misc_feature
<222> LOCATION: (1)..(11)
<223> OTHER INFORMATION: Cyclic
<220> FEATURE:
<221> NAME/KEY: MOD_RES
<222> LOCATION: (11)..(11)
<223> OTHER INFORMATION: Dap

<400> SEQUENCE: 577

Glu Tyr Phe Asp Asp Ser Ser Asn Val Leu Xaa Lys Lys Tyr Arg Ser
1               5                   10                  15

<210> SEQ ID NO 578
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (3)..(9)
<223> OTHER INFORMATION: Cyclic
<220> FEATURE:
<221> NAME/KEY: MOD_RES
<222> LOCATION: (3)..(3)
<223> OTHER INFORMATION: Dap

<400> SEQUENCE: 578

Leu Tyr Xaa Asp Asp Ser Ser Asn Gly Leu Leu Lys Lys Tyr Arg Ser
1               5                   10                  15

<210> SEQ ID NO 579
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (3)..(9)
<223> OTHER INFORMATION: Cyclic
<220> FEATURE:
<221> NAME/KEY: MOD_RES
<222> LOCATION: (9)..(9)
<223> OTHER INFORMATION: Dap

<400> SEQUENCE: 579

Leu Tyr Asp Asp Asp Ser Ser Asn Xaa Leu Leu Lys Lys Tyr Arg Ser
1               5                   10                  15

<210> SEQ ID NO 580
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(10)
<223> OTHER INFORMATION: Cyclic
<220> FEATURE:
<221> NAME/KEY: MOD_RES
<222> LOCATION: (10)..(10)
<223> OTHER INFORMATION: Dab

<400> SEQUENCE: 580

Leu Glu Phe Asp Asp Ser Ser Asn Val Xaa Leu Lys Lys Tyr Arg Ser
1               5                   10                  15
```

<210> SEQ ID NO 581
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(9)
<223> OTHER INFORMATION: Cyclic

<400> SEQUENCE: 581

Asp Tyr Phe Asp Asp Ser Ser Asn Lys Leu Leu Lys Lys Tyr Arg Ser
1               5                   10                  15

<210> SEQ ID NO 582
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (3)..(11)
<223> OTHER INFORMATION: Cyclic

<400> SEQUENCE: 582

Asp Tyr Lys Asp Asp Ser Ser Asn Lys Leu Glu Lys Lys Tyr Arg Ser
1               5                   10                  15

<210> SEQ ID NO 583
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(11)
<223> OTHER INFORMATION: Cyclic
<220> FEATURE:
<221> NAME/KEY: MOD_RES
<222> LOCATION: (1)..(1)
<223> OTHER INFORMATION: Dap
<220> FEATURE:
<221> NAME/KEY: misc_feature
<222> LOCATION: (3)..(9)
<223> OTHER INFORMATION: Cyclic
<220> FEATURE:
<221> NAME/KEY: MOD_RES
<222> LOCATION: (9)..(9)
<223> OTHER INFORMATION: Dap

<400> SEQUENCE: 583

Xaa Tyr Asp Asp Asp Ser Ser Asn Xaa Leu Asp Lys Lys Tyr Arg Ser
1               5                   10                  15

<210> SEQ ID NO 584
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(21)
<223> OTHER INFORMATION: Cyclic

```
<220> FEATURE:
<221> NAME/KEY: misc_feature
<222> LOCATION: (6)..(16)
<223> OTHER INFORMATION: Cyclic
<220> FEATURE:
<221> NAME/KEY: MOD_RES
<222> LOCATION: (16)..(16)
<223> OTHER INFORMATION: Dab

<400> SEQUENCE: 584

Asn Ala Ile Ser Val Asp Tyr Phe Asp Asp Ser Ser Asn Val Leu Xaa
1               5                   10                  15

Lys Lys Tyr Arg Asn
            20

<210> SEQ ID NO 585
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(11)
<223> OTHER INFORMATION: Cyclic
<220> FEATURE:
<221> NAME/KEY: MOD_RES
<222> LOCATION: (1)..(1)
<223> OTHER INFORMATION: Dap
<220> FEATURE:
<221> NAME/KEY: misc_feature
<222> LOCATION: (11)..(21)
<223> OTHER INFORMATION: Cyclic

<400> SEQUENCE: 585

Xaa Tyr Phe Asp Asp Ser Ser Asn Val Leu Gly Lys Lys Tyr Arg Asn
1               5                   10                  15

Asn Ala Ile Ser Val
            20

<210> SEQ ID NO 586
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (3)..(9)
<223> OTHER INFORMATION: Cyclic
<220> FEATURE:
<221> NAME/KEY: misc_feature
<222> LOCATION: (11)..(21)
<223> OTHER INFORMATION: Cyclic
<220> FEATURE:
<221> NAME/KEY: MOD_RES
<222> LOCATION: (11)..(11)
<223> OTHER INFORMATION: Dab

<400> SEQUENCE: 586

Leu Tyr Glu Asp Asp Ser Ser Asn Lys Leu Xaa Lys Lys Tyr Arg Asn
1               5                   10                  15

Asn Ala Ile Ser Val
            20

<210> SEQ ID NO 587
<211> LENGTH: 21
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(11)
<223> OTHER INFORMATION: Cyclic
<220> FEATURE:
<221> NAME/KEY: misc_feature
<222> LOCATION: (3)..(21)
<223> OTHER INFORMATION: Cyclic
<220> FEATURE:
<221> NAME/KEY: MOD_RES
<222> LOCATION: (11)..(11)
<223> OTHER INFORMATION: Orn

<400> SEQUENCE: 587

Asp Tyr Lys Asp Asp Ser Ser Asn Val Leu Xaa Lys Lys Tyr Arg Asn
1               5                   10                  15

Asn Ala Ile Ser Val
            20

<210> SEQ ID NO 588
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(21)
<223> OTHER INFORMATION: Cyclic
<220> FEATURE:
<221> NAME/KEY: misc_feature
<222> LOCATION: (3)..(9)
<223> OTHER INFORMATION: Cyclic
<220> FEATURE:
<221> NAME/KEY: MOD_RES
<222> LOCATION: (3)..(3)
<223> OTHER INFORMATION: Dap

<400> SEQUENCE: 588

Leu Lys Xaa Asp Asp Ser Ser Asn Glu Leu Leu Lys Lys Tyr Arg Asn
1               5                   10                  15

Asn Ala Ile Ser Val
            20

<210> SEQ ID NO 589
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(11)
<223> OTHER INFORMATION: Cyclic
<220> FEATURE:
<221> NAME/KEY: MOD_RES
<222> LOCATION: (1)..(1)
<223> OTHER INFORMATION: Dap
<220> FEATURE:
<221> NAME/KEY: MOD_RES
<222> LOCATION: (11)..(11)
<223> OTHER INFORMATION: Dap

<400> SEQUENCE: 589

Xaa Tyr Phe Asp Asp Ser Ser Asn Val Leu Xaa Lys Lys Tyr Arg Ser
1               5                   10                  15
```

```
<210> SEQ ID NO 590
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(11)
<223> OTHER INFORMATION: Cyclic

<400> SEQUENCE: 590

Glu Tyr Phe Asp Asp Ser Ser Asn Val Leu Glu Lys Lys Tyr Arg Ser
1               5                   10                  15

<210> SEQ ID NO 591
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(10)
<223> OTHER INFORMATION: Cyclic

<400> SEQUENCE: 591

Leu Ser Phe Asp Asp Ser Ser Asn Val Lys Leu Lys Lys Tyr Arg Ser
1               5                   10                  15

<210> SEQ ID NO 592
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (3)..(9)
<223> OTHER INFORMATION: Cyclic
<220> FEATURE:
<221> NAME/KEY: MOD_RES
<222> LOCATION: (3)..(3)
<223> OTHER INFORMATION: Dab
<220> FEATURE:
<221> NAME/KEY: MOD_RES
<222> LOCATION: (9)..(9)
<223> OTHER INFORMATION: Dap

<400> SEQUENCE: 592

Leu Tyr Xaa Asp Asp Ser Ser Asn Xaa Leu Leu Lys Lys Tyr Arg Ser
1               5                   10                  15

<210> SEQ ID NO 593
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (3)..(9)
<223> OTHER INFORMATION: Cyclic

<400> SEQUENCE: 593

Leu Tyr Asp Asp Asp Ser Ser Asn Glu Leu Leu Lys Lys Tyr Arg Ser
```

```
<210> SEQ ID NO 594
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(9)
<223> OTHER INFORMATION: Cyclic

<400> SEQUENCE: 594

Thr Tyr Phe Asp Asp Ser Ser Asn Ser Leu Leu Lys Lys Tyr Arg Ser
1               5                   10                  15

<210> SEQ ID NO 595
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (3)..(9)
<223> OTHER INFORMATION: Cyclic
<220> FEATURE:
<221> NAME/KEY: MOD_RES
<222> LOCATION: (3)..(3)
<223> OTHER INFORMATION: p-Phe

<400> SEQUENCE: 595

Leu Tyr Phe Asp Asp Ser Ser Asn Lys Leu Leu Lys Lys Tyr Arg Ser
1               5                   10                  15

<210> SEQ ID NO 596
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (3)..(9)
<223> OTHER INFORMATION: Cyclic
<220> FEATURE:
<221> NAME/KEY: MOD_RES
<222> LOCATION: (3)..(3)
<223> OTHER INFORMATION: p-Phe

<400> SEQUENCE: 596

Leu Tyr Phe Asp Asp Ser Ser Asn Asp Leu Leu Lys Lys Tyr Arg Ser
1               5                   10                  15

<210> SEQ ID NO 597
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(10)
<223> OTHER INFORMATION: Cyclic
<220> FEATURE:
<221> NAME/KEY: MOD_RES
<222> LOCATION: (10)..(10)
```

```
<223> OTHER INFORMATION: Dap

<400> SEQUENCE: 597

Leu Tyr Phe Asp Asp Ser Ser Asn Val Xaa Leu Lys Lys Tyr Arg Ser
1               5                   10                  15

<210> SEQ ID NO 598
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (3)..(9)
<223> OTHER INFORMATION: Cyclic
<220> FEATURE:
<221> NAME/KEY: MOD_RES
<222> LOCATION: (3)..(3)
<223> OTHER INFORMATION: o-Tyr

<400> SEQUENCE: 598

Leu Tyr Tyr Asp Asp Ser Ser Asn Ser Leu Leu Lys Lys Tyr Arg Ser
1               5                   10                  15

<210> SEQ ID NO 599
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(11)
<223> OTHER INFORMATION: Cyclic
<220> FEATURE:
<221> NAME/KEY: MOD_RES
<222> LOCATION: (1)..(1)
<223> OTHER INFORMATION: o-Phe
<220> FEATURE:
<221> NAME/KEY: MOD_RES
<222> LOCATION: (11)..(11)
<223> OTHER INFORMATION: Dap

<400> SEQUENCE: 599

Phe Tyr Phe Asp Asp Ser Ser Asn Val Leu Xaa Lys Lys Tyr Arg Ser
1               5                   10                  15

<210> SEQ ID NO 600
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(11)
<223> OTHER INFORMATION: Cyclic

<400> SEQUENCE: 600

Gly Tyr Phe Asp Asp Ser Ser Asn Val Leu Cys Lys Lys Tyr Arg Ser
1               5                   10                  15

<210> SEQ ID NO 601
<211> LENGTH: 16
<212> TYPE: PRT
<213> ORGANISM: Artificial Sequence
<220> FEATURE:
```

<223> OTHER INFORMATION: Description of Artificial Sequence: Synthetic
      peptide
<220> FEATURE:
<221> NAME/KEY: misc_feature
<222> LOCATION: (1)..(11)
<223> OTHER INFORMATION: Cyclic

<400> SEQUENCE: 601

Cys Tyr Phe Asp Asp Ser Ser Asn Val Leu Gly Lys Lys Tyr Arg Ser
1               5                   10                  15

<210> SEQ ID NO 602
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(10)
<223> OTHER INFORMATION: Cyclic

<400> SEQUENCE: 602

Leu Tyr Phe Asp Asp Ser Ser Asn Val Gly Leu Lys Lys Tyr Arg Ser
1               5                   10                  15

<210> SEQ ID NO 603
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(10)
<223> OTHER INFORMATION: Cyclic

<400> SEQUENCE: 603

Leu Tyr Phe Asp Asp Ser Ser Asn Val Ser Leu Lys Lys Tyr Arg Ser
1               5                   10                  15

<210> SEQ ID NO 604
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (3)..(9)
<223> OTHER INFORMATION: Cyclic

<400> SEQUENCE: 604

Leu Tyr Ser Asp Asp Ser Ser Asn Thr Leu Lys Lys Tyr Arg Ser
1               5                   10                  15

<210> SEQ ID NO 605
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (3)..(9)
<223> OTHER INFORMATION: Cyclic

```
<400> SEQUENCE: 605

Leu Tyr Gly Asp Asp Ser Ser Asn Gly Leu Leu Lys Lys Tyr Arg Ser
1               5                   10                  15

<210> SEQ ID NO 606
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(9)
<223> OTHER INFORMATION: Cyclic

<400> SEQUENCE: 606

Gly Tyr Phe Asp Asp Ser Ser Asn Lys Leu Leu Lys Lys Tyr Arg Ser
1               5                   10                  15

<210> SEQ ID NO 607
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(11)
<223> OTHER INFORMATION: Cyclic

<400> SEQUENCE: 607

Asn Tyr Phe Asp Asp Ser Ser Asn Val Leu Asn Lys Lys Tyr Arg Ser
1               5                   10                  15

<210> SEQ ID NO 608
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(10)
<223> OTHER INFORMATION: Cyclic

<400> SEQUENCE: 608

Leu Tyr Phe Asp Asp Ser Ser Asn Val Gln Leu Lys Lys Tyr Arg Ser
1               5                   10                  15

<210> SEQ ID NO 609
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(9)
<223> OTHER INFORMATION: Cyclic

<400> SEQUENCE: 609

Gly Tyr Phe Asp Asp Ser Ser Asn Lys Leu Leu Lys Lys Tyr Arg Ser
1               5                   10                  15

<210> SEQ ID NO 610
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(9)
<223> OTHER INFORMATION: Cyclic

<400> SEQUENCE: 610

Tyr Phe Asp Asp Ser Ser Asn Val Leu
1               5

<210> SEQ ID NO 611
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(9)
<223> OTHER INFORMATION: Cyclic

<400> SEQUENCE: 611

Tyr Phe Asp Asp Ser Ser Asn Val Leu
1               5

<210> SEQ ID NO 612
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(7)
<223> OTHER INFORMATION: Disulfide bridge

<400> SEQUENCE: 612

Cys Asp Asp Ser Ser Asn Cys Leu Leu Lys Lys Tyr Arg Ser
1               5                   10

<210> SEQ ID NO 613
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(9)
<223> OTHER INFORMATION: Cyclic

<400> SEQUENCE: 613

Asn Ser Ser Asp Asp Phe Tyr Cys Cys Lys Lys Tyr Arg Ser
1               5                   10

<210> SEQ ID NO 614
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: misc_feature
<222> LOCATION: (3)..(9)
<223> OTHER INFORMATION: Disulfide bridge

<400> SEQUENCE: 614

Leu Tyr Cys Asp Asp Ser Ser Asn Cys
1               5
```